United States Patent
Schell et al.

(10) Patent No.: US 11,035,006 B2
(45) Date of Patent: Jun. 15, 2021

(54) COLORECTAL CANCER RECURRENCE GENE EXPRESSION SIGNATURE

(71) Applicants: H. LEE MOFFITT CANCER CENTER AND RESEARCH INSTITUTE, INC., Tampa, FL (US); GIBBS CANCER CENTER, Spartanburg, SC (US)

(72) Inventors: Michael Schell, Temple Terrace, FL (US); Timothy Yeatman, Greenville, SC (US)

(73) Assignees: H. Lee Moffitt Cancer Center and Research Institute, Inc., Tampa, FL (US); Gibbs Cancer Center & Research Institute, Spartanburg, SC (US)

( * ) Notice: Subject to any disclaimer, the term of this patent is extended or adjusted under 35 U.S.C. 154(b) by 549 days.

(21) Appl. No.: 14/907,372

(22) PCT Filed: Jul. 30, 2014

(86) PCT No.: PCT/US2014/048887
§ 371 (c)(1),
(2) Date: Jan. 25, 2016

(87) PCT Pub. No.: WO2015/017537
PCT Pub. Date: Feb. 5, 2015

(65) Prior Publication Data
US 2016/0208333 A1    Jul. 21, 2016

Related U.S. Application Data

(60) Provisional application No. 61/859,959, filed on Jul. 30, 2013.

(51) Int. Cl.
*G01N 33/48* (2006.01)
*C12Q 1/6886* (2018.01)
*G06G 7/58* (2006.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

WO    2012061515 A2    5/2012

OTHER PUBLICATIONS

Loboda, A, et al., BMC Med Genomics, 2011, 4:9.
Eschrich, S. et al. J Clin Oncol. 2005 23(15):3526-35.
Jorissen, R. N. et al. Clin Cancer Res. 2009 15(24):7642-7651.
Sotiriou, C. et al. J Natl Cancer Inst. 2006 98(4):262-72.
Farmer, P. et al. Nat Med. 2009 15(1):68-74).
Roth, A.D. et al. J Natl Cancer Inst. 2012 104(21):1635-46.
Popovici, V. et al. J Clin Oncol. 2012 30(12):1288-95.
Budinska, E. et al. J Pathol. 2013 231(1):63-76.
Sadanandam, A. et al. Nat Med. 2013 19(5):619-25.
Zhang, B. et al. Nature. Jul. 20, 2014 (in press)).
Greaves, M. et al. Clonal evolution in cancer. Nature 2012 481:306-313.
Vanharanta, S. et al. Cancer Cell. 2013 24(4):410-21.
Tsuji, T et al. Cancer Res. 2009 69(18):7135-9.
Tsuji, T. et al. Cancer Res. 2008 68(24):10377-86.
Giancotti, F.G. Cell. 2013 155(4):750-64.
Oskarsson, T., Cell Stem Cell. 2014 14(3):306-21.
Chui, M. H. Int J Cancer. 2013 132(7):1487-95.
Smith, S.C. et al. Cancer Res. 2006 66(4):1917-22.
Ashley, N. et al. Cancer Res. 2013 73(18):5798-809.
Liu, S. et al. Stem Cell Reports. 2013 2(1):78-91.
Guinney, J. et al. Clin Cancer Res. 2014 20(1):265-72.
Cancer Genome Atlas Network. Nature. 2012 487(7407):330-7.
Karhemo, P.R. et al. J Proteomics. 2012 77:87-100.
Emori, M. et al. PLoS One. 2013 8(12):e84187.
Subramanian, A, et al. (2005). Proc. Natl. Acad. Sci 102:15545-15550.
Yu, G. et al. J Cancer Res Clin Oncol. 2011 137(1):73-80.
Gao, Q. et al. Hum Pathol. 2014 45(2):372-81.
Knopfova, L. et al. Mol Cancer. 2012 11:15.
Favre, C., et al. Oncogene. 2010 29(27):3964-76.
O'Connell, M.J. et al. J Clin Oncol. 2010 28(25):3937-44.
Nieto, M.A. Science. 2013 342(6159):1234850.
Staub E1, et al. (2009). J Mol Med (Berl). 87:633-44.
Kennedy, R. D. et al. J Clin Oncol. 2011 29(35):4620-6.
Marisa, L. et al. PLoS Med. 2013 10(5):e1001453.
Sheffer, M. et al. Proc Natl Acad Sci U S A. 2009 106(17):7131-6.
International Search Report and Written Opinion, issued in International Application No. PCT/US/14/48887 dated Jan. 14, 2015.
Loboda, A. et al. BMC Med Genomics. 2010 3:26.
Dry, J. R. et al. Cancer Res. 2010 70(6):2264-73.
Schetter AJ, et al. (2009). Clin Cancer Res. 15:5878-87.
Jiang, Y. et al. J Mol Diagn. 2008 10(4):346-5.
Oh, S. C. et al. Gut. 2012 61(9):1291-8.
Moertel, C., "Chemotherapy for Colorectal Cancer", N Engl J Med, 1994, vol. 330, No. 16, pp. 1136-1142.
Huang, S. et al. Cell. 2012 151(5):937-50.

(Continued)

*Primary Examiner* — Eric S Dejong
(74) *Attorney, Agent, or Firm* — Meunier Carlin & Curfman LLC

(57) ABSTRACT

Disclosed are gene signatures that may be used to predict the recurrence of colorectal cancer in a human patient. These signatures can be used to determine when to treat a patient with post-operative adjuvant chemotherapy, i.e., when a high risk of colorectal cancer recurrence is predicted.

29 Claims, 42 Drawing Sheets
Specification includes a Sequence Listing.

(56) References Cited

OTHER PUBLICATIONS

Kalady, M., "Gene Signature is Associated with Early Stage Rectal Cancer Recurrence", Journal of the American College of Surgeons, 2010, vol. 211, No. 2, pp. 187-195.
Coppola D, et al. (2011). Am J Pathol. 179:37-45.
Peng J, et al. (2010). Int J Colorectal Dis. 25:1277-85.

| PCI.EMT | ONCO-TYPETX | MAMMA PRINT | FLAS. MERCK | RAS. ASTRA | GH | VERIDEX | MDA | DGN | EMT | MED12 | BRAF | COPPOLA | PENG | SCHETTER | STAUB | ALM | |
|---|---|---|---|---|---|---|---|---|---|---|---|---|---|---|---|---|---|
| PCI.EMT | .25 | -.16 | .17 | .03 | .36 | -.11 | .42 | .27 | .24 | .47 | .40 | -.26 | .20 | .30 | .07 | .90 | PCI.EMT |
|  | ONCO-TYPETX | .37 | -.07 | .15 | -.47 | .00 | -.30 | -.31 | -.46 | -.34 | -.24 | .18 | -.38 | -.01 | .12 | .08 | ONCO-TYPETX |
|  |  | MAMMA PRINT | .09 | .52 | -.05 | -.09 | .13 | .19 | -.09 | .02 | -04 | -.24 | -.06 | -.03 | .59 | .07 | MAMMA PRINT |
|  |  |  | FLAS. MERCK | .26 | .37 | -.24 | .53 | .90 | .13 | .47 | .41 | -.38 | .17 | .19 | .23 | .11 | FLAS. MERCK |
|  |  |  |  | RAS. ASTRA | .15 | -.01 | .15 | .29 | -.09 | .25 | .02 | -.20 | .09 | .17 | .59 | .25 | RAS. ASTRA |
|  |  |  |  |  | GH | -.24 | .56 | .75 | .68 | .74 | .27 | .50 | .50 | .19 | .27 | .23 | GH |
|  |  |  |  |  |  | VERIDEX | -.42 | -.29 | -.33 | -.31 | -.32 | .44 | -.27 | -.11 | -.25 | -.01 | VERIDEX |
|  |  |  |  |  |  |  | MDA | .51 | .45 | .68 | .85 | -.53 | .39 | .29 | .26 | .14 | MDA |
|  |  |  |  |  |  |  |  | DCN | .80 | .82 | .10 | -.56 | .53 | .16 | .49 | .25 | DGN |
|  |  |  |  |  |  |  |  |  | EMT | .68 | .13 | -.49 | .52 | .06 | .19 | .09 | EMT |
|  |  |  |  |  |  |  |  |  |  | MED12 | .28 | -.54 | .49 | .27 | .42 | .27 | MED12 |
|  |  |  |  |  |  |  |  |  |  |  | BRAF | -.27 | .24 | .28 | .01 | .09 | BRAF |
|  |  |  |  |  |  |  |  |  |  |  |  | COPPOLA | -.37 | -.01 | -.39 | -.09 | COPPOLA |
|  |  |  |  |  |  |  |  |  |  |  |  |  | PENG | .11 | .11 | .06 | PENG |
|  |  |  |  |  |  |  |  |  |  |  |  |  |  | SCHETTER | .10 | .16 | SCHETTER |
|  |  |  |  |  |  |  |  |  |  |  |  |  |  |  | STAUB | .26 | STAUB |
|  |  |  |  |  |  |  |  |  |  |  |  |  |  |  |  | ALM | ALM |

FIG. 6A

| PCI.EMT | ONCO-TYPETX | MAMMA PRINT | FLAS. MERCK | RAS. ASTRA | GH | VERIDEX | MDA | DGN | EMT | MED12 | BRAF | COPPOLA | PENG | SCHETTER | STAUB | ALM | |
|---|---|---|---|---|---|---|---|---|---|---|---|---|---|---|---|---|---|
| PCI.EMT | -.05 | -.04 | .25 | .20 | .31 | -.16 | .31 | .29 | .14 | .53 | .28 | -.22 | .03 | .32 | .21 | .21 | PCI.EMT |
| | ONCO-TYPETX | .43 | .07 | .34 | -.33 | -.05 | -.12 | -.23 | -.50 | -.26 | -.06 | .06 | -.37 | -.02 | .27 | -.04 | ONCO-TYPETX |
| | | MAMMA PRINT | .06 | .63 | -.03 | -.12 | .30 | .15 | -.27 | -.04 | .16 | -.20 | -.18 | .10 | .60 | .24 | MAMMA PRINT |
| | | | FLAS. MERCK | .14 | .30 | -.28 | .57 | .10 | -.01 | .35 | .55 | -.28 | .02 | .11 | .14 | .17 | FLAS. MERCK |
| | | | | RAS. ASTRA | .17 | -.08 | .20 | .27 | -.28 | .16 | .05 | -.13 | -.20 | .22 | .63 | .33 | RAS. ASTRA |
| | | | | | GH | -.30 | .44 | .71 | .57 | .62 | .19 | -.38 | .37 | .21 | .21 | .29 | GH |
| | | | | | | VERIDEX | -.43 | -.33 | -.25 | -.34 | -.32 | .42 | -.09 | .00 | -.28 | -.07 | VERIDEX |
| | | | | | | | MDA | .41 | .25 | .47 | .87 | -.54 | -.18 | .16 | .32 | .25 | MDA |
| | | | | | | | | DCN | .70 | .75 | .03 | -.45 | .33 | .24 | .44 | .30 | DGN |
| | | | | | | | | | EMT | .54 | .02 | -.38 | .50 | .10 | -.05 | .08 | EMT |
| | | | | | | | | | | MED12 | .23 | -.44 | .26 | .23 | .32 | .26 | MED12 |
| | | | | | | | | | | | BRAF | -.32 | .10 | .09 | .12 | .13 | BRAF |
| | | | | | | | | | | | | COPPOLA | -.21 | .08 | -.32 | -.12 | COPPOLA |
| | | | | | | | | | | | | | PENG | .12 | -.10 | .04 | PENG |
| | | | | | | | | | | | | | | SCHETTER | .18 | .17 | SCHETTER |
| | | | | | | | | | | | | | | | STAUB | .34 | STAUB |
| | | | | | | | | | | | | | | | | ALM | ALM |

FIG. 6B

| PC1.EMT | ONCO-TYPETX | MAMMA PRINT | FLAS. MERCK | RAS. ASTRA | GH | VERIDEX | MDA | DGN | EMT | MED12 | BRAF | COPPOLA | PENG | SCHETTER | STAUB | ALM | |
|---|---|---|---|---|---|---|---|---|---|---|---|---|---|---|---|---|---|
| PC1.EMT | -.29 | .11 | .21 | .27 | .68 | -.39 | .74 | .60 | .62 | .54 | .57 | -.54 | .37 | .35 | .38 | .41 | PC1.EMT |
| | ONCO-TYPETX | .62 | .06 | .08 | -.58 | .05 | -.28 | -.30 | -.34 | -.40 | -.23 | .21 | -.45 | -.18 | -.22 | -.37 | ONCO-TYPETX |
| | | MAMMA PRINT | .11 | .31 | -.23 | -.06 | .21 | -.01 | -.05 | -.13 | .21 | -.07 | -.14 | .14 | .05 | -.05 | MAMMA PRINT |
| | | | FLAS. MERCK | .42 | .30 | -.20 | .49 | .19 | .00 | .40 | .50 | -.38 | -.13 | .30 | .33 | .21 | FLAS. MERCK |
| | | | | RAS. ASTRA | .28 | .01 | .41 | .26 | .09 | .37 | .41 | .22 | .13 | .28 | .37 | .28 | RAS. ASTRA |
| | | | | | GH | -.22 | .64 | .82 | .74 | .78 | .39 | -.57 | .54 | .33 | .49 | .48 | GH |
| | | | | | | VERIDEX | -.43 | -.25 | -.33 | -.22 | -.35 | .44 | -.00 | -.11 | -.35 | -.11 | VERIDEX |
| | | | | | | | MDA | .55 | .43 | .59 | .90 | -.60 | .22 | .43 | .51 | .47 | MDA |
| | | | | | | | | DCN | .89 | .80 | .21 | -.63 | .65 | .21 | .59 | .35 | DGN |
| | | | | | | | | | EMT | .64 | .10 | -.61 | .65 | .13 | .51 | .31 | EMT |
| | | | | | | | | | | MED12 | .38 | -.66 | .52 | .32 | .70 | .47 | MED12 |
| | | | | | | | | | | | BRAF | -.40 | -.00 | .41 | .38 | .43 | BRAF |
| | | | | | | | | | | | | COPPOLA | -.39 | -.09 | -.69 | -.30 | COPPOLA |
| | | | | | | | | | | | | | PENG | .15 | .33 | .22 | PENG |
| | | | | | | | | | | | | | | SCHETTER | .15 | .29 | SCHETTER |
| | | | | | | | | | | | | | | | STAUB | .47 | STAUB |
| | | | | | | | | | | | | | | | | ALM | ALM |

FIG. 6C

| PCI.EMT | ONCO-TYPETX | MAMMA PRINT | FLAS. MERCK | RAS. ASTRA | GH | VERIDEX | MDA | DGN | EMT | MED12 | BRAF | COPPOLA | PENG | SCHETTER | STAUB | ALM | |
|---|---|---|---|---|---|---|---|---|---|---|---|---|---|---|---|---|---|
| PCI.EMT | -.27 | .00 | .27 | .08 | .69 | -.13 | .76 | .63 | .52 | .61 | .61 | -.49 | .19 | -.07 | .18 | .44 | PCI.EMT |
|  | ONCO-TYPETX | .63 | .19 | .20 | -.45 | .12 | -.22 | -.25 | -.46 | -.34 | -.15 | .16 | -.32 | -.00 | -.29 | -.35 | ONCO-TYPETX |
|  |  | MAMMA PRINT | .27 | .27 | -.16 | .19 | .12 | -.05 | -.23 | -.16 | .15 | .06 | -.12 | .05 | -.18 | -.22 | MAMMA PRINT |
|  |  |  | FLAS. MERCK | .36 | .21 | .00 | .46 | .12 | -.12 | .32 | .50 | -.24 | -.15 | .21 | .03 | .05 | FLAS. MERCK |
|  |  |  |  | RAS. ASTRA | .04 | .27 | .17 | .08 | -.18 | .14 | .25 | .07 | -.06 | .01 | -.06 | -.04 | RAS. ASTRA |
|  |  |  |  |  | GH | -.19 | .60 | .73 | .62 | .69 | .40 | -.53 | .24 | -.09 | .30 | .39 | GH |
|  |  |  |  |  |  | VERIDEX | -.14 | -.08 | -.17 | -.14 | -.10 | .29 | -.06 | -.06 | -.13 | .01 | VERIDEX |
|  |  |  |  |  |  |  | MDA | .51 | .31 | .53 | .91 | -.49 | .14 | .00 | .23 | .33 | MDA |
|  |  |  |  |  |  |  |  | DCN | .81 | .80 | .23 | -.60 | .27 | -.13 | .37 | .36 | DGN |
|  |  |  |  |  |  |  |  |  | EMT | .60 | .03 | -.56 | .35 | -.06 | .32 | .35 | EMT |
|  |  |  |  |  |  |  |  |  |  | MED12 | .33 | -.58 | .20 | -.06 | .43 | .37 | MED12 |
|  |  |  |  |  |  |  |  |  |  |  | BRAF | -.30 | .04 | .05 | .17 | .22 | BRAF |
|  |  |  |  |  |  |  |  |  |  |  |  | COPPOLA | -.19 | .14 | -.35 | -.14 | COPPOLA |
|  |  |  |  |  |  |  |  |  |  |  |  |  | PENG | .09 | .14 | .06 | PENG |
|  |  |  |  |  |  |  |  |  |  |  |  |  |  | SCHETTER | -.07 | -.10 | SCHETTER |
|  |  |  |  |  |  |  |  |  |  |  |  |  |  |  | STAUB | .17 | STAUB |
|  |  |  |  |  |  |  |  |  |  |  |  |  |  |  |  | ALM | ALM |

FIG. 6D

| PC1.EMT | ONCO-TYPETX | MAMMA PRINT | FLAS. MERCK | RAS. ASTRA | GH | VERIDEX | MDA | DGN | EMT | MED12 | BRAF | COPPOLA | PENG | SCHETTER | STAUB | ALM | |
|---|---|---|---|---|---|---|---|---|---|---|---|---|---|---|---|---|---|
| PC1.EMT | -.47 | .03 | .37 | .10 | .78 | -.26 | .68 | .60 | .57 | .71 | .52 | -.47 | .41 | .53 | .30 | .40 | PC1.EMT |
| | ONCO-TYPETX | .53 | -.01 | -.04 | -.69 | .17 | -.29 | -.40 | -.47 | -.61 | -.23 | .22 | -.39 | -.24 | -.15 | -.39 | ONCO-TYPETX |
| | | MAMMA PRINT | .22 | .29 | -.13 | -.00 | .34 | .13 | -.00 | -.13 | .25 | -.15 | .11 | .15 | .24 | .07 | MAMMA PRINT |
| | | | FLAS. MERCK | .50 | .32 | -.17 | .57 | .25 | .05 | .41 | .48 | -.29 | .06 | .36 | .37 | .17 | FLAS. MERCK |
| | | | | RAS. ASTRA | .21 | .12 | .29 | .22 | -.06 | .24 | .29 | .06 | .09 | .24 | .30 | .33 | RAS. ASTRA |
| | | | | | GH | -.28 | .60 | .77 | .75 | .81 | .38 | -.43 | .53 | .40 | .39 | .41 | GH |
| | | | | | | VERIDEX | -.32 | -.29 | -.39 | -.26 | -.22 | .48 | -.33 | -.09 | -.45 | -.04 | VERIDEX |
| | | | | | | | MDA | .53 | .38 | .54 | .87 | -.55 | .45 | .57 | .51 | .30 | MDA |
| | | | | | | | | DCN | .83 | .76 | .19 | -.44 | .69 | .30 | .49 | .28 | DGN |
| | | | | | | | | | EMT | .64 | .05 | -.52 | .63 | .19 | .41 | .25 | EMT |
| | | | | | | | | | | MED12 | .31 | -.41 | .49 | .41 | .38 | .29 | MED12 |
| | | | | | | | | | | | BRAF | -.35 | .23 | .55 | .37 | .25 | BRAF |
| | | | | | | | | | | | | COPPOLA | -.50 | -.14 | -.52 | .00 | COPPOLA |
| | | | | | | | | | | | | | PENG | .19 | .64 | .07 | PENG |
| | | | | | | | | | | | | | | SCHETTER | .22 | .41 | SCHETTER |
| | | | | | | | | | | | | | | | STAUB | .29 | STAUB |
| | | | | | | | | | | | | | | | | ALM | ALM |

FIG. 6E

| PC1.EMT | ONCO-TYPETX | MAMMA PRINT | FLAS. MERCK | RAS. ASTRA | GH | VERIDEX | MDA | DGN | EMT | MED12 | BRAF | COPPOLA | PENG | SCHETTER | STAUB | ALM | |
|---|---|---|---|---|---|---|---|---|---|---|---|---|---|---|---|---|---|
| PC1.EMT | -.16 | .24 | .41 | .45 | .55 | -.32 | .71 | .45 | .28 | .47 | .61 | -.44 | .31 | .19 | .37 | .36 | PC1.EMT |
| | ONCO-TYPETX | .25 | -.17 | -.26 | -.48 | .09 | -.30 | -.30 | -.28 | -.44 | -.26 | .18 | -.46 | -.11 | -.40 | -.32 | ONCO-TYPETX |
| | | MAMMA PRINT | .11 | .20 | -.19 | -.01 | .40 | -.03 | .08 | -.18 | .34 | -.21 | .06 | .03 | -.14 | .01 | MAMMA PRINT |
| | | | FLAS. MERCK | .54 | .48 | -.41 | .57 | .23 | .04 | .50 | .56 | -.45 | .06 | .44 | .37 | .18 | FLAS. MERCK |
| | | | | RAS. ASTRA | .47 | -.09 | .48 | .25 | .13 | .44 | .51 | -.26 | .24 | .20 | .34 | .40 | RAS. ASTRA |
| | | | | | GH | -.30 | .50 | .77 | .56 | .78 | .32 | -.52 | .53 | .17 | .66 | .40 | GH |
| | | | | | | VERIDEX | -.51 | -.31 | -.30 | -.30 | -.45 | .59 | -.20 | -.15 | -.41 | .05 | VERIDEX |
| | | | | | | | MDA | .39 | .27 | .44 | .91 | -.58 | .31 | .21 | .41 | .30 | MDA |
| | | | | | | | | DCN | .82 | .78 | .11 | -.58 | .72 | .09 | .72 | .31 | DGN |
| | | | | | | | | | EMT | .57 | -.01 | -.48 | .64 | -.01 | .59 | .22 | EMT |
| | | | | | | | | | | MED12 | .29 | -.50 | .58 | .21 | .74 | .41 | MED12 |
| | | | | | | | | | | | BRAF | -.39 | .10 | .18 | .29 | .27 | BRAF |
| | | | | | | | | | | | | COPPOLA | -.53 | -.12 | -.56 | -.09 | COPPOLA |
| | | | | | | | | | | | | | PENG | .12 | .55 | .26 | PENG |
| | | | | | | | | | | | | | | SCHETTER | .15 | .04 | SCHETTER |
| | | | | | | | | | | | | | | | STAUB | .35 | STAUB |
| | | | | | | | | | | | | | | | | ALM | ALM |

SEQUENCE LISTING

```
<160> NUMBER OF SEQ ID NOS: 508

<210> SEQ ID NO 1
<211> LENGTH: 60
<212> TYPE: DNA
<213> ORGANISM: Artificial Sequence
<220> FEATURE:
<223> OTHER INFORMATION: Synthetic

<400> SEQUENCE: 1
ttgagtcatt tttatcacaa taatcctact gtgaagctgt cgttgagaac ttaggttggc     60

<210> SEQ ID NO 2
<211> LENGTH: 60
<212> TYPE: DNA
<213> ORGANISM: Artificial Sequence
<220> FEATURE:
<223> OTHER INFORMATION: Synthetic

<400> SEQUENCE: 2
ttcttcttct tatcttgtta ttacggtttt attaattttg tagagggaca gggagtgggc     60

<210> SEQ ID NO 3
<211> LENGTH: 60
<212> TYPE: DNA
<213> ORGANISM: Artificial Sequence
<220> FEATURE:
<223> OTHER INFORMATION: Synthetic

<400> SEQUENCE: 3
```
tagacctgaa atctttgttt ttcctattga caagggcttg gtccgtctgt tggccaggaa      60

<210> SEQ ID NO 4
<211> LENGTH: 60
<212> TYPE: DNA
<213> ORGANISM: Artificial Sequence
<220> FEATURE:
<223> OTHER INFORMATION: Synthetic

<400> SEQUENCE: 4
tttcacgagt cttcaagctt tcaggctatc ttctagtcaa gatgagtgat aagccagact      60

<210> SEQ ID NO 5
<211> LENGTH: 60
<212> TYPE: DNA
<213> ORGANISM: Artificial Sequence
<220> FEATURE:
<223> OTHER INFORMATION: Synthetic

<400> SEQUENCE: 5
tttaaatgta acagatctga aaacttacca gattgggtgg gatacattct gtgtcaaatg      60

<210> SEQ ID NO 6
<211> LENGTH: 60
<212> TYPE: DNA
<213> ORGANISM: Artificial Sequence
<220> FEATURE:
<223> OTHER INFORMATION: Synthetic

<400> SEQUENCE: 6
tggattgata ttacagatgt aaaacctgga aactatatcc taaaggtcag tgtaaacccc      60

<210> SEQ ID NO 7
<211> LENGTH: 60
<212> TYPE: DNA
<213> ORGANISM: Artificial Sequence
<220> FEATURE:
<223> OTHER INFORMATION: Synthetic

<400> SEQUENCE: 7
tatagacatt ctcacataag cccagttcat caccatttcc tcctttacct ttcagtgcag      60

<210> SEQ ID NO 8
<211> LENGTH: 60
<212> TYPE: DNA
<213> ORGANISM: Artificial Sequence
<220> FEATURE:
<223> OTHER INFORMATION: Synthetic

<400> SEQUENCE: 8
tttatctcaa gtgaacctgg agaagcaaca ataatggacc ttctcccta gtcaaatagc      60

<210> SEQ ID NO 9
<211> LENGTH: 60
<212> TYPE: DNA
<213> ORGANISM: Artificial Sequence
<220> FEATURE:
<223> OTHER INFORMATION: Synthetic

<400> SEQUENCE: 9
cagcattctt acgtgagaat ttcacttacg ggagagttct tacaggattt caagaaggaa      60

<210> SEQ ID NO 10
<211> LENGTH: 60
<212> TYPE: DNA
<213> ORGANISM: Artificial Sequence

```
<220> FEATURE:
<223> OTHER INFORMATION: Synthetic

<400> SEQUENCE: 10
ttgccttaac attgcaattg catttaacag tgttactttt aacattgcct cgtggcctca      60

<210> SEQ ID NO 11
<211> LENGTH: 60
<212> TYPE: DNA
<213> ORGANISM: Artificial Sequence
<220> FEATURE:
<223> OTHER INFORMATION: Synthetic

<400> SEQUENCE: 11
tttctctctg cattgtgtag tgagtggtgt cacccaggac tttcatgtga gaaaaagcac      60

<210> SEQ ID NO 12
<211> LENGTH: 60
<212> TYPE: DNA
<213> ORGANISM: Artificial Sequence
<220> FEATURE:
<223> OTHER INFORMATION: Synthetic

<400> SEQUENCE: 12
tcttcattcg ccaggctttg aggccatttc cctattcatt aaagactaat gtttaaaaag      60

<210> SEQ ID NO 13
<211> LENGTH: 60
<212> TYPE: DNA
<213> ORGANISM: Artificial Sequence
<220> FEATURE:
<223> OTHER INFORMATION: Synthetic

<400> SEQUENCE: 13
ttatccctca ggatggtgat tatagagaat ttcccattcc tgaacagttc aagacagcat      60

<210> SEQ ID NO 14
<211> LENGTH: 60
<212> TYPE: DNA
<213> ORGANISM: Artificial Sequence
<220> FEATURE:
<223> OTHER INFORMATION: Synthetic

<400> SEQUENCE: 14
tgaaaaggcg gtactagttc agacactttg gaagtttgtg ttctgtttgt taaaactggc      60

<210> SEQ ID NO 15
<211> LENGTH: 60
<212> TYPE: DNA
<213> ORGANISM: Artificial Sequence
<220> FEATURE:
<223> OTHER INFORMATION: Synthetic

<400> SEQUENCE: 15
tagttaccat tttcagtgtt atttcaaagg ttctttgaag aattttgggg cagggcatca      60

<210> SEQ ID NO 16
<211> LENGTH: 60
<212> TYPE: DNA
<213> ORGANISM: Artificial Sequence
<220> FEATURE:
<223> OTHER INFORMATION: Synthetic

<400> SEQUENCE: 16
tttgttcgtg gtagcaccct caaagaaatc cccgtgactg tctatagaga agtatgacaa      60
```

<210> SEQ ID NO 17
<211> LENGTH: 60
<212> TYPE: DNA
<213> ORGANISM: Artificial Sequence
<220> FEATURE:
<223> OTHER INFORMATION: Synthetic

<400> SEQUENCE: 17
ttgtgatttc atgtttgtaa tctacaactt ttcaaaagca ttcagtcatg gtctgctagg    60

<210> SEQ ID NO 18
<211> LENGTH: 60
<212> TYPE: DNA
<213> ORGANISM: Artificial Sequence
<220> FEATURE:
<223> OTHER INFORMATION: Synthetic

<400> SEQUENCE: 18
cacaagtttt agccttttc acaagggaac tcatactgtc tacacatcag accatagttg    60

<210> SEQ ID NO 19
<211> LENGTH: 60
<212> TYPE: DNA
<213> ORGANISM: Artificial Sequence
<220> FEATURE:
<223> OTHER INFORMATION: Synthetic

<400> SEQUENCE: 19
ttcaacctga ttgacacttt tcccttgaga aagaagaga tggtcctaca agccgaaatg    60

<210> SEQ ID NO 20
<211> LENGTH: 60
<212> TYPE: DNA
<213> ORGANISM: Artificial Sequence
<220> FEATURE:
<223> OTHER INFORMATION: Synthetic

<400> SEQUENCE: 20
tccagatata aaatatggtg caatatccac ttcatcactt ggagaaaaag tgctgagtgc    60

<210> SEQ ID NO 21
<211> LENGTH: 60
<212> TYPE: DNA
<213> ORGANISM: Artificial Sequence
<220> FEATURE:
<223> OTHER INFORMATION: Synthetic

<400> SEQUENCE: 21
tttcaatatt ttaactttt gttttattt cttttagaaa aggccaatat acctatcgcg    60

<210> SEQ ID NO 22
<211> LENGTH: 60
<212> TYPE: DNA
<213> ORGANISM: Artificial Sequence
<220> FEATURE:
<223> OTHER INFORMATION: Synthetic

<400> SEQUENCE: 22
tcactatacc atgctatagg agactgggca aaacctgtac aatgacaacc ctggaagttg    60

<210> SEQ ID NO 23
<211> LENGTH: 60
<212> TYPE: DNA
<213> ORGANISM: Artificial Sequence
<220> FEATURE:
<223> OTHER INFORMATION: Synthetic -continued

<400> SEQUENCE: 23
ttgtagatgg cagttatgaa tgtatattta tattttgatt aagatttcta ttaactttt      60

<210> SEQ ID NO 24
<211> LENGTH: 60
<212> TYPE: DNA
<213> ORGANISM: Artificial Sequence
<220> FEATURE:
<223> OTHER INFORMATION: Synthetic

<400> SEQUENCE: 24
ttcctgggat tgatggagtt aaaggtgaca aaggaaatcc aggctggcca ggagcacccg      60

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25
tctgtgtatt ttcaaatgtt actatatatt aaagcagaaa tataaccaaa ggttaaaaaa      60

<210> SEQ ID NO 26
<211> LENGTH: 60
<212> TYPE: DNA
<213> ORGANISM: Artificial Sequence
<220> FEATURE:
<223> OTHER INFORMATION: Synthetic

<400> SEQUENCE: 26
ttgggactgt gttagcaact attattgtgg aataacccag aacattggat ttataccaac      60

<210> SEQ ID NO 27
<211> LENGTH: 60
<212> TYPE: DNA
<213> ORGANISM: Artificial Sequence
<220> FEATURE:
<223> OTHER INFORMATION: Synthetic

<400> SEQUENCE: 27
tgagaatgca cgcgtgcata tgctacacat atgtgcttct cagttgcaga aaatgaactg      60

<210> SEQ ID NO 28
<211> LENGTH: 60
<212> TYPE: DNA
<213> ORGANISM: Artificial Sequence
<220> FEATURE:
<223> OTHER INFORMATION: Synthetic

<400> SEQUENCE: 28
tttggactaa tacaattcag gaaagaaaaa acccaaaaac caacctcatt cacatatggc      60

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29
ttggcactga ggggaccagc tggcccgatg ggtctcacag ggagacctgg ccctgtgcaa      60

<210> SEQ ID NO 30

<211> LENGTH: 60
<212> TYPE: DNA
<213> ORGANISM: Artificial Sequence
<220> FEATURE:
<223> OTHER INFORMATION: Synthetic

<400> SEQUENCE: 30
gcttgaaaaa gattagcata catctaatgt gaaaagacca catttgattc aactgagacc    60

<210> SEQ ID NO 31
<211> LENGTH: 60
<212> TYPE: DNA
<213> ORGANISM: Artificial Sequence
<220> FEATURE:
<223> OTHER INFORMATION: Synthetic

<400> SEQUENCE: 31
tttagccttt tagaatgatt catgtcaaca cttaagacaa agttcatgaa aagtcccagc    60

<210> SEQ ID NO 32
<211> LENGTH: 60
<212> TYPE: DNA
<213> ORGANISM: Artificial Sequence
<220> FEATURE:
<223> OTHER INFORMATION: Synthetic

<400> SEQUENCE: 32
gtcgcgatgc ctattttagt caaagcggct gcgggcttgg ggacccggcc cgggcagcgg    60

<210> SEQ ID NO 33
<211> LENGTH: 60
<212> TYPE: DNA
<213> ORGANISM: Artificial Sequence
<220> FEATURE:
<223> OTHER INFORMATION: Synthetic

<400> SEQUENCE: 33
tttgctgtag ccttcagtgt cctgctgtta agctgtaagg atcacgtggg gtacattttt    60

<210> SEQ ID NO 34
<211> LENGTH: 60
<212> TYPE: DNA
<213> ORGANISM: Artificial Sequence
<220> FEATURE:
<223> OTHER INFORMATION: Synthetic

<400> SEQUENCE: 34
ttgccatttg gacttggtac tcggcttagt gattagaggc cctgaacagg tggtggtatc    60

<210> SEQ ID NO 35
<211> LENGTH: 60
<212> TYPE: DNA
<213> ORGANISM: Artificial Sequence
<220> FEATURE:
<223> OTHER INFORMATION: Synthetic

<400> SEQUENCE: 35
tgtggcagta atggcaagac ctacctcaac cactgtgaac tgcatcgaga tgcctgcctc    60

<210> SEQ ID NO 36
<211> LENGTH: 60
<212> TYPE: DNA
<213> ORGANISM: Artificial Sequence
<220> FEATURE:
<223> OTHER INFORMATION: Synthetic

<400> SEQUENCE: 36

```
ggctagagat atatcttaat gcaatccatt ttctgatgga ttgttacgag ttggctatat      60

<210> SEQ ID NO 37
<211> LENGTH: 60
<212> TYPE: DNA
<213> ORGANISM: Artificial Sequence
<220> FEATURE:
<223> OTHER INFORMATION: Synthetic

<400> SEQUENCE: 37
tttgaaccgg ggacagagtc taggtgagct ggggcttggg agctattagc gtagaggatc      60

<210> SEQ ID NO 38
<211> LENGTH: 60
<212> TYPE: DNA
<213> ORGANISM: Artificial Sequence
<220> FEATURE:
<223> OTHER INFORMATION: Synthetic

<400> SEQUENCE: 38
aagaaaaaga gagggcatgg gttgcggagc cgacatcacg gccggggtct ttgctgttta      60

<210> SEQ ID NO 39
<211> LENGTH: 60
<212> TYPE: DNA
<213> ORGANISM: Artificial Sequence
<220> FEATURE:
<223> OTHER INFORMATION: Synthetic

<400> SEQUENCE: 39
ttctattttc gtataacatt gtcaagtgga aacatgctga aatctattaa accatctttg      60

<210> SEQ ID NO 40
<211> LENGTH: 60
<212> TYPE: DNA
<213> ORGANISM: Artificial Sequence
<220> FEATURE:
<223> OTHER INFORMATION: Synthetic

<400> SEQUENCE: 40
tttttagata cagagacttg gggaaattgc ttttcctctt gaaccacagt tctacccctg      60

<210> SEQ ID NO 41
<211> LENGTH: 60
<212> TYPE: DNA
<213> ORGANISM: Artificial Sequence
<220> FEATURE:
<223> OTHER INFORMATION: Synthetic

<400> SEQUENCE: 41
ttccaaatgg aaactgctaa tttttgaagc agaaggttga cagcttcagt aagatctcaa      60

<210> SEQ ID NO 42
<211> LENGTH: 60
<212> TYPE: DNA
<213> ORGANISM: Artificial Sequence
<220> FEATURE:
<223> OTHER INFORMATION: Synthetic

<400> SEQUENCE: 42
ttctactaca ctgcgggctc tagctccccg actcatgcga agagtgccca cgtataagag      60

<210> SEQ ID NO 43
<211> LENGTH: 60
<212> TYPE: DNA
```

<213> ORGANISM: Artificial Sequence
<220> FEATURE:
<223> OTHER INFORMATION: Synthetic

<400> SEQUENCE: 43
taaaagagcc aagttcaaag aaccctagca caaatttgct ttgggatttt cttttctgga    60

<210> SEQ ID NO 44
<211> LENGTH: 60
<212> TYPE: DNA
<213> ORGANISM: Artificial Sequence
<220> FEATURE:
<223> OTHER INFORMATION: Synthetic

<400> SEQUENCE: 44
tggtttcatc ttaatattag ttatatttgt aaccggtctg cttttgcgta agccaaacac    60

<210> SEQ ID NO 45
<211> LENGTH: 60
<212> TYPE: DNA
<213> ORGANISM: Artificial Sequence
<220> FEATURE:
<223> OTHER INFORMATION: Synthetic

<400> SEQUENCE: 45
attaaaaacc cttttcctat gtttattgta tacaagaatt atgcaataaa atttctttat    60

<210> SEQ ID NO 46
<211> LENGTH: 60
<212> TYPE: DNA
<213> ORGANISM: Artificial Sequence
<220> FEATURE:
<223> OTHER INFORMATION: Synthetic

<400> SEQUENCE: 46
gctttcctgt ttctaacctt aggaaaccag aatagcgttt ggcagacacg acgttttcag    60

<210> SEQ ID NO 47
<211> LENGTH: 60
<212> TYPE: DNA
<213> ORGANISM: Artificial Sequence
<220> FEATURE:
<223> OTHER INFORMATION: Synthetic

<400> SEQUENCE: 47
tgaagaatgc aaattgcaca tcagattttg aggaatactt tgccaaaaga aaactggagg    60

<210> SEQ ID NO 48
<211> LENGTH: 60
<212> TYPE: DNA
<213> ORGANISM: Artificial Sequence
<220> FEATURE:
<223> OTHER INFORMATION: Synthetic

<400> SEQUENCE: 48
ttttcagcta taacacggat tcccgccaga cgtgtgctaa caacagacac cagtgctcgg    60

<210> SEQ ID NO 49
<211> LENGTH: 60
<212> TYPE: DNA
<213> ORGANISM: Artificial Sequence
<220> FEATURE:
<223> OTHER INFORMATION: Synthetic

<400> SEQUENCE: 49
gctgaaaatg aactttatga accttttcca agttgatcta tccagtgacg tggcctggtg    60

<210> SEQ ID NO 50
<211> LENGTH: 60
<212> TYPE: DNA
<213> ORGANISM: Artificial Sequence
<220> FEATURE:
<223> OTHER INFORMATION: Synthetic

<400> SEQUENCE: 50
gctgttttga gtgttgatga aaagcaatgc aattatgcca aacagtattg agcagaataa    60

<210> SEQ ID NO 51
<211> LENGTH: 60
<212> TYPE: DNA
<213> ORGANISM: Artificial Sequence
<220> FEATURE:
<223> OTHER INFORMATION: Synthetic

<400> SEQUENCE: 51
gtgttttgga aatatttgct gtgtctcagg ggattgtagg aatacgagga gttttcagca    60

<210> SEQ ID NO 52
<211> LENGTH: 60
<212> TYPE: DNA
<213> ORGANISM: Artificial Sequence
<220> FEATURE:
<223> OTHER INFORMATION: Synthetic

<400> SEQUENCE: 52
ggttctttac aaatggtatt ttgatagata ctggattgtg tttgtgccat atttgtgcca    60

<210> SEQ ID NO 53
<211> LENGTH: 60
<212> TYPE: DNA
<213> ORGANISM: Artificial Sequence
<220> FEATURE:
<223> OTHER INFORMATION: Synthetic

<400> SEQUENCE: 53
agatggctga ctactaacag gtcattgcca ggtgtatttc tatactcttt gaagaataac    60

<210> SEQ ID NO 54
<211> LENGTH: 60
<212> TYPE: DNA
<213> ORGANISM: Artificial Sequence
<220> FEATURE:
<223> OTHER INFORMATION: Synthetic

<400> SEQUENCE: 54
tcttgcctta acatcccttg catttggctg caaagaaatc tgcttggaag aaggggttac    60

<210> SEQ ID NO 55
<211> LENGTH: 60
<212> TYPE: DNA
<213> ORGANISM: Artificial Sequence
<220> FEATURE:
<223> OTHER INFORMATION: Synthetic

<400> SEQUENCE: 55
tctcctatat atgaatgatg actttgaagg aggagaattc atattcacag agatggatgc    60

<210> SEQ ID NO 56
<211> LENGTH: 60
<212> TYPE: DNA
<213> ORGANISM: Artificial Sequence
<220> FEATURE:

<223> OTHER INFORMATION: Synthetic

<400> SEQUENCE: 56
ttgtggtttg aatgttcata agcagtgttc caagatggtc ccaaatgact gtaagccaga    60

<210> SEQ ID NO 57
<211> LENGTH: 60
<212> TYPE: DNA
<213> ORGANISM: Artificial Sequence
<220> FEATURE:
<223> OTHER INFORMATION: Synthetic

<400> SEQUENCE: 57
ttcttcttgc caagcaatcc aaagatgaac tttctgaagc ccgagaactt ggcaacatgg    60

<210> SEQ ID NO 58
<211> LENGTH: 60
<212> TYPE: DNA
<213> ORGANISM: Artificial Sequence
<220> FEATURE:
<223> OTHER INFORMATION: Synthetic

<400> SEQUENCE: 58
ttcatagatg ttgacaattt cctgactaat ccacagaccc tcaatctact gattgcagaa    60

<210> SEQ ID NO 59
<211> LENGTH: 60
<212> TYPE: DNA
<213> ORGANISM: Artificial Sequence
<220> FEATURE:
<223> OTHER INFORMATION: Synthetic

<400> SEQUENCE: 59
ctccgttatt ttagtgtgct tccttctctt gtctggattt ctgcattgcc ctaggaagtc    60

<210> SEQ ID NO 60
<211> LENGTH: 60
<212> TYPE: DNA
<213> ORGANISM: Artificial Sequence
<220> FEATURE:
<223> OTHER INFORMATION: Synthetic

<400> SEQUENCE: 60
ggggagttga tagtctcata aaactaattt ggcttcaagt ttcatgaatc tgtaactaga    60

<210> SEQ ID NO 61
<211> LENGTH: 60
<212> TYPE: DNA
<213> ORGANISM: Artificial Sequence
<220> FEATURE:
<223> OTHER INFORMATION: Synthetic

<400> SEQUENCE: 61
tgccgcctgt ccgtatcagc aggatgctac tgctgctgct gatacctggg gaattgccag    60

<210> SEQ ID NO 62
<211> LENGTH: 60
<212> TYPE: DNA
<213> ORGANISM: Artificial Sequence
<220> FEATURE:
<223> OTHER INFORMATION: Synthetic

<400> SEQUENCE: 62
tttggagaag gggatggcat tattagagag ttatgcatct catatggagg cgttggtcca    60

-continued

<210> SEQ ID NO 63
<211> LENGTH: 60
<212> TYPE: DNA
<213> ORGANISM: Artificial Sequence
<220> FEATURE:
<223> OTHER INFORMATION: Synthetic

<400> SEQUENCE: 63
gacagtttat tgttgagag tgtgaccaaa agttacatgt ttgcaccttt ctagttgaaa      60

<210> SEQ ID NO 64
<211> LENGTH: 60
<212> TYPE: DNA
<213> ORGANISM: Artificial Sequence
<220> FEATURE:
<223> OTHER INFORMATION: Synthetic

<400> SEQUENCE: 64
ctgctcaaca tccggaggga attcattgag aaatatgaca agtctctcca ccaagccatt      60

<210> SEQ ID NO 65
<211> LENGTH: 60
<212> TYPE: DNA
<213> ORGANISM: Artificial Sequence
<220> FEATURE:
<223> OTHER INFORMATION: Synthetic

<400> SEQUENCE: 65
ttgtctttgg tgaagggtct gctgtgcacc atccccatc ctacgtggcc cacctggcct      60

<210> SEQ ID NO 66
<211> LENGTH: 60
<212> TYPE: DNA
<213> ORGANISM: Artificial Sequence
<220> FEATURE:
<223> OTHER INFORMATION: Synthetic

<400> SEQUENCE: 66
tttatgggac tgtgtaaagt agctaagtcg gttgaaatgc tgatcctggg tcgcttggtt      60

<210> SEQ ID NO 67
<211> LENGTH: 60
<212> TYPE: DNA
<213> ORGANISM: Artificial Sequence
<220> FEATURE:
<223> OTHER INFORMATION: Synthetic

<400> SEQUENCE: 67
tcagcggcag cagccgccgc cgagatgtcc cggcgaaagc aaagcaaacc ccggcagatc      60

<210> SEQ ID NO 68
<211> LENGTH: 60
<212> TYPE: DNA
<213> ORGANISM: Artificial Sequence
<220> FEATURE:
<223> OTHER INFORMATION: Synthetic

<400> SEQUENCE: 68
tttgccaagc attgcgtgaa gtgcaacaag gacaagtgtg aaccatgaga agtatgacaa      60

<210> SEQ ID NO 69
<211> LENGTH: 60
<212> TYPE: DNA
<213> ORGANISM: Artificial Sequence
<220> FEATURE:
<223> OTHER INFORMATION: Synthetic

<400> SEQUENCE: 69
cttcggggag ctcatcatgt ctggcaagaa catgcggctg agctctctcg cgctctccag        60

<210> SEQ ID NO 70
<211> LENGTH: 60
<212> TYPE: DNA
<213> ORGANISM: Artificial Sequence
<220> FEATURE:
<223> OTHER INFORMATION: Synthetic

<400> SEQUENCE: 70
gtccggacac tgtttgtcag cggcctccct gtggacatta aacccagaga actctacttg        60

<210> SEQ ID NO 71
<211> LENGTH: 60
<212> TYPE: DNA
<213> ORGANISM: Artificial Sequence
<220> FEATURE:
<223> OTHER INFORMATION: Synthetic

<400> SEQUENCE: 71
tttgaccctg aatttgacct acttgctggg gtacagttgc ttccttttga acctccaaca        60

<210> SEQ ID NO 72
<211> LENGTH: 60
<212> TYPE: DNA
<213> ORGANISM: Artificial Sequence
<220> FEATURE:
<223> OTHER INFORMATION: Synthetic

<400> SEQUENCE: 72
tggtgacaaa ggtgaaacag gtgaacgtgg agctgctggc atcaaaggac atcgaggatt        60

<210> SEQ ID NO 73
<211> LENGTH: 60
<212> TYPE: DNA
<213> ORGANISM: Artificial Sequence
<220> FEATURE:
<223> OTHER INFORMATION: Synthetic

<400> SEQUENCE: 73
ttaaacactt cttttccttc tcttcctcgt tttgattgca ccgtttccat ctgggggcta        60

<210> SEQ ID NO 74
<211> LENGTH: 60
<212> TYPE: DNA
<213> ORGANISM: Artificial Sequence
<220> FEATURE:
<223> OTHER INFORMATION: Synthetic

<400> SEQUENCE: 74
tttggacact gtgctactga aactcccagc cacagcattt atagactgcg gtgaacattt        60

<210> SEQ ID NO 75
<211> LENGTH: 60
<212> TYPE: DNA
<213> ORGANISM: Artificial Sequence
<220> FEATURE:
<223> OTHER INFORMATION: Synthetic

<400> SEQUENCE: 75
tcttatgttt ttagaggctt ttccgtaaac atatatctta catataataa acttttcaaa        60

<210> SEQ ID NO 76
<211> LENGTH: 60

```
<212> TYPE: DNA
<213> ORGANISM: Artificial Sequence
<220> FEATURE:
<223> OTHER INFORMATION: Synthetic

<400> SEQUENCE: 76
tgacggtgac ttcaagatca aatgtgtggc ctttgactga aatcagccag cccatggccc    60

<210> SEQ ID NO 77
<211> LENGTH: 60
<212> TYPE: DNA
<213> ORGANISM: Artificial Sequence
<220> FEATURE:
<223> OTHER INFORMATION: Synthetic

<400> SEQUENCE: 77
tgctagtggt ttacaaatat gcaactgaca aaagaggatc actttcaggc attggtcctg    60

<210> SEQ ID NO 78
<211> LENGTH: 60
<212> TYPE: DNA
<213> ORGANISM: Artificial Sequence
<220> FEATURE:
<223> OTHER INFORMATION: Synthetic

<400> SEQUENCE: 78
tgatcatgga gaccgaggcg acagaggtca gaagggccac agaggcttta ctggtcttca    60

<210> SEQ ID NO 79
<211> LENGTH: 60
<212> TYPE: DNA
<213> ORGANISM: Artificial Sequence
<220> FEATURE:
<223> OTHER INFORMATION: Synthetic

<400> SEQUENCE: 79
ttcctgagga tttcagagat ggagagtatg aagctgctgt tactttagag aagcaggagg    60

<210> SEQ ID NO 80
<211> LENGTH: 60
<212> TYPE: DNA
<213> ORGANISM: Artificial Sequence
<220> FEATURE:
<223> OTHER INFORMATION: Synthetic

<400> SEQUENCE: 80
tcgtgacacc accaaggctg cgggagaaga agtttgacca tcaccctcag cagttcagct    60

<210> SEQ ID NO 81
<211> LENGTH: 60
<212> TYPE: DNA
<213> ORGANISM: Artificial Sequence
<220> FEATURE:
<223> OTHER INFORMATION: Synthetic

<400> SEQUENCE: 81
tccgccggga aacttctgcg ggcgccgggc tgaagctccg ggcagggctg ggaaggaaag    60

<210> SEQ ID NO 82
<211> LENGTH: 60
<212> TYPE: DNA
<213> ORGANISM: Artificial Sequence
<220> FEATURE:
<223> OTHER INFORMATION: Synthetic

<400> SEQUENCE: 82
```
acttgatcat tctcagtatc cactgtctat gtacaataaa ggatgtttat aagcaaaaaa    60

<210> SEQ ID NO 83
<211> LENGTH: 60
<212> TYPE: DNA
<213> ORGANISM: Artificial Sequence
<220> FEATURE:
<223> OTHER INFORMATION: Synthetic

<400> SEQUENCE: 83
tctgttttat tactcctggt gcgagtcccg cggactccgg cccgctattt gtcatcagct    60

<210> SEQ ID NO 84
<211> LENGTH: 60
<212> TYPE: DNA
<213> ORGANISM: Artificial Sequence
<220> FEATURE:
<223> OTHER INFORMATION: Synthetic

<400> SEQUENCE: 84
gactgtcaaa attcattgat gaaaagggtc tttgatacct acatgctctt tttccaagtc    60

<210> SEQ ID NO 85
<211> LENGTH: 60
<212> TYPE: DNA
<213> ORGANISM: Artificial Sequence
<220> FEATURE:
<223> OTHER INFORMATION: Synthetic

<400> SEQUENCE: 85
tgtccccaaa ctcagcatga ctcctgtcct cttcaataaa gacgtttcta tggccaaaaa    60

<210> SEQ ID NO 86
<211> LENGTH: 60
<212> TYPE: DNA
<213> ORGANISM: Artificial Sequence
<220> FEATURE:
<223> OTHER INFORMATION: Synthetic

<400> SEQUENCE: 86
tgtggggacc aaggggacac aatatgagac caacagcatg gacttcaaag ttggggcaga    60

<210> SEQ ID NO 87
<211> LENGTH: 60
<212> TYPE: DNA
<213> ORGANISM: Artificial Sequence
<220> FEATURE:
<223> OTHER INFORMATION: Synthetic

<400> SEQUENCE: 87
tggtcatcac tgacgggcgc tcagacactc agagggacac cacaccgctc aacgtgctct    60

<210> SEQ ID NO 88
<211> LENGTH: 60
<212> TYPE: DNA
<213> ORGANISM: Artificial Sequence
<220> FEATURE:
<223> OTHER INFORMATION: Synthetic

<400> SEQUENCE: 88
ttgttgtagt aaagtatctt cattagcgtt atactccatc atatctggtg taaactgctc    60

<210> SEQ ID NO 89
<211> LENGTH: 60
<212> TYPE: DNA
<213> ORGANISM: Artificial Sequence
<220> FEATURE:
<223> OTHER INFORMATION: Synthetic

<400> SEQUENCE: 89
tttctatgat cagagatatt cgagagaggg agattcggat ctatacggat gcaggccgta    60

<210> SEQ ID NO 90
<211> LENGTH: 60
<212> TYPE: DNA
<213> ORGANISM: Artificial Sequence
<220> FEATURE:
<223> OTHER INFORMATION: Synthetic

<400> SEQUENCE: 90
tctccttaga cactttggaa tctaaccact taaggacctt tttaaagaga tagcttctct    60

<210> SEQ ID NO 91
<211> LENGTH: 60
<212> TYPE: DNA
<213> ORGANISM: Artificial Sequence
<220> FEATURE:
<223> OTHER INFORMATION: Synthetic

<400> SEQUENCE: 91
ggtcgcttgg accctgatct tacccgtggg caccctgcgc tctgcctgcc gcgaagaccg    60

<210> SEQ ID NO 92
<211> LENGTH: 46
<212> TYPE: DNA
<213> ORGANISM: Artificial Sequence
<220> FEATURE:
<223> OTHER INFORMATION: Synthetic

<400> SEQUENCE: 92
ctagtgttgt ggaggttggt ccctgcactc ctaatctttt tttttt    46

<210> SEQ ID NO 93
<211> LENGTH: 60
<212> TYPE: DNA
<213> ORGANISM: Artificial Sequence
<220> FEATURE:
<223> OTHER INFORMATION: Synthetic

<400> SEQUENCE: 93
tttttaactg aaagctgaat ccttccattt cttctgcaca tctacttgct taaattgtgg    60

<210> SEQ ID NO 94
<211> LENGTH: 60
<212> TYPE: DNA
<213> ORGANISM: Artificial Sequence
<220> FEATURE:
<223> OTHER INFORMATION: Synthetic

<400> SEQUENCE: 94
tttggaattg ggagcacgat gactctgagt ttgagctatt aaagtacttc ttacacattg    60

<210> SEQ ID NO 95
<211> LENGTH: 60
<212> TYPE: DNA
<213> ORGANISM: Artificial Sequence
<220> FEATURE:
<223> OTHER INFORMATION: Synthetic

<400> SEQUENCE: 95
gagacaattc tctattttac agtgtataca gatacaacta tttcccctaa tagggtggga    60

<210> SEQ ID NO 96
<211> LENGTH: 60
<212> TYPE: DNA
<213> ORGANISM: Artificial Sequence
<220> FEATURE:
<223> OTHER INFORMATION: Synthetic

<400> SEQUENCE: 96
tgttgcttag taacatttat gattttgtgt ttctcgtgac agcatgagca gagatcatta    60

<210> SEQ ID NO 97
<211> LENGTH: 60
<212> TYPE: DNA
<213> ORGANISM: Artificial Sequence
<220> FEATURE:
<223> OTHER INFORMATION: Synthetic

<400> SEQUENCE: 97
tgcggctgtt agggacagag gcaaagaagg gcaggacggt ccggtttccc gtggatgttc    60

<210> SEQ ID NO 98
<211> LENGTH: 60
<212> TYPE: DNA
<213> ORGANISM: Artificial Sequence
<220> FEATURE:
<223> OTHER INFORMATION: Synthetic

<400> SEQUENCE: 98
tgtggtttct acggaatgta tgataagatc ctgcttttc gccatgaccc tacctctgaa    60

<210> SEQ ID NO 99
<211> LENGTH: 60
<212> TYPE: DNA
<213> ORGANISM: Artificial Sequence
<220> FEATURE:
<223> OTHER INFORMATION: Synthetic

<400> SEQUENCE: 99
ttcttcaagg gtgcctatta cctgaagctg gagaaccaaa gtctgaagag cgtgaagttt    60

<210> SEQ ID NO 100
<211> LENGTH: 60
<212> TYPE: DNA
<213> ORGANISM: Artificial Sequence
<220> FEATURE:
<223> OTHER INFORMATION: Synthetic

<400> SEQUENCE: 100
tagctgtttt tcgtcttccc taggctattt ctgccgggcg ctccgcgaag atgcagctca    60

<210> SEQ ID NO 101
<211> LENGTH: 60
<212> TYPE: DNA
<213> ORGANISM: Artificial Sequence
<220> FEATURE:
<223> OTHER INFORMATION: Synthetic

<400> SEQUENCE: 101
tgtcacgtcc cctacaagta aattttgttt ctttgaacat ttattaaaat gccaagaccc    60

<210> SEQ ID NO 102
<211> LENGTH: 60
<212> TYPE: DNA
<213> ORGANISM: Artificial Sequence
<220> FEATURE:
<223> OTHER INFORMATION: Synthetic

<400> SEQUENCE: 102
ataaacatac ggattttgtt aacgtttatg ttaatttcga caaactggtg atcacccac    60

<210> SEQ ID NO 103
<211> LENGTH: 60
<212> TYPE: DNA
<213> ORGANISM: Artificial Sequence
<220> FEATURE:
<223> OTHER INFORMATION: Synthetic

<400> SEQUENCE: 103
ttgcagtatc aaatctgaat gactctgata agttacagct tctaagtctg gtgacaaaaa    60

<210> SEQ ID NO 104
<211> LENGTH: 60
<212> TYPE: DNA
<213> ORGANISM: Artificial Sequence
<220> FEATURE:
<223> OTHER INFORMATION: Synthetic

<400> SEQUENCE: 104
ttcctcatcg tctactccgt cactgacaag gccagctttg agcacgtgga ccgcttccac    60

<210> SEQ ID NO 105
<211> LENGTH: 60
<212> TYPE: DNA
<213> ORGANISM: Artificial Sequence
<220> FEATURE:
<223> OTHER INFORMATION: Synthetic

<400> SEQUENCE: 105
ttgcctccat gcatgtgtgt gtgtgtctgt gaggactggt gtgcgtggac acgtctgaag    60

<210> SEQ ID NO 106
<211> LENGTH: 60
<212> TYPE: DNA
<213> ORGANISM: Artificial Sequence
<220> FEATURE:
<223> OTHER INFORMATION: Synthetic

<400> SEQUENCE: 106
gctgcatatt tcttttacca ttgaccatta ttatagggac ccatgaagta aatgtcacaa    60

<210> SEQ ID NO 107
<211> LENGTH: 60
<212> TYPE: DNA
<213> ORGANISM: Artificial Sequence
<220> FEATURE:
<223> OTHER INFORMATION: Synthetic

<400> SEQUENCE: 107
gtttcatgga agatttgaga aagtgtaaaa ttattttcat aattgtgaga agtatgacaa    60

<210> SEQ ID NO 108
<211> LENGTH: 60
<212> TYPE: DNA
<213> ORGANISM: Artificial Sequence
<220> FEATURE:
<223> OTHER INFORMATION: Synthetic

<400> SEQUENCE: 108
ttggcatcta tacagtcaag gattgctatc ctgtccagga aacctttacc ataaactaca    60

<210> SEQ ID NO 109

```
<211> LENGTH: 60
<212> TYPE: DNA
<213> ORGANISM: Artificial Sequence
<220> FEATURE:
<223> OTHER INFORMATION: Synthetic

<400> SEQUENCE: 109
tgtcttagat gatgagggca gaaacctgag gcagcagaag cttgatcggc agtttttttt    60

<210> SEQ ID NO 110
<211> LENGTH: 60
<212> TYPE: DNA
<213> ORGANISM: Artificial Sequence
<220> FEATURE:
<223> OTHER INFORMATION: Synthetic

<400> SEQUENCE: 110
ttctcaccca gagacatcac cctgaaatgg ttcaaaatg ggaatgagct ctcagacttc    60

<210> SEQ ID NO 111
<211> LENGTH: 60
<212> TYPE: DNA
<213> ORGANISM: Artificial Sequence
<220> FEATURE:
<223> OTHER INFORMATION: Synthetic

<400> SEQUENCE: 111
ttctaagact tactctaaga tcttagattc tctgtgtcta agattctaga tcagatgctc    60

<210> SEQ ID NO 112
<211> LENGTH: 60
<212> TYPE: DNA
<213> ORGANISM: Artificial Sequence
<220> FEATURE:
<223> OTHER INFORMATION: Synthetic

<400> SEQUENCE: 112
ttccgaacat ctgtgtcttt ggaacttgcc acaacctccc tggcctgttc cgctgtgagt    60

<210> SEQ ID NO 113
<211> LENGTH: 60
<212> TYPE: DNA
<213> ORGANISM: Artificial Sequence
<220> FEATURE:
<223> OTHER INFORMATION: Synthetic

<400> SEQUENCE: 113
ctgaagtaga ttataaaggt aattctacaa acatgcctga acatctcac atcgtagctt    60

<210> SEQ ID NO 114
<211> LENGTH: 60
<212> TYPE: DNA
<213> ORGANISM: Artificial Sequence
<220> FEATURE:
<223> OTHER INFORMATION: Synthetic

<400> SEQUENCE: 114
tcggaatggg acaagctctt catcatgctg gagaactcgc agatgagaga gcgcatgctg    60

<210> SEQ ID NO 115
<211> LENGTH: 60
<212> TYPE: DNA
<213> ORGANISM: Artificial Sequence
<220> FEATURE:
<223> OTHER INFORMATION: Synthetic

<400> SEQUENCE: 115
```
ttgttgtctt ctgattatgt ggagattcac tacgaaaatg ggaaaccaca gtactctaag    60

<210> SEQ ID NO 116
<211> LENGTH: 60
<212> TYPE: DNA
<213> ORGANISM: Artificial Sequence
<220> FEATURE:
<223> OTHER INFORMATION: Synthetic

<400> SEQUENCE: 116
ccaggatatt ttcaatatta agtcagtgca tagctgcacc actaacaaat tggtgcctgt    60

<210> SEQ ID NO 117
<211> LENGTH: 60
<212> TYPE: DNA
<213> ORGANISM: Artificial Sequence
<220> FEATURE:
<223> OTHER INFORMATION: Synthetic

<400> SEQUENCE: 117
ttttcgcaaa tgtacagaag ccatttgtca cctcagcatt cgctgccgaa atgagcaact    60

<210> SEQ ID NO 118
<211> LENGTH: 60
<212> TYPE: DNA
<213> ORGANISM: Artificial Sequence
<220> FEATURE:
<223> OTHER INFORMATION: Synthetic

<400> SEQUENCE: 118
ttttaatgtc acctataaca aaatgtgttt ggtagcagat tgtccagaaa gcattttaaa    60

<210> SEQ ID NO 119
<211> LENGTH: 60
<212> TYPE: DNA
<213> ORGANISM: Artificial Sequence
<220> FEATURE:
<223> OTHER INFORMATION: Synthetic

<400> SEQUENCE: 119
taggacaaac cattgtagga ttttagcaat gtgtatctgt gtgtccctca cacctttttcc   60

<210> SEQ ID NO 120
<211> LENGTH: 60
<212> TYPE: DNA
<213> ORGANISM: Artificial Sequence
<220> FEATURE:
<223> OTHER INFORMATION: Synthetic

<400> SEQUENCE: 120
gggggaatta ctcaattatt ctatcagaac ctattataaa gactgtatttt cccatagacg   60

<210> SEQ ID NO 121
<211> LENGTH: 60
<212> TYPE: DNA
<213> ORGANISM: Artificial Sequence
<220> FEATURE:
<223> OTHER INFORMATION: Synthetic

<400> SEQUENCE: 121
ttctcaaaca gctgtcaagt cgccaggata ctaaagtgtg aaccatgaga agtatgacaa    60

<210> SEQ ID NO 122
<211> LENGTH: 60
<212> TYPE: DNA

```
<213> ORGANISM: Artificial Sequence
<220> FEATURE:
<223> OTHER INFORMATION: Synthetic

<400> SEQUENCE: 122
ttgcaggagg agatgcttca gagagaggaa gccgaaaaca ccctgcaatc tttcagacag      60

<210> SEQ ID NO 123
<211> LENGTH: 60
<212> TYPE: DNA
<213> ORGANISM: Artificial Sequence
<220> FEATURE:
<223> OTHER INFORMATION: Synthetic

<400> SEQUENCE: 123
ttcctgatct gtccacttct ggtgtcaaag attttactca tcttcttagt acattctatg      60

<210> SEQ ID NO 124
<211> LENGTH: 60
<212> TYPE: DNA
<213> ORGANISM: Artificial Sequence
<220> FEATURE:
<223> OTHER INFORMATION: Synthetic

<400> SEQUENCE: 124
tttaacatgc cacatgatga tgcaaagcag tgtgccagcc ttaatggtgt gaaccaggat      60

<210> SEQ ID NO 125
<211> LENGTH: 60
<212> TYPE: DNA
<213> ORGANISM: Artificial Sequence
<220> FEATURE:
<223> OTHER INFORMATION: Synthetic

<400> SEQUENCE: 125
ttactatact ttaaagttct atattatgaa aatatataat agcttgtacg cttcaaaaaa      60

<210> SEQ ID NO 126
<211> LENGTH: 60
<212> TYPE: DNA
<213> ORGANISM: Artificial Sequence
<220> FEATURE:
<223> OTHER INFORMATION: Synthetic

<400> SEQUENCE: 126
ttccgaggag gctcttactc actcaagaaa gtggtgatga tgatccgacc gaaccccaac      60

<210> SEQ ID NO 127
<211> LENGTH: 60
<212> TYPE: DNA
<213> ORGANISM: Artificial Sequence
<220> FEATURE:
<223> OTHER INFORMATION: Synthetic

<400> SEQUENCE: 127
tttatgttgc ttttagtcg tcagggaaag cttcgactgc aaaaatggta tgtcccacta       60

<210> SEQ ID NO 128
<211> LENGTH: 60
<212> TYPE: DNA
<213> ORGANISM: Artificial Sequence
<220> FEATURE:
<223> OTHER INFORMATION: Synthetic

<400> SEQUENCE: 128
tgctgagaaa gcctaccatg aacagctttc tgtagcagac atcaccaatg cttgctttga      60
```

<210> SEQ ID NO 129
<211> LENGTH: 60
<212> TYPE: DNA
<213> ORGANISM: Artificial Sequence
<220> FEATURE:
<223> OTHER INFORMATION: Synthetic

<400> SEQUENCE: 129
ttttgcagaa tcctgctata ggaaaaatgg agctgttcgg tgcatttgta acgaaaatta    60

<210> SEQ ID NO 130
<211> LENGTH: 60
<212> TYPE: DNA
<213> ORGANISM: Artificial Sequence
<220> FEATURE:
<223> OTHER INFORMATION: Synthetic

<400> SEQUENCE: 130
ttgggggatg agatctgctc tgcctgtgag tccttccatt tcctctgctc ctgtgccagt    60

<210> SEQ ID NO 131
<211> LENGTH: 60
<212> TYPE: DNA
<213> ORGANISM: Artificial Sequence
<220> FEATURE:
<223> OTHER INFORMATION: Synthetic

<400> SEQUENCE: 131
ttgataacat cagcactgat gacctgaaca ccacatcctc tgtcagctct tactccaaca    60

<210> SEQ ID NO 132
<211> LENGTH: 60
<212> TYPE: DNA
<213> ORGANISM: Artificial Sequence
<220> FEATURE:
<223> OTHER INFORMATION: Synthetic

<400> SEQUENCE: 132
tttttcttac tgtcatgtat ctgctctcaa tatggctggg taacaagtat atgaagaaca    60

<210> SEQ ID NO 133
<211> LENGTH: 60
<212> TYPE: DNA
<213> ORGANISM: Artificial Sequence
<220> FEATURE:
<223> OTHER INFORMATION: Synthetic

<400> SEQUENCE: 133
tatgacaaag gtactctcaa aattcattac aatgctgttc acctgaagat caaacatcga    60

<210> SEQ ID NO 134
<211> LENGTH: 60
<212> TYPE: DNA
<213> ORGANISM: Artificial Sequence
<220> FEATURE:
<223> OTHER INFORMATION: Synthetic

<400> SEQUENCE: 134
tgattgacaa gcagatgccc gtcatcatgg tcattatgaa ggatccttgc ttcgccaaat    60

<210> SEQ ID NO 135
<211> LENGTH: 60
<212> TYPE: DNA
<213> ORGANISM: Artificial Sequence
<220> FEATURE:

<223> OTHER INFORMATION: Synthetic

<400> SEQUENCE: 135
tttcttaaaa cagaaagggt ggaaaatcac tatacagaag caatatccaa agatctcctg    60

<210> SEQ ID NO 136
<211> LENGTH: 60
<212> TYPE: DNA
<213> ORGANISM: Artificial Sequence
<220> FEATURE:
<223> OTHER INFORMATION: Synthetic

<400> SEQUENCE: 136
tatgaatgat gcattgtttt tgcaattgac ctatgacaaa ctgtgaacct gcagatttca    60

<210> SEQ ID NO 137
<211> LENGTH: 60
<212> TYPE: DNA
<213> ORGANISM: Artificial Sequence
<220> FEATURE:
<223> OTHER INFORMATION: Synthetic

<400> SEQUENCE: 137 cctgatttt atggaatttt agggatatt ttgagctttg ggttctcagt agtgaattga    60

<210> SEQ ID NO 138
<211> LENGTH: 60
<212> TYPE: DNA
<213> ORGANISM: Artificial Sequence
<220> FEATURE:
<223> OTHER INFORMATION: Synthetic

<400> SEQUENCE: 138
ccagttagta ttatcatatg tttgtacccg tcacagtttt catagtgctt tcaaatacac    60

<210> SEQ ID NO 139
<211> LENGTH: 60
<212> TYPE: DNA
<213> ORGANISM: Artificial Sequence
<220> FEATURE:
<223> OTHER INFORMATION: Synthetic

<400> SEQUENCE: 139
tgagcatgac acttctttca gtatattgct tgatgcttca ataaagtttt gtcttggga    60

<210> SEQ ID NO 140
<211> LENGTH: 60
<212> TYPE: DNA
<213> ORGANISM: Artificial Sequence
<220> FEATURE:
<223> OTHER INFORMATION: Synthetic

<400> SEQUENCE: 140
tcattgcatt cctggtgggt ttgatttcta tctgcgtggg atctcgaagg cgtttctata    60

<210> SEQ ID NO 141
<211> LENGTH: 60
<212> TYPE: DNA
<213> ORGANISM: Artificial Sequence
<220> FEATURE:
<223> OTHER INFORMATION: Synthetic

<400> SEQUENCE: 141
tttggctgaa tgcaggcatc cattcccgag agtggatctc ccaggccact gcaatctgga    60

<210> SEQ ID NO 142
<211> LENGTH: 60
<212> TYPE: DNA
<213> ORGANISM: Artificial Sequence
<220> FEATURE:
<223> OTHER INFORMATION: Synthetic

<400> SEQUENCE: 142
tgactgatgt tggttgtaat ggttgggttt aggatgaacc attttaagga tgccaaatga    60

<210> SEQ ID NO 143
<211> LENGTH: 60
<212> TYPE: DNA
<213> ORGANISM: Artificial Sequence
<220> FEATURE:
<223> OTHER INFORMATION: Synthetic

<400> SEQUENCE: 143
gtctcttctc ttgtttagtt acttacggca ataaatcatc tatgagttag tgcaccgtga    60

<210> SEQ ID NO 144
<211> LENGTH: 60
<212> TYPE: DNA
<213> ORGANISM: Artificial Sequence
<220> FEATURE:
<223> OTHER INFORMATION: Synthetic

<400> SEQUENCE: 144
ttgatctatg ccattcacgc cgaggagatc ctggagaagc acccgcgagg gggcagcttc    60

<210> SEQ ID NO 145
<211> LENGTH: 46
<212> TYPE: DNA
<213> ORGANISM: Artificial Sequence
<220> FEATURE:
<223> OTHER INFORMATION: Synthetic

<400> SEQUENCE: 145
gattctgatg gggaagagtc cgacaggaac cgggcctttt tttttt    46

<210> SEQ ID NO 146
<211> LENGTH: 60
<212> TYPE: DNA
<213> ORGANISM: Artificial Sequence
<220> FEATURE:
<223> OTHER INFORMATION: Synthetic

<400> SEQUENCE: 146
gctgtgtttt tgatactgat attttcctat gctgaatagt tttcttactt tcagggaagg    60

<210> SEQ ID NO 147
<211> LENGTH: 60
<212> TYPE: DNA
<213> ORGANISM: Artificial Sequence
<220> FEATURE:
<223> OTHER INFORMATION: Synthetic

<400> SEQUENCE: 147
gtgtgatatc agcagtcttc agctccttac aaattaccaa aagtggttct aatatgctag    60

<210> SEQ ID NO 148
<211> LENGTH: 60
<212> TYPE: DNA
<213> ORGANISM: Artificial Sequence
<220> FEATURE:
<223> OTHER INFORMATION: Synthetic

<400> SEQUENCE: 148
tggggaacct ctcacgttgc tgtgtcctgg tgagcagccc gaccaataaa cctgcttttc     60

<210> SEQ ID NO 149
<211> LENGTH: 60
<212> TYPE: DNA
<213> ORGANISM: Artificial Sequence
<220> FEATURE:
<223> OTHER INFORMATION: Synthetic

<400> SEQUENCE: 149
ttagttttgt aatacctttt ttatttgtga ataaaattat cacctggtat tcttaaaaaa     60

<210> SEQ ID NO 150
<211> LENGTH: 60
<212> TYPE: DNA
<213> ORGANISM: Artificial Sequence
<220> FEATURE:
<223> OTHER INFORMATION: Synthetic

<400> SEQUENCE: 150
ttttgtttaa caaataatt gtaggtttct ctctgtaata caacgctgg aaaggccgag       60

<210> SEQ ID NO 151
<211> LENGTH: 60
<212> TYPE: DNA
<213> ORGANISM: Artificial Sequence
<220> FEATURE:
<223> OTHER INFORMATION: Synthetic

<400> SEQUENCE: 151
tccatgcttc ctactaggat cctgaggctg ttggagtttg tggggttttc aggaaacaag     60

<210> SEQ ID NO 152
<211> LENGTH: 60
<212> TYPE: DNA
<213> ORGANISM: Artificial Sequence
<220> FEATURE:
<223> OTHER INFORMATION: Synthetic

<400> SEQUENCE: 152
tacaaatgtt agagactgta tacgccttcg aggtcttccc tatgcagcca caattgagga     60

<210> SEQ ID NO 153
<211> LENGTH: 60
<212> TYPE: DNA
<213> ORGANISM: Artificial Sequence
<220> FEATURE:
<223> OTHER INFORMATION: Synthetic

<400> SEQUENCE: 153
ttgccataag aaggtgatga aggagcgcta cgtggaggtg gtcccctgtt ccacagagga     60

<210> SEQ ID NO 154
<211> LENGTH: 60
<212> TYPE: DNA
<213> ORGANISM: Artificial Sequence
<220> FEATURE:
<223> OTHER INFORMATION: Synthetic

<400> SEQUENCE: 154
tggggagatg acatcacttg ggtacaaact tatgaagaag gtctctttta tgctcaaaaa     60

<210> SEQ ID NO 155
<211> LENGTH: 60

```
<212> TYPE: DNA
<213> ORGANISM: Artificial Sequence
<220> FEATURE:
<223> OTHER INFORMATION: Synthetic

<400> SEQUENCE: 155
tttgtatctc actagcccct cttattttca tatctgccag tgtgctgagg aatggagtgg    60

<210> SEQ ID NO 156
<211> LENGTH: 60
<212> TYPE: DNA
<213> ORGANISM: Artificial Sequence
<220> FEATURE:
<223> OTHER INFORMATION: Synthetic

<400> SEQUENCE: 156
ttccacctta ctcggctctt ctgtggggcg accctcatca gtgaccgctg gctgctcaca    60

<210> SEQ ID NO 157
<211> LENGTH: 60
<212> TYPE: DNA
<213> ORGANISM: Artificial Sequence
<220> FEATURE:
<223> OTHER INFORMATION: Synthetic

<400> SEQUENCE: 157
tttagtatgc tacttctatg tttattttt gttcttctaa taaaatgcat aaacttcttg    60

<210> SEQ ID NO 158
<211> LENGTH: 60
<212> TYPE: DNA
<213> ORGANISM: Artificial Sequence
<220> FEATURE:
<223> OTHER INFORMATION: Synthetic

<400> SEQUENCE: 158
gctcagaatt catctgaaga gagacttaag atgaaagcaa atgattcagc tcccttatac    60

<210> SEQ ID NO 159
<211> LENGTH: 60
<212> TYPE: DNA
<213> ORGANISM: Artificial Sequence
<220> FEATURE:
<223> OTHER INFORMATION: Synthetic

<400> SEQUENCE: 159
tgtcaaactg tcttggctgt ggggctaggg gctggggcca aataaagtct cttcctccaa    60

<210> SEQ ID NO 160
<211> LENGTH: 60
<212> TYPE: DNA
<213> ORGANISM: Artificial Sequence
<220> FEATURE:
<223> OTHER INFORMATION: Synthetic

<400> SEQUENCE: 160
tcaggagttt gacattgcca ggaacgttct agaactgatc tatgcacaaa ctctggtgtg    60

<210> SEQ ID NO 161
<211> LENGTH: 60
<212> TYPE: DNA
<213> ORGANISM: Artificial Sequence
<220> FEATURE:
<223> OTHER INFORMATION: Synthetic

<400> SEQUENCE: 161
```
tccaaagttc tcatctatgg gaatttgtac gagacctgct tctatctcct gaagaaaact    60

<210> SEQ ID NO 162
<211> LENGTH: 60
<212> TYPE: DNA
<213> ORGANISM: Artificial Sequence
<220> FEATURE:
<223> OTHER INFORMATION: Synthetic

<400> SEQUENCE: 162
tcttgtctac aacaagctaa ctttccagct ggaacccaat ccccacacca agtatcagta    60

<210> SEQ ID NO 163
<211> LENGTH: 60
<212> TYPE: DNA
<213> ORGANISM: Artificial Sequence
<220> FEATURE:
<223> OTHER INFORMATION: Synthetic

<400> SEQUENCE: 163
tgtacgtcta ggcctaggta accagtggag tgattatatt agcaaatgtg tttgtatcca    60

<210> SEQ ID NO 164
<211> LENGTH: 60
<212> TYPE: DNA
<213> ORGANISM: Artificial Sequence
<220> FEATURE:
<223> OTHER INFORMATION: Synthetic

<400> SEQUENCE: 164
tggcacttaa accttggtag atctgggttt ataatcggcc attcttaagc acgtggggtt    60

<210> SEQ ID NO 165
<211> LENGTH: 60
<212> TYPE: DNA
<213> ORGANISM: Artificial Sequence
<220> FEATURE:
<223> OTHER INFORMATION: Synthetic

<400> SEQUENCE: 165
ttcgaatgaa aagaaatgca tgtttcctgc tcttccctca ttaaattgct tttaattcca    60

<210> SEQ ID NO 166
<211> LENGTH: 60
<212> TYPE: DNA
<213> ORGANISM: Artificial Sequence
<220> FEATURE:
<223> OTHER INFORMATION: Synthetic

<400> SEQUENCE: 166
tatataaact agatagtcct caaatactgt ttgaatttaa taaatgtcaa tttaaaaatt    60

<210> SEQ ID NO 167
<211> LENGTH: 60
<212> TYPE: DNA
<213> ORGANISM: Artificial Sequence
<220> FEATURE:
<223> OTHER INFORMATION: Synthetic

<400> SEQUENCE: 167
gggtaatccg gttataatat gtttttcaca ggaattaata aatctatttt cattttgaat    60

<210> SEQ ID NO 168
<211> LENGTH: 60
<212> TYPE: DNA
<213> ORGANISM: Artificial Sequence

```
<220> FEATURE:
<223> OTHER INFORMATION: Synthetic

<400> SEQUENCE: 168
ttttaatcaa gctgcccaaa gtcccccaat cactcctgga atacacagag agaggcagca    60

<210> SEQ ID NO 169
<211> LENGTH: 60
<212> TYPE: DNA
<213> ORGANISM: Artificial Sequence
<220> FEATURE:
<223> OTHER INFORMATION: Synthetic

<400> SEQUENCE: 169
tgtgattggg ttattcaaca gcgtaattca gattcatctc ctcctgataa tgaacaaggc    60

<210> SEQ ID NO 170
<211> LENGTH: 60
<212> TYPE: DNA
<213> ORGANISM: Artificial Sequence
<220> FEATURE:
<223> OTHER INFORMATION: Synthetic

<400> SEQUENCE: 170
tggagttgtt atgagaatta cattagattt tgtacgtaaa actcagcatc aagcacacag    60

<210> SEQ ID NO 171
<211> LENGTH: 60
<212> TYPE: DNA
<213> ORGANISM: Artificial Sequence
<220> FEATURE:
<223> OTHER INFORMATION: Synthetic

<400> SEQUENCE: 171
tggctgggat ctgccacaac atcctggtct gctgccccaa ggagctgctg aacagaagg    60

<210> SEQ ID NO 172
<211> LENGTH: 60
<212> TYPE: DNA
<213> ORGANISM: Artificial Sequence
<220> FEATURE:
<223> OTHER INFORMATION: Synthetic

<400> SEQUENCE: 172
ttgcactcta cctgacacag ctgcagcctg caattcactc ccactgcctg ggattgcact    60

<210> SEQ ID NO 173
<211> LENGTH: 60
<212> TYPE: DNA
<213> ORGANISM: Artificial Sequence
<220> FEATURE:
<223> OTHER INFORMATION: Synthetic

<400> SEQUENCE: 173
ttggtgtgaa cttaggtctt ggcgtcggga tccctttttcg tcacactcag gtgacctaca    60

<210> SEQ ID NO 174
<211> LENGTH: 60
<212> TYPE: DNA
<213> ORGANISM: Artificial Sequence
<220> FEATURE:
<223> OTHER INFORMATION: Synthetic

<400> SEQUENCE: 174
ggactttttt ccatatcaaa agaatatttt gagtatattg gaagctatga tgaagaaatg    60
```

<210> SEQ ID NO 175
<211> LENGTH: 60
<212> TYPE: DNA
<213> ORGANISM: Artificial Sequence
<220> FEATURE:
<223> OTHER INFORMATION: Synthetic

<400> SEQUENCE: 175
ttccctaaat cacaaagcct acagagatgc attcaaaaag atgaagccac caaaaatccc    60

<210> SEQ ID NO 176
<211> LENGTH: 60
<212> TYPE: DNA
<213> ORGANISM: Artificial Sequence
<220> FEATURE:
<223> OTHER INFORMATION: Synthetic

<400> SEQUENCE: 176
ttcttggaat acagcctttc aagcagagga cagaagggtc cttctcctta tgtgggaaat    60

<210> SEQ ID NO 177
<211> LENGTH: 60
<212> TYPE: DNA
<213> ORGANISM: Artificial Sequence
<220> FEATURE:
<223> OTHER INFORMATION: Synthetic

<400> SEQUENCE: 177
ttcaggcagc aagaacaaat cagtagagct ggaggatgta aaattccacc agtgcgtgcg    60

<210> SEQ ID NO 178
<211> LENGTH: 60
<212> TYPE: DNA
<213> ORGANISM: Artificial Sequence
<220> FEATURE:
<223> OTHER INFORMATION: Synthetic

<400> SEQUENCE: 178
tacacctaca atggggtggt tgcttactcc atccatagcc aagaaccaaa ggacccacac    60

<210> SEQ ID NO 179
<211> LENGTH: 60
<212> TYPE: DNA
<213> ORGANISM: Artificial Sequence
<220> FEATURE:
<223> OTHER INFORMATION: Synthetic

<400> SEQUENCE: 179
tggtggacca ccaagtggag gagcataaca tcttccacaa tgaggtcaag gccatcgggc    60

<210> SEQ ID NO 180
<211> LENGTH: 60
<212> TYPE: DNA
<213> ORGANISM: Artificial Sequence
<220> FEATURE:
<223> OTHER INFORMATION: Synthetic

<400> SEQUENCE: 180
ttggacatct tatgaatgtc agaaaatacc ttttggaggg ttagaagatc aggggacatg    60

<210> SEQ ID NO 181
<211> LENGTH: 60
<212> TYPE: DNA
<213> ORGANISM: Artificial Sequence
<220> FEATURE:
<223> OTHER INFORMATION: Synthetic

<400> SEQUENCE: 181
gttatctgtg gaaaacgttt taagttgtca tgtgacagaa acttttcctt tgtccatcga     60

<210> SEQ ID NO 182
<211> LENGTH: 60
<212> TYPE: DNA
<213> ORGANISM: Artificial Sequence
<220> FEATURE:
<223> OTHER INFORMATION: Synthetic

<400> SEQUENCE: 182
tgcctaccat tttacagtat ttgtcttcta ttttggagcc tttttattgg aagcagcagc     60

<210> SEQ ID NO 183
<211> LENGTH: 60
<212> TYPE: DNA
<213> ORGANISM: Artificial Sequence
<220> FEATURE:
<223> OTHER INFORMATION: Synthetic

<400> SEQUENCE: 183
ttgtgacagg atttggagca ctgaaaaatg atggttacag tcaaaatcat cttcgacaag     60

<210> SEQ ID NO 184
<211> LENGTH: 60
<212> TYPE: DNA
<213> ORGANISM: Artificial Sequence
<220> FEATURE:
<223> OTHER INFORMATION: Synthetic

<400> SEQUENCE: 184
gacttcggaa ctaaaggaga acttcatccg cttctccaaa tctctgggcc tccctgaaaa     60

<210> SEQ ID NO 185
<211> LENGTH: 60
<212> TYPE: DNA
<213> ORGANISM: Artificial Sequence
<220> FEATURE:
<223> OTHER INFORMATION: Synthetic

<400> SEQUENCE: 185
tgtaccgcat tacattatgc ctgtgaaatg aaaaaccagt ctcttatccc tctgctcttg     60

<210> SEQ ID NO 186
<211> LENGTH: 60
<212> TYPE: DNA
<213> ORGANISM: Artificial Sequence
<220> FEATURE:
<223> OTHER INFORMATION: Synthetic

<400> SEQUENCE: 186
tctctctaga ggtccttta ccttcttcat cataaggata cctatctgaa tggtaaaccc     60

<210> SEQ ID NO 187
<211> LENGTH: 60
<212> TYPE: DNA
<213> ORGANISM: Artificial Sequence
<220> FEATURE:
<223> OTHER INFORMATION: Synthetic

<400> SEQUENCE: 187
ttgtgctgta aagagttgct ttttgtttat ttaatgctgt ggcatgggtg aagaggaggg     60

<210> SEQ ID NO 188

```
<211> LENGTH: 60
<212> TYPE: DNA
<213> ORGANISM: Artificial Sequence
<220> FEATURE:
<223> OTHER INFORMATION: Synthetic

<400> SEQUENCE: 188
ttgctaccta cccctctgga cacttggata tgatcaatgg cttctttgac cagttcatag     60

<210> SEQ ID NO 189
<211> LENGTH: 60
<212> TYPE: DNA
<213> ORGANISM: Artificial Sequence
<220> FEATURE:
<223> OTHER INFORMATION: Synthetic

<400> SEQUENCE: 189
tttgggtgag atatctttgc acagataaca tgtatacatc atagttcaaa acccagtagt     60

<210> SEQ ID NO 190
<211> LENGTH: 60
<212> TYPE: DNA
<213> ORGANISM: Artificial Sequence
<220> FEATURE:
<223> OTHER INFORMATION: Synthetic

<400> SEQUENCE: 190
gttcactgct ttggtggaaa ttggtggaaa ttgctagcag gttccacgat gtttattttt     60

<210> SEQ ID NO 191
<211> LENGTH: 60
<212> TYPE: DNA
<213> ORGANISM: Artificial Sequence
<220> FEATURE:
<223> OTHER INFORMATION: Synthetic

<400> SEQUENCE: 191
tgaggtttga ctgggacaag tctctgctta aaatctactc tgggtcctcc catcagtggc     60

<210> SEQ ID NO 192
<211> LENGTH: 60
<212> TYPE: DNA
<213> ORGANISM: Artificial Sequence
<220> FEATURE:
<223> OTHER INFORMATION: Synthetic

<400> SEQUENCE: 192
tgagaggcgt gaagggcctg gagccactct gctagaagag accaataaag ggcaggtgtg     60

<210> SEQ ID NO 193
<211> LENGTH: 60
<212> TYPE: DNA
<213> ORGANISM: Artificial Sequence
<220> FEATURE:
<223> OTHER INFORMATION: Synthetic

<400> SEQUENCE: 193
tttttcggga ctctgtattc cctcttgggc tgaccacagc ttctcccttt cccaaccaat     60

<210> SEQ ID NO 194
<211> LENGTH: 60
<212> TYPE: DNA
<213> ORGANISM: Artificial Sequence
<220> FEATURE:
<223> OTHER INFORMATION: Synthetic

<400> SEQUENCE: 194
```
tcgctcttca acggcctctc gttccactgc gcgggtgtcc tggtggacca gagttgggtg    60

<210> SEQ ID NO 195
<211> LENGTH: 60
<212> TYPE: DNA
<213> ORGANISM: Artificial Sequence
<220> FEATURE:
<223> OTHER INFORMATION: Synthetic

<400> SEQUENCE: 195
tgctcaggaa ttcagtgatg tggagagggc cattgagacc ctcatcaaga actttcacca    60

<210> SEQ ID NO 196
<211> LENGTH: 60
<212> TYPE: DNA
<213> ORGANISM: Artificial Sequence
<220> FEATURE:
<223> OTHER INFORMATION: Synthetic

<400> SEQUENCE: 196
gttggcaatt attcccctag gctgagcctg ctcatgtacc tctgattaat aaatgcttat    60

<210> SEQ ID NO 197
<211> LENGTH: 60
<212> TYPE: DNA
<213> ORGANISM: Artificial Sequence
<220> FEATURE:
<223> OTHER INFORMATION: Synthetic

<400> SEQUENCE: 197
tggaattctt cctcctctgc tgggactcct ttgcatggca gggcctcatc tcacctctcg    60

<210> SEQ ID NO 198
<211> LENGTH: 60
<212> TYPE: DNA
<213> ORGANISM: Artificial Sequence
<220> FEATURE:
<223> OTHER INFORMATION: Synthetic

<400> SEQUENCE: 198
ttggcacatg ttctgtgttt cagtaaagag agacctgatc acccatctgt gtgcttccat    60

<210> SEQ ID NO 199
<211> LENGTH: 60
<212> TYPE: DNA
<213> ORGANISM: Artificial Sequence
<220> FEATURE:
<223> OTHER INFORMATION: Synthetic

<400> SEQUENCE: 199
tcctgcaata acttcatcta tggaggctgc cggggcaata agaacagcta ccgctctgag    60

<210> SEQ ID NO 200
<211> LENGTH: 60
<212> TYPE: DNA
<213> ORGANISM: Artificial Sequence
<220> FEATURE:
<223> OTHER INFORMATION: Synthetic

<400> SEQUENCE: 200 taatttatc tttggaagat agctatatgg taactcatca ttaaccagaa cacctctccc    60

<210> SEQ ID NO 201
<211> LENGTH: 60
<212> TYPE: DNA

<213> ORGANISM: Artificial Sequence
<220> FEATURE:
<223> OTHER INFORMATION: Synthetic

<400> SEQUENCE: 201
ttaaaagaag ctgaaaatgc caagcgagag ggtgaaacta gaattcgacg aaatgctgaa        60

<210> SEQ ID NO 202
<211> LENGTH: 60
<212> TYPE: DNA
<213> ORGANISM: Artificial Sequence
<220> FEATURE:
<223> OTHER INFORMATION: Synthetic

<400> SEQUENCE: 202
tgtttgatca gtaccagcgg agcactgggc aagagctgga ggaggctgtc cagaaccgtt        60

<210> SEQ ID NO 203
<211> LENGTH: 60
<212> TYPE: DNA
<213> ORGANISM: Artificial Sequence
<220> FEATURE:
<223> OTHER INFORMATION: Synthetic

<400> SEQUENCE: 203
ttcggtctct gcggggacgt ccacgtgcgg ctgcgccagc gcatcatctt gtacgaatta        60

<210> SEQ ID NO 204
<211> LENGTH: 60
<212> TYPE: DNA
<213> ORGANISM: Artificial Sequence
<220> FEATURE:
<223> OTHER INFORMATION: Synthetic

<400> SEQUENCE: 204
tgctgcacta tcgcatcgac aaagacaaga cagggaagct ctccatcccc gagggaaaga        60

<210> SEQ ID NO 205
<211> LENGTH: 60
<212> TYPE: DNA
<213> ORGANISM: Artificial Sequence
<220> FEATURE:
<223> OTHER INFORMATION: Synthetic

<400> SEQUENCE: 205
ttgatgagta aagaaatatt gagctctcct ccaaatgatg ctgttggaga attggagcaa        60

<210> SEQ ID NO 206
<211> LENGTH: 60
<212> TYPE: DNA
<213> ORGANISM: Artificial Sequence
<220> FEATURE:
<223> OTHER INFORMATION: Synthetic

<400> SEQUENCE: 206
tggatgtgtt cacggatgtg gagatcttct gtgacattct agaggcagcc aacaagcgtg        60

<210> SEQ ID NO 207
<211> LENGTH: 60
<212> TYPE: DNA
<213> ORGANISM: Artificial Sequence
<220> FEATURE:
<223> OTHER INFORMATION: Synthetic

<400> SEQUENCE: 207
ttgagcaggt ggctccaaaa ggagatgaag aaggtgttcc tgctgttgtt attgacatgt        60

<210> SEQ ID NO 208
<211> LENGTH: 60
<212> TYPE: DNA
<213> ORGANISM: Artificial Sequence
<220> FEATURE:
<223> OTHER INFORMATION: Synthetic

<400> SEQUENCE: 208
tgaggcatta ttatataaat tcaagctcgc tcgtgatcct tagtaccctg agttgcctga    60

<210> SEQ ID NO 209
<211> LENGTH: 60
<212> TYPE: DNA
<213> ORGANISM: Artificial Sequence
<220> FEATURE:
<223> OTHER INFORMATION: Synthetic

<400> SEQUENCE: 209
ggttgcttca atcagctttt gtatgacatc cgaactaatg cagtcaccgt gggtggtgtg    60

<210> SEQ ID NO 210
<211> LENGTH: 60
<212> TYPE: DNA
<213> ORGANISM: Artificial Sequence
<220> FEATURE:
<223> OTHER INFORMATION: Synthetic

<400> SEQUENCE: 210
tgcagacgtc tggttcaaag agttggatat caacactgat ggtgcagtta acttccagga    60

<210> SEQ ID NO 211
<211> LENGTH: 60
<212> TYPE: DNA
<213> ORGANISM: Artificial Sequence
<220> FEATURE:
<223> OTHER INFORMATION: Synthetic

<400> SEQUENCE: 211
ttaaatccaa gctgggtttc atcaactggg atgccataaa caaggaccag agaagctctc    60

<210> SEQ ID NO 212
<211> LENGTH: 60
<212> TYPE: DNA
<213> ORGANISM: Artificial Sequence
<220> FEATURE:
<223> OTHER INFORMATION: Synthetic

<400> SEQUENCE: 212
ggtggttttt gctgaagaca aaagcagaga agatcagtta aggcattgga agtactggca    60

<210> SEQ ID NO 213
<211> LENGTH: 60
<212> TYPE: DNA
<213> ORGANISM: Artificial Sequence
<220> FEATURE:
<223> OTHER INFORMATION: Synthetic

<400> SEQUENCE: 213
ttctggctac tttgatgaga ggtatgtatt gtcctctaga gtcagaactg gccgaagcat    60

<210> SEQ ID NO 214
<211> LENGTH: 60
<212> TYPE: DNA
<213> ORGANISM: Artificial Sequence
<220> FEATURE:

<223> OTHER INFORMATION: Synthetic

<400> SEQUENCE: 214
tagatgttta caacggactc cttcctccct atgcttcttg ccacttgacg gaattgtact    60

<210> SEQ ID NO 215
<211> LENGTH: 60
<212> TYPE: DNA
<213> ORGANISM: Artificial Sequence
<220> FEATURE:
<223> OTHER INFORMATION: Synthetic

<400> SEQUENCE: 215
gtgacttggt agtgatacgc tctgtttctt cacttctgca attgccagac agcatagagg    60

<210> SEQ ID NO 216
<211> LENGTH: 60
<212> TYPE: DNA
<213> ORGANISM: Artificial Sequence
<220> FEATURE:
<223> OTHER INFORMATION: Synthetic

<400> SEQUENCE: 216
tggacctgga tagcatcatc gctgaggtca aggcccagta tgaggagatt gccaaccgca    60

<210> SEQ ID NO 217
<211> LENGTH: 60
<212> TYPE: DNA
<213> ORGANISM: Artificial Sequence
<220> FEATURE:
<223> OTHER INFORMATION: Synthetic

<400> SEQUENCE: 217
tttatattct ttggctttgt ttattaaaaa gcatgatttt gctgtgcatg taccattttg    60

<210> SEQ ID NO 218
<211> LENGTH: 60
<212> TYPE: DNA
<213> ORGANISM: Artificial Sequence
<220> FEATURE:
<223> OTHER INFORMATION: Synthetic

<400> SEQUENCE: 218
ttttaaagca gatctctggg acagatggag agggaaacaa cgtgccttca ggtgactttt    60

<210> SEQ ID NO 219
<211> LENGTH: 60
<212> TYPE: DNA
<213> ORGANISM: Artificial Sequence
<220> FEATURE:
<223> OTHER INFORMATION: Synthetic

<400> SEQUENCE: 219
tcacgggcag ttactcggtg tctgagtctc ccttcttcag ccccatccac ctacactcaa    60

<210> SEQ ID NO 220
<211> LENGTH: 60
<212> TYPE: DNA
<213> ORGANISM: Artificial Sequence
<220> FEATURE:
<223> OTHER INFORMATION: Synthetic

<400> SEQUENCE: 220
tgaattcatt aattacattt ctgcaagatg gggtggcatg ttgtcatctt cagccatttt    60

<210> SEQ ID NO 221
<211> LENGTH: 60
<212> TYPE: DNA
<213> ORGANISM: Artificial Sequence
<220> FEATURE:
<223> OTHER INFORMATION: Synthetic

<400> SEQUENCE: 221
ggtgcaacat tagaaatttc ttgttagttt gcactgagtt tattactgta gatagcagac    60

<210> SEQ ID NO 222
<211> LENGTH: 60
<212> TYPE: DNA
<213> ORGANISM: Artificial Sequence
<220> FEATURE:
<223> OTHER INFORMATION: Synthetic

<400> SEQUENCE: 222
tttctttggg ggtggaaaag gaaacaatt caagctgaga aaagtattct caaagatgca    60

<210> SEQ ID NO 223
<211> LENGTH: 60
<212> TYPE: DNA
<213> ORGANISM: Artificial Sequence
<220> FEATURE:
<223> OTHER INFORMATION: Synthetic

<400> SEQUENCE: 223
ttgtgaaata aaaacttaaa ttgtatattt tgaaaaataa aacactgaaa agaaaccaac    60

<210> SEQ ID NO 224
<211> LENGTH: 60
<212> TYPE: DNA
<213> ORGANISM: Artificial Sequence
<220> FEATURE:
<223> OTHER INFORMATION: Synthetic

<400> SEQUENCE: 224
ttggggaagg atcaagtgaa ccatccctag tcttccttca ataaataact tttaactcca    60

<210> SEQ ID NO 225
<211> LENGTH: 60
<212> TYPE: DNA
<213> ORGANISM: Artificial Sequence
<220> FEATURE:
<223> OTHER INFORMATION: Synthetic

<400> SEQUENCE: 225
ttttaaaaaa tgctatttgg aagactattt atttctcgtg tatataatgt atataaaaaa    60

<210> SEQ ID NO 226
<211> LENGTH: 60
<212> TYPE: DNA
<213> ORGANISM: Artificial Sequence
<220> FEATURE:
<223> OTHER INFORMATION: Synthetic

<400> SEQUENCE: 226
tgtagagtgg tgctgcttta attcataaat cacaaataaa agccaattag ctctataact    60

<210> SEQ ID NO 227
<211> LENGTH: 60
<212> TYPE: DNA
<213> ORGANISM: Artificial Sequence
<220> FEATURE:
<223> OTHER INFORMATION: Synthetic

<400> SEQUENCE: 227
tttctactgg gaattagaat ggtgcataca caatgtatta ttatcactgt cagatgagca        60

<210> SEQ ID NO 228
<211> LENGTH: 60
<212> TYPE: DNA
<213> ORGANISM: Artificial Sequence
<220> FEATURE:
<223> OTHER INFORMATION: Synthetic

<400> SEQUENCE: 228
gtagtacttc tgttcactga agagttatgt tacatgagga taaaatggtt ttgtcgtgtt        60

<210> SEQ ID NO 229
<211> LENGTH: 60
<212> TYPE: DNA
<213> ORGANISM: Artificial Sequence
<220> FEATURE:
<223> OTHER INFORMATION: Synthetic

<400> SEQUENCE: 229
ttctcccacc tctgtgtgat tggactcgtt tatggcacag ccattatcat gtatgttgga        60

<210> SEQ ID NO 230
<211> LENGTH: 60
<212> TYPE: DNA
<213> ORGANISM: Artificial Sequence
<220> FEATURE:
<223> OTHER INFORMATION: Synthetic

<400> SEQUENCE: 230
tttgtttaaa tcaacatagc atgaaacacc aaataaaatg tttgacatag ttttaaaaaa        60

<210> SEQ ID NO 231
<211> LENGTH: 60
<212> TYPE: DNA
<213> ORGANISM: Artificial Sequence
<220> FEATURE:
<223> OTHER INFORMATION: Synthetic

<400> SEQUENCE: 231
ttgtttacca atgatttatt tacaagatat ttactcaaat aaatggagct gcttacaaaa        60

<210> SEQ ID NO 232
<211> LENGTH: 60
<212> TYPE: DNA
<213> ORGANISM: Artificial Sequence
<220> FEATURE:
<223> OTHER INFORMATION: Synthetic

<400> SEQUENCE: 232
tgggtcagtt ccttattcaa gtctgcagcc ggctcccagg gagatctcgg tggaacttca        60

<210> SEQ ID NO 233
<211> LENGTH: 60
<212> TYPE: DNA
<213> ORGANISM: Artificial Sequence
<220> FEATURE:
<223> OTHER INFORMATION: Synthetic

<400> SEQUENCE: 233
tgccactggt gttaagatat attttgagtg gatggaggag aaataaactt attcctcctt        60

<210> SEQ ID NO 234
<211> LENGTH: 60

<212> TYPE: DNA
<213> ORGANISM: Artificial Sequence
<220> FEATURE:
<223> OTHER INFORMATION: Synthetic

<400> SEQUENCE: 234
tcagttcaac atgttaaact gaagaaaatg aagtactctt ttcagttgtg gatcgcaatg    60

<210> SEQ ID NO 235
<211> LENGTH: 60
<212> TYPE: DNA
<213> ORGANISM: Artificial Sequence
<220> FEATURE:
<223> OTHER INFORMATION: Synthetic

<400> SEQUENCE: 235
ttgcacccca atatcatgcc ctggtgagct atgtccccaa gacaatggca cagcctgtgg    60

<210> SEQ ID NO 236
<211> LENGTH: 60
<212> TYPE: DNA
<213> ORGANISM: Artificial Sequence
<220> FEATURE:
<223> OTHER INFORMATION: Synthetic

<400> SEQUENCE: 236
ttttgacaaa ttagagacag agacccattg ggtgccagtg agctggttac attcataact    60

<210> SEQ ID NO 237
<211> LENGTH: 60
<212> TYPE: DNA
<213> ORGANISM: Artificial Sequence
<220> FEATURE:
<223> OTHER INFORMATION: Synthetic

<400> SEQUENCE: 237
ttcgtaaagc caatgcccct gaaatgctca gtgatggcga atatatctca gatgttgaag    60

<210> SEQ ID NO 238
<211> LENGTH: 60
<212> TYPE: DNA
<213> ORGANISM: Artificial Sequence
<220> FEATURE:
<223> OTHER INFORMATION: Synthetic

<400> SEQUENCE: 238
gttccttgta aatccaaatg tttctatatt gtagctttgc ttaaaatggg gtcggcccca    60

<210> SEQ ID NO 239
<211> LENGTH: 60
<212> TYPE: DNA
<213> ORGANISM: Artificial Sequence
<220> FEATURE:
<223> OTHER INFORMATION: Synthetic

<400> SEQUENCE: 239
ttttcctcat cttgtactgg agaaaattct tgtgagtctc actatgaaaa actgtaaagc    60

<210> SEQ ID NO 240
<211> LENGTH: 60
<212> TYPE: DNA
<213> ORGANISM: Artificial Sequence
<220> FEATURE:
<223> OTHER INFORMATION: Synthetic

<400> SEQUENCE: 240
tgctgtatgc tctgttcgga gggtgtgtta gtatctccct agaggtgatc ttccgggacc    60

<210> SEQ ID NO 241
<211> LENGTH: 60
<212> TYPE: DNA
<213> ORGANISM: Artificial Sequence
<220> FEATURE:
<223> OTHER INFORMATION: Synthetic

<400> SEQUENCE: 241
tgaagctgct gtacagcgga gtcccattcc tgggcccta ccacaaggag tcggctgtga    60

<210> SEQ ID NO 242
<211> LENGTH: 60
<212> TYPE: DNA
<213> ORGANISM: Artificial Sequence
<220> FEATURE:
<223> OTHER INFORMATION: Synthetic

<400> SEQUENCE: 242
tttttctcat tgacttcctt cctgttctaa ctgccagtac tcagaagtca gagttgagag    60

<210> SEQ ID NO 243
<211> LENGTH: 60
<212> TYPE: DNA
<213> ORGANISM: Artificial Sequence
<220> FEATURE:
<223> OTHER INFORMATION: Synthetic

<400> SEQUENCE: 243
cagaaatatc ctgcttttta tttcagagct gacgtttgca atcctagtgc actagcggaa    60

<210> SEQ ID NO 244
<211> LENGTH: 60
<212> TYPE: DNA
<213> ORGANISM: Artificial Sequence
<220> FEATURE:
<223> OTHER INFORMATION: Synthetic

<400> SEQUENCE: 244
ttgaatatca gcgtgctaag tcagaaaagg tgcgaggatg cttacccgag acagatagat    60

<210> SEQ ID NO 245
<211> LENGTH: 60
<212> TYPE: DNA
<213> ORGANISM: Artificial Sequence
<220> FEATURE:
<223> OTHER INFORMATION: Synthetic

<400> SEQUENCE: 245
tctggctaaa caatttctgt atggcgaaag aaaaattcta acttgtacgc cctcttcatg    60

<210> SEQ ID NO 246
<211> LENGTH: 60
<212> TYPE: DNA
<213> ORGANISM: Artificial Sequence
<220> FEATURE:
<223> OTHER INFORMATION: Synthetic

<400> SEQUENCE: 246
ggtatttatg tatcaagatc ggacagagta atatataaat cactccaccg atttggcccc    60

<210> SEQ ID NO 247
<211> LENGTH: 60
<212> TYPE: DNA
<213> ORGANISM: Artificial Sequence

```
<220> FEATURE:
<223> OTHER INFORMATION: Synthetic

<400> SEQUENCE: 247
tttgtaaaat gttctcttat gatcaccatg tattttgtaa ataataaaat agtatctgtt    60

<210> SEQ ID NO 248
<211> LENGTH: 60
<212> TYPE: DNA
<213> ORGANISM: Artificial Sequence
<220> FEATURE:
<223> OTHER INFORMATION: Synthetic

<400> SEQUENCE: 248
gtaatctcat taccctggac tgttctcata atgtaacaga tcactaacac tgaatcttaa    60

<210> SEQ ID NO 249
<211> LENGTH: 60
<212> TYPE: DNA
<213> ORGANISM: Artificial Sequence
<220> FEATURE:
<223> OTHER INFORMATION: Synthetic

<400> SEQUENCE: 249
tgtgtagttt ggtgacaaga tttgcattca cctggcccaa acccttttg tctctttggg     60

<210> SEQ ID NO 250
<211> LENGTH: 60
<212> TYPE: DNA
<213> ORGANISM: Artificial Sequence
<220> FEATURE:
<223> OTHER INFORMATION: Synthetic

<400> SEQUENCE: 250
acccatgaat gcttcctttt ctgtaaaatg ggacaatgac aggacctgta accacacagg    60

<210> SEQ ID NO 251
<211> LENGTH: 60
<212> TYPE: DNA
<213> ORGANISM: Artificial Sequence
<220> FEATURE:
<223> OTHER INFORMATION: Synthetic

<400> SEQUENCE: 251
ttcaaagctg gagtctgtcc tcctaagaaa tctgcccagt gccttagata caagaaacct    60

<210> SEQ ID NO 252
<211> LENGTH: 60
<212> TYPE: DNA
<213> ORGANISM: Artificial Sequence
<220> FEATURE:
<223> OTHER INFORMATION: Synthetic

<400> SEQUENCE: 252
tgtgcctcct caggtatggc agtgactcac ctggttttaa taaaacaacc tgcaacatct    60

<210> SEQ ID NO 253
<211> LENGTH: 60
<212> TYPE: DNA
<213> ORGANISM: Artificial Sequence
<220> FEATURE:
<223> OTHER INFORMATION: Synthetic

<400> SEQUENCE: 253
tgacctgctc catggcaaac tgtcagtatg gctgtgatgt tgttaaagga caaatacggt    60
```

<210> SEQ ID NO 254
<211> LENGTH: 60
<212> TYPE: DNA
<213> ORGANISM: Artificial Sequence
<220> FEATURE:
<223> OTHER INFORMATION: Synthetic

<400> SEQUENCE: 254
tgccactcct gctcagaaga cagtggctct gacgtctcca gcatctccca ccccacttcg    60

<210> SEQ ID NO 255
<211> LENGTH: 60
<212> TYPE: DNA
<213> ORGANISM: Artificial Sequence
<220> FEATURE:
<223> OTHER INFORMATION: Synthetic

<400> SEQUENCE: 255
tggagttgga ttcttcagat caccaagtgc attgatgttc atctgaaaga aaatgctgcc    60

<210> SEQ ID NO 256
<211> LENGTH: 60
<212> TYPE: DNA
<213> ORGANISM: Artificial Sequence
<220> FEATURE:
<223> OTHER INFORMATION: Synthetic

<400> SEQUENCE: 256
tttttctgtt tgtactcttg gggaatcact tctttgccat ctgttagcaa tgcagtcaac    60

<210> SEQ ID NO 257
<211> LENGTH: 60
<212> TYPE: DNA
<213> ORGANISM: Artificial Sequence
<220> FEATURE:
<223> OTHER INFORMATION: Synthetic

<400> SEQUENCE: 257
tggcttagtt gctctatcat cttacaataa gttcaaaaac aactgcttct ctgatgccat    60

<210> SEQ ID NO 258
<211> LENGTH: 60
<212> TYPE: DNA
<213> ORGANISM: Artificial Sequence
<220> FEATURE:
<223> OTHER INFORMATION: Synthetic

<400> SEQUENCE: 258 gggcttttc cctgtcgcct tcggcttcct gggcaatgtc tgcaacatcc ccttcctggg    60

<210> SEQ ID NO 259
<211> LENGTH: 60
<212> TYPE: DNA
<213> ORGANISM: Artificial Sequence
<220> FEATURE:
<223> OTHER INFORMATION: Synthetic

<400> SEQUENCE: 259
ttttgatgac attgacctgc cctcagcagt caagtacctc atggcttcag accccaacct    60

<210> SEQ ID NO 260
<211> LENGTH: 60
<212> TYPE: DNA
<213> ORGANISM: Artificial Sequence
<220> FEATURE:
<223> OTHER INFORMATION: Synthetic

<400> SEQUENCE: 260
ctcatattac atagcagtat gtttacaaaa ggcttataaa aataaaatga actatcagtt        60

<210> SEQ ID NO 261
<211> LENGTH: 60
<212> TYPE: DNA
<213> ORGANISM: Artificial Sequence
<220> FEATURE:
<223> OTHER INFORMATION: Synthetic

<400> SEQUENCE: 261
tttatatttc tgggaggaaa tgaattcata tctagaagtc tggagtgagc aaacaagagc        60

<210> SEQ ID NO 262
<211> LENGTH: 60
<212> TYPE: DNA
<213> ORGANISM: Artificial Sequence
<220> FEATURE:
<223> OTHER INFORMATION: Synthetic

<400> SEQUENCE: 262
tgcaactagc aaattcggct tttgccgttg atctgttcaa acaactatgt gaaaggagc         60

<210> SEQ ID NO 263
<211> LENGTH: 60
<212> TYPE: DNA
<213> ORGANISM: Artificial Sequence
<220> FEATURE:
<223> OTHER INFORMATION: Synthetic

<400> SEQUENCE: 263
ttataataaa taaaccatgt aagttgaggc ttctggtgct ataaaggact tttccctcag        60

<210> SEQ ID NO 264
<211> LENGTH: 60
<212> TYPE: DNA
<213> ORGANISM: Artificial Sequence
<220> FEATURE:
<223> OTHER INFORMATION: Synthetic

<400> SEQUENCE: 264
tcgcctatat gaaatatggt tgcttttgtg gcttgggagg ccatggccag ccccgcgatg        60

<210> SEQ ID NO 265
<211> LENGTH: 60
<212> TYPE: DNA
<213> ORGANISM: Artificial Sequence
<220> FEATURE:
<223> OTHER INFORMATION: Synthetic

<400> SEQUENCE: 265
tgtgcctaca tcttctatcc gcggccccag aacgtggagt actgtgacta cagaaagcac        60

<210> SEQ ID NO 266
<211> LENGTH: 60
<212> TYPE: DNA
<213> ORGANISM: Artificial Sequence
<220> FEATURE:
<223> OTHER INFORMATION: Synthetic

<400> SEQUENCE: 266
tttcaagaag gctgttcaaa aaatcaaata tcagaaccag gagtgaaagc atcagatcac        60

<210> SEQ ID NO 267

```
<211> LENGTH: 60
<212> TYPE: DNA
<213> ORGANISM: Artificial Sequence
<220> FEATURE:
<223> OTHER INFORMATION: Synthetic

<400> SEQUENCE: 267
tgcgctgtgc tctcaataag agcagagaat tcaacctgat gtatgatggc accaaggagg    60

<210> SEQ ID NO 268
<211> LENGTH: 60
<212> TYPE: DNA
<213> ORGANISM: Artificial Sequence
<220> FEATURE:
<223> OTHER INFORMATION: Synthetic

<400> SEQUENCE: 268
ttcaaatcaa ctccagacct ccttcgagac cagcaggagg cagccccacc aggcagtgtg    60

<210> SEQ ID NO 269
<211> LENGTH: 60
<212> TYPE: DNA
<213> ORGANISM: Artificial Sequence
<220> FEATURE:
<223> OTHER INFORMATION: Synthetic

<400> SEQUENCE: 269
tctgtgcctt tctacaactg attgcaacag actgttgagt tatgataaca ccagtgggaa    60

<210> SEQ ID NO 270
<211> LENGTH: 60
<212> TYPE: DNA
<213> ORGANISM: Artificial Sequence
<220> FEATURE:
<223> OTHER INFORMATION: Synthetic

<400> SEQUENCE: 270
ttacaatcga aacctctatc agtctgcaga ggacagctgt ggagggttgt attaccatga    60

<210> SEQ ID NO 271
<211> LENGTH: 46
<212> TYPE: DNA
<213> ORGANISM: Artificial Sequence
<220> FEATURE:
<223> OTHER INFORMATION: Synthetic

<400> SEQUENCE: 271
aagttgggtt taggacaggt gctgttccga gactcatttt tttttt                   46

<210> SEQ ID NO 272
<211> LENGTH: 60
<212> TYPE: DNA
<213> ORGANISM: Artificial Sequence
<220> FEATURE:
<223> OTHER INFORMATION: Synthetic

<400> SEQUENCE: 272
tgtgcattta taaatgatgt gtattttata tagacctgct tgcattggct gatgctcctc    60

<210> SEQ ID NO 273
<211> LENGTH: 60
<212> TYPE: DNA
<213> ORGANISM: Artificial Sequence
<220> FEATURE:
<223> OTHER INFORMATION: Synthetic

<400> SEQUENCE: 273
```
ttgagtctgg tgaggagtct ttgcgagagc gaggagcagc ggttactgga acaggtgcat    60

<210> SEQ ID NO 274
<211> LENGTH: 60
<212> TYPE: DNA
<213> ORGANISM: Artificial Sequence
<220> FEATURE:
<223> OTHER INFORMATION: Synthetic

<400> SEQUENCE: 274 tttttttacaa catcaaaaac tttgtccgat tccagctgag cacgagcatc tccgccctga    60

<210> SEQ ID NO 275
<211> LENGTH: 60
<212> TYPE: DNA
<213> ORGANISM: Artificial Sequence
<220> FEATURE:
<223> OTHER INFORMATION: Synthetic

<400> SEQUENCE: 275
caggacgctg tggctgaaat gaatgatttt tcaatgtaat caatgtttaa actggtacta    60

<210> SEQ ID NO 276
<211> LENGTH: 60
<212> TYPE: DNA
<213> ORGANISM: Artificial Sequence
<220> FEATURE:
<223> OTHER INFORMATION: Synthetic

<400> SEQUENCE: 276
tgttcacagc accctcaggg tcttaaggtc ttcatgccct atcacaaata cctcttttat    60

<210> SEQ ID NO 277
<211> LENGTH: 60
<212> TYPE: DNA
<213> ORGANISM: Artificial Sequence
<220> FEATURE:
<223> OTHER INFORMATION: Synthetic

<400> SEQUENCE: 277
ggggtttttc ctcttccttc tttgtggttt ctgttttgta atttaagaag agctattcat    60

<210> SEQ ID NO 278
<211> LENGTH: 60
<212> TYPE: DNA
<213> ORGANISM: Artificial Sequence
<220> FEATURE:
<223> OTHER INFORMATION: Synthetic

<400> SEQUENCE: 278
ggatggtggt ttattctcag aagaaaaaga tatgtaagtc ttttagctcc taagagtgaa    60

<210> SEQ ID NO 279
<211> LENGTH: 60
<212> TYPE: DNA
<213> ORGANISM: Artificial Sequence
<220> FEATURE:
<223> OTHER INFORMATION: Synthetic

<400> SEQUENCE: 279
ttctgctgtc ctttggaggg tgtcttctgg gtagagggat gggaaggaag ggacccttac    60

<210> SEQ ID NO 280
<211> LENGTH: 60
<212> TYPE: DNA

<213> ORGANISM: Artificial Sequence
<220> FEATURE:
<223> OTHER INFORMATION: Synthetic

<400> SEQUENCE: 280
tggagctgct tttaatttta gcaaaatgtt ttatgcaagg cacaatagga agtcagttct    60

<210> SEQ ID NO 281
<211> LENGTH: 60
<212> TYPE: DNA
<213> ORGANISM: Artificial Sequence
<220> FEATURE:
<223> OTHER INFORMATION: Synthetic

<400> SEQUENCE: 281
tgagctgcct ctaccacagc ctcctgccca ccagctggcc tcacctcctg aaggcccggg    60

<210> SEQ ID NO 282
<211> LENGTH: 60
<212> TYPE: DNA
<213> ORGANISM: Artificial Sequence
<220> FEATURE:
<223> OTHER INFORMATION: Synthetic

<400> SEQUENCE: 282
tttttgaaga agggatgtgg ctacgatata actttcaggc accagcaaca aatgccagag    60

<210> SEQ ID NO 283
<211> LENGTH: 60
<212> TYPE: DNA
<213> ORGANISM: Artificial Sequence
<220> FEATURE:
<223> OTHER INFORMATION: Synthetic

<400> SEQUENCE: 283
ttctctttta tgtattgagc cctgtgttaa catttcactt aagaagagca ccagtgcttt    60

<210> SEQ ID NO 284
<211> LENGTH: 60
<212> TYPE: DNA
<213> ORGANISM: Artificial Sequence
<220> FEATURE:
<223> OTHER INFORMATION: Synthetic

<400> SEQUENCE: 284
cggccgggct tggcaggatt ccaggcgcg acttggggac gaagccaagt tcattcccag    60

<210> SEQ ID NO 285
<211> LENGTH: 60
<212> TYPE: DNA
<213> ORGANISM: Artificial Sequence
<220> FEATURE:
<223> OTHER INFORMATION: Synthetic

<400> SEQUENCE: 285
tgggatatca gatctttagt gtgaagatac atctacatta aaccaggaat cactagaact    60

<210> SEQ ID NO 286
<211> LENGTH: 60
<212> TYPE: DNA
<213> ORGANISM: Artificial Sequence
<220> FEATURE:
<223> OTHER INFORMATION: Synthetic

<400> SEQUENCE: 286
ttcttttagc attttaatta gcagatagca tattatacat actgtttgga actttgcatt    60

<210> SEQ ID NO 287
<211> LENGTH: 60
<212> TYPE: DNA
<213> ORGANISM: Artificial Sequence
<220> FEATURE:
<223> OTHER INFORMATION: Synthetic

<400> SEQUENCE: 287
tataatattg taataatata ttttacctgt ggtatgtggg catgtttact gccactggcc        60

<210> SEQ ID NO 288
<211> LENGTH: 60
<212> TYPE: DNA
<213> ORGANISM: Artificial Sequence
<220> FEATURE:
<223> OTHER INFORMATION: Synthetic

<400> SEQUENCE: 288
tggcgttctc tgcaagccat ggtatgctgg agcctgtgat cgaaagtctg ctgaagaggc        60

<210> SEQ ID NO 289
<211> LENGTH: 60
<212> TYPE: DNA
<213> ORGANISM: Artificial Sequence
<220> FEATURE:
<223> OTHER INFORMATION: Synthetic

<400> SEQUENCE: 289
ttcctccttg gtcaaccttg actcgttggt caaggcaccc caggttgcaa agacccggaa        60

<210> SEQ ID NO 290
<211> LENGTH: 60
<212> TYPE: DNA
<213> ORGANISM: Artificial Sequence
<220> FEATURE:
<223> OTHER INFORMATION: Synthetic

<400> SEQUENCE: 290
tctcctgtga atggaggcag agacctccaa taaagtgcct tctgggcttt ttctaaaaaa        60

<210> SEQ ID NO 291
<211> LENGTH: 60
<212> TYPE: DNA
<213> ORGANISM: Artificial Sequence
<220> FEATURE:
<223> OTHER INFORMATION: Synthetic

<400> SEQUENCE: 291
gcagagtact gtgttgttgg tgctgtccat gctgtagctc aaaataaaga agctatttta        60

<210> SEQ ID NO 292
<211> LENGTH: 60
<212> TYPE: DNA
<213> ORGANISM: Artificial Sequence
<220> FEATURE:
<223> OTHER INFORMATION: Synthetic

<400> SEQUENCE: 292
tttgatgagt gaatattctg gctggcgaac tcctacacat ccttcaaaac ccacctggta        60

<210> SEQ ID NO 293
<211> LENGTH: 60
<212> TYPE: DNA
<213> ORGANISM: Artificial Sequence
<220> FEATURE:

<223> OTHER INFORMATION: Synthetic

<400> SEQUENCE: 293
ttatcaggga gttacagtta caattgttac agtactgttc ccaactcagc tgccacgggt    60

<210> SEQ ID NO 294
<211> LENGTH: 60
<212> TYPE: DNA
<213> ORGANISM: Artificial Sequence
<220> FEATURE:
<223> OTHER INFORMATION: Synthetic

<400> SEQUENCE: 294
tgcacagtat tcttggctga ttgatgggaa catccagcaa cacacacaag agctctttat    60

<210> SEQ ID NO 295
<211> LENGTH: 60
<212> TYPE: DNA
<213> ORGANISM: Artificial Sequence
<220> FEATURE:
<223> OTHER INFORMATION: Synthetic

<400> SEQUENCE: 295
ttgtcaaaat tttaaacctt tatactcccc tgaatgaatt tgaagaacgg gtaacagtgg    60

<210> SEQ ID NO 296
<211> LENGTH: 60
<212> TYPE: DNA
<213> ORGANISM: Artificial Sequence
<220> FEATURE:
<223> OTHER INFORMATION: Synthetic

<400> SEQUENCE: 296
gtacaagaag aacttgaagg ccctctacgt ggtgcacccc accagcttca tcaaggtcct    60

<210> SEQ ID NO 297
<211> LENGTH: 60
<212> TYPE: DNA
<213> ORGANISM: Artificial Sequence
<220> FEATURE:
<223> OTHER INFORMATION: Synthetic

<400> SEQUENCE: 297
tgtgcttttt gggaccatca ctgagagtca ggagttttac tgcctgtagc aatggccaga    60

<210> SEQ ID NO 298
<211> LENGTH: 60
<212> TYPE: DNA
<213> ORGANISM: Artificial Sequence
<220> FEATURE:
<223> OTHER INFORMATION: Synthetic

<400> SEQUENCE: 298
ttcagatctt tacatgtata atctcatttc tttcatgcag ttactctggg atactgttcc    60

<210> SEQ ID NO 299
<211> LENGTH: 60
<212> TYPE: DNA
<213> ORGANISM: Artificial Sequence
<220> FEATURE:
<223> OTHER INFORMATION: Synthetic

<400> SEQUENCE: 299
ttcctgggga agcataacct tcggcaaagg gagagttccc aggagcagag ttctgttgtc    60

```
<210> SEQ ID NO 300
<211> LENGTH: 60
<212> TYPE: DNA
<213> ORGANISM: Artificial Sequence
<220> FEATURE:
<223> OTHER INFORMATION: Synthetic

<400> SEQUENCE: 300
tgcaaagttc cctacttcct gtgacttcag ctctgtttta caataaaatc ttgaaaatgc      60

<210> SEQ ID NO 301
<211> LENGTH: 60
<212> TYPE: DNA
<213> ORGANISM: Artificial Sequence
<220> FEATURE:
<223> OTHER INFORMATION: Synthetic

<400> SEQUENCE: 301
taaagaactt cttgcctaaa cctgaattac cgcaatttgc tgagtgactt tgagaaaaat      60

<210> SEQ ID NO 302
<211> LENGTH: 60
<212> TYPE: DNA
<213> ORGANISM: Artificial Sequence
<220> FEATURE:
<223> OTHER INFORMATION: Synthetic

<400> SEQUENCE: 302
tgttgggtaa cactgagcat caccccattg attaccccat tgccaggcgt gggcacgagt      60

<210> SEQ ID NO 303
<211> LENGTH: 60
<212> TYPE: DNA
<213> ORGANISM: Artificial Sequence
<220> FEATURE:
<223> OTHER INFORMATION: Synthetic

<400> SEQUENCE: 303 tattttctg gaaattgaag tgtcaattgg gttctcaata tttcatgact ccaaggatgc       60

<210> SEQ ID NO 304
<211> LENGTH: 60
<212> TYPE: DNA
<213> ORGANISM: Artificial Sequence
<220> FEATURE:
<223> OTHER INFORMATION: Synthetic

<400> SEQUENCE: 304 tgacctttc actgtgcaaa gggagatttc tagccaggca ttgactatta caatttcatt      60

<210> SEQ ID NO 305
<211> LENGTH: 60
<212> TYPE: DNA
<213> ORGANISM: Artificial Sequence
<220> FEATURE:
<223> OTHER INFORMATION: Synthetic

<400> SEQUENCE: 305
gggctgatct tgttggactt taattaatgg tatccttttt cacacacctt aaactccaaa      60

<210> SEQ ID NO 306
<211> LENGTH: 60
<212> TYPE: DNA
<213> ORGANISM: Artificial Sequence
<220> FEATURE:
<223> OTHER INFORMATION: Synthetic
```

```
<400> SEQUENCE: 306
ttgggcattg gaaagaaggg agttggaccc atcgtggagt ggaaggcacc gtagctctag      60

<210> SEQ ID NO 307
<211> LENGTH: 60
<212> TYPE: DNA
<213> ORGANISM: Artificial Sequence
<220> FEATURE:
<223> OTHER INFORMATION: Synthetic

<400> SEQUENCE: 307
tgtaaaggag tcaaactata aatcaagtat tgggaagtg aagactggaa gctaatttgc       60

<210> SEQ ID NO 308
<211> LENGTH: 60
<212> TYPE: DNA
<213> ORGANISM: Artificial Sequence
<220> FEATURE:
<223> OTHER INFORMATION: Synthetic

<400> SEQUENCE: 308
ttttgaagaa agcaacaata ttgtcaggtt tcttgctgtg gttctggatg tccagtagca      60

<210> SEQ ID NO 309
<211> LENGTH: 60
<212> TYPE: DNA
<213> ORGANISM: Artificial Sequence
<220> FEATURE:
<223> OTHER INFORMATION: Synthetic

<400> SEQUENCE: 309
ttctgagccc tcaagaaaga tcagaacaga ttcatgggtg atttagccta tctgtcccag      60

<210> SEQ ID NO 310
<211> LENGTH: 60
<212> TYPE: DNA
<213> ORGANISM: Artificial Sequence
<220> FEATURE:
<223> OTHER INFORMATION: Synthetic

<400> SEQUENCE: 310
ttccagttgc ctggtgagcg cagctaccat gtctactacc agatcctctc agggaggaag      60

<210> SEQ ID NO 311
<211> LENGTH: 60
<212> TYPE: DNA
<213> ORGANISM: Artificial Sequence
<220> FEATURE:
<223> OTHER INFORMATION: Synthetic

<400> SEQUENCE: 311
ttgagtacat tcggcgccag aagcaaccca ggccaccccc aagcagaagg aggaggcccg      60

<210> SEQ ID NO 312
<211> LENGTH: 60
<212> TYPE: DNA
<213> ORGANISM: Artificial Sequence
<220> FEATURE:
<223> OTHER INFORMATION: Synthetic

<400> SEQUENCE: 312
tttgactatt tgaaactact aggtaaaggc acttttggga aagttatttt ggttcgagag      60

<210> SEQ ID NO 313
<211> LENGTH: 60
```

```
<212> TYPE: DNA
<213> ORGANISM: Artificial Sequence
<220> FEATURE:
<223> OTHER INFORMATION: Synthetic

<400> SEQUENCE: 313
ttgaagatcc tctttgtaac ttccactccc caaacttcct gaggatctca gaggtggaaa    60

<210> SEQ ID NO 314
<211> LENGTH: 60
<212> TYPE: DNA
<213> ORGANISM: Artificial Sequence
<220> FEATURE:
<223> OTHER INFORMATION: Synthetic

<400> SEQUENCE: 314
tgccaataag ggccatcttc ctgtggtcca gatcttgctg aaggctggct gcgaccttga    60

<210> SEQ ID NO 315
<211> LENGTH: 60
<212> TYPE: DNA
<213> ORGANISM: Artificial Sequence
<220> FEATURE:
<223> OTHER INFORMATION: Synthetic

<400> SEQUENCE: 315
tgggtaccaa ctctattgcg cagctcgctg ccgtgcgttt aacccaggcg aggaggagga    60

<210> SEQ ID NO 316
<211> LENGTH: 60
<212> TYPE: DNA
<213> ORGANISM: Artificial Sequence
<220> FEATURE:
<223> OTHER INFORMATION: Synthetic

<400> SEQUENCE: 316
ttatatgtaa ttgtataaat ggtgcaacag taataaagtt aaacaattaa aaagaaaaaa    60

<210> SEQ ID NO 317
<211> LENGTH: 60
<212> TYPE: DNA
<213> ORGANISM: Artificial Sequence
<220> FEATURE:
<223> OTHER INFORMATION: Synthetic

<400> SEQUENCE: 317
tgcagaacaa cgacatctcc gagctccgca aggatgactt caagggtctc cagcacctct    60

<210> SEQ ID NO 318
<211> LENGTH: 60
<212> TYPE: DNA
<213> ORGANISM: Artificial Sequence
<220> FEATURE:
<223> OTHER INFORMATION: Synthetic

<400> SEQUENCE: 318
ttgttcaggt ggggatgtat ttcatgtaga aggtggaaga aggctgctat gactctttgg    60

<210> SEQ ID NO 319
<211> LENGTH: 60
<212> TYPE: DNA
<213> ORGANISM: Artificial Sequence
<220> FEATURE:
<223> OTHER INFORMATION: Synthetic

<400> SEQUENCE: 319
```
tgctgttatt gaggctgttt tggctggcat tgcatgttat gctaaaactt ccagtctaac    60

<210> SEQ ID NO 320
<211> LENGTH: 60
<212> TYPE: DNA
<213> ORGANISM: Artificial Sequence
<220> FEATURE:
<223> OTHER INFORMATION: Synthetic

<400> SEQUENCE: 320
catggcagat aggtatcaat atgttttcaa tgcctgatga cctataagaa gaaagtattg    60

<210> SEQ ID NO 321
<211> LENGTH: 60
<212> TYPE: DNA
<213> ORGANISM: Artificial Sequence
<220> FEATURE:
<223> OTHER INFORMATION: Synthetic

<400> SEQUENCE: 321
ctgatctgtt aaattcttag tgaagtttcc ttgatttcca gtggctgctg ttgtttgagt    60

<210> SEQ ID NO 322
<211> LENGTH: 60
<212> TYPE: DNA
<213> ORGANISM: Artificial Sequence
<220> FEATURE:
<223> OTHER INFORMATION: Synthetic

<400> SEQUENCE: 322
ttggttgatc gtgtttttga tgaaagcctc aacttccgaa agattcctcc attagttcat    60

<210> SEQ ID NO 323
<211> LENGTH: 60
<212> TYPE: DNA
<213> ORGANISM: Artificial Sequence
<220> FEATURE:
<223> OTHER INFORMATION: Synthetic

<400> SEQUENCE: 323
tggatataat caaaatcatg gaagaaagtt tgtacagggt aaatctatag acgttgcctg    60

<210> SEQ ID NO 324
<211> LENGTH: 60
<212> TYPE: DNA
<213> ORGANISM: Artificial Sequence
<220> FEATURE:
<223> OTHER INFORMATION: Synthetic

<400> SEQUENCE: 324
tttttcagta ttatttatag ttggcacttg attgcagttc tgtgaggctt gagcattcat    60

<210> SEQ ID NO 325
<211> LENGTH: 60
<212> TYPE: DNA
<213> ORGANISM: Artificial Sequence
<220> FEATURE:
<223> OTHER INFORMATION: Synthetic

<400> SEQUENCE: 325
gagtgcgcga gaaacagaag ctcttccagg aggacaatga catcccgttg tacctgaagg    60

<210> SEQ ID NO 326
<211> LENGTH: 60
<212> TYPE: DNA
<213> ORGANISM: Artificial Sequence

```
<220> FEATURE:
<223> OTHER INFORMATION: Synthetic

<400> SEQUENCE: 326
tccccagagg aactcaaagt taaggtgttg ggagatgtga ttgaggtgca tggaaaacat    60

<210> SEQ ID NO 327
<211> LENGTH: 60
<212> TYPE: DNA
<213> ORGANISM: Artificial Sequence
<220> FEATURE:
<223> OTHER INFORMATION: Synthetic

<400> SEQUENCE: 327
tggaaaccta actgcaatgt ggatgtttta cccacatgac ttattatgca tgttatgatc    60

<210> SEQ ID NO 328
<211> LENGTH: 60
<212> TYPE: DNA
<213> ORGANISM: Artificial Sequence
<220> FEATURE:
<223> OTHER INFORMATION: Synthetic

<400> SEQUENCE: 328
cttggtttat ttttcttaga atctgttgct aagactgggg acgctgtttt cttttacaaa    60

<210> SEQ ID NO 329
<211> LENGTH: 60
<212> TYPE: DNA
<213> ORGANISM: Artificial Sequence
<220> FEATURE:
<223> OTHER INFORMATION: Synthetic

<400> SEQUENCE: 329
tgttgggttt tagatctctt ttcatttgtc aaccttttca gtaaagccct ctgttacatc    60

<210> SEQ ID NO 330
<211> LENGTH: 60
<212> TYPE: DNA
<213> ORGANISM: Artificial Sequence
<220> FEATURE:
<223> OTHER INFORMATION: Synthetic

<400> SEQUENCE: 330
ggggcatatc attctctgag agaattattt ctggatcaca atgacttaaa atctatacca    60

<210> SEQ ID NO 331
<211> LENGTH: 60
<212> TYPE: DNA
<213> ORGANISM: Artificial Sequence
<220> FEATURE:
<223> OTHER INFORMATION: Synthetic

<400> SEQUENCE: 331
ggttataaaa cagtccagaa gtaccccact ttcaaatcat gcctgaagaa agaacttcac    60

<210> SEQ ID NO 332
<211> LENGTH: 60
<212> TYPE: DNA
<213> ORGANISM: Artificial Sequence
<220> FEATURE:
<223> OTHER INFORMATION: Synthetic

<400> SEQUENCE: 332
ttgggggaga ttttactcct ttcttcaaca actattcact ggacaagttc tctgctccca    60
```

<210> SEQ ID NO 333
<211> LENGTH: 60
<212> TYPE: DNA
<213> ORGANISM: Artificial Sequence
<220> FEATURE:
<223> OTHER INFORMATION: Synthetic

<400> SEQUENCE: 333
tccatattca gactatatag agaatattct atgcatctat gacgtgctta ctactgcagt    60

<210> SEQ ID NO 334
<211> LENGTH: 60
<212> TYPE: DNA
<213> ORGANISM: Artificial Sequence
<220> FEATURE:
<223> OTHER INFORMATION: Synthetic

<400> SEQUENCE: 334
tggctcaagt tccacattgg tatcaaccgg tacgagctgt actccagaca caacccggcc    60

<210> SEQ ID NO 335
<211> LENGTH: 60
<212> TYPE: DNA
<213> ORGANISM: Artificial Sequence
<220> FEATURE:
<223> OTHER INFORMATION: Synthetic

<400> SEQUENCE: 335
gcgtgctgta tgaatctaga aagccttaat ttactaccaa gaaataaagc aatatgttcg    60

<210> SEQ ID NO 336
<211> LENGTH: 60
<212> TYPE: DNA
<213> ORGANISM: Artificial Sequence
<220> FEATURE:
<223> OTHER INFORMATION: Synthetic

<400> SEQUENCE: 336
ttctctttgc catgaaggag gataatgaga aggtgcctac tttgctaacg gactacattt    60

<210> SEQ ID NO 337
<211> LENGTH: 60
<212> TYPE: DNA
<213> ORGANISM: Artificial Sequence
<220> FEATURE:
<223> OTHER INFORMATION: Synthetic

<400> SEQUENCE: 337
tcggcgccgg taggaagagt cagaggggtg accagagagc ccaacgcctg gtgctcaaga    60

<210> SEQ ID NO 338
<211> LENGTH: 60
<212> TYPE: DNA
<213> ORGANISM: Artificial Sequence
<220> FEATURE:
<223> OTHER INFORMATION: Synthetic

<400> SEQUENCE: 338
tggaccatgt caacgattac catgtcaagc ccgagaagga tgcggggtac tgctgccact    60

<210> SEQ ID NO 339
<211> LENGTH: 60
<212> TYPE: DNA
<213> ORGANISM: Artificial Sequence
<220> FEATURE:
<223> OTHER INFORMATION: Synthetic

<400> SEQUENCE: 339
tcctgtatct tatatggata tatgtatgtg tttgcattga ctgggacctc tttcacaatt        60

<210> SEQ ID NO 340
<211> LENGTH: 60
<212> TYPE: DNA
<213> ORGANISM: Artificial Sequence
<220> FEATURE:
<223> OTHER INFORMATION: Synthetic

<400> SEQUENCE: 340
ttctgttttc atctataaaa tcttcaagat tgacattgtg ctttggtaca gggattcctg        60

<210> SEQ ID NO 341
<211> LENGTH: 60
<212> TYPE: DNA
<213> ORGANISM: Artificial Sequence
<220> FEATURE:
<223> OTHER INFORMATION: Synthetic

<400> SEQUENCE: 341
ttttggatta gaggggatt tttgatggga gaaagctgga gatctgaacc cagcccattt        60

<210> SEQ ID NO 342
<211> LENGTH: 60
<212> TYPE: DNA
<213> ORGANISM: Artificial Sequence
<220> FEATURE:
<223> OTHER INFORMATION: Synthetic

<400> SEQUENCE: 342
ttttatagca tgaagattta atgcctataa ttaggaagga gttttcacag aaaccctccc        60

<210> SEQ ID NO 343
<211> LENGTH: 60
<212> TYPE: DNA
<213> ORGANISM: Artificial Sequence
<220> FEATURE:
<223> OTHER INFORMATION: Synthetic

<400> SEQUENCE: 343
catatgtgaa tgttattact ctcagtgaat tgttattgtt tgcaaaaatg cactgggcag        60

<210> SEQ ID NO 344
<211> LENGTH: 60
<212> TYPE: DNA
<213> ORGANISM: Artificial Sequence
<220> FEATURE:
<223> OTHER INFORMATION: Synthetic

<400> SEQUENCE: 344
tgaggaaaca gagctgacaa cacctgtact tccagaagaa acacaggaag aagatgccaa        60

<210> SEQ ID NO 345
<211> LENGTH: 60
<212> TYPE: DNA
<213> ORGANISM: Artificial Sequence
<220> FEATURE:
<223> OTHER INFORMATION: Synthetic

<400> SEQUENCE: 345
tttttgaaga tgacgccaca ttaacccttt cattttgttt ggaagatgga ccaaagcgat        60

<210> SEQ ID NO 346

```
<211> LENGTH: 60
<212> TYPE: DNA
<213> ORGANISM: Artificial Sequence
<220> FEATURE:
<223> OTHER INFORMATION: Synthetic

<400> SEQUENCE: 346 tggactttctg gagaatgagt tgaaactgat ggaagaattt gtcaagcaat ataagagcga    60

<210> SEQ ID NO 347
<211> LENGTH: 60
<212> TYPE: DNA
<213> ORGANISM: Artificial Sequence
<220> FEATURE:
<223> OTHER INFORMATION: Synthetic

<400> SEQUENCE: 347
ttgccaatga actggctaaa cataccaaag ggccagtgtt tgctggggat gtaagttctt    60

<210> SEQ ID NO 348
<211> LENGTH: 60
<212> TYPE: DNA
<213> ORGANISM: Artificial Sequence
<220> FEATURE:
<223> OTHER INFORMATION: Synthetic

<400> SEQUENCE: 348
ctccaaaatg ggcaagagcg aagacttctt ctacatcaag gtcagccaga aagcccgggg    60

<210> SEQ ID NO 349
<211> LENGTH: 60
<212> TYPE: DNA
<213> ORGANISM: Artificial Sequence
<220> FEATURE:
<223> OTHER INFORMATION: Synthetic

<400> SEQUENCE: 349
ttattatttg cagtcatgga gaaccaccta ccctgactt ctgtttagtc tccttttaa    60

<210> SEQ ID NO 350
<211> LENGTH: 60
<212> TYPE: DNA
<213> ORGANISM: Artificial Sequence
<220> FEATURE:
<223> OTHER INFORMATION: Synthetic

<400> SEQUENCE: 350
tgtaaaagag agtcacaggt accccaagga gtagatgcca gggtcctaag ttgaaaatga    60

<210> SEQ ID NO 351
<211> LENGTH: 60
<212> TYPE: DNA
<213> ORGANISM: Artificial Sequence
<220> FEATURE:
<223> OTHER INFORMATION: Synthetic

<400> SEQUENCE: 351
gttttcacat acaggattaa ccttgctgca gtgcgtgtgc aagattaaaa aagatgtcac    60

<210> SEQ ID NO 352
<211> LENGTH: 60
<212> TYPE: DNA
<213> ORGANISM: Artificial Sequence
<220> FEATURE:
<223> OTHER INFORMATION: Synthetic

<400> SEQUENCE: 352
```
tgtccctagc tgaactcagg acaacgtgca gcgagaatga gctggctgcg gagttcacca    60

<210> SEQ ID NO 353
<211> LENGTH: 60
<212> TYPE: DNA
<213> ORGANISM: Artificial Sequence
<220> FEATURE:
<223> OTHER INFORMATION: Synthetic

<400> SEQUENCE: 353
tgcagtgagg gtcaaaggag agtcaacata tgtgattgtt ccataataaa cttctggtgt    60

<210> SEQ ID NO 354
<211> LENGTH: 60
<212> TYPE: DNA
<213> ORGANISM: Artificial Sequence
<220> FEATURE:
<223> OTHER INFORMATION: Synthetic

<400> SEQUENCE: 354
gtccccaatc cttccaaaaa tattgatggt gatttgtgct accatttact cgtttattta    60

<210> SEQ ID NO 355
<211> LENGTH: 60
<212> TYPE: DNA
<213> ORGANISM: Artificial Sequence
<220> FEATURE:
<223> OTHER INFORMATION: Synthetic

<400> SEQUENCE: 355
tttattagcc ttctgaagac agcaaagatg acagtaaaac ttaccatcca tgctgagaat    60

<210> SEQ ID NO 356
<211> LENGTH: 60
<212> TYPE: DNA
<213> ORGANISM: Artificial Sequence
<220> FEATURE:
<223> OTHER INFORMATION: Synthetic

<400> SEQUENCE: 356
tgcatgggga accatgaact atacatgcgc cgtcgcaagc ctgataccat tgaggtgcag    60

<210> SEQ ID NO 357
<211> LENGTH: 60
<212> TYPE: DNA
<213> ORGANISM: Artificial Sequence
<220> FEATURE:
<223> OTHER INFORMATION: Synthetic

<400> SEQUENCE: 357
gctgaccatt cactctctgt gtctgttgtt ggatccaaat acgagtgttt ttcttcaaa    60

<210> SEQ ID NO 358
<211> LENGTH: 60
<212> TYPE: DNA
<213> ORGANISM: Artificial Sequence
<220> FEATURE:
<223> OTHER INFORMATION: Synthetic

<400> SEQUENCE: 358
gaaaatacaa agaaagttat tcagtacctt gcccatgttg cttcttcaca taaggaaga    60

<210> SEQ ID NO 359
<211> LENGTH: 60
<212> TYPE: DNA

```
<213> ORGANISM: Artificial Sequence
<220> FEATURE:
<223> OTHER INFORMATION: Synthetic

<400> SEQUENCE: 359
tttatgaagc acaacacatc tcgccagaat gaacactgcc tcaccaattt tgacctggct    60

<210> SEQ ID NO 360
<211> LENGTH: 60
<212> TYPE: DNA
<213> ORGANISM: Artificial Sequence
<220> FEATURE:
<223> OTHER INFORMATION: Synthetic

<400> SEQUENCE: 360
tgtgtgtgat cttgaaggga acagagtcaa gggtccagag aaggaggaga agttgagaca    60

<210> SEQ ID NO 361
<211> LENGTH: 60
<212> TYPE: DNA
<213> ORGANISM: Artificial Sequence
<220> FEATURE:
<223> OTHER INFORMATION: Synthetic

<400> SEQUENCE: 361
tggatgtttc ttatggcatt tgctctgggg tggagatcat atagacaatc aagtgcaaac    60

<210> SEQ ID NO 362
<211> LENGTH: 60
<212> TYPE: DNA
<213> ORGANISM: Artificial Sequence
<220> FEATURE:
<223> OTHER INFORMATION: Synthetic

<400> SEQUENCE: 362
gaaaagccca cggtcataga cagcaccata caatcaggta tcaaataaaa tacgaaatgt    60

<210> SEQ ID NO 363
<211> LENGTH: 60
<212> TYPE: DNA
<213> ORGANISM: Artificial Sequence
<220> FEATURE:
<223> OTHER INFORMATION: Synthetic

<400> SEQUENCE: 363
tggacatccc agaaatacat gagagagaag gatatgaaga tgaaattgat ggtatgacaa    60

<210> SEQ ID NO 364
<211> LENGTH: 60
<212> TYPE: DNA
<213> ORGANISM: Artificial Sequence
<220> FEATURE:
<223> OTHER INFORMATION: Synthetic

<400> SEQUENCE: 364
ttctgtctgc agtgtgcacg gccttgttct aacccggaat aaaggtgatt gattgtattg    60

<210> SEQ ID NO 365
<211> LENGTH: 60
<212> TYPE: DNA
<213> ORGANISM: Artificial Sequence
<220> FEATURE:
<223> OTHER INFORMATION: Synthetic

<400> SEQUENCE: 365
ttgtttttat ttcagttgct gcgaggtctg tcttacatcc accagcgtta tattttgcac    60
```

<210> SEQ ID NO 366
<211> LENGTH: 60
<212> TYPE: DNA
<213> ORGANISM: Artificial Sequence
<220> FEATURE:
<223> OTHER INFORMATION: Synthetic

<400> SEQUENCE: 366
tggccacaat attgacacct gttaccatgt atcaatcaca gagaagacct gccgaggatt        60

<210> SEQ ID NO 367
<211> LENGTH: 60
<212> TYPE: DNA
<213> ORGANISM: Artificial Sequence
<220> FEATURE:
<223> OTHER INFORMATION: Synthetic

<400> SEQUENCE: 367
tggtagctat aggaattaac atatacagaa catcaaatgt ggaggtgcta ctacagtttc        60

<210> SEQ ID NO 368
<211> LENGTH: 60
<212> TYPE: DNA
<213> ORGANISM: Artificial Sequence
<220> FEATURE:
<223> OTHER INFORMATION: Synthetic

<400> SEQUENCE: 368
tttaagttaa tatgaggttc tggttcaagg aaaacttacg ttggatctga accaatgagc        60

<210> SEQ ID NO 369
<211> LENGTH: 60
<212> TYPE: DNA
<213> ORGANISM: Artificial Sequence
<220> FEATURE:
<223> OTHER INFORMATION: Synthetic

<400> SEQUENCE: 369
tttcatcgtc attgatatca tgttggacat ggccgaaagg gaaggggtcg tagacatcta        60

<210> SEQ ID NO 370
<211> LENGTH: 60
<212> TYPE: DNA
<213> ORGANISM: Artificial Sequence
<220> FEATURE:
<223> OTHER INFORMATION: Synthetic

<400> SEQUENCE: 370
ggactttgtc tgtttattaa cctttatatg tttaattaaa ataaacaaat aaagacaaaa        60

<210> SEQ ID NO 371
<211> LENGTH: 60
<212> TYPE: DNA
<213> ORGANISM: Artificial Sequence
<220> FEATURE:
<223> OTHER INFORMATION: Synthetic

<400> SEQUENCE: 371
tttcattcat tggctcccat gtactatcga ggctcagctg cagctgttat cgtgtatgat        60

<210> SEQ ID NO 372
<211> LENGTH: 60
<212> TYPE: DNA
<213> ORGANISM: Artificial Sequence
<220> FEATURE:

<223> OTHER INFORMATION: Synthetic

<400> SEQUENCE: 372
tgcctgagga aggaggccgc tttgcacggg cacaaagact tccaccccccg cgtcacctgc    60

<210> SEQ ID NO 373
<211> LENGTH: 60
<212> TYPE: DNA
<213> ORGANISM: Artificial Sequence
<220> FEATURE:
<223> OTHER INFORMATION: Synthetic

<400> SEQUENCE: 373
ttgagtgatg tctcttcccc aagatcaata acttcgactc cactatcggg aaaggaatcg    60

<210> SEQ ID NO 374
<211> LENGTH: 60
<212> TYPE: DNA
<213> ORGANISM: Artificial Sequence
<220> FEATURE:
<223> OTHER INFORMATION: Synthetic

<400> SEQUENCE: 374
tgtgtagatc atcctagaat acctgtgtgg tgctgtcctt cctcaagact acctcattct    60

<210> SEQ ID NO 375
<211> LENGTH: 60
<212> TYPE: DNA
<213> ORGANISM: Artificial Sequence
<220> FEATURE:
<223> OTHER INFORMATION: Synthetic

<400> SEQUENCE: 375
ttttatcctc tatccttttt tcctttccta aaagcactct gagtcaagat gagtgggaaa    60

<210> SEQ ID NO 376
<211> LENGTH: 60
<212> TYPE: DNA
<213> ORGANISM: Artificial Sequence
<220> FEATURE:
<223> OTHER INFORMATION: Synthetic

<400> SEQUENCE: 376
ttagttaagt gtcttcaaat cttttgggct ggtgtggcag cttatgtctg taatcccagc    60

<210> SEQ ID NO 377
<211> LENGTH: 60
<212> TYPE: DNA
<213> ORGANISM: Artificial Sequence
<220> FEATURE:
<223> OTHER INFORMATION: Synthetic

<400> SEQUENCE: 377
tgaagttcct ttttagatgt gctattaaca ttctgttgga ttcagagggt tccttgaaag    60

<210> SEQ ID NO 378
<211> LENGTH: 60
<212> TYPE: DNA
<213> ORGANISM: Artificial Sequence
<220> FEATURE:
<223> OTHER INFORMATION: Synthetic

<400> SEQUENCE: 378
tccattgaag aagcttcagg agtgtatcct attgatgacg atgactacgc ttctgcgtct    60

<210> SEQ ID NO 379
<211> LENGTH: 60
<212> TYPE: DNA
<213> ORGANISM: Artificial Sequence
<220> FEATURE:
<223> OTHER INFORMATION: Synthetic

<400> SEQUENCE: 379
tttgattcac cagactttag caagatcaca ggcaaaccca tcaagctgac tcaggtggaa    60

<210> SEQ ID NO 380
<211> LENGTH: 60
<212> TYPE: DNA
<213> ORGANISM: Artificial Sequence
<220> FEATURE:
<223> OTHER INFORMATION: Synthetic

<400> SEQUENCE: 380
tgatggcata aatggaacag ttaactggaa gaccagacag gccaacaatt ttattatcag    60

<210> SEQ ID NO 381
<211> LENGTH: 60
<212> TYPE: DNA
<213> ORGANISM: Artificial Sequence
<220> FEATURE:
<223> OTHER INFORMATION: Synthetic

<400> SEQUENCE: 381
ttgcaattca gtgcttggag acagttttta agatcagccc agaagataca cacctagcag    60

<210> SEQ ID NO 382
<211> LENGTH: 60
<212> TYPE: DNA
<213> ORGANISM: Artificial Sequence
<220> FEATURE:
<223> OTHER INFORMATION: Synthetic

<400> SEQUENCE: 382
tttgctttct ttgtatgata atcaaattac tacagttgca ccaggggcat ttgatactct    60

<210> SEQ ID NO 383
<211> LENGTH: 60
<212> TYPE: DNA
<213> ORGANISM: Artificial Sequence
<220> FEATURE:
<223> OTHER INFORMATION: Synthetic

<400> SEQUENCE: 383
tttcagagat tgttcgtgag ttcaagtcga ctaaccgctt gctcctaact ggaacacctt    60

<210> SEQ ID NO 384
<211> LENGTH: 60
<212> TYPE: DNA
<213> ORGANISM: Artificial Sequence
<220> FEATURE:
<223> OTHER INFORMATION: Synthetic

<400> SEQUENCE: 384
ctgtatgaaa ctgagatgtt gtctatagct atgtctataa acaacctgaa gacttgtgaa    60

<210> SEQ ID NO 385
<211> LENGTH: 60
<212> TYPE: DNA
<213> ORGANISM: Artificial Sequence
<220> FEATURE:
<223> OTHER INFORMATION: Synthetic

<400> SEQUENCE: 385
ttgcaatgtt tttattgtta atgtagcata tataaaaaag tatctcataa ttttaaaaaa    60

<210> SEQ ID NO 386
<211> LENGTH: 60
<212> TYPE: DNA
<213> ORGANISM: Artificial Sequence
<220> FEATURE:
<223> OTHER INFORMATION: Synthetic

<400> SEQUENCE: 386
tgtgaaaact gtcaagtgct ctgtggatac aagtcgagtg actcttaatg gccaataggc    60

<210> SEQ ID NO 387
<211> LENGTH: 60
<212> TYPE: DNA
<213> ORGANISM: Artificial Sequence
<220> FEATURE:
<223> OTHER INFORMATION: Synthetic

<400> SEQUENCE: 387
ttttaacaga gtcaacctat ttgatttctt gacaagacca caatctgatc ccaaagatgt    60

<210> SEQ ID NO 388
<211> LENGTH: 60
<212> TYPE: DNA
<213> ORGANISM: Artificial Sequence
<220> FEATURE:
<223> OTHER INFORMATION: Synthetic

<400> SEQUENCE: 388
tgtttatgga cagtgctcta gatgtgaaaa cagatagaac tggtttgtgg gacaggggca    60

<210> SEQ ID NO 389
<211> LENGTH: 60
<212> TYPE: DNA
<213> ORGANISM: Artificial Sequence
<220> FEATURE:
<223> OTHER INFORMATION: Synthetic

<400> SEQUENCE: 389
tgcctgcctg gattgcacct ttctgcccct tcccctcat tattaaatgt ttcttttgc    60

<210> SEQ ID NO 390
<211> LENGTH: 60
<212> TYPE: DNA
<213> ORGANISM: Artificial Sequence
<220> FEATURE:
<223> OTHER INFORMATION: Synthetic

<400> SEQUENCE: 390
gggcttacac gatatcccat acctttaatg cctttggcct tccattctga tttctctgat    60

<210> SEQ ID NO 391
<211> LENGTH: 60
<212> TYPE: DNA
<213> ORGANISM: Artificial Sequence
<220> FEATURE:
<223> OTHER INFORMATION: Synthetic

<400> SEQUENCE: 391
tttgtatcat tcttgagcaa tcgctcggtc cgtggacaat aaacagtatt atcaaagaga    60

<210> SEQ ID NO 392
<211> LENGTH: 60

<210> SEQ ID NO 393
<211> LENGTH: 60
<212> TYPE: DNA
<213> ORGANISM: Artificial Sequence
<220> FEATURE:
<223> OTHER INFORMATION: Synthetic

<400> SEQUENCE: 392
ttaccagaag acggatccag ccagaagtat gacaagtgtg aaccatgaga agtatgacaa    60

<210> SEQ ID NO 393
<211> LENGTH: 60
<212> TYPE: DNA
<213> ORGANISM: Artificial Sequence
<220> FEATURE:
<223> OTHER INFORMATION: Synthetic

<400> SEQUENCE: 393
ttcttacatt atgacgtttg ttttcaagga gagggtttaa aaatgggatc ctgtaagcag    60

<210> SEQ ID NO 394
<211> LENGTH: 60
<212> TYPE: DNA
<213> ORGANISM: Artificial Sequence
<220> FEATURE:
<223> OTHER INFORMATION: Synthetic

<400> SEQUENCE: 394
tttcatgatt ttgctgatcg gaaggattgg gatgcattcc atcctacact ggtggcagaa    60

<210> SEQ ID NO 395
<211> LENGTH: 60
<212> TYPE: DNA
<213> ORGANISM: Artificial Sequence
<220> FEATURE:
<223> OTHER INFORMATION: Synthetic

<400> SEQUENCE: 395
gtttcttaat ggctaccaat aaggcaaata tcacaataat aaacgccaaa ttccttaggg    60

<210> SEQ ID NO 396
<211> LENGTH: 60
<212> TYPE: DNA
<213> ORGANISM: Artificial Sequence
<220> FEATURE:
<223> OTHER INFORMATION: Synthetic

<400> SEQUENCE: 396
ctggttgttc tacttggtaa tttgacaccc tgttaataac gcaattattt ctgtgttctt    60

<210> SEQ ID NO 397
<211> LENGTH: 60
<212> TYPE: DNA
<213> ORGANISM: Artificial Sequence
<220> FEATURE:
<223> OTHER INFORMATION: Synthetic

<400> SEQUENCE: 397
tttttgtcct caagaaaata cggaagaagc cctgttgtta ttgctgatta gtgaatcaat    60

<210> SEQ ID NO 398
<211> LENGTH: 60
<212> TYPE: DNA
<213> ORGANISM: Artificial Sequence
<220> FEATURE:
<223> OTHER INFORMATION: Synthetic

<400> SEQUENCE: 398
gggcacgagg gcagagccag ttcctagcgc agagccgcgc ccgccatgag ggagatcgtg        60

<210> SEQ ID NO 399
<211> LENGTH: 60
<212> TYPE: DNA
<213> ORGANISM: Artificial Sequence
<220> FEATURE:
<223> OTHER INFORMATION: Synthetic

<400> SEQUENCE: 399
tgtatagtct ttgctatgac ttctggccag atgtggaacc atatccgtgg acctccatat        60

<210> SEQ ID NO 400
<211> LENGTH: 60
<212> TYPE: DNA
<213> ORGANISM: Artificial Sequence
<220> FEATURE:
<223> OTHER INFORMATION: Synthetic

<400> SEQUENCE: 400
tgggtccggc tttcggtgac tagacggtcc gcaggggaca tcccgtccct ggggcctccc        60

<210> SEQ ID NO 401
<211> LENGTH: 60
<212> TYPE: DNA
<213> ORGANISM: Artificial Sequence
<220> FEATURE:
<223> OTHER INFORMATION: Synthetic

<400> SEQUENCE: 401
ttgttgggga tcttaaataa gattccttttt gatctaccgg aatatacatg tacagagtac       60

<210> SEQ ID NO 402
<211> LENGTH: 60
<212> TYPE: DNA
<213> ORGANISM: Artificial Sequence
<220> FEATURE:
<223> OTHER INFORMATION: Synthetic

<400> SEQUENCE: 402
tcccttatga tttctgctct ggctttgcag ttttcagcct ttcccaagag cagcagaaaa        60

<210> SEQ ID NO 403
<211> LENGTH: 60
<212> TYPE: DNA
<213> ORGANISM: Artificial Sequence
<220> FEATURE:
<223> OTHER INFORMATION: Synthetic

<400> SEQUENCE: 403
ttgtgctttt tcttttagaa gctactaaag ggtgttgggg atgcttctga ctattatgaa        60

<210> SEQ ID NO 404
<211> LENGTH: 60
<212> TYPE: DNA
<213> ORGANISM: Artificial Sequence
<220> FEATURE:
<223> OTHER INFORMATION: Synthetic

<400> SEQUENCE: 404
gtaaaactat tgtctaacat atatgcttta tgtggtcagg acccttaga attgttgatg         60

<210> SEQ ID NO 405
<211> LENGTH: 60
<212> TYPE: DNA
<213> ORGANISM: Artificial Sequence

```
<220> FEATURE:
<223> OTHER INFORMATION: Synthetic

<400> SEQUENCE: 405
gtggccaaaa tcaacagccg atttggatac cttcaagaca cctgaaacct tatcatgagc    60

<210> SEQ ID NO 406
<211> LENGTH: 60
<212> TYPE: DNA
<213> ORGANISM: Artificial Sequence
<220> FEATURE:
<223> OTHER INFORMATION: Synthetic

<400> SEQUENCE: 406
ttcttgctca gaggcctaga agggtacaca aaatgtcttc taaactagaa aacctaaggc    60

<210> SEQ ID NO 407
<211> LENGTH: 60
<212> TYPE: DNA
<213> ORGANISM: Artificial Sequence
<220> FEATURE:
<223> OTHER INFORMATION: Synthetic

<400> SEQUENCE: 407
ctgctagtga tagttacctg gaacttctaa aagaggctac caagcgagat ctaaatcttt    60

<210> SEQ ID NO 408
<211> LENGTH: 60
<212> TYPE: DNA
<213> ORGANISM: Artificial Sequence
<220> FEATURE:
<223> OTHER INFORMATION: Synthetic

<400> SEQUENCE: 408
tttgccaatc tctattttgt gggcattgcg gttctgaatt ttatccctgt ggtcaatgct    60

<210> SEQ ID NO 409
<211> LENGTH: 60
<212> TYPE: DNA
<213> ORGANISM: Artificial Sequence
<220> FEATURE:
<223> OTHER INFORMATION: Synthetic

<400> SEQUENCE: 409
ttggttgtca cttactttt ctgtggggaa gaaattccat accggaggat gctgaaggct    60

<210> SEQ ID NO 410
<211> LENGTH: 60
<212> TYPE: DNA
<213> ORGANISM: Artificial Sequence
<220> FEATURE:
<223> OTHER INFORMATION: Synthetic

<400> SEQUENCE: 410
ttctccaagg agaggcacat catggacagg accccgaga aactgaagaa ggagctggag    60

<210> SEQ ID NO 411
<211> LENGTH: 60
<212> TYPE: DNA
<213> ORGANISM: Artificial Sequence
<220> FEATURE:
<223> OTHER INFORMATION: Synthetic

<400> SEQUENCE: 411
gcctaatacc taggaagatg ttgctattca cgttagtaaa cagcctaaag aaactcttag    60
```

<210> SEQ ID NO 412
<211> LENGTH: 60
<212> TYPE: DNA
<213> ORGANISM: Artificial Sequence
<220> FEATURE:
<223> OTHER INFORMATION: Synthetic

<400> SEQUENCE: 412
tggcagaagt gaacctttgg ggcacagtgc ggatgacgaa atcctttctc cccctcatcc    60

<210> SEQ ID NO 413
<211> LENGTH: 60
<212> TYPE: DNA
<213> ORGANISM: Artificial Sequence
<220> FEATURE:
<223> OTHER INFORMATION: Synthetic

<400> SEQUENCE: 413
ttttcttgtt tcagaagttc ttggccaggc tgactgagag atttgtgctg ggagtggata    60

<210> SEQ ID NO 414
<211> LENGTH: 60
<212> TYPE: DNA
<213> ORGANISM: Artificial Sequence
<220> FEATURE:
<223> OTHER INFORMATION: Synthetic

<400> SEQUENCE: 414
cctcctgaca tgagtctgct ggaaagagca tccaaacaaa caagtaataa ataaataaat    60

<210> SEQ ID NO 415
<211> LENGTH: 60
<212> TYPE: DNA
<213> ORGANISM: Artificial Sequence
<220> FEATURE:
<223> OTHER INFORMATION: Synthetic

<400> SEQUENCE: 415
tgtatcaatg acccacatat caatgaccca cgtatcaatg acccgcatat gaatgaaaaa    60

<210> SEQ ID NO 416
<211> LENGTH: 60
<212> TYPE: DNA
<213> ORGANISM: Artificial Sequence
<220> FEATURE:
<223> OTHER INFORMATION: Synthetic

<400> SEQUENCE: 416
ccacccagaa atccactcaa atttggggat tgtcattcct tttgtgaata attaatacaa    60

<210> SEQ ID NO 417
<211> LENGTH: 60
<212> TYPE: DNA
<213> ORGANISM: Artificial Sequence
<220> FEATURE:
<223> OTHER INFORMATION: Synthetic

<400> SEQUENCE: 417
gtgatgagtg gcgtctttcc tgcctctgat gatggactca ataaacagca ctggacaagg    60

<210> SEQ ID NO 418
<211> LENGTH: 60
<212> TYPE: DNA
<213> ORGANISM: Artificial Sequence
<220> FEATURE:
<223> OTHER INFORMATION: Synthetic

<400> SEQUENCE: 418
tgtttgatac caaaataaat ttacgtagag atccttaact taaaataaat taatttttc    60

<210> SEQ ID NO 419
<211> LENGTH: 60
<212> TYPE: DNA
<213> ORGANISM: Artificial Sequence
<220> FEATURE:
<223> OTHER INFORMATION: Synthetic

<400> SEQUENCE: 419
ttcagggaag cagatatcga acccaatggc aaagtgaagt atgatgaatt tatccacaag    60

<210> SEQ ID NO 420
<211> LENGTH: 60
<212> TYPE: DNA
<213> ORGANISM: Artificial Sequence
<220> FEATURE:
<223> OTHER INFORMATION: Synthetic

<400> SEQUENCE: 420
tgtgccggta cttcacggac atcatcaagt gccgcgtgat caacacatcc cacctgagca    60

<210> SEQ ID NO 421
<211> LENGTH: 60
<212> TYPE: DNA
<213> ORGANISM: Artificial Sequence
<220> FEATURE:
<223> OTHER INFORMATION: Synthetic

<400> SEQUENCE: 421
ttggtactca tgtctcatgg catcctagag ggaatctgcg gaactgcgca taaaaagaaa    60

<210> SEQ ID NO 422
<211> LENGTH: 60
<212> TYPE: DNA
<213> ORGANISM: Artificial Sequence
<220> FEATURE:
<223> OTHER INFORMATION: Synthetic

<400> SEQUENCE: 422
tttttaaagg tttttgaaat ccaggaatta aatcatccct taataaaata ttcgaaattc    60

<210> SEQ ID NO 423
<211> LENGTH: 60
<212> TYPE: DNA
<213> ORGANISM: Artificial Sequence
<220> FEATURE:
<223> OTHER INFORMATION: Synthetic

<400> SEQUENCE: 423
tgctgctcaa gggagcccca agggctggaa gggggttgtg aaaccgaaat aaactgccaa    60

<210> SEQ ID NO 424
<211> LENGTH: 60
<212> TYPE: DNA
<213> ORGANISM: Artificial Sequence
<220> FEATURE:
<223> OTHER INFORMATION: Synthetic

<400> SEQUENCE: 424
tctatcagac agcaattgaa agcgccagac aagctggaga cagcgccaag atgcggcgct    60

<210> SEQ ID NO 425

```
<211> LENGTH: 60
<212> TYPE: DNA
<213> ORGANISM: Artificial Sequence
<220> FEATURE:
<223> OTHER INFORMATION: Synthetic

<400> SEQUENCE: 425
gatttaagaa tctcctccta cctcctgact cagcaccatg taatcattaa actctctgct    60

<210> SEQ ID NO 426
<211> LENGTH: 60
<212> TYPE: DNA
<213> ORGANISM: Artificial Sequence
<220> FEATURE:
<223> OTHER INFORMATION: Synthetic

<400> SEQUENCE: 426
gcgcgggccg gggattagga gacggaggcg gactcggagc cagggaacca ggggtccggg    60

<210> SEQ ID NO 427
<211> LENGTH: 60
<212> TYPE: DNA
<213> ORGANISM: Artificial Sequence
<220> FEATURE:
<223> OTHER INFORMATION: Synthetic

<400> SEQUENCE: 427
ggacaggtgt tgtatataga gtggaatctc ttggatgcag cttcaagaat aaattttct    60

<210> SEQ ID NO 428
<211> LENGTH: 60
<212> TYPE: DNA
<213> ORGANISM: Artificial Sequence
<220> FEATURE:
<223> OTHER INFORMATION: Synthetic

<400> SEQUENCE: 428
catgtcgcgc tgggcaggga ccggcagccc tggaaggggc acttgatatt tttcaataaa    60

<210> SEQ ID NO 429
<211> LENGTH: 60
<212> TYPE: DNA
<213> ORGANISM: Artificial Sequence
<220> FEATURE:
<223> OTHER INFORMATION: Synthetic

<400> SEQUENCE: 429
ttaataacta ttgtattaaa ttgtcatgaa ggaacttgtt taataaatgg acgtgtaagg    60

<210> SEQ ID NO 430
<211> LENGTH: 60
<212> TYPE: DNA
<213> ORGANISM: Artificial Sequence
<220> FEATURE:
<223> OTHER INFORMATION: Synthetic

<400> SEQUENCE: 430
tatttctata ttttttacca gaaaaccaaa ctctccatcg ctgaaagaga ttccagtggg    60

<210> SEQ ID NO 431
<211> LENGTH: 60
<212> TYPE: DNA
<213> ORGANISM: Artificial Sequence
<220> FEATURE:
<223> OTHER INFORMATION: Synthetic

<400> SEQUENCE: 431
```
tgccatttga ctcaaacatg aataggacaa agaacagacc gctggttcgt ggacagatca    60

<210> SEQ ID NO 432
<211> LENGTH: 60
<212> TYPE: DNA
<213> ORGANISM: Artificial Sequence
<220> FEATURE:
<223> OTHER INFORMATION: Synthetic

<400> SEQUENCE: 432
tgggaacctt tttagcttgg agcttggtga catatctgca gttcttatta ctggcttgcc    60

<210> SEQ ID NO 433
<211> LENGTH: 60
<212> TYPE: DNA
<213> ORGANISM: Artificial Sequence
<220> FEATURE:
<223> OTHER INFORMATION: Synthetic

<400> SEQUENCE: 433
ttgggccttt aggttccaca atccccatgg cttattatcc agtcggtccc atctatccac    60

<210> SEQ ID NO 434
<211> LENGTH: 60
<212> TYPE: DNA
<213> ORGANISM: Artificial Sequence
<220> FEATURE:
<223> OTHER INFORMATION: Synthetic

<400> SEQUENCE: 434
tttttgtggg cctttccaaa aggacaaatc aacgaggtgc tgaaatcttg gctgatactt    60

<210> SEQ ID NO 435
<211> LENGTH: 60
<212> TYPE: DNA
<213> ORGANISM: Artificial Sequence
<220> FEATURE:
<223> OTHER INFORMATION: Synthetic

<400> SEQUENCE: 435
tcctgcaaaa ccatctatgg agagaagacg gggacccagc cccagggaaa gatggaggta    60

<210> SEQ ID NO 436
<211> LENGTH: 60
<212> TYPE: DNA
<213> ORGANISM: Artificial Sequence
<220> FEATURE:
<223> OTHER INFORMATION: Synthetic

<400> SEQUENCE: 436
ttcttttcct ttttcatcgg gctctttcct aaaaagctga gctgtaaaat attttacatc    60

<210> SEQ ID NO 437
<211> LENGTH: 60
<212> TYPE: DNA
<213> ORGANISM: Artificial Sequence
<220> FEATURE:
<223> OTHER INFORMATION: Synthetic

<400> SEQUENCE: 437
tccactgctc atcgttattc tagtgttttt ggctctagca gcaagcttcc tgctcatctt    60

<210> SEQ ID NO 438
<211> LENGTH: 60
<212> TYPE: DNA

<213> ORGANISM: Artificial Sequence
<220> FEATURE:
<223> OTHER INFORMATION: Synthetic

<400> SEQUENCE: 438
ttccaattct agaaggggaa gtttttgatt ctgtgaagcc aggactttct gcttttgtag    60

<210> SEQ ID NO 439
<211> LENGTH: 60
<212> TYPE: DNA
<213> ORGANISM: Artificial Sequence
<220> FEATURE:
<223> OTHER INFORMATION: Synthetic

<400> SEQUENCE: 439
tttcctcagt aatagtcctg taaaggtacg tgtttgtcct ggctacttgt gctcttcctg    60

<210> SEQ ID NO 440
<211> LENGTH: 60
<212> TYPE: DNA
<213> ORGANISM: Artificial Sequence
<220> FEATURE:
<223> OTHER INFORMATION: Synthetic

<400> SEQUENCE: 440
tttttaatga caatgaagtg acactttgac atttcctacc ttttgaggac ttgatccttc    60

<210> SEQ ID NO 441
<211> LENGTH: 60
<212> TYPE: DNA
<213> ORGANISM: Artificial Sequence
<220> FEATURE:
<223> OTHER INFORMATION: Synthetic

<400> SEQUENCE: 441
agtaaccacc tatttatttt acctctttcc caaacctgga gcatttatgc ctaggcttgt    60

<210> SEQ ID NO 442
<211> LENGTH: 60
<212> TYPE: DNA
<213> ORGANISM: Artificial Sequence
<220> FEATURE:
<223> OTHER INFORMATION: Synthetic

<400> SEQUENCE: 442
tggtgggcat tgagcctctc tacatcaagg cagagccggc cagccctgac agtccaaagg    60

<210> SEQ ID NO 443
<211> LENGTH: 60
<212> TYPE: DNA
<213> ORGANISM: Artificial Sequence
<220> FEATURE:
<223> OTHER INFORMATION: Synthetic

<400> SEQUENCE: 443
tgctcccatc cactattaat gcactaggtg ggaggagagg gcggcaatga cactgcacct    60

<210> SEQ ID NO 444
<211> LENGTH: 60
<212> TYPE: DNA
<213> ORGANISM: Artificial Sequence
<220> FEATURE:
<223> OTHER INFORMATION: Synthetic

<400> SEQUENCE: 444
tttcttaaat gacgaagagg ccgggaagat ccttcaggtg ctggaaagga atgaggagtt    60

<210> SEQ ID NO 445
<211> LENGTH: 60
<212> TYPE: DNA
<213> ORGANISM: Artificial Sequence
<220> FEATURE:
<223> OTHER INFORMATION: Synthetic

<400> SEQUENCE: 445
ttactcttca agttcaacca ctgttaagac ctcctattga gttttccagg tcctcagatg     60

<210> SEQ ID NO 446
<211> LENGTH: 60
<212> TYPE: DNA
<213> ORGANISM: Artificial Sequence
<220> FEATURE:
<223> OTHER INFORMATION: Synthetic

<400> SEQUENCE: 446
taaaaagtac aagtgtggcc tcatcaagcc ctgcccagcc aactactttg cgtttaaaat     60

<210> SEQ ID NO 447
<211> LENGTH: 60
<212> TYPE: DNA
<213> ORGANISM: Artificial Sequence
<220> FEATURE:
<223> OTHER INFORMATION: Synthetic

<400> SEQUENCE: 447
ttgtcgtttt tgttatctaa cggtaattac ggagtccaga agagaattg gaaatgccgg     60

<210> SEQ ID NO 448
<211> LENGTH: 60
<212> TYPE: DNA
<213> ORGANISM: Artificial Sequence
<220> FEATURE:
<223> OTHER INFORMATION: Synthetic

<400> SEQUENCE: 448
gagtgtctga aattgtggtg gtcctgattt ataggatttc ataattaaaa tgtctgctga     60

<210> SEQ ID NO 449
<211> LENGTH: 60
<212> TYPE: DNA
<213> ORGANISM: Artificial Sequence
<220> FEATURE:
<223> OTHER INFORMATION: Synthetic

<400> SEQUENCE: 449
ttgctggcga tggcattgag ggctcacctg ccaaagattt tgctctactc acacagtgta     60

<210> SEQ ID NO 450
<211> LENGTH: 60
<212> TYPE: DNA
<213> ORGANISM: Artificial Sequence
<220> FEATURE:
<223> OTHER INFORMATION: Synthetic

<400> SEQUENCE: 450
gtcaagatgt caagtcattt ttgaatgtgt ctcagggatt tctatgctac acattctttt     60

<210> SEQ ID NO 451
<211> LENGTH: 60
<212> TYPE: DNA
<213> ORGANISM: Artificial Sequence
<220> FEATURE:

```
<223> OTHER INFORMATION: Synthetic

<400> SEQUENCE: 451
tgcagagaga taatcaccgc accgtttcca gatgtaatac tgcaaagaaa accaatgatg      60

<210> SEQ ID NO 452
<211> LENGTH: 60
<212> TYPE: DNA
<213> ORGANISM: Artificial Sequence
<220> FEATURE:
<223> OTHER INFORMATION: Synthetic

<400> SEQUENCE: 452
tggcaaatta ttatttgttc cttgttctcg tgttggacat atctaccgtc ttgagggctg      60

<210> SEQ ID NO 453
<211> LENGTH: 60
<212> TYPE: DNA
<213> ORGANISM: Artificial Sequence
<220> FEATURE:
<223> OTHER INFORMATION: Synthetic

<400> SEQUENCE: 453
tgccttgtga agatcattaa tgaagtaaag cccacagaga tctacaacct tggagcccag      60

<210> SEQ ID NO 454
<211> LENGTH: 60
<212> TYPE: DNA
<213> ORGANISM: Artificial Sequence
<220> FEATURE:
<223> OTHER INFORMATION: Synthetic

<400> SEQUENCE: 454
tattgctatc ttttctggat gatcagaaaa ataattccat aaatctattg tctacttgcg      60

<210> SEQ ID NO 455
<211> LENGTH: 60
<212> TYPE: DNA
<213> ORGANISM: Artificial Sequence
<220> FEATURE:
<223> OTHER INFORMATION: Synthetic

<400> SEQUENCE: 455
tacataacca gcaagctctc agatgccaac tgctgcctgg acgccatctg ctactactac      60

<210> SEQ ID NO 456
<211> LENGTH: 60
<212> TYPE: DNA
<213> ORGANISM: Artificial Sequence
<220> FEATURE:
<223> OTHER INFORMATION: Synthetic

<400> SEQUENCE: 456
gcggcctttg tcacctactg tgataataaa gcagtgagtg ctgagctctc acccttcccc      60

<210> SEQ ID NO 457
<211> LENGTH: 60
<212> TYPE: DNA
<213> ORGANISM: Artificial Sequence
<220> FEATURE:
<223> OTHER INFORMATION: Synthetic

<400> SEQUENCE: 457
cacaaactac ctctggacag ttgtgttgtt ttttgttcaa tgttccattc ttcgacatcc      60
```

<210> SEQ ID NO 458
<211> LENGTH: 60
<212> TYPE: DNA
<213> ORGANISM: Artificial Sequence
<220> FEATURE:
<223> OTHER INFORMATION: Synthetic

<400> SEQUENCE: 458
ttccaggagc tgcagatcga tgacaatgag tatgcctacc tcaaagccat catcttcttt    60

<210> SEQ ID NO 459
<211> LENGTH: 60
<212> TYPE: DNA
<213> ORGANISM: Artificial Sequence
<220> FEATURE:
<223> OTHER INFORMATION: Synthetic

<400> SEQUENCE: 459
tttctttggg ggtgattgtc tcgcttgttt tcagttgtcg attatatggg agggttctgg    60

<210> SEQ ID NO 460
<211> LENGTH: 60
<212> TYPE: DNA
<213> ORGANISM: Artificial Sequence
<220> FEATURE:
<223> OTHER INFORMATION: Synthetic

<400> SEQUENCE: 460
gctactcatg gacacattca gctgtgaact ccttccctgg ggggtcaagg tcagcatcat    60

<210> SEQ ID NO 461
<211> LENGTH: 60
<212> TYPE: DNA
<213> ORGANISM: Artificial Sequence
<220> FEATURE:
<223> OTHER INFORMATION: Synthetic

<400> SEQUENCE: 461
ctttaacata taaaaaacac ttattcccac agagaaaatg taaaattaaa aatcatcatc    60

<210> SEQ ID NO 462
<211> LENGTH: 60
<212> TYPE: DNA
<213> ORGANISM: Artificial Sequence
<220> FEATURE:
<223> OTHER INFORMATION: Synthetic

<400> SEQUENCE: 462
ttcaacataa tgaaatagac ttgaaagtct ctaaggctct atcagttctg acattctagg    60

<210> SEQ ID NO 463
<211> LENGTH: 60
<212> TYPE: DNA
<213> ORGANISM: Artificial Sequence
<220> FEATURE:
<223> OTHER INFORMATION: Synthetic

<400> SEQUENCE: 463
ggggttcctt ctgggcatta catcgcatag aaatcaataa tttgtggtga tttggatctg    60

<210> SEQ ID NO 464
<211> LENGTH: 60
<212> TYPE: DNA
<213> ORGANISM: Artificial Sequence
<220> FEATURE:
<223> OTHER INFORMATION: Synthetic

<400> SEQUENCE: 464
ttgttcctga ggtgggaggc ggtacccgtg gctgagaaga aggaggcctg agagcgacat    60

<210> SEQ ID NO 465
<211> LENGTH: 60
<212> TYPE: DNA
<213> ORGANISM: Artificial Sequence
<220> FEATURE:
<223> OTHER INFORMATION: Synthetic

<400> SEQUENCE: 465
gcacgctctc tctttctctc tttaattttg gtttctctca agcttccaaa tggtgctcag    60

<210> SEQ ID NO 466
<211> LENGTH: 60
<212> TYPE: DNA
<213> ORGANISM: Artificial Sequence
<220> FEATURE:
<223> OTHER INFORMATION: Synthetic

<400> SEQUENCE: 466
gttcttcgtg aactttgtgg ttgggcagga tccgggctca gacgtcgcct tccacttcaa    60

<210> SEQ ID NO 467
<211> LENGTH: 60
<212> TYPE: DNA
<213> ORGANISM: Artificial Sequence
<220> FEATURE:
<223> OTHER INFORMATION: Synthetic

<400> SEQUENCE: 467
tgtcaacaag tgtctagatt tgaataactg tggattaaca acagcggaca tgaaagaaat    60

<210> SEQ ID NO 468
<211> LENGTH: 60
<212> TYPE: DNA
<213> ORGANISM: Artificial Sequence
<220> FEATURE:
<223> OTHER INFORMATION: Synthetic

<400> SEQUENCE: 468
tatgtgcctg ccatggctga tgaaaacatc attgtacgca agcagggtac cattttcttg    60

<210> SEQ ID NO 469
<211> LENGTH: 60
<212> TYPE: DNA
<213> ORGANISM: Artificial Sequence
<220> FEATURE:
<223> OTHER INFORMATION: Synthetic

<400> SEQUENCE: 469
tttcaccaag agagtgtttc ttcactcaac tcaggtggca tttggggtga catctcaaag    60

<210> SEQ ID NO 470
<211> LENGTH: 60
<212> TYPE: DNA
<213> ORGANISM: Artificial Sequence
<220> FEATURE:
<223> OTHER INFORMATION: Synthetic

<400> SEQUENCE: 470
cggaaagaac acccggaaat gaaaggccac caagaagaaa gaccatgaga agtatgacaa    60

<210> SEQ ID NO 471
<211> LENGTH: 60

<212> TYPE: DNA
<213> ORGANISM: Artificial Sequence
<220> FEATURE:
<223> OTHER INFORMATION: Synthetic

<400> SEQUENCE: 471
ctttggggac aggaagtcgg cacatctcca ggtcttcatg tgcacaatat agagtttatt     60

<210> SEQ ID NO 472
<211> LENGTH: 60
<212> TYPE: DNA
<213> ORGANISM: Artificial Sequence
<220> FEATURE:
<223> OTHER INFORMATION: Synthetic

<400> SEQUENCE: 472
ttctctccat gaattttcag ggagctaggg gtgtcagtat cccgccatgt agcatttccc     60

<210> SEQ ID NO 473
<211> LENGTH: 60
<212> TYPE: DNA
<213> ORGANISM: Artificial Sequence
<220> FEATURE:
<223> OTHER INFORMATION: Synthetic

<400> SEQUENCE: 473
tgtgtgcaaa tgagtgcaca cacacagaag gggtccagag gggagaatgc caccaacaga     60

<210> SEQ ID NO 474
<211> LENGTH: 60
<212> TYPE: DNA
<213> ORGANISM: Artificial Sequence
<220> FEATURE:
<223> OTHER INFORMATION: Synthetic

<400> SEQUENCE: 474
gtatgtatca cccaactcac taattatcaa cttatgtgct atcagatatc ctctctaccc     60

<210> SEQ ID NO 475
<211> LENGTH: 60
<212> TYPE: DNA
<213> ORGANISM: Artificial Sequence
<220> FEATURE:
<223> OTHER INFORMATION: Synthetic

<400> SEQUENCE: 475
tgaacggcat gctgattcgt gaggcccgga gctacatctt gcgctgccat ggctgtttca     60

<210> SEQ ID NO 476
<211> LENGTH: 60
<212> TYPE: DNA
<213> ORGANISM: Artificial Sequence
<220> FEATURE:
<223> OTHER INFORMATION: Synthetic

<400> SEQUENCE: 476
ttttcctggt tcaacaacct gttgacttcc ctggaacagg agatggagga attaggcaaa     60

<210> SEQ ID NO 477
<211> LENGTH: 60
<212> TYPE: DNA
<213> ORGANISM: Artificial Sequence
<220> FEATURE:
<223> OTHER INFORMATION: Synthetic

<400> SEQUENCE: 477

```
tgtagccctg ggtttaatgt caaatcaagg caaaaggaat taaataatgt acttttggct    60
```

<210> SEQ ID NO 478
<211> LENGTH: 60
<212> TYPE: DNA
<213> ORGANISM: Artificial Sequence
<220> FEATURE:
<223> OTHER INFORMATION: Synthetic

<400> SEQUENCE: 478

```
tgaagttttc tttattacgg attcaaagac ttattttgaa agttggaagg agaagggagg    60
```

<210> SEQ ID NO 479
<211> LENGTH: 60
<212> TYPE: DNA
<213> ORGANISM: Artificial Sequence
<220> FEATURE:
<223> OTHER INFORMATION: Synthetic

<400> SEQUENCE: 479

```
tggctgctct gatctggtct cagcgcggag ggagcagagg gagtccatgg aggatccctc    60
```

<210> SEQ ID NO 480
<211> LENGTH: 60
<212> TYPE: DNA
<213> ORGANISM: Artificial Sequence
<220> FEATURE:
<223> OTHER INFORMATION: Synthetic

<400> SEQUENCE: 480

```
ttttgtgttt ttaaggcat taataaagcc ttcgataata ttaaatacaa aatgaaaaaa    60
```

<210> SEQ ID NO 481
<211> LENGTH: 60
<212> TYPE: DNA
<213> ORGANISM: Artificial Sequence
<220> FEATURE:
<223> OTHER INFORMATION: Synthetic

<400> SEQUENCE: 481

```
gtaagtcaca tttctattag gactacttac aaggacaagg tttccatttt tccagttgta    60
```

<210> SEQ ID NO 482
<211> LENGTH: 60
<212> TYPE: DNA
<213> ORGANISM: Artificial Sequence
<220> FEATURE:
<223> OTHER INFORMATION: Synthetic

<400> SEQUENCE: 482

```
tgtggctatc ttatgtgagg actagaggtg aagaggagat ggacactgcc tctggagcca    60
```

<210> SEQ ID NO 483
<211> LENGTH: 60
<212> TYPE: DNA
<213> ORGANISM: Artificial Sequence
<220> FEATURE:
<223> OTHER INFORMATION: Synthetic

<400> SEQUENCE: 483

```
ttgcagatgc tttagtgatc tttcagctct atgagatgat ccgagtgcca gtcaactgga    60
```

<210> SEQ ID NO 484
<211> LENGTH: 60
<212> TYPE: DNA
<213> ORGANISM: Artificial Sequence -continued

```
<220> FEATURE:
<223> OTHER INFORMATION: Synthetic

<400> SEQUENCE: 484
ttccttgtcg aatgatactg taatgacctt ccaaagtgaa gagtagcaca ttaaagtgat     60

<210> SEQ ID NO 485
<211> LENGTH: 60
<212> TYPE: DNA
<213> ORGANISM: Artificial Sequence
<220> FEATURE:
<223> OTHER INFORMATION: Synthetic

<400> SEQUENCE: 485
tcattgattc ctaaaggatt atcagagttt acaaaacagc aaatacgcta cattctgcag     60

<210> SEQ ID NO 486
<211> LENGTH: 60
<212> TYPE: DNA
<213> ORGANISM: Artificial Sequence
<220> FEATURE:
<223> OTHER INFORMATION: Synthetic

<400> SEQUENCE: 486
tgcgttttgt gctttgatgc caggaatgcc gcctagttta tgtccccggt ggggcacaca     60

<210> SEQ ID NO 487
<211> LENGTH: 60
<212> TYPE: DNA
<213> ORGANISM: Artificial Sequence
<220> FEATURE:
<223> OTHER INFORMATION: Synthetic

<400> SEQUENCE: 487 tattttaca atacaggttt gcagaaccag cgagtattat atgtacagga ttccttagag     60

<210> SEQ ID NO 488
<211> LENGTH: 60
<212> TYPE: DNA
<213> ORGANISM: Artificial Sequence
<220> FEATURE:
<223> OTHER INFORMATION: Synthetic

<400> SEQUENCE: 488
gggaagctcc tgttcctctt attccaatgt tcttggtttt tctttatata acttgatgaa     60

<210> SEQ ID NO 489
<211> LENGTH: 60
<212> TYPE: DNA
<213> ORGANISM: Artificial Sequence
<220> FEATURE:
<223> OTHER INFORMATION: Synthetic

<400> SEQUENCE: 489
ttgcttgttg ctcactgtgc tgcttttcca tgagctcttg gaggcaccaa gaaataaact     60

<210> SEQ ID NO 490
<211> LENGTH: 60
<212> TYPE: DNA
<213> ORGANISM: Artificial Sequence
<220> FEATURE:
<223> OTHER INFORMATION: Synthetic

<400> SEQUENCE: 490
ttctgcgcgg ggtgtgaggt ggatactttg aacattctga gaacccaata aaactagaag     60
```

<210> SEQ ID NO 491
<211> LENGTH: 60
<212> TYPE: DNA
<213> ORGANISM: Artificial Sequence
<220> FEATURE:
<223> OTHER INFORMATION: Synthetic

<400> SEQUENCE: 491
tgtactacga gtccaaggca catatccact gctcggtgaa agcagagaac tcggtggcgg    60

<210> SEQ ID NO 492
<211> LENGTH: 60
<212> TYPE: DNA
<213> ORGANISM: Artificial Sequence
<220> FEATURE:
<223> OTHER INFORMATION: Synthetic

<400> SEQUENCE: 492
ttttgacata caatatggag tagtggttat tcgcctaaaa gaaggtctgg atatatctca    60

<210> SEQ ID NO 493
<211> LENGTH: 60
<212> TYPE: DNA
<213> ORGANISM: Artificial Sequence
<220> FEATURE:
<223> OTHER INFORMATION: Synthetic

<400> SEQUENCE: 493
ttgtaggaaa tttgcatacc cgtaaaggga gactttttta aataacagtt gagtctttgc    60

<210> SEQ ID NO 494
<211> LENGTH: 60
<212> TYPE: DNA
<213> ORGANISM: Artificial Sequence
<220> FEATURE:
<223> OTHER INFORMATION: Synthetic

<400> SEQUENCE: 494
ttcctcctct tcaacatcat ggactggctg ggacggagcc tgacctctta cttcctgtgg    60

<210> SEQ ID NO 495
<211> LENGTH: 60
<212> TYPE: DNA
<213> ORGANISM: Artificial Sequence
<220> FEATURE:
<223> OTHER INFORMATION: Synthetic

<400> SEQUENCE: 495
tttgaactat caagcatata ctgtatacag ttagaaagtt attaaatgaa cattttactc    60

<210> SEQ ID NO 496
<211> LENGTH: 60
<212> TYPE: DNA
<213> ORGANISM: Artificial Sequence
<220> FEATURE:
<223> OTHER INFORMATION: Synthetic

<400> SEQUENCE: 496
tgatccgcct catacacaag gagctgagct gcccagggtc agctacgggg gaccaagttc    60

<210> SEQ ID NO 497
<211> LENGTH: 60
<212> TYPE: DNA
<213> ORGANISM: Artificial Sequence
<220> FEATURE:
<223> OTHER INFORMATION: Synthetic

<400> SEQUENCE: 497
tggtgctcat cttcctgcgg cagcggattc gtattgccat cgccctcctg aaggaggcca    60

<210> SEQ ID NO 498
<211> LENGTH: 60
<212> TYPE: DNA
<213> ORGANISM: Artificial Sequence
<220> FEATURE:
<223> OTHER INFORMATION: Synthetic

<400> SEQUENCE: 498
tgtggtttat aatccttgaa tattgtttta gaaactttgg tctccctggt tcctgccact    60

<210> SEQ ID NO 499
<211> LENGTH: 60
<212> TYPE: DNA
<213> ORGANISM: Artificial Sequence
<220> FEATURE:
<223> OTHER INFORMATION: Synthetic

<400> SEQUENCE: 499
ttgtttgatc atgtgaagac tggaattgaa gatgtttgtg gacattgggg tcacaacttt    60

<210> SEQ ID NO 500
<211> LENGTH: 60
<212> TYPE: DNA
<213> ORGANISM: Artificial Sequence
<220> FEATURE:
<223> OTHER INFORMATION: Synthetic

<400> SEQUENCE: 500
ttttaaataa gaaatgctaa cgtttactgt tactgctgtg tgctatgcac tttgctaagc    60

<210> SEQ ID NO 501
<211> LENGTH: 60
<212> TYPE: DNA
<213> ORGANISM: Artificial Sequence
<220> FEATURE:
<223> OTHER INFORMATION: Synthetic

<400> SEQUENCE: 501
ttttggtaga ttttatcta tacaaattta ataaaatta tgttttgtaa gctgaaaaaa    60

<210> SEQ ID NO 502
<211> LENGTH: 60
<212> TYPE: DNA
<213> ORGANISM: Artificial Sequence
<220> FEATURE:
<223> OTHER INFORMATION: Synthetic

<400> SEQUENCE: 502
tgtctgtagt tgattgaaac gagggcagtt atgaattgat ttgggcaatc aaatgaattt    60

<210> SEQ ID NO 503
<211> LENGTH: 60
<212> TYPE: DNA
<213> ORGANISM: Artificial Sequence
<220> FEATURE:
<223> OTHER INFORMATION: Synthetic

<400> SEQUENCE: 503
ttttctggaa aatggtgcag tcccgcgtgg gtgactcctt ctacatccgc actcactttg    60

<210> SEQ ID NO 504

```
<211> LENGTH: 60
<212> TYPE: DNA
<213> ORGANISM: Artificial Sequence
<220> FEATURE:
<223> OTHER INFORMATION: Synthetic

<400> SEQUENCE: 504
tggcggagaa cgtgtttgct gtacgctgtg ctcagctcac ccaccagctg ctggagctga     60

<210> SEQ ID NO 505
<211> LENGTH: 60
<212> TYPE: DNA
<213> ORGANISM: Artificial Sequence
<220> FEATURE:
<223> OTHER INFORMATION: Synthetic

<400> SEQUENCE: 505
ttgcaagaat gaaatgaatg attctacagc taggacttaa ccttgaaatg gaaagtcttg     60

<210> SEQ ID NO 506
<211> LENGTH: 60
<212> TYPE: DNA
<213> ORGANISM: Artificial Sequence
<220> FEATURE:
<223> OTHER INFORMATION: Synthetic

<400> SEQUENCE: 506
ggccccgcct cctttctgtt ttatttttga ggaaataaaa taaccaagtg ctaaatcttg     60

<210> SEQ ID NO 507
<211> LENGTH: 60
<212> TYPE: DNA
<213> ORGANISM: Artificial Sequence
<220> FEATURE:
<223> OTHER INFORMATION: Synthetic

<400> SEQUENCE: 507
ggtaaaggtt attcctttcc tttcctggag ctacacctttt ctttgtaaaa ctgtactgtg     60

<210> SEQ ID NO 508
<211> LENGTH: 60
<212> TYPE: DNA
<213> ORGANISM: Artificial Sequence
<220> FEATURE:
<223> OTHER INFORMATION: Synthetic

<400> SEQUENCE: 508
tgcatctact ttcagtcagg caacaatgaa gagccttatg tcagtatcac caagaagagg     60
```

COLORECTAL CANCER RECURRENCE GENE EXPRESSION SIGNATURE

CROSS-REFERENCE TO RELATED APPLICATIONS

This application claims benefit of U.S. Provisional Application No. 61/859,959, filed Jul. 30, 2013, which is hereby incorporated herein by reference in its entirety.

STATEMENT REGARDING FEDERALLY SPONSORED RESEARCH OR DEVELOPMENT

This invention was made with Government Support under Grant No. U01CA157960 awarded by the National Institutes of Health. The Government has certain rights in the invention.

BACKGROUND

Colon cancers that are confined within the wall of the colon are often curable with surgery. However, colon cancers that have spread widely around the body are usually not curable and management then focuses on extending the person's life via chemotherapy and improving quality of life. Survival rates for early stage detection is about 5 times that of late stage cancers. For example, patients with a tumor that has not breached the muscularis mucosa (TNM stage Tis, N0, M0) have an average 5-year survival of 100%, while those with an invasive cancer, i.e. T1 (within the submucosal layer) or T2 (within the muscular layer) cancer have an average 5-year survival of approximately 90%. Those with a more invasive tumor, yet without node involvement (T3-4, N0, M0) have an average 5-year survival of approximately 70%. Patients with positive regional lymph nodes (any T, N1-3, M0) have an average 5-year survival of approximately 40%, while those with distant metastases (any T, any N, M1) have an average 5-year survival of approximately 5%. Moreover, more than 50% of patients experience recurrence of the disease after initial treatment of colorectal cancer. Therefore, there is a need in the art for methods that can predict colorectal cancer recurrence, metastasis, and overall survival.

SUMMARY

Disclosed are gene signatures that may be used to predict the recurrence of colorectal cancer in a human patient. A dominant pattern of intrinsic gene expression in colon cancer (referred to herein as "PC1 signature" or "CRC signature") has been shown to be tightly correlated with a group of genes associated with epithelial-mesenchymal transition (referred to herein as "EMT signature"). There is a 92% correlation (85% r-squared) between the two signatures in a cohort of 326 colorectal cancer tissues. However, as disclosed herein, that the difference between these two scores is much more predictive of metastasis and overall survival than either the CRC signature or EMT signature.

Therefore, disclosed is a method for predicting the recurrence of colorectal cancer in a human patient that involves assaying colorectal cells obtained from the human patient for the expression level of 5, 10, 20, 30, 40, 50, 60, 70, 80, 90, 100, 110, 115, 116, 117, 118, 119, 120, 121, 122, 123, or more genes listed in TABLE 2A, or their corresponding expression products, and 5, 10, 20, 30, 40, 50, 60, 70, 80, 90, 100, 110, 111, 112, 113, 114, 115, 116, 117, 118, or more genes listed in TABLE 2B, or their corresponding expression products, and using normalized values of the expression levels to calculate a CRC signature score. For example, in some embodiments, increased expression of the genes listed in TABLE 2A, or their corresponding expression products, increases the CRC score; and increased expression of the genes listed in TABLE 2B, or their corresponding products, decreases the CRC score.

The method further comprises assaying colorectal cells obtained from the human patient for the expression levels of 5, 10, 20, 30, 40, 50, 60, 70, 80, 90, 100, 110, 120, 130, 140, 141, 142, 143, 144, 145, 146, 147, 148, or more genes listed in TABLE 1A, or their corresponding expression products, and 5, 10, 20, 30, 40, 50, 60, 70, 80, 90, 100, 110, 120, 130, 140, 150, 151, 152, 153, 154, 155, 156, 157, 158, 159, 160, or more genes listed TABLE 1B, or their corresponding expression products, and using normalized values of the expression levels to calculate an EMT signature score. In some embodiments, gene expression values are first compared to control values to derive differential expression values that are then used to calculate signature scores. For example, in some embodiments, increased expression of the genes listed in TABLE 1A, or their corresponding expression products, increases the EMT score; and increased expression of the genes listed in TABLE 1B, or their corresponding products, decreases the EMT score.

The expression levels for each assayed gene are preferably normalized, such as by quantile normalization, to compensate for differences in sample preparation and measurement techniques. Once normalized, each gene expression value can be given equal weight in an algorithm that calculates each signature score. However, in some cases, different weighting coefficients are assigned to each gene based on multivariate analysis of the gene signature.

The difference between the CRC signature score and the EMT signature score can then be used to arrive at a Recurrence Signature Score (also referred to herein as "ΔPC1.EMT score") that predicts risk of colorectal cancer recurrence. In some embodiments, the higher the Recurrence Signature Score, the higher the risk of colorectal cancer recurrence.

Also disclosed is a method for analyzing a colorectal cancer tissue sample to determine adjuvant chemotherapy is needed to prevent colorectal cancer recurrence in a human patient that involves first assaying colorectal cells obtained from the human patient for normalized expression values of ten (10) or more genes listed in TABLE 1A, ten (10) or more genes listed in TABLE 1B, ten (10) or more genes listed in TABLE 2A, and ten (10) or more genes listed in TABLE 2B. The method then involves inputting the normalized expression values into a computer programmed to execute an algorithm to convert the normalized expression values to a Recurrence Signature Score indicative of a likelihood of the risk of colorectal cancer recurrence, wherein the algorithm gives reduced weight to the normalized expression values for genes that are listed in more than one of TABLE 1A, TABLE 1B, TABLE 1C, and TABLE 1D.

In some embodiments, the method further involves displaying or outputting to a user, user interface device, computer readable storage medium, or local or remote computer system the calculated risk of colorectal cancer recurrence.

Importantly, the disclosed Recurrence Signature Score may be used to identify patients who may not need adjuvant chemotherapy. Currently Dukes B (stage II) CRC is generally treated by surgical resection alone whereas Dukes C (stage III) CRC is treated with 6 months of post-operative adjuvant chemotherapy. Therefore, the disclosed Recurrence Signature Score may be used to discern a population of stage II CRC patients who might benefit from adjuvant chemotherapy and a population of stage III CRC patients who may not benefit from adjuvant chemotherapy. By using the disclosed Recurrence Signature Score, one can avoid giving chemotherapy to a portion of stage III patients and instead deliver adjuvant therapy selectively to those patients who might actually derive benefit. For example, 54% of people are cured with surgical resection alone in stage III CRC when >10 lymph nodes are involved with metastatic cancer. Adjuvant chemotherapy, while effective, only cures about 14% of these patients; thus, 100 patients are treated to help only 14. The disclosed Recurrence Signature Score can be used to identify the 14% of patients who might actually benefit from adjuvant chemotherapy. For stage 2 patients, approximately 87% of patients are cured with surgery alone; however, it is estimated that 2-10% additional patients might benefit from adjuvant therapy. The disclosed Recurrence Signature Score can be used to identify which of the stage 2 patients might actually benefit from adjuvant chemotherapy. Patients undergoing liver resection for metastatic disease can also benefit from adjuvant chemotherapy. Again, the disclosed Recurrence Signature Score predicting further metastasis and survival can be used to determine which patients might actually benefit from adjuvant chemotherapy following resection. For example, the chemotherapy comprises a 5-fluorouracil (5-FU) therapy.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a graph of PC1 scores as a function of EMT scores. PC1 vs. EMT shows strong correlation but metastatic tumor (○) and primary tumors with metastatic potential (■) displayed higher PC1 scores than EMT scores as indicated by two separate regression lines. Tumors with "d_meta" are defined as both primary tumors with evidence of synchronous metastasis [stage 4] as well as sampled metastatic lesions. FIGS. 1B and 1C are graphs of ΔPC1.EMT scores as a function of PC1 scores (FIG. 1B) or EMT scores (FIG. 1C). ΔPC1.EMT outperformed EMT and PC1 in predicting metastasis. While solid lines represent median lines, the dash line (EMT=0) is the dividing line as defined (EMT<0, non-EMT epithelial-like; EMT>0, EMT mesenchymal-like). Metastatic lesions (M) (n=101) shown as open circles (○). Primary tumors (P) with d_meta (n=60) shown as filled squares (■). Regression line for M and P with d_meta (n=161) shown. Primary tumors without d_meta is shown as plus symbol (+) with a regression line (n=307) (below regression line for M and P with d_meta). FIG. 1D shows EMT score (left), PC1 score (middle) and ΔPC1.EMT score (right) for Stage 1, Stage 2, Stage 3, Stage 4, and Metastatic lesions. ΔPC1.EMT outperformed PCT and EMT in progressively deciphering metastatic potential of primary CRCs. Six samples that lack stage information were removed.

FIGS. 3A to 3D are graph showing ΔPC1.EMT score (in quartiles) remarkably improved the trends (relative to PC1 and EMT) for identifying tumors harboring APC (truncated, FIG. 3A) and BRAF (V600E, FIG. 3B) mutations, and for tumors identified as MSI-H (FIG. 3C) and Stage 4 (FIG. 3D). FIGS. 3E to 3H are graph showing ΔPC1.EMT and EMT trended in opposite directions of the distant metastasis rate in the subgroups of combined mutations KRAS&TP53 (FIG. 3F) or BRAF&TP53 (FIG. 3E) as well as in MSI-H (FIG. 3G) and Stage 1 (FIG. 3H) cases. EMT (▲), PC1 (■), ΔPC1-EMT (●). FIG. 3I shows weighted analysis of genes contributing to PC1 and EMT vs. ΔPC1.EMT signatures on additional five datasets, suggesting that ΔPC1.EMT is represented by more epithelial (non-EMT) than mesenchymal (EMT) components when compared with the other two scores. The genes that were the most changed from EMT or PC1 to ΔPC1.EMT are shown.

FIGS. 6A to 6F are pairs plots of the signature scores in PETACC (FIG. 6A), ALAMC (FIG. 6B), French (FIG. 6C), GSE14333 (FIG. 6D), GEO41258 (FIG. 6E), and TCGA (FIG. 6F) datasets.

DETAILED DESCRIPTION

Figure 1A:
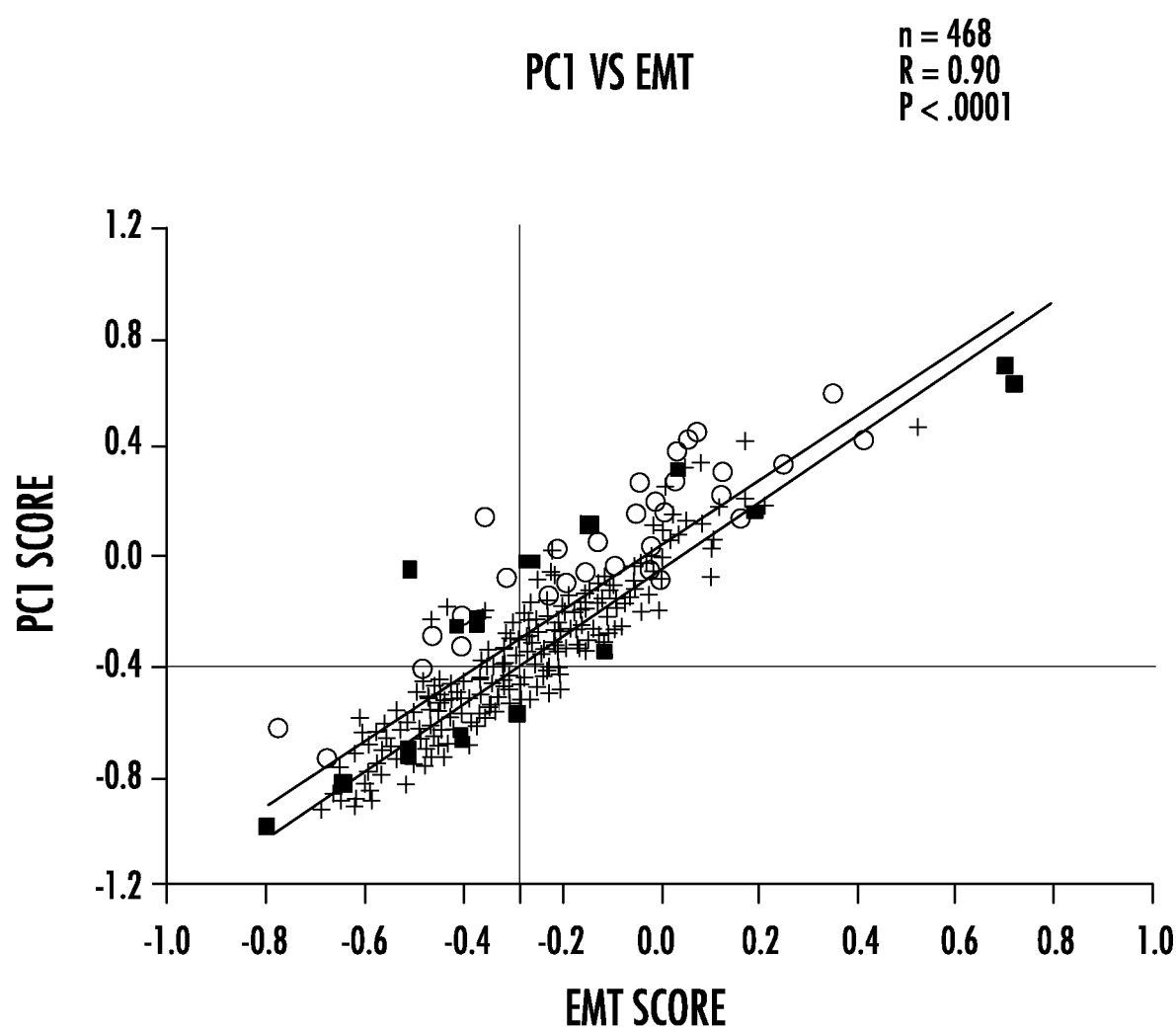
FIGS. 1A to 1D show correlation of PC1, EMT and ΔPC1.EMT scores with each other and with stage, metastasis on Moffitt468 CRC dataset.

A dominant pattern of intrinsic gene expression in colon cancer (referred to herein as "PC1 signature" score or "CRC signature" score) is tightly correlated with a group of genes associated with epithelial-mesenchymal transition (referred to herein as "EMT signature" score) (Loboda A, et al. BMC Med Genomics. 2011 4:9). There is a 92% correlation (85% r-squared) between the two signatures in a cohort of 326 colorectal cancer tissues. As disclosed herein, an independent analysis of a subset of 468 of the tissues (which was very strongly validated on the 1563 independent patients that were not part of the subset), demonstrated that the difference between these two scores was much more predictive of metastasis and overall survival than either of the two original signatures, and especially much more statistically significant than the EMT-lung derived signature. This suggests that the 15% (100%-85%) of unexplained variability between the two gene signatures holds the key for predicting metastasis and poor overall survival. Of further surprise, the difference score was significantly positively associated with the EMT signature itself (typically one would expect a negative association between the difference score and the signature being subtracted off in order to obtain it). Liver metastatic tissues were also found to be highly associated with this difference score. However, similar findings were seen when only primary tissue samples were studied, lending further credibility to this signature difference as predictive of distant metastasis and overall survival. Thus, the disclosed "ΔPC1.EMT" score is also referred to herein as a "Recurrence Signature Score" since it can be used to predict the recurrence of colorectal cancer and overall survival.

Methods of "determining gene expression levels" include methods that quantify levels of gene transcripts as well as methods that determine whether a gene of interest is expressed at all. A measured expression level may be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix, nuclease protection, RT-PCR, microarray profiling, differential display, 2D gel electrophoresis, SELDI-TOF, ICAT, enzyme assay, antibody assay, and MNAzyme-based detection methods. Optionally a gene whose level of expression is to be detected may be amplified, for example by methods that may include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

A number of suitable high throughput formats exist for evaluating expression patterns and profiles of the disclosed genes. Numerous technological platforms for performing high throughput expression analysis are known. Generally, such methods involve a logical or physical array of either the subject samples, the biomarkers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, Tex.), the SECTOR® Imager with MULTI-ARRAY® and MULTI-SPOT® technologies from Meso Scale Discovery (Gaithersburg, Md.), the ORCA™ system from Beckman-Coulter, Inc. (Fullerton, Calif.) and the ZYMATE™ systems from Zymark Corporation (Hopkinton, Mass.), miRCURY LNA™ microRNA Arrays (Exiqon, Woburn, Mass.).

Alternatively, a variety of solid phase arrays can favorably be employed to determine expression patterns in the context of the disclosed methods, assays and kits. Exemplary formats include membrane or filter arrays (e.g., nitrocellulose, nylon), pin arrays, and bead arrays (e.g., in a liquid "slurry").

Typically, probes corresponding to nucleic acid or protein reagents that specifically interact with (e.g., hybridize to or bind to) an expression product corresponding to a member of the candidate library, are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In one embodiment, the array is a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Microarray expression may be detected by scanning the microarray with a variety of laser or CCD-based scanners, and extracting features with numerous software packages, for example, IMAGENE™ (Biodiscovery), Feature Extraction Software (Agilent), SCANLYZE™ (Stanford Univ., Stanford, Calif.), GENEPIX™ (Axon Instruments).

In some embodiments, the gene expression values involve numerous data points that are best managed and stored in a computer readable form. Prior to analysis, the data in each dataset can be collected by measuring expression values for each gene, usually in duplicate or triplicate or in multiple replicates. The data may be manipulated, for example raw data may be transformed using standard curves, and the average of replicate measurements used to calculate the average and standard deviation for each gene expression value. These values may be transformed before being used in the models, e.g. log-transformed, Box-Cox transformed, etc.

The disclosed signature scores (CRC signature score and/or EMT signature score) can be determined using standard statistical methods. In some embodiments, the signature score is a ession value. For example, gene expression values (e.g., differential values from controls) may be analyzed by multivariate, regression analysis (e.g., determined by linear regression) or principal component analysis to derive a signature score.

In some embodiments, the gene expression values are analyzed by principal component analysis (PCA) to derive the signature scores. PCA is a mathematical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it be orthogonal to (i.e., uncorrelated with) the preceding components. When used in the disclosed methods, a PCA score can be a numeric value that summarizes the gene expression of the entire panel (e.g., Tables 4A and/or 4B for CRC signature score) for that patient's biological sample. Therefore, in these embodiments, a "high" signature score (e.g., high CRC signature score) may be a PCA score above the median value, and a "low" risk score (e.g., low CRC signature score) may be a PCA score below the median value.

PCA can be used to reduce gene expression values into a small set of uncorrelated principal components based on their ability to account for variation. The first principal component (1st PCA), as it accounts for the largest variability in the data, can be to represent the overall expression level for the set of genes.

In some cases, the signature scores are calculated as a weighted average expression among the normalized expression values, e.g., by the formula $\Sigma w_i x_i$, where $x_i$ represents gene i expression level, $w_i$ is the corresponding weight (loading coefficient) with $\Sigma w^2_i = 1$, and the $w_i$ values maximize the variance of $\Sigma w_i x_i$.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

Table 1A lists the 149 gene markers that were found to be up-regulated in lung cancer cell lines that were classified as mesenchymal cell-like, as compared to the lung cancer cell lines that were classified as epithelial cell-like, and were also found to be down-regulated in the lung tumor cell lines that were classified as epithelial cell-like as compared to the lung cancer cell lines that were classified as mesenchymal cell-like. Table 1A provides for each of the 149 gene markers, the gene symbol; the Genbank reference number for each gene symbol as of Oct. 1, 2010, each of which is hereby incorporated herein by reference; and the SEQ ID NO: corresponding to an exemplary 60-mer sequence that corresponds to a portion of the corresponding cDNA, which may be used as a probe.

TABLE 1A

149 EMT Signature Genes: Up-Regulated Arm.

| Gene Symbol | Genbank Ref. Number | SEQ ID NO: |
|---|---|---|
| FAM171A1 | AY683003 | 1 |
| ZCCHC24 | BC028617 | 2 |
| GLIPR2 | AK091288 | 3 |
| TMSB15A | BG471140 | 4 |
| COL12A1 | NM_004370 | 5 |
| LOX | NM_002317 | 6 |
| SPARC | AK126525 | 7 |
| CDH11 | D21255 | 8 |
| ZEB 1 | BX647794 | 9 |
| EML1 | NM_001008707 | 10 |
| ZNF788 | AK128700 | 11 |
| WIPF1 | NM_001077269 | 12 |
| CAP2 | NM_006366 | 13 |
| TGFB2 | AB209842 | 14 |

TABLE 1A-continued

149 EMT Signature Genes: Up-Regulated Arm.

| Gene Symbol | Genbank Ref. Number | SEQ ID NO: |
|---|---|---|
| DLC1 | NM_182643 | 15 |
| POSTN | NM_006475 | 16 |
| NEGR1 | NM_173808 | 17 |
| JAM3 | AK027435 | 18 |
| SRPX | BC020684 | 19 |
| BICC1 | NM_001080512 | 20 |
| HAS2 | NM_005328 | 21 |
| ANTXR1 | NM_032208 | 22 |
| GNB4 | NM_021629 | 23 |
| COL4A1 | NM_001845 | 24 |
| SRGN | CD359027 | 25 |
| SUSD5 | NM_015551 | 26 |
| DIO2 | NM_013989 | 27 |
| GLIPR1 | NM_006851 | 28 |
| COL5A1 | NM_000093 | 29 |
| NAP1L3 | BC094729 | 30 |
| RBMS3 | BQ214991 | 31 |
| BVES | BC040502 | 32 |
| SLC47A1 | BC010661 | 33 |
| FGFR1 | NM_023110 | 34 |
| FSTL1 | NM_007085 | 35 |
| FGF2 | NM_002006 | 36 |
| DKK3 | NM_015881 | 37 |
| CMTM3 | AK056324 | 38 |
| PTGIS | NM_000961 | 39 |
| CCL2 | BU570769 | 40 |
| WNT5B | BC001749 | 41 |
| CLDN11 | AK098766 | 42 |
| MAP1B | NM_005909 | 43 |
| IL13RA2 | AK308523 | 44 |
| MSRB3 | NM_001031679 | 45 |
| FAM101B | AK093557 | 46 |
| ZEB2 | NM_014795 | 47 |
| NID1 | NM_002508 | 48 |
| TMEM158 | NM_015444 | 49 |
| ST3GAL2 | AK127322 | 50 |
| FGF5 | NM_004464 | 51 |
| AKAP12 | NM_005100 | 52 |
| GPR176 | BC067106 | 53 |
| PMP22 | NM_000304 | 54 |
| LEPREL1 | NM_018192 | 55 |
| CHN1 | NM_001822 | 56 |
| TTC28 | NM_001145418 | 57 |
| GLT25D2 | NM_015101 | 58 |
| RECK | BX648668 | 59 |
| GREM1 | NM_013372 | 60 |
| C16orf45 | AK092923 | 61 |
| AOX1 | LI 1005 | 62 |
| CTGF | NM_001901 | 63 |
| ANXA6 | NM_001155 | 64 |
| SERPINE1 | NM_000602 | 65 |
| SLC2A3 | AB209607 | 66 |
| ZFPM2 | NM_012082 | 67 |
| FHL1 | NM_001159704 | 68 |
| ATP8B2 | NM_020452 | 69 |
| RBPMS2 | AY369207 | 70 |
| TBXA2R | NM_001060 | 71 |
| COL3A1 | NM_000090 | 72 |
| GPC6 | NM_005708 | 73 |
| AFF3 | NM_002285 | 74 |
| PLAGL1 | CR749329 | 75 |
| LGALS1 | BF570935 | 76 |
| TTLL7 | NM_024686 | 77 |
| COL5A2 | NM_000393 | 78 |
| ANKRD1 | NM_014391 | 79 |
| NRG1 | NM_013960 | 80 |
| POPDC3 | NM_022361 | 81 |
| C1S | NM_201442 | 82 |
| CDH2 | NM_001792 | 83 |
| DOCK10 | NM_014689 | 84 |
| CLIP3 | AK094738 | 85 |
| CDH4 | AL834206 | 86 |
| COL6A1 | NM_001848 | 87 |
| HEG1 | NM_020733 | 88 |
| IGFBP7 | BX648756 | 89 |
| DAB2 | NM_001343 | 90 |
| F2R | NM_001992 | 91 |
| EDIL3 | BX648583 | 92 |
| COL1A2 | J03464 | 93 |
| HTRA1 | NM_002775 | 94 |
| NDN | NM_002487 | 95 |
| BDNF | EF689009 | 96 |
| LHFP | NM_005780 | 97 |
| PRKD1 | X75756 | 98 |
| MMP2 | NM_004530 | 99 |
| UCHL1 | AB209038 | 100 |
| DPYSL3 | BC077077 | 101 |
| RBM24 | AL832199 | 102 |
| DFNA5 | AK094714 | 103 |
| MRAS | NM_012219 | 104 |
| SYDE1 | AK128870 | 105 |
| FLRT2 | NM_013231 | 106 |
| AK5 | NM_012093 | 107 |
| EPDR1 | XM_002342700 | 108 |
| TUB | NM_003320 | 109 |
| SIRPA | NM_001040022 | 110 |
| AXL | NM_021913 | 111 |
| FBN1 | NM_000138 | 112 |
| EVI2A | NM_001003927 | 113 |
| PTX3 | NM_002852 | 114 |
| ADAM23 | AK091800 | 115 |
| PNMA2 | NM_007257 | 116 |
| PDE7B | AB209990 | 117 |
| TCF4 | NM_001083962 | 118 |
| KIRREL | AK090554 | 119 |
| NEXN | NM_144573 | 120 |
| ALPK2 | BX647796 | 121 |
| VIM | NM_003380 | 122 |
| LIX1L | AK128733 | 123 |
| ADAMTS1 | NM_006988 | 124 |
| PAPPA | NM_002581 | 125 |
| ANGPTL2 | NM_012098 | 126 |
| AP1S2 | BX647483 | 127 |
| TUBA1A | BI083878 | 128 |
| LAMA4 | NM_001105206 | 129 |
| EPB41L5 | BC054508 | 130 |
| NAV3 | NM_014903 | 131 |
| ELOVL2 | BC050278 | 132 |
| BNC2 | NM_017637 | 133 |
| GFPT2 | BC000012 | 134 |
| TRPA1 | Y10601 | 135 |
| PRR16 | AF242769 | 136 |
| CYBRD1 | NM_024843 | 137 |
| HS3ST3A1 | NM_006042 | 138 |
| GNG11 | BF971151 | 139 |
| TMEM47 | BC039242 | 140 |
| CPA4 | NM_016352 | 141 |
| ARMCX1 | CR933662 | 142 |
| RFTN1 | NM_015150 | 143 |
| EMP3 | BM556279 | 144 |
| ATP8B3 | AK125969 | 145 |
| FAT4 | NM_024582 | 146 |
| NUDT11 | NM_018159 | 147 |
| PTRF | NM_012232 | 148 |
| TNFRSF19 | NM_148957 | 149 |

Table 1B lists the 161 gene markers that were found to be down-regulated in the lung tumor cell lines that were classified as mesenchymal cell-like, as compared to the lung cancer cell lines that were classified as epithelial cell-like, and were also found to be up-regulated in the lung cancer cell lines that were classified as epithelial cell-like as compared to the lung cancer cell lines that were classified as mesenchymal cell-like. Table 1B provides for each of the 161 gene markers, the gene symbol; the Genbank reference number for each gene symbol as of Oct. 1, 2010, each of which is hereby incorporated herein by reference; and the SEQ ID NO: corresponding to an exemplary 60-mer sequence that corresponds to a portion of the corresponding cDNA, which may be used as a probe.

TABLE 1B

161 EMT Signature Genes: Down-Regulated Arm.

| Gene Symbol | Genbank Ref. Number | SEQ ID NO: |
|---|---|---|
| PRR15L | BC002865 | 150 |
| TTC39A | AB007921 | 151 |
| ESRP1 | NM_017697 | 152 |
| RBM35B | CR607695 | 153 |
| AGR3 | BG540617 | 154 |
| TMEM125 | BC072393 | 155 |
| KLK8 | DQ267420 | 156 |
| MBNL3 | NM_001170704 | 157 |
| SPRR1B | AI541215 | 158 |
| S100A9 | BQ927179 | 159 |
| TMC5 | NM_001105248 | 160 |
| ELF5 | NM_198381 | 161 |
| ERBB3 | NM_001982 | 162 |
| WDR72 | NM_182758 | 163 |
| FAM84B | NM_174911 | 164 |
| SPRR3 | EF553525 | 165 |
| TMEM30B | NM_001017970 | 166 |
| C1orf210 | NM_182517 | 167 |
| TMPRSS4 | NM_019894 | 168 |
| ERP27 | BC030218 | 169 |
| TTC22 | NM_017904 | 170 |
| CNKSR1 | BC012797 | 171 |
| FGFBP1 | NM_005130 | 172 |
| FUT3 | NM_000149 | 173 |
| GALNT3 | NM_004482 | 174 |
| RAPGEF5 | NM_012294 | 175 |
| MAPK13 | AB209586 | 176 |
| AP1M2 | BC005021 | 177 |
| CDH3 | NM_001793 | 178 |
| PPL | NM_002705 | 179 |
| GCNT3 | EF152283 | 180 |
| EPPK1 | AB051895 | 181 |
| MAL2 | NM_052886 | 182 |
| TMPRSS11E | NM_014058 | 183 |
| LCN2 | AK307311 | 184 |
| ANKRD22 | NM_144590 | 185 |
| POU2F3 | AF162715 | 186 |
| SPINT1 | BC018702 | 187 |
| AQP3 | NM_004925 | 188 |
| GPR110 | CR627234 | 189 |
| FAM84A | NM_145175 | 190 |
| TMPRSS13 | NM_001077263 | 191 |
| GPX2 | BE512691 | 192 |
| WFDC2 | BM921431 | 193 |
| KLK10 | NM_002776 | 194 |
| S100A14 | BG674026 | 195 |
| S100P | BG571732 | 196 |
| FXYD3 | BF676327 | 197 |
| MUC20 | XR_078298 | 198 |
| SPINT2 | NM_021102 | 199 |
| C1orf116 | NM_023938 | 200 |
| SPINK5 | NM_001127698 | 201 |
| ANXA9 | NMJX568 | 202 |
| TMC4 | NM_001145303 | 203 |
| SYK | NM_003177 | 204 |
| HOOK1 | NM_015888 | 205 |
| FAM83A | DQ280323 | 206 |
| LCP1 | NM_002298 | 207 |
| HS6ST2 | NM_001077188 | 208 |
| TSPAN1 | NM_005727 | 209 |
| S100A8 | BG739729 | 210 |
| DMKN | BC035311 | 211 |
| GRHL1 | NM_198182 | 212 |
| CKMT1B | AK094322 | 213 |
| ACPP | NM_001099 | 214 |
| PTAFR | NM_000952 | 215 |
| KRT5 | M21389 | 216 |
| DAPP1 | NM_014395 | 217 |
| LAMA3 | NM_198129 | 218 |
| C19orf21 | NM_173481 | 219 |
| SH2D3A | AK024368 | 220 |

TABLE 1B-continued

161 EMT Signature Genes: Down-Regulated Arm.

| Gene Symbol | Genbank Ref. Number | SEQ ID NO: |
|---|---|---|
| TOX3 | AK095095 | 221 |
| CDH1 | NM_004360 | 222 |
| FA2H | NM_024306 | 223 |
| SPRR1A | NM_005987 | 224 |
| LIPG | BC060825 | 225 |
| CEACAM6 | NM_002483 | 226 |
| PROM2 | NM_001165978 | 227 |
| ITGB6 | AL831998 | 228 |
| OR2A4 | BC120953 | 229 |
| MAP7 | NM_003980 | 230 |
| PPPR14C | AF407165 | 231 |
| PVRL4 | NM_030916 | 232 |
| FBP1 | NM_00507 | 233 |
| FAAH2 | NM_174912 | 234 |
| LAMB3 | NM_001017402 | 235 |
| MPP7 | NM_173496 | 236 |
| ANK3 | NM_020987 | 237 |
| SYT7 | NM_004200 | 238 |
| TRIP29 | BX648072 | 239 |
| TMEM45B | AK098106 | 240 |
| ST14 | NM_021978 | 241 |
| ARHGDIB | AK125625 | 242 |
| HS3ST1 | AK096823 | 243 |
| KLK5 | AY359010 | 244 |
| GJB6 | NM_001110219 | 245 |
| CCDC64B | NM_001103175 | 246 |
| PAK6 | AK131522 | 247 |
| MARVELD3 | NM_001017967 | 248 |
| CLDN7 | NM_001307 | 249 |
| SH3YL1 | AK123829 | 250 |
| SLPI | BG483345 | 251 |
| MB | BF670653 | 252 |
| NPNT | NM_001033047 | 253 |
| C1orf106 | NM_001142569 | 254 |
| DSP | NM_004415 | 255 |
| STEAP4 | NM_024636 | 256 |
| SLC6A14 | NM_007231 | 257 |
| GOLT1A | AB075871 | 258 |
| PKP3 | NM_007183 | 259 |
| SCEL | BC047536 | 260 |
| VTCN1 | BX648021 | 261 |
| SERPEMB5 | BX640597 | 262 |
| DEND2D | AL713773 | 263 |
| PLA2G10 | NM_003561 | 264 |
| SCNN1A | AK172792 | 265 |
| GPR87 | NM_023915 | 266 |
| IRF6 | NM_006147 | 267 |
| CGN | BC146657 | 268 |
| LAMC2 | NM_005562 | 269 |
| RASGEF1B | BX648337 | 270 |
| KRTCAP3 | AY358993 | 271 |
| GRAMD2 | BC038451 | 272 |
| BSPRY | NM_017688 | 273 |
| ATP2C2 | AB014603 | 274 |
| SORBS2 | BC069025 | 275 |
| RAB25 | BE612887 | 276 |
| CLDN4 | AK126462 | 277 |
| EHF | NM_012153 | 278 |
| KRT19 | BQ073256 | 279 |
| CDS1 | NM_001263 | 280 |
| KRT16 | NM_005557 | 281 |
| CNTNAP2 | NM_014141 | 282 |
| MARVELD2 | AK055094 | 283 |
| RASEF | NM_152573 | 284 |
| INPP4B | NM_003866 | 285 |
| OVOL2 | AK022284 | 286 |
| GRHL2 | NM_024915 | 287 |
| BLNK | AK225546 | 288 |
| EPN3 | NM_017957 | 289 |
| ELF3 | NM_001114309 | 290 |
| STX19 | NM_001001850 | 291 |
| B3GNT3 | NM_014256 | 292 |
| FUT1 | NM_000148 | 293 |
| CEACAM5 | NM_004363 | 294 |
| MY05B | NM_001080467 | 295 |

TABLE 1B-continued

161 EMT Signature Genes: Down-Regulated Arm.

| Gene Symbol | Genbank Ref. Number | SEQ ID NO: |
|---|---|---|
| ARHGAP8 | BC059382 | 296 |
| PRSS8 | NM_002773 | 297 |
| TTC9 | NM_015351 | 298 |
| KLK6 | NM_002774 | 299 |
| IL1RN | BC068441 | 300 |
| FAM110C | NM_001077710 | 301 |
| ALDH3B2 | AK092464 | 302 |
| PRR15 | NM_175887 | 303 |
| DSC2 | NM_004949 | 304 |
| C11orf52 | BC110872 | 305 |
| ILDR1 | BC044240 | 306 |
| CD24 | AK125531 | 307 |
| CTAGE4 | DB515636 | 308 |
| FGD2 | BC023645 | 309 |
| MYH14 | NM_001145809 | 310 |

The 60mer sequences provided in Tables 2A and 2B are non-limiting examples of exemplary probes that correspond to a portion of the corresponding cDNA.

A refined set of CRC Signature genes were selected from the about 5000 first principal component (PC1) genes identified by performing Principal Component Analysis ("PCA") on robust multi-array (RMA)—normalized data obtained from the U133 Plus 2.0 Affymetrix arrays. The RMA-normalized dataset consisted of the 326 CRC tumor profiles. A first principal component (PC1) was selected and for each probe-set, (i.e., gene transcript represented on the array), a Spearman correlation was computed to the PC1. Then, the 200 probe-sets with the highest value of correlation coefficient to PC1 were selected, and the list of unique markers for these probe-sets was used to generate the 124 CRC Signature Mesenchymal marker list shown in Table 2A. Table 2A provides for each of the 124 CRC Signature Mesenchymal markers, the gene symbol; the Genbank reference number for each gene symbol as of Oct. 1, 2010, each of which is hereby incorporated herein by reference; and the SEQ ID NO: corresponding to an exemplary 60-mer sequence that corresponds to a portion of the corresponding cDNA, which may be used as a probe.

TABLE 2A

124 CRC Signature Genes: The Mesenchymal or Up-Regulated Arm.

| Gene Symbol | Genbank Ref. Number | SEQ ID NO: |
|---|---|---|
| SPARC | AK126525 | 7 |
| CAP2 | NM_006366 | 13 |
| JAM3 | AK027435 | 18 |
| SRPX | BC020684 | 19 |
| NAP1L3 | BC094729 | 30 |
| CMTM3 | AK056324 | 38 |
| MAP1B | NM_005909 | 43 |
| MSRB3 | NM_001031679 | 45 |
| AKAP12 | NM_005100 | 52 |
| RECK | BX648668 | 59 |
| ZFPM2 | NM_012082 | 67 |
| ATP8B2 | NM_020452 | 69 |
| LGALS1 | BF570935 | 76 |
| HTRA1 | NM_002775 | 94 |
| NDN | NM_002487 | 95 |
| LHFP | NM_005780 | 97 |
| PRKD1 | X75756 | 98 |
| UCHL1 | AB209038 | 100 |
| DPYSL3 | BC077077 | 101 |
| DFNA5 | AK094714 | 103 |
| MRAS | NM_012219 | 104 |
| FLRT2 | NM_013231 | 106 |
| VIM | NM_003380 | 122 |
| LIX1L | AK128733 | 123 |
| AP1S2 | BX647483 | 127 |
| GFPT2 | BC000012 | 134 |
| TRPA1 | Y10601 | 135 |
| GNG11 | BF971151 | 139 |
| ARMCX1 | CR933662 | 142 |
| PTRF | NM_012232 | 148 |
| AEBP1 | NM_001129 | 311 |
| AKT3 | NM_005465 | 312 |
| AMOTL1 | NM_130847 | 313 |
| ANKRD6 | NM_014942 | 314 |
| ARMCX2 | NM_014782 | 315 |
| BASP1 | NM_006317 | 316 |
| BGN | NM_001711 | 317 |
| C1orf54 | NM_024579 | 318 |
| C20orf194 | NM_001009984 | 319 |
| CALD1 | NM_004342 | 320 |
| CCDC80 | NM_199511 | 321 |
| CEP170 | NM_001042404 | 322 |
| CFH | NM_000186 | 323 |
| CFL2 | NM_021914 | 324 |
| COX7A1 | NM_001864 | 325 |
| CRYAB | NM_001885 | 326 |
| DCN | NM_001920 | 327 |
| DNAJB4 | NM_007034 | 328 |
| DZIP1 | NM_014934 | 329 |
| ECM2 | NM_001393 | 330 |
| EFHA2 | NM_181723 | 331 |
| EFS | NM_005864 | 332 |
| EHD3 | NM_014600 | 333 |
| FAM20C | NM_020223 | 334 |
| FBXL7 | NM_012304 | 335 |
| FEZ1 | NM_005103 | 336 |
| FRMD6 | NM_001042481 | 337 |
| GLIS2 | NM_032575 | 338 |
| HECTD2 | NM_173497 | 339 |
| IL1R1 | NM_000877 | 340 |
| KCNE4 | NM_080671 | 341 |
| KIAA1462 | NM_020848 | 342 |
| KLHL5 | NM_001007075 | 343 |
| LAYN | NM_178834 | 344 |
| LDB2 | NM_001130834 | 345 |
| LMCD1 | NM_014583 | 346 |
| LPHN2 | NM_012302 | 347 |
| LZTS1 | NM_021020 | 348 |
| MAF | NM_001031804 | 349 |
| MAGEH1 | NM_014061 | 350 |
| MAP9 | NM_001039580 | 351 |
| MCC | NM_001085377 | 352 |
| MGP | NM_000900 | 353 |
| MLLT11 | NM_006818 | 354 |
| MPDZ | NM_003829 | 355 |
| MSN | NM_002444 | 356 |
| MXRA7 | NM_001008528 | 357 |
| MYH10 | NM_005964 | 358 |
| MYO5A | NM_000259 | 359 |
| NNMT | NM_006169 | 360 |
| NR3C1 | NM_000176 | 361 |
| NRP1 | NM_001024628 | 362 |
| NRP2 | NM_003872 | 363 |
| PEA15 | NM_003768 | 364 |
| PFTK1 | NM_012395 | 365 |
| PHLDB2 | NM_001134437 | 366 |
| PKD2 | NM_000297 | 367 |
| PRICKLE1 | NM_001144881 | 368 |
| PTPRM | NM_001105244 | 369 |
| QKI | NM_006775 | 370 |
| RAB31 | NM_006868 | 371 |
| RAB34 | NM_001142624 | 372 |
| RAI14 | NM_001145520 | 373 |
| RASSF8 | NM_001164746 | 374 |
| RGS4 | NM_001102445 | 375 |
| RNF180 | NM_001113561 | 376 |

TABLE 2A-continued

124 CRC Signature Genes: The Mesenchymal or Up-Regulated Arm.

| Gene Symbol | Genbank Ref. Number | SEQ ID NO: |
|---|---|---|
| SCHIP1 | NM_014575 | 377 |
| SDC2 | NM_002998 | 378 |
| SERPINF1 | NM_002615 | 379 |
| SGCE | NM_001099400 | 380 |
| SGTB | NM_019072 | 381 |
| SLIT2 | NM_004787 | 382 |
| SMARCA1 | NM_003069 | 383 |
| SNAI2 | NM_003068 | 384 |
| SPG20 | NM_001142294 | 385 |
| SRGAP2 | NM_001042758 | 386 |
| STON1 | NM_006873 | 387 |
| SYT11 | NM_152280 | 388 |
| TCEA2 | NM_003195 | 389 |
| TCEAL3 | NM_001006933 | 390 |
| TIMP2 | NM_003255 | 391 |
| TNS1 | NM_022648 | 392 |
| TPST1 | NM_003596 | 393 |
| TRPC1 | NM_003304 | 394 |
| TRPS1 | NM_014112 | 395 |
| TSPYL5 | NM_033512 | 396 |
| TTC7B | NM_001010854 | 397 |
| TUBB6 | NM_032525 | 398 |
| TUSC3 | NM_006765 | 399 |
| UBE2E2 | NM_152653 | 400 |
| WWTR1 | NM_001168278 | 401 |
| ZNF25 | NM_145011 | 402 |
| ZNF532 | NM_018181 | 403 |
| ZNF677 | NM_182609 | 404 |

Similarly, 200 probe-sets with the most negative correlation coefficient to PC1 were taken, and the corresponding list of 119 unique markers was used to generate the CRC Signature Epithelial marker list shown in Table 2B. Table 2B provides for each of the 119 CRC Signature Epithelial markers, the gene symbol; the Genbank reference number for each gene symbol as of Oct. 1, 2010, each of which is hereby incorporated herein by reference; and the SEQ ID NO: corresponding to an exemplary 60-mer sequence that corresponds to a portion of the corresponding cDNA, which may be used as a probe.

TABLE 2B

119 CRC Signature Genes: The Epithelial or Down-Regulated Arm.

| Gene Symbol | Genbank Ref. Number | SEQ ID NO: |
|---|---|---|
| TMC5 | NM_001105248 | 160 |
| FUT3 | NM_000149 | 173 |
| AP1M2 | BC005021 | 177 |
| FAM84A | NM_145175 | 190 |
| GPX2 | BE512691 | 192 |
| CKMT1B | AK094322 | 213 |
| FA2H | NM_024306 | 223 |
| MAP7 | NM_003980 | 230 |
| ST14 | NM_021978 | 241 |
| MARVELD3 | NM_001017967 | 248 |
| RAB25 | BE612887 | 276 |
| CDS1 | NM_001263 | 280 |
| EPN3 | NM_017957 | 289 |
| MY05B | NM_001080467 | 295 |
| MYH14 | NM_001145809 | 310 |
| ACOT11 | NM_015547 | 405 |
| AGMAT | NM_024758 | 406 |
| ANKS4B | NM_145865 | 407 |
| ATP10B | NM_025153 | 408 |
| AXIN2 | NM_004655 | 409 |
| BCAR3 | NM_003567 | 410 |
| BCL2L14 | NM_030766 | 411 |
| BDH1 | NM_004051 | 412 |
| BRI3BP | NM_080626 | 413 |
| C10orf99 | NM_207373 | 414 |
| C4orf19 | NM_001104629 | 415 |
| C9orf152 | NM_001012993 | 416 |
| C9orf75 | NM_001128228 | 417 |
| C9orf82 | NM_001167575 | 418 |
| CALML4 | NM_001031733 | 419 |
| CAPN5 | NM_004055 | 420 |
| CASP5 | NM_001136109 | 421 |
| CASP6 | NM_001226 | 422 |
| CBLC | NM_001130852 | 423 |
| CC2D1A | NM_017721 | 424 |
| CCL28 | NM_148672 | 425 |
| CDC42EP5 | NM_145057 | 426 |
| CDX1 | NM_001804 | 427 |
| CLDN3 | NM_001306 | 428 |
| CMTM4 | NM_178818 | 429 |
| COR02A | NM_003389 | 430 |
| COX10 | NM_001303 | 431 |
| CYP2J2 | NM_000775 | 432 |
| DAZAP2 | NM_001136264 | 433 |
| DDAH1 | NM_001134445 | 434 |
| DTX2 | NM_001102594 | 435 |
| DUOX2 | NM_014080 | 436 |
| DUOXA2 | NM_207581 | 437 |
| ENTPD5 | NM_001249 | 438 |
| EPB41L4B | NM_018424 | 439 |
| EPHB2 | NM_004442 | 440 |
| EPS8L3 | NM_024526 | 441 |
| ESRRA | NM_004451 | 442 |
| ETHE1 | NM_014297 | 443 |
| EXPH5 | NM_001144763 | 444 |
| F2RL1 | NM_005242 | 445 |
| FAM3D | NM_138805 | 446 |
| FAM83F | NM_138435 | 447 |
| FRAT2 | NM_012083 | 448 |
| FUT2 | NM_000511 | 449 |
| FUT5 | NM_002033 | 450 |
| FUT6 | NM_000150 | 451 |
| GALNT7 | NM_017423 | 452 |
| GMDS | NM_001500 | 453 |
| GPA33 | NM_005814 | 454 |
| GPR35 | NM_005301 | 455 |
| HDHD3 | NM_031219 | 456 |
| HMGA1 | NM_002131 | 457 |
| HNF4A | NM_000457 | 458 |
| HOXB9 | NM_024017 | 459 |
| HSD11B2 | NM_000196 | 460 |
| KALRN | NM_001024660 | 461 |
| KCNE3 | NM_005472 | 462 |
| KCNQ1 | NM_000218 | 463 |
| KIAA0152 | NM_014730 | 464 |
| LENG9 | NM_198988 | 465 |
| LGALS4 | NM_006149 | 466 |
| LRRC31 | NM_024727 | 467 |
| MCCC2 | NM_022132 | 468 |
| MPST | NM_001013436 | 469 |
| MRPS35 | NM_021821 | 470 |
| MUC3B | XM_001125753.2 | 471 |
| MYB | NM_001130172 | 472 |
| MY07B | NM_001080527 | 473 |
| NAT2 | NM_000015 | 474 |
| NOB1 | NM_014062 | 475 |
| NOX1 | NM_007052 | 476 |
| NR1I2 | NM_003889 | 477 |
| PAQR8 | NM_133367 | 478 |
| PI4K2B | NM_018323 | 479 |
| PKP2 | NM_001005242 | 480 |
| PLA2G12A | NM_030821 | 481 |
| PLEKHA6 | NM_014935 | 482 |
| PLS1 | NM_001145319 | 483 |
| PMM2 | NM_000303 | 484 |
| POF1B | NM_024921 | 485 |
| PPP1R1B | NM_032192 | 486 |
| PREP | NM_002726 | 487 |

TABLE 2B-continued

119 CRC Signature Genes: The Epithelial or Down-Regulated Arm.

| Gene Symbol | Genbank Ref. Number | SEQ ID NO: |
|---|---|---|
| RNF186 | NM_019062 | 488 |
| SELENBP1 | NM_003944 | 489 |
| SH3RF2 | NM_152550 | 490 |
| SHH | NM_000193 | 491 |
| SLC12A2 | NM_001046 | 492 |
| SLC27A2 | NM_001159629 | 493 |
| SLC29A2 | NM_001532 | 494 |
| SLC35A3 | NM_012243 | 495 |
| SLC37A1 | NM_018964 | 496 |
| SLC44A4 | NM_001178044 | 497 |
| SLC5A1 | NM_000343 | 498 |
| SLC9A2 | NM_003048 | 499 |
| STRBP | NM_001171137 | 500 |
| SUCLG2 | NM_001177599 | 501 |
| SULT1B1 | NM_014465 | 502 |
| TJP3 | NM_014428 | 503 |
| TMEM54 | NM_033504 | 504 |
| TMPRSS2 | NM_001135099 | 505 |
| TST | NM_003312 | 506 |
| USP54 | NM_152586 | 507 |
| XK | NM_021083 | 508 |

The markers represented in Tables 2A and 2B are collectively referred to as CRC Signature genes. Markers that are also present in the EMT Signature lists (Tables 1A and 1B) are indicated at the beginning of both Tables 2A and 2B. In total, 30 gene markers listed in Tables 4A are also present in Table 1A, and 15 gene markers listed in Table 2B are also present in Table 1B. The 60mer sequences provided in Tables 2A and 2B are non-limiting examples of exemplary probes that correspond to a portion of the corresponding cDNA.

As disclosed herein, the result of subtracting the EMT signature score from its strongly related PC1 signature score produces a best in class "difference score" ($\Delta$PC1.EMT) that is far more predictive of metastasis and outcome than either score alone. Table 3A below lists the genes that are common to both the CRC and EMT signature gene panels. Table 3B lists the genes that do not overlap.

TABLE 3A

Overlapping CRC-EMT genes

| CRC.EMT Up-Regulated | | CRC.EMT Down-Regulated |
|---|---|---|
| AKAP12 | MAP1B | AP1M2 |
| AP1S2 | MRAS | CDS1 |
| ARMCX1 | MSRB3 | CKMT1B |
| ATP8B2 | NAP1L3 | EPN3 |
| CAP2 | NDN | FA2H |
| CMTM3 | PRKD1 | FAM84A |
| DFNA5 | PTRF | FUT3 |
| DPYSL3 | RECK | GPX2 |
| FLRT2 | SERPINF1 | MAP7 |
| GFPT2 | SPARC | MARVELD3 |
| GNG11 | SRPX | MYH14 |
| HTRA1 | TRPA1 | MYO5B |
| JAM3 | UCHL1 | RAB25 |
| LGALS1 | VIM | ST14 |
| LHFP | ZFPM2 | TMC5 |
| LIX1L | | |

TABLE 3B

Non-overlapping CRC-EMT genes

| EMT (Lung) UP | | EMT (Lung) DOWN | | CRC UP | | CRC DOWN | |
|---|---|---|---|---|---|---|---|
| ADAM23 | LOX | ACPP | KRT16 | AEBP1 | SPG20 | ACOT11 | PAQR8 |
| ADAMTS1 | MMP2 | AGR3 | KRT19 | AKT3 | SRGAP2 | AGMAT | PI4K2B |
| AFF3 | NAV3 | ALDH3B2 | KRT5 | AMOTL1 | STON1 | ANKS4B | PKP2 |
| AK5 | NEGR1 | ANK3 | KRTCAP3 | ANKRD6 | SYT11 | ATP10B | PLA2G12A |
| ALPK2 | NEXN | ANKRD22 | LAMA3 | ARMCX2 | TCEA2 | AXIN2 | PLEKHA6 |
| ANGPTL2 | NID1 | ANXA9 | LAMB3 | BASP1 | TCEAL3 | BCAR3 | PLS1 |
| ANKRD1 | NRG1 | AQP3 | LAMC2 | BGN | TIMP2 | BCL2L14 | PMM2 |
| ANTXR1 | NUDT11 | ARHGAP8 | LCN2 | C1orf54 | TNS1 | BDH1 | POF1B |
| ANXA6 | PAPPA | ARHGDIB | LCP1 | C20orf194 | TPST1 | BRI3BP | PPP1R1B |
| AOX1 | PDE7B | ATAD4 | LIPG | CALD1 | TRPC1 | C10orf99 | PREP |
| ATP8B3 | PLAGL1 | ATP2C2 | MAL2 | CCDC80 | TRPS1 | C4orf19 | RNF186 |
| AXL | PMP22 | B3GNT3 | MAPK13 | CEP170 | TSPYL5 | C9orf152 | SELENBP1 |
| BDNF | PNMA2 | BLNK | MARVELD2 | CFH | TTC7B | C9orf75 | SH3RF2 |
| BICC1 | POPDC3 | BSPRY | MB | CFL2 | TUBB6 | C9orf82 | SHH |
| BNC2 | POSTN | C11orf52 | MBNL3 | COX7A1 | TUSC3 | CALML4 | SLC12A2 |
| BVES | PRR16 | C19orf21 | MPP7 | CRYAB | UBE2E2 | CAPN5 | SLC27A2 |
| C10orf38 | PTGIS | C1orf106 | MUC20 | DCN | WWTR1 | CASP5 | SLC29A2 |
| C10orf56 | PTX3 | C1orf116 | NPNT | DNAJB4 | ZNF25 | CASP6 | SLC35A3 |
| C16orf45 | RBM24 | C1orf210 | OR2A4 | DZIP1 | ZNF532 | CBLC | SLC37A1 |
| C1S | RBMS3 | C1orf34 | OVOL2 | ECM2 | ZNF677 | CC2D1A | SLC44A4 |
| C9orf19 | RBPMS2 | CCDC64B | PAK6 | EFHA2 | | CCL28 | SLC5A1 |
| CCL2 | RFTN1 | CD24 | PKP3 | EFS | | CDC42EP5 | SLC9A2 |
| CDH11 | SIRPA | CDH1 | PLA2G10 | EHD3 | | CDX1 | STRBP |
| CDH2 | SLC2A3 | CDH3 | POU2F3 | FAM20C | | CLDN3 | SUCLG2 |
| CDH4 | SLC47A1 | CEACAM5 | PPL | FBXL7 | | CMTM4 | SULT1B1 |
| CHN1 | SRGN | CEACAM6 | PPP1R14C | FEZ1 | | CORO2A | TJP3 |
| CLDN11 | ST3GAL2 | CGN | PROM2 | FRMD6 | | COX10 | TMEM54 |
| CLIP3 | SUSD5 | CLDN4 | PRR15 | GLIS2 | | CYP2J2 | TMPRSS2 |
| COL12A1 | SYDE1 | CLDN7 | PRSS8 | HECTD2 | | DAZAP2 | TST |
| COL1A2 | TBXA2R | CNKSR1 | PTAFR | IL1R1 | | DDAH1 | USP54 |
| COL3A1 | TCF4 | CNTNAP2 | PVRL4 | KCNE4 | | DTX2 | XK |
| COL4A1 | TGFB2 | CTAGE4 | RAPGEF5 | KIAA1462 | | DUOX2 | |
| COL5A1 | TMEM158 | DAPP1 | RASEF | KLHL5 | | DUOXA2 | |
| COL5A2 | TMEM47 | DENND2D | RASGEF1B | LAYN | | ENTPD5 | |
| COL6A1 | TMSL8 | DMKN | RBM35A | LDB2 | | EPB41L4B | |
| CPA4 | TNFRSF19 | DSC2 | RBM35B | LMCD1 | | EPHB2 | |

TABLE 3B-continued

Non-overlapping CRC-EMT genes

| EMT (Lung) UP | | EMT (Lung) DOWN | | CRC UP | CRC DOWN |
|---|---|---|---|---|---|
| CTGF | TTC28 | DSP | S100A14 | LPHN2 | EPS8L3 |
| CYBRD1 | TTLL7 | EHF | S100A8 | LZTS1 | ESRRA |
| DAB2 | TUB | ELF3 | S100A9 | MAF | ETHE1 |
| DIO2 | TUBA1A | ELF5 | S100P | MAGEH1 | EXPH5 |
| DKK3 | WIPF1 | EPPK1 | SCEL | MAP9 | F2RL1 |
| DLC1 | WNT5B | ERBB3 | SCNN1A | MCC | FAM3D |
| DOCK10 | ZEB1 | ERP27 | SERPINB5 | MGP | FAM83F |
| EDIL3 | ZEB2 | FAAH2 | SH2D3A | MLLT11 | FRAT2 |
| ELOVL2 | ZNF788 | FAM110C | SH3YL1 | MPDZ | FUT2 |
| EML1 | | FAM83A | SLC6A14 | MSN | FUT4 |
| EMP3 | | FAM84B | SLPI | MXRA7 | FUT 6 |
| EPB41L5 | | FBP1 | SORBS2 | MYH10 | GALNT7 |
| EPDR1 | | FGD2 | SPINK5 | MYO5A | GMDS |
| EVI2A | | FGFBP1 | SPINT1 | NNMT | GPA33 |
| F2R | | FUT1 | SPINT2 | NR3C1 | GPR35 |
| FAM101B | | FXYD3 | SPRR1A | NRP1 | HDHD3 |
| FAT4 | | GALNT3 | SPRR1B | NRP2 | HMGA1 |
| FBN1 | | GCNT3 | SPRR3 | PEA15 | HNF4A |
| FGF2 | | GJB6 | STEAP4 | PFTK1 | HOXB9 |
| FGF5 | | GOLT1A | STX19 | PHLDB2 | HSD11B2 |
| FGFR1 | | GPR110 | SYK | PKD2 | KALRN |
| FHL1 | | GPR87 | SYT7 | PRICKLE1 | KCNE3 |
| FSTL1 | | GRAMD2 | TMC4 | PTPRM | KCNQ1 |
| GLIPR1 | | GRHL1 | TMEM125 | QKI | KIAA0152 |
| GLT25D2 | | GRHL2 | TMEM30B | RAB31 | LENG9 |
| GNB4 | | HOOK1 | TMEM45B | RAB34 | LGALS4 |
| GPC6 | | HS3ST1 | TMPRSS11E | RAI14 | LRRC31 |
| GPR176 | | HS6ST2 | TMPRSS13 | RASSF8 | MCCC2 |
| GREM1 | | IL1RN | TMPRSS4 | RGS4 | MPST |
| HAS2 | | ILDR1 | TOX3 | RNF180 | MRPS35 |
| HEG1 | | INPP4B | TRIM29 | SCHIP1 | MUC3B |
| HS3ST3A1 | | IRF6 | TSPAN1 | SDC2 | MYB |
| IGFBP7 | | ITGB6 | TTC22 | SGCE | MYO7B |
| IL13RA2 | | KLK10 | TTC9 | SGTB | NAT2 |
| KIRREL | | KLK5 | VTCN1 | SLIT2 | NOB1 |
| LAMA4 | | KLK6 | WDR72 | SMARCA1 | NOX1 |
| LEPREL1 | | KLK8 | WFDC2 | SNAI2 | NR1I2 |

In some embodiments of the disclosed methods, a low Recurrence signature score can be an indication of a favorable prognosis for the patient. A favorable prognosis can involve an increased likelihood of survival after treatment with chemotherapy. For example, a favorable prognosis can be a greater than 47%, 48%, 49%, 50%, 60%, 70%, 80%, or 90% chance of survival for at least five years.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "cancer" or "malignant neoplasm" refers to a cell that displays uncontrolled growth, invasion upon adjacent tissues, and often metastasis to other locations of the body.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

A number of embodiments of the invention have been described. Nevertheless, it will be understood that various modifications may be made without departing from the spirit and scope of the invention.

EXAMPLES

Example 1

Non-EMT Features Optimize Prediction of Colorectal Cancer Metastasis

Colorectal cancer (CRC) still represents a prognostic challenge because it is difficult to identify which patients will ultimately progress and succumb to their disease. An EMT signature is highly correlated to the first principal component (PC1) of a large CRC gene expression data set (Loboda, A. et al. BMC Med Genomics. 2011 4:9). Both EMT and PC1 were prognostic for survival and recurrence of disease. However, as disclosed herein, the result of subtracting the EMT signature score from its strongly related PC1 signature score produces a best in class "difference score" (ΔPC1.EMT) that is far more predictive of metastasis and outcome than either score alone. This result was highly reproducible on six independent test sets (n>4000 CRC tumors), performing well in Stages 1-3, amongst MSI subtypes, and across multiple mutation-based subclasses. The improved performance of ΔPC1.EMT to predict metastasis appears to be related to its bias to identify epithelial (non-EMT) as well as mesenchymal (EMT) subpopulations, supporting a cooperative model for metastatic progression involving both cell types. While EMT is a dominant differential molecular program of CRC and sufficient to predict outcome, non-EMT features, including epithelial cancer stem cell-related properties, are necessary to optimally predict metastatic potential, and may need to be targeted to overcome distant disease.

The heterogeneity of colorectal cancer makes it difficult to determine which patients will benefit from adjuvant therapy and which patients do not require further therapy beyond surgical resection. To address this problem, several gene expression signatures have been developed to identify molecular subpopulations of human CRC with poor prognosis (Loboda, A. et al. BMC Med Genomics. 2011 4:9; Eschrich, S. et al. J Clin Oncol. 2005 23(15):3526-35; Jorissen, R. N. et al. Clin Cancer Res. 2009 15(24):7642-7651; Sotiriou, C. et al. J Natl Cancer Inst. 2006 98(4):262-72; Farmer, P. et al. Nat Med. 2009 15(1):68-74; Roth, A. D. et al. J Natl Cancer Inst. 2012 104(21):1635-46; Popovici, V. et al. J Clin Oncol. 2012 30(12):1288-95; Budinska, E. et al. J Pathol. 2013 231(1):63-76; Sadanandam, A. et al. Nat Med. 2013 19(5):619-25; Zhang, B. et al. Nature. 2014 Jul. 20 (in press)). In an unsupervised analysis, a "PC1 signature" (PC1) was generated (Tables 2A and 2B) by selecting a list of top-ranked genes bearing positive and negative correlation with the first principal component of 326 CRC tumors. Of many signatures tested, an "EMT signature" (Tables 1A and 1B), derived from a gene expression analysis of 93 lung cancer cell lines sorted (based on their expression of CDH1 or VIM) into epithelial or mesenchymal groups, showed a very strong correlation (Pearson R=0.92, P<$10^{-135}$) with PC1 (Loboda, A. et al. BMC Med Genomics. 2011 4:9). This colon PC1 and lung EMT association was verified in 38 CRC cell lines and by assessment of other known EMT-related genes and microRNAs in CRC tumors (Loboda, A. et al. BMC Med Genomics. 2011 4:9).

To further assess the respective prognostic values of PC1 and EMT scores, outcomes were evaluated on a new set of 468 CRC tumors (Moffitt468) including all stages (1-4) as well as metastatic lesions, and found that both PC1 and EMT were predictive of overall survival (OS), albeit to different degrees (Table 4).

TABLE 4

Univariable models on EMT, PC1 and ΔPC1.EMT scores

| Variable | Hazard Ratio | 95% CI lower limit | 95% CI Upper limit | p value |
|---|---|---|---|---|
| EMT score | 1.13 | 0.96 | 1.34 | 0.1438 |
| PC1 score | 1.40 | 1.18 | 1.66 | 0.0001 |
| ΔPC1.EMT score | 1.82 | 1.51 | 2.18 | <.0001 |

While it was clear that PC1 and EMT were highly correlated (Pearson R=0.90, P<0.0001), tumors from metastatic patients ("d_meta") appeared to cluster, to some degree, more so towards PC1 rather than EMT (FIG. 1A, indicated by two separate regression lines for tumors with and without d_meta). This suggested that the PC1 score might contribute to better identify patients with metastatic disease or metastatic potential. Interestingly in bivariate survival models, the coefficients for PC1 and EMT were both highly significant—but of opposite sign (Table 5)—reinforcing the graphical observation showing their differential propensities for metastasis (indicating poor survival). This suggested that a signature combining both scores could predict survival better than either alone.

TABLE 5

OS Multivariable Model: PC1 and EMT scores
Analysis of Maximum Likelihood Estimates

| Parameter | DF | Parameter Estimate | Standard Error | Chi-Square | Pr > ChiSq | Hazard Ratio | 95% Hazard Ratio Confidence Limits | |
|---|---|---|---|---|---|---|---|---|
| EMT score | 1 | −1.02847 | 0.20329 | 25.5941 | <.0001 | 0.358 | 0.240 | 0.533 |
| PC1 score | 1 | 1.32160 | 0.20542 | 41.3931 | <.0001 | 3.749 | 2.507 | 5.608 |

Figure 1B:
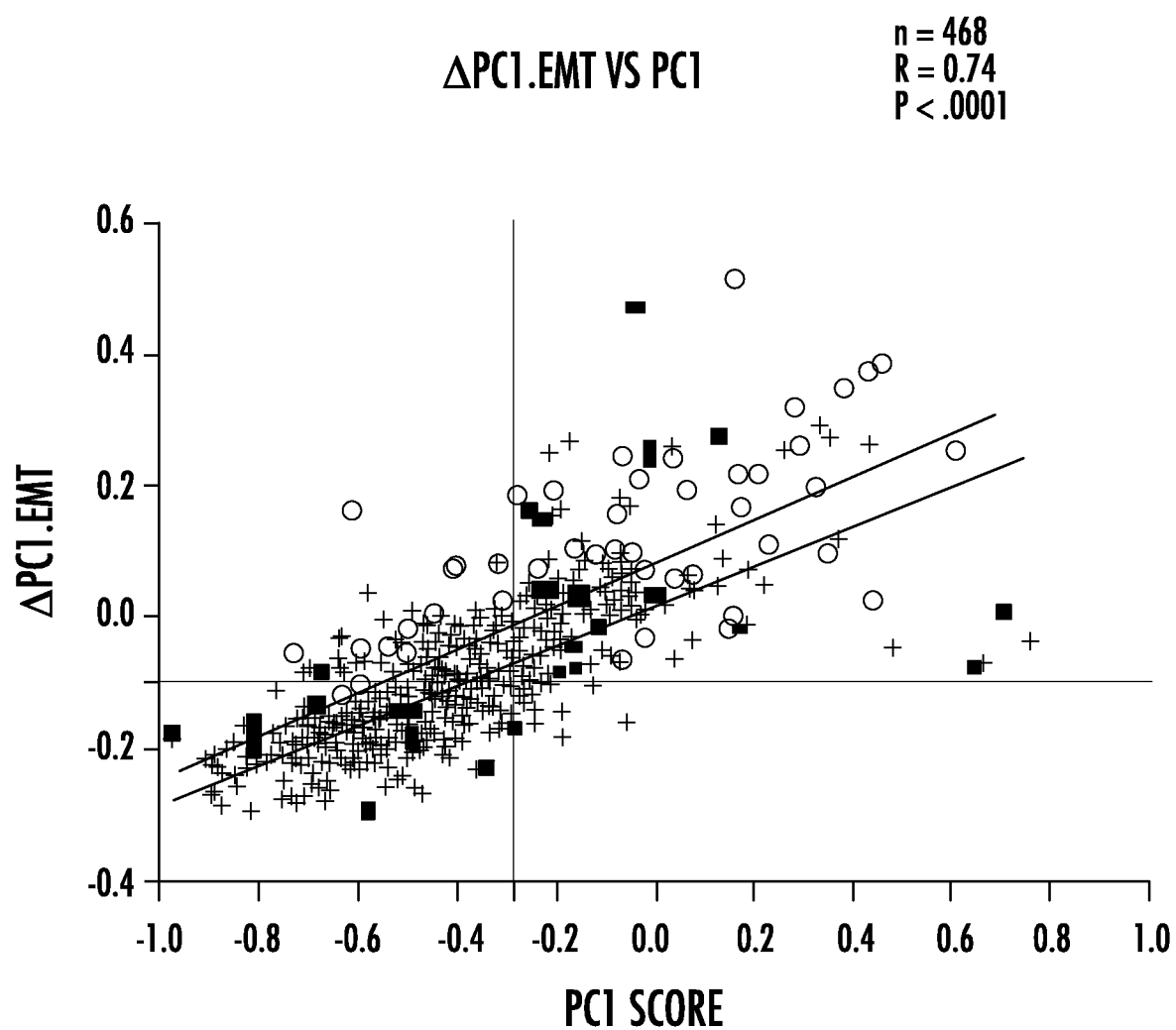
Figure 1C:
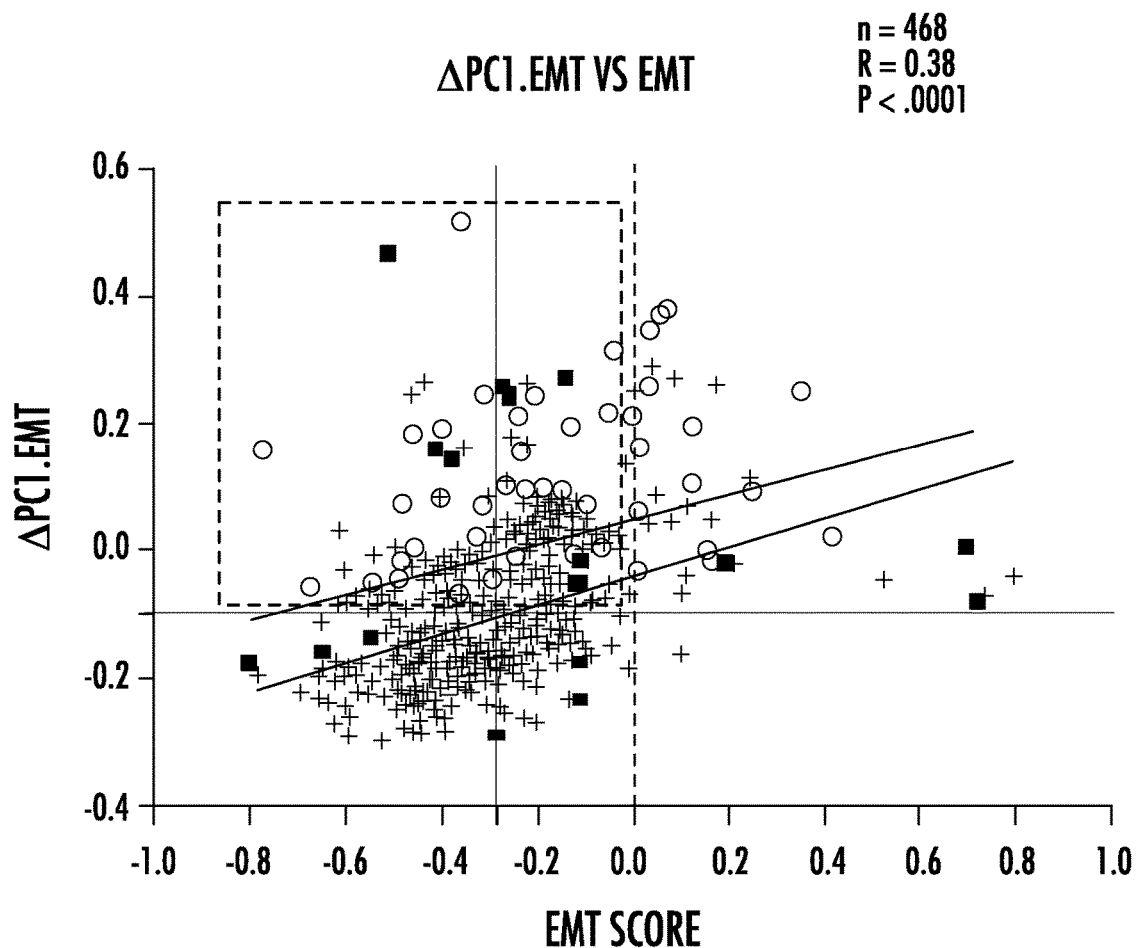
Figure 1D:
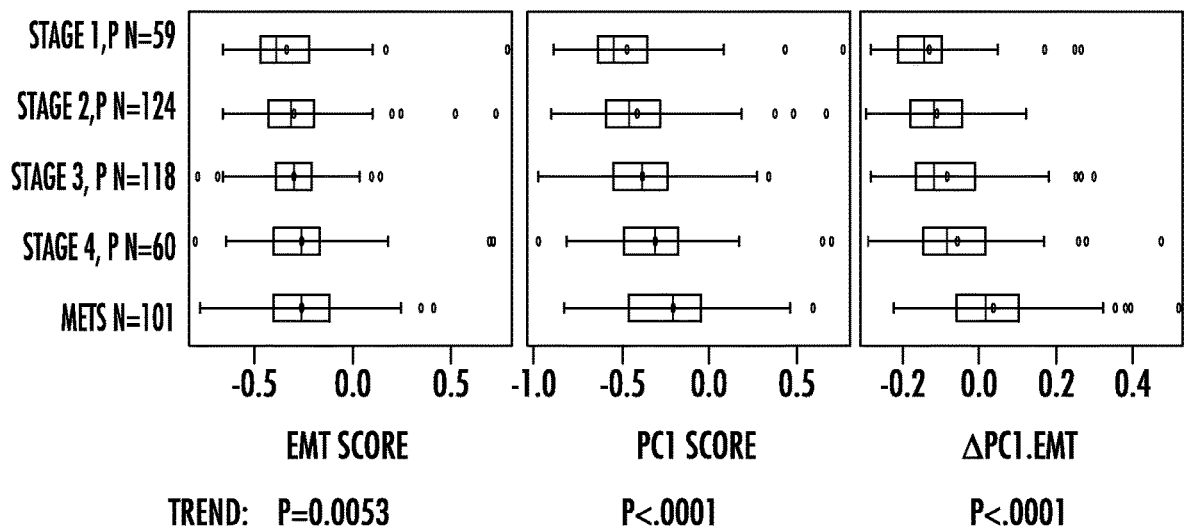
Figure 2A:
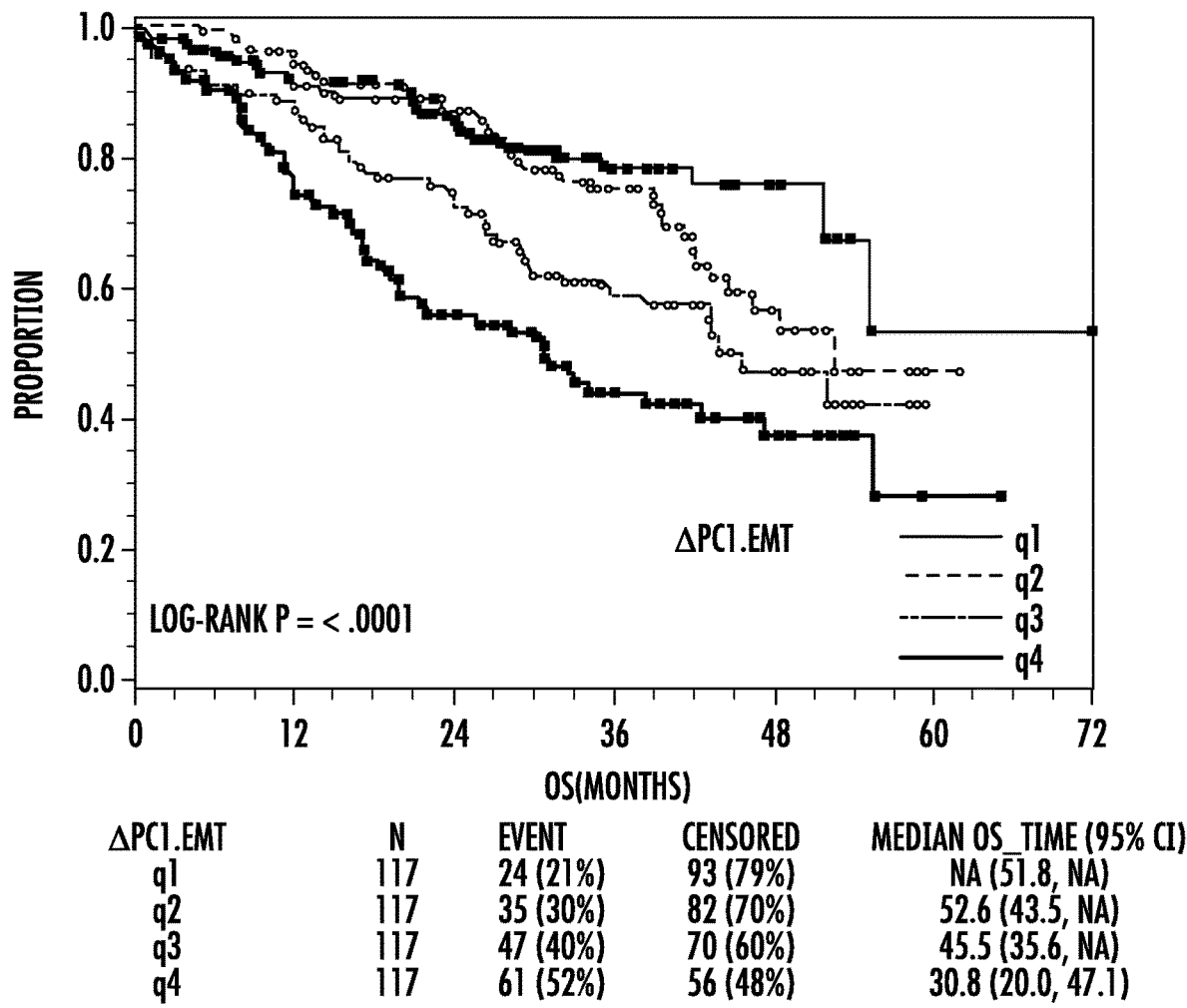
FIGS. 2A to 2C are Kaplan Meier survival graphs of quartile scores on Moffitt468 showing that a higher ΔPC1.EMT predicted poorer overall survival (OS) for all 468 patients (FIG. 2A), for 61 MSI patients (FIG. 2B) and for 407 MSS patients (FIG. 2C).
Figure 2B:
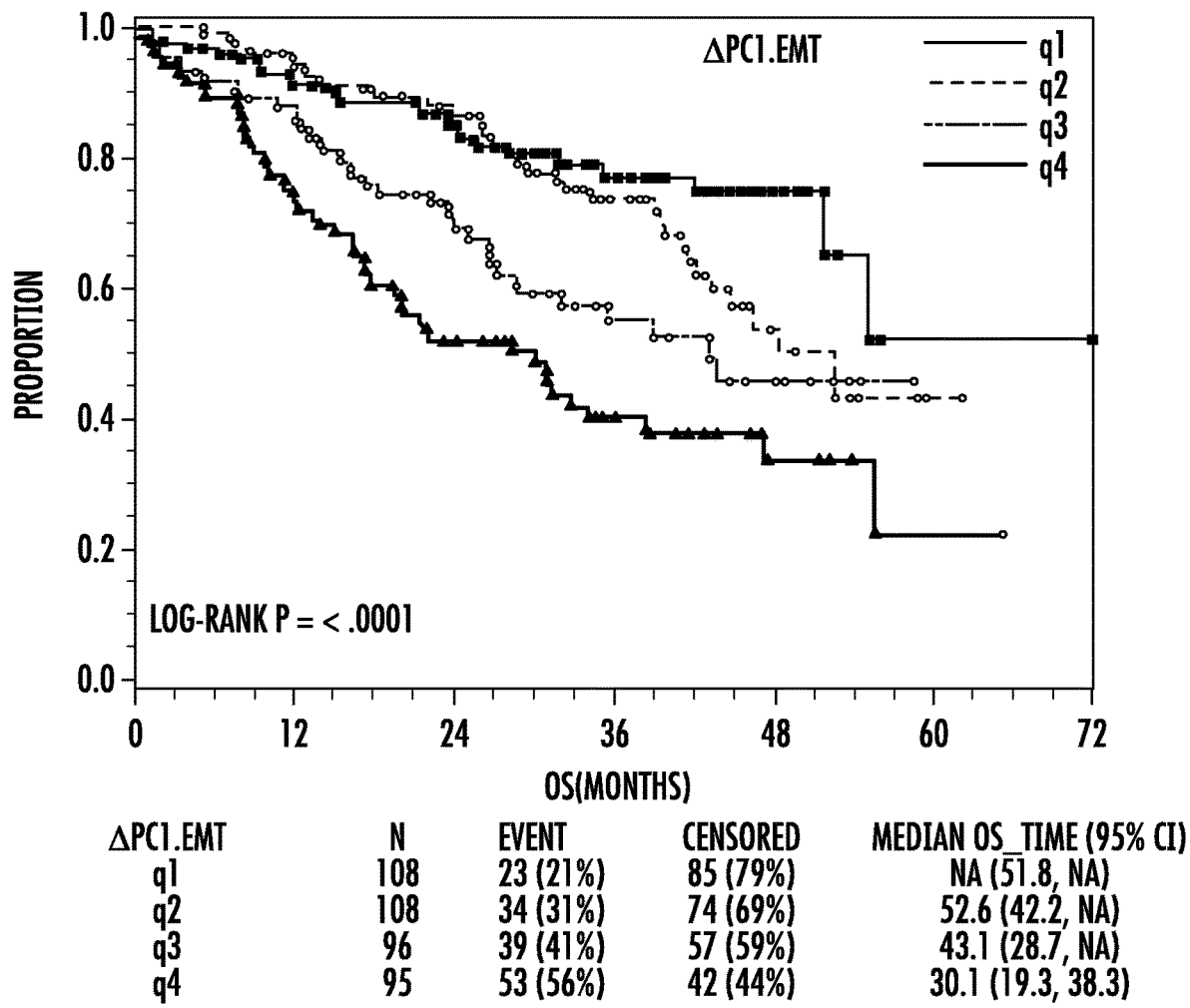
Figure 2C:
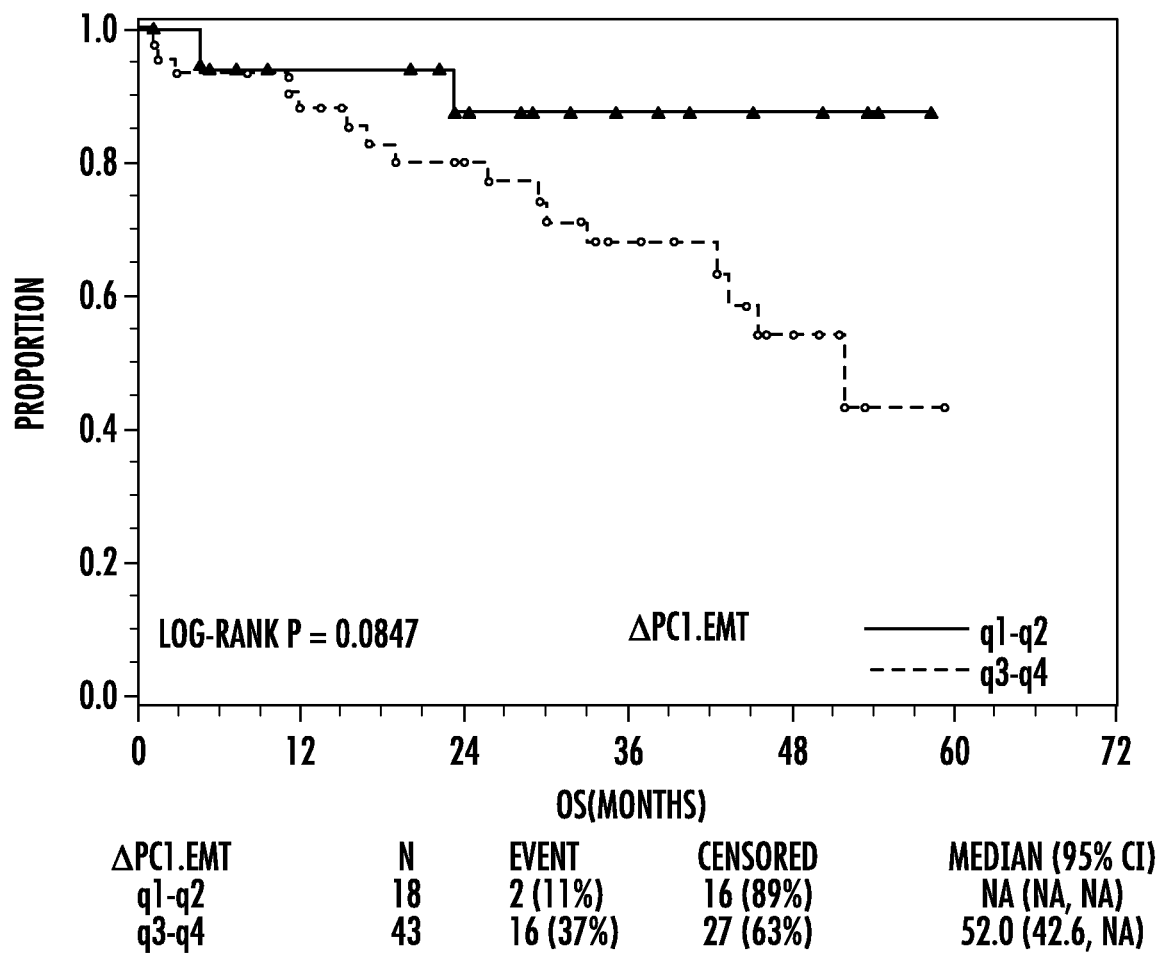

To better understand the relationship of the two scores, the EMT score was subtracted from the PC1 score to produce a "difference" score (ΔPC1.EMT) (see Tables 3A and 3B for overlapping and non-overlapping genes). As shown in FIGS. 1B and 1C, ΔPC1.EMT clearly outperformed not only EMT, but also PC1, in predicting metastasis. Correlation analysis shows that ΔPC1.EMT score had a good association with EMT (Pearson R=0.38, P<0.0001), but displayed even a stronger correlation with PC1 (Pearson R=0.74, P<0.0001), suggesting that PC1 might also include a "non-EMT" biological component. While EMT is a dominant differential molecular program in CRC (Loboda, A. et al. BMC Med Genomics. 2011 4:9), ΔPC1.EMT appeared to capture predominantly non-EMT contributions to predict metastasis (FIG. 1C, highlighted by box). Moreover, it was clear that PC1, and especially ΔPC1.EMT, outperformed EMT in progressively deciphering the degree of tumor progression of primary CRCs (stages 1 vs. 2 vs. 3 vs. 4) vs. metastatic lesions (FIG. 1D), further supporting the non-EMT bias of ΔPC1.EMT. Metastatic tumors may represent homogeneous clonal expansions of subpopulations of non-EMT (epithelial) tumor cells (Greaves, M. et al. Clonal evolution in cancer. Nature 2012 481:306-313) which might explain their higher ΔPC1.EMT score. Higher ΔPC1.EMT scores were also correlated with a higher percentage of deaths in stages 1-3 tumors (Table 6), suggesting clinical utility in predicting the use of adjunct therapy. Kaplan Meier survival analysis of quartile scores shows that a higher ΔPC1.EMT predicted poorer OS for all 468 patients (Logrank P=0.0004), and for 61 MSI patients (P=0.085) as well as 407 MSS patients (P<0.0001), respectively (FIG. 2). This result was confirmed by a Cox regression analysis in an expanded Moffitt dataset with 1988 CRC (Moffitt1988) patients (representing an additional 1520 independent cases) with both primary and metastatic tumor-derived profiles, showing that ΔPC1.EMT robustly predicted worse overall survival (beta (Cox)=2.35, i.e. HR=10.5, P=$3.0 \times 10^{-22}$). Collectively, these data suggested that ΔPC1.EMT appeared to be measuring EMT as well as non-EMT biological programs that together have significant prognostic value.

TABLE 6

ΔPC1.EMT predicts deaths in Stages 1-3 CRC

| Stage | Q1 | Q2 | Q3 | Q4 | Avg. | Deaths/N | Deaths/N |
|---|---|---|---|---|---|---|---|
| 1 | 9 | 9 | 17 | 17 | 10 | 6/58 | 4/42 (10%) |
| 2 | 14 | 21 | 32 | 36 | 24 | 29/123 | 14/82 (17%) |
| 3 | 20 | 34 | 31 | 55 | 34 | 39/116 | 26/80 (32%) |

These findings proved to be extremely robust when ΔPC1.EMT was further tested in five additional independent datasets (n=2153 CRC tumors) (Table 7) using both univariate and multivariate Cox Proportional Hazard Regression models.

TABLE 7

List of datasets used for the validation

| Dataset | Accession | N of sample | Stage | Treatment | Platform | RNA-material | Follow-up Information |
|---|---|---|---|---|---|---|---|
| PETACC-3 | E-MTAB-990 | 752 | 2, 3 | 5-FU/FA and FOLFIRI | Almac | FFPE | OS, RFS, SAR |
| ALMAC | E-MTAB-863, E-MTAB-864 | 359 | 2 | Untreated[a] | Almac | FFPE | OS, RFS |
| LNCC | E-GEOD-39582 | 566 | 1, 4 | Treated-Untreated | HGU133plus2 | Frozen | RFS |
| GEO41258 | E-GEOD-41258 | 186 | 1, 4 | Unknown | HGU133a | Frozen | OS, RFS |
| GSE14333 | GSE14333 | 290 | A-D | Unknown[b] | HGU133plus2 | Frozen | RFS |

[a]no preoperative or postoperative cancer therapy within 1 year of surgery (although therapy given after recurrence was acceptable)
[b]standard adjuvant chemotherapy (either single agent 5-uouracil/capecitabine or 5-uouracil and oxaliplatin) or postoperative concurrent chemoradiotherapy (50.4 Gy in 28 fractions with concurrent 5-uorouracil)
*related references were given in "methods"

Overall, while EMT, PC1 and ΔPC1.EMT all had hazard ratios>1.0 in univariate models, and PC1 performed better than EMT, ΔPC1.EMT consistently outperformed both in predicting OS and relapse free survival (RFS) (FIGS. 4A to 4F, and Tables 8 and 9). Moreover, the independent prognostic values of PC1 and ΔPC1.EMT were confirmed when analyzed together in a multivariate model, including other clinopathological variables (Tables 10 and 11).

TABLE 8

Univariable Cox Proportional Hazard Regression models for Overall Survival (OS), Relapse Free Survival (RFS) and Survival After Relapse (SAR) by ΔPC1.EMT score on PETACC dataset

| Covariates | HR | 1.95 | u.95 | p | n |
|---|---|---|---|---|---|
| Univariate model for OS in Stage 2 and 3 patients | | | | | |
| ΔPC1.EMT | 1.56 | 1.32 | 1.84 | 1.16e−07 | 752 |
| Univariate model for OS in Stage 3 patients | | | | | |
| ΔPC1.EMT | 1.69 | 1.42 | 2.03 | 8.22e−09 | 644 |
| Univariate model for RFS in Stage 2 and 3 patients | | | | | |
| ΔPC1.EMT | 1.47 | 1.28 | 1.69 | 8.98e−08 | 752 |
| Univariate model for RFS in Stage 3 patients | | | | | |
| ΔPC1.EMT | 1.55 | 1.33 | 1.81 | 3.99e−08 | 644 |
| Univariate model for SAR in Stage 2 and 3 patients | | | | | |
| ΔPC1.EMT | 1.20 | 1.02 | 1.42 | 3.11e−02 | 291 |
| Univariate model for SAR in Stage 3 patients | | | | | |
| ΔPC1.EMT | 1.26 | 1.04 | 1.51 | 1.54e−02 | 241 |

TABLE 9

Univariable Cox Proportional Hazard Regression models for Overall Survival (OS) and Relapse Free Survival (RFS) - Univariate model for OS in Stage 2 and 3 - PETACC dataset

| Covariates | HR (95% CI) | p | n |
|---|---|---|---|
| ΔPC1.EMT | 1.56 (1.32-1.84) | 1.16e−07 | 752 |
| PC1 | 1.35 (1.15-1.57) | 1.54e−04 | 752 |
| EMT | 1.24 (1.05-1.47) | 1.28e−02 | 752 |
| MSI (MSS vs. MSI-H) | 1.98 (1.10-3.55) | 2.22e−02 | 752 |
| BRAF (wt vs. mut) | 0.57 (0.36-0.91) | 1.89e−02 | 752 |
| site (right vs. left) | 1.26 (0.96-1.65) | 1.03e−01 | 752 |
| T stage (T12 vs. T3) | 0.37 (0.16-0.83) | 1.60e−02 | 752 |

TABLE 9-continued

Univariable Cox Proportional Hazard Regression models for Overall Survival (OS) and Relapse Free Survival (RFS) - Univariate model for OS in Stage 2 and 3 - PETACC dataset

| Covariates | HR (95% CI) | p | n |
|---|---|---|---|
| T stage (T4 vs. T3) | 2.00 (1.47-2.72) | 9.69e−06 | 752 |
| N stage (N2 vs. N1) | 2.31 (1.73-3.09) | 1.85e−08 | 752 |

TABLE 9-continued

Univariable Cox Proportional Hazard Regression models for Overall Survival (OS) and Relapse Free Survival (RFS) - Univariate model for OS in Stage 2 and 3 - PETACC dataset

| Covariates | HR (95% CI) | p | n |
|---|---|---|---|
| N stage (N0 vs. N1) | 1.42 (0.94-2.13) | 9.63e-02 | 752 |
| stage (3 vs. 2) | 0.99 (0.68-1.45) | 9.7e-01 | 752 |
| grade (G-34 vs. G-12) | 1.83 (1.24-2.72) | 2.43e-03 | 752 |
| SMAD4 (Any Loss vs. No Loss) | 1.56 (1.15-2.11) | 3.88e-03 | 752 |
| BRAF.score | 1.26 (1.13-1.39) | 1.3e-05 | 752 |
| Age | 1.11 (0.97-1.26) | 1.24e-01 | 752 |
| LN | 0.79 (0.67-0.93) | 3.74e-03 | 750 |

TABLE 10

Multivariable models for Overall Survival (OS) and Relapse Free Survival (RFS) including PC1 and EMT scores - Multivariable Cox Proportional Hazard Regression model for OS in Stage2 and 3 - PETACC dataset

| Covariates | HR | 1.95 | u.95 | p | n |
|---|---|---|---|---|---|
| PC1 | 2.62 | 1.53 | 4.46 | 4.08E-004 | 750 |
| EMT | 0.44 | 0.25 | 0.78 | 4.83E-003 | 750 |
| Age | 1.11 | 0.96 | 1.27 | 1.53E-001 | 750 |
| tstage (T12 vs T3) | 0.47 | 0.2 | 1.08 | 7.42E-002 | 750 |
| tstage (T4 vs T3) | 2.04 | 1.49 | 2.78 | 8.13E-006 | 750 |
| nstage (N2 vs N1) | 2.13 | 1.58 | 2.87 | 7.20E-007 | 750 |
| nstage (N0 vs N1) | 1.45 | 0.95 | 2.2 | 8.35E-002 | 750 |
| LN | 0.72 | 0.61 | 0.86 | 2.54E-004 | 750 |
| site (right vs left) | 1.6 | 1.19 | 2.15 | 2.07E-003 | 750 |
| MSI (MSS vs MSI-H) | 2.48 | 1.33 | 4.63 | 4.19E-003 | 750 |
| BRAF (wt vs mut) | 0.74 | 0.45 | 1.22 | 2.37E-001 | 750 |

TABLE 11

Multivariable models for Overall Survival (OS) and Relapse Free Survival (RFS) including PC1.EMT score - Multivariable Cox Proportional Hazard Regression model for OS in Stage2 and 3 - PETACC dataset

| Covariates | HR | 1.95 | u.95 | p | n |
|---|---|---|---|---|---|
| ΔPC1.EMT | 1.40 | 1.18 | 1.66 | 9.72e-05 | 750 |
| Age | 1.10 | 0.96 | 1.26 | 1.71e-01 | 750 |
| tstage (T12 vs T3) | 0.46 | 0.20 | 1.04 | 6.27e-02 | 750 |
| tstage (T4 vs T3) | 2.04 | 1.49 | 2.79 | 7.63e-06 | 750 |
| nstage (N2 vs N1) | 2.12 | 1.58 | 2.86 | 7.69e-07 | 750 |
| nstage (N0 vs N1) | 1.44 | 0.95 | 2.19 | 8.64e-02 | 750 |
| LN | 0.72 | 0.61 | 0.86 | 2.33e-04 | 750 |
| site (right vs left) | 1.60 | 1.19 | 2.16 | 1.79e-03 | 750 |
| MSI (MSS vs MSI-H) | 2.47 | 1.32 | 4.60 | 4.47e-03 | 750 |
| BRAF (wt vs mut) | 0.74 | 0.45 | 1.23 | 2.48e-01 | 750 |

To explore the molecular basis for the observed prognostic improvement of ΔPC1.EMT from its parent PC1 and EMT scores, quartile trends of these three scores vs. the number of tumors harboring observed mutations of several driver genes were examined in the Moffitt468 dataset. The ΔPC1.EMT remarkably improved the trends (relative to PC1 and EMT) to identify better prognosis tumors harboring APC mutations and worse prognosis tumors harboring BRAF (V600E) mutations, as well as tumors identified as MSI-H or Stage 4 (FIGS. 3A to 3D). This suggested the potential for ΔPC1.EMT to refine the prediction of metastasis. Moreover, it was observed that in some subgroups of combined mutations (KRAS & TP53 or BRAF & TP53), as well as in MSI-H and Stage 1 cases, ΔPC1.EMT and EMT trended in opposite directions for distant metastasis rate (FIGS. 3E to 3H), supporting the hypothesis that ΔPC1.EMT might be measuring non-EMT components of metastasis. These data also suggested a previously dismissed role for driver genes in predicting distant metastatic potential (Vanharanta, S. et al. Cancer Cell. 2013 24(4):410-21).

The improved survival prediction with ΔPC1.EMT through capture of non-EMT components is also consistent with the hypothesis that both EMT (mesenchymal) as well as non-EMT (epithelial) cellular phenotypes must cooperate to produce metastasis (Tsuji, T et al. Cancer Res. 2009 69(18):7135-9). Tsuji et al. found that primary tumors were heterogeneous and contained both cell types (with mesenchymal cells populating the invasive front), but metastatic tumors contained only the cells originating from the epithelial type (Tsuji, T et al. Cancer Res. 2009 69(18):7135-9). Recently, new evidence has suggested a critical role for non-EMT "epithelial-like" cells in the multi-step process of metastasis (Tsuji, T. et al. Cancer Res. 2008 68(24):10377-86; Giancotti, F. G. Cell. 2013 155(4):750-64; Oskarsson, T., Cell Stem Cell. 2014 14(3):306-21). For instance, cohesive epithelial migration was often observed as the predominant pattern in CRC (Chui, M. H. Int J Cancer. 2013 132(7): 1487-95).

Figure 3A:
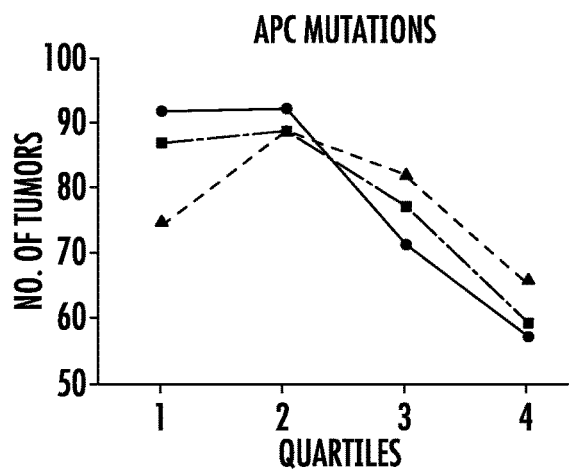
FIGS. 3A to 3I show that ΔPC1.EMT appears to measure "non-EMT" components of metastasis in addition to EMT components, improving its capacity to predict outcomes.
Figure 3B:
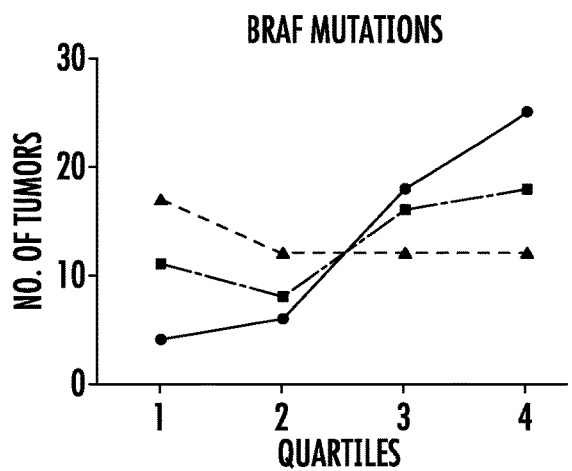
Figure 3C:
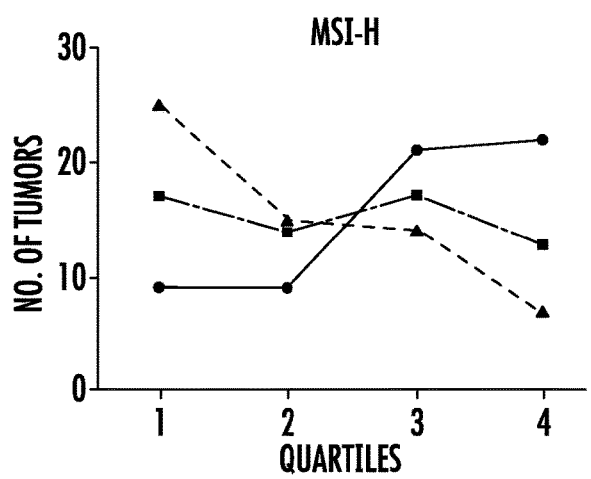
Figure 3D:
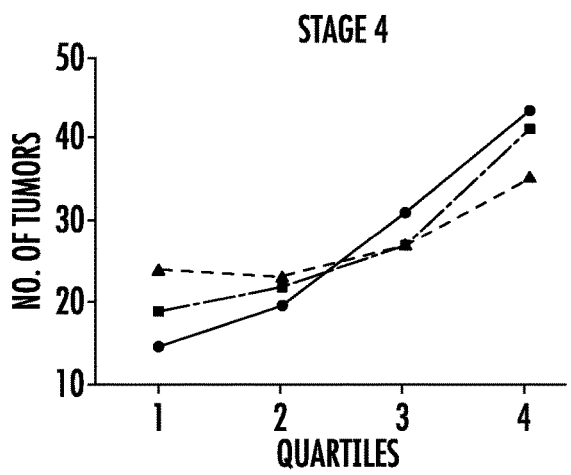
Figure 3E:
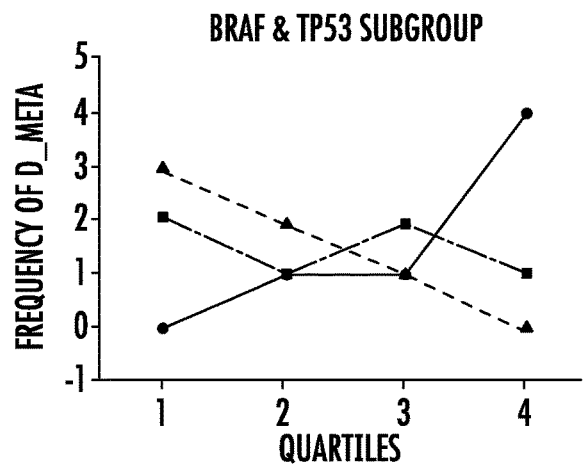
Figure 3F:
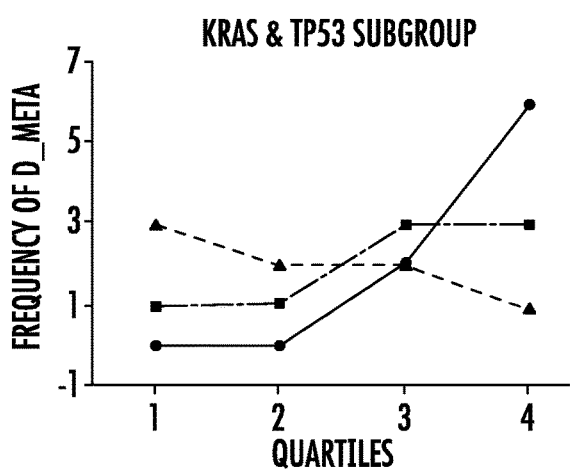
Figure 3G:
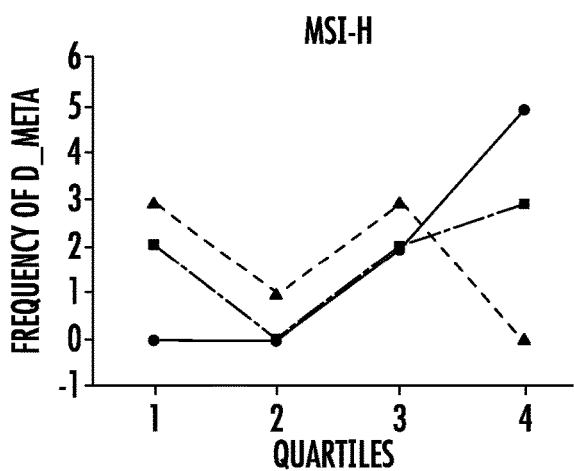
Figure 3H:
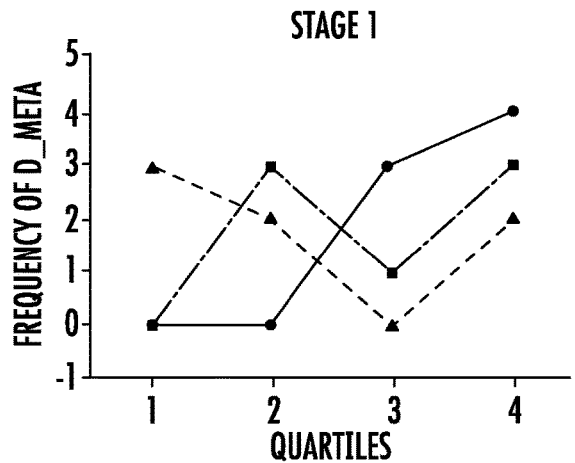
Figure 3I:
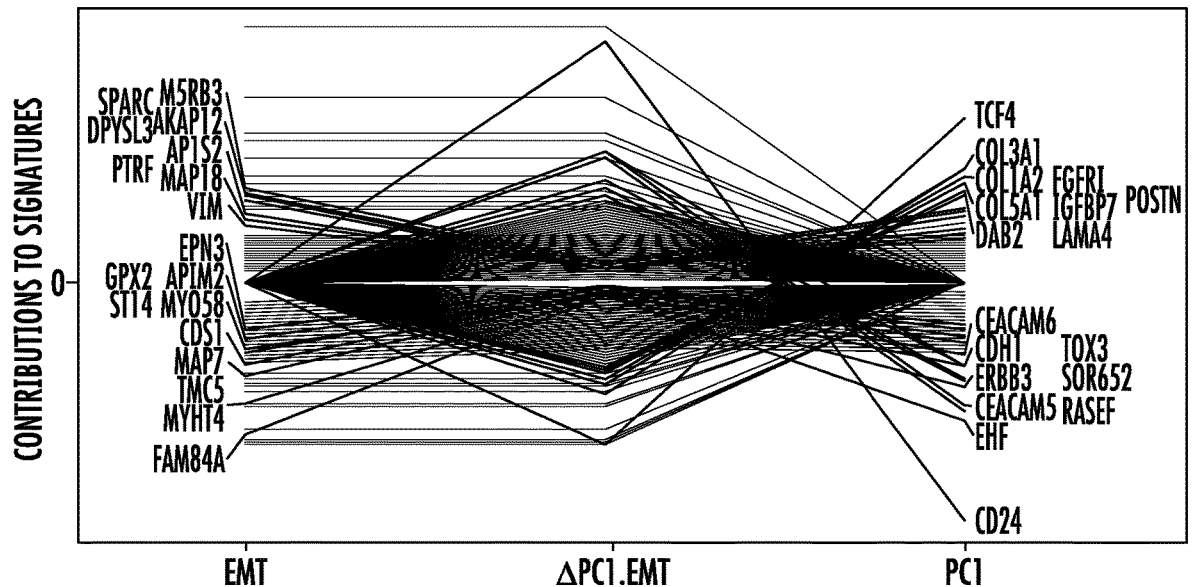
Figure 4A:
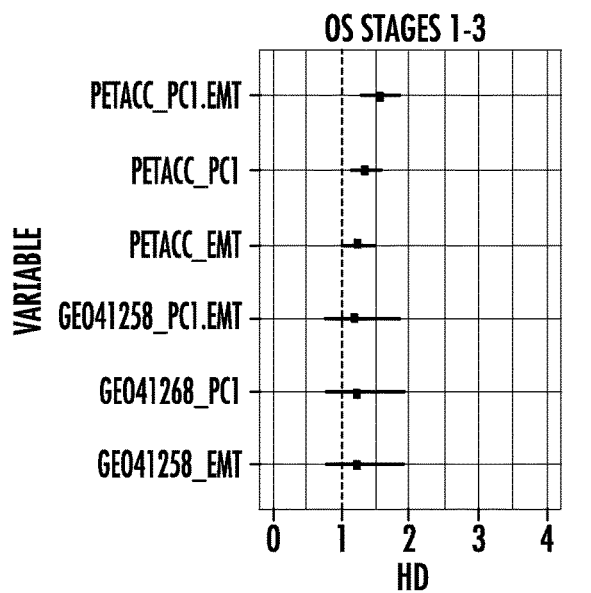
FIGS. 4A to 4F are forest plot summaries of OS Stages 1-3 (FIG. 4A), OS Stage 2 (FIG. 4C), OS Stage 3 (FIG. 4E), RFS Stages 1-3 (FIG. 4B), RFS Stage 2 (FIG. 4D), and RFS Stage 3 (FIG. 4F) analyses of EMT, PC1 and ΔPC1.EMT scores on PETACC, ALMAC, LNCC, GSE14333 and GEO41258 data sets.
Figure 4B:
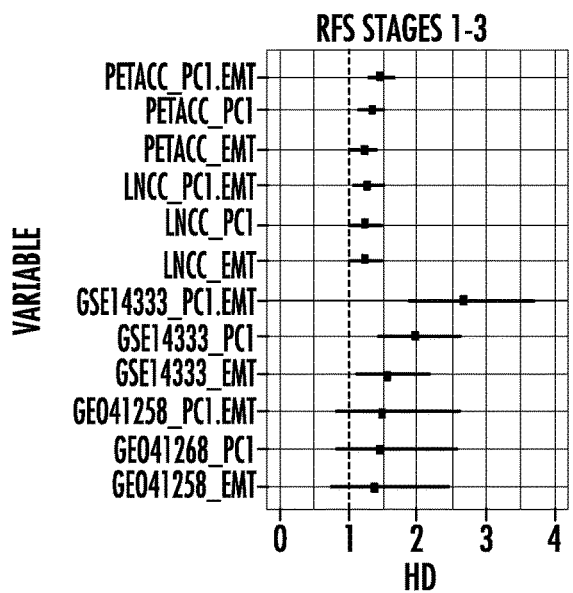
Figure 4C:
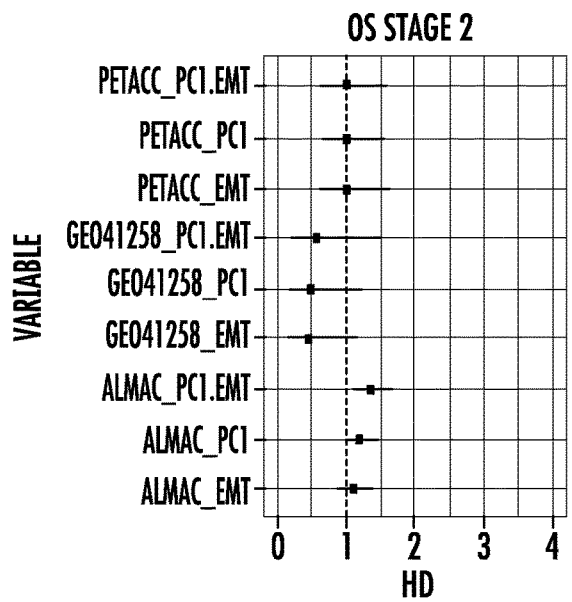
Figure 4D:
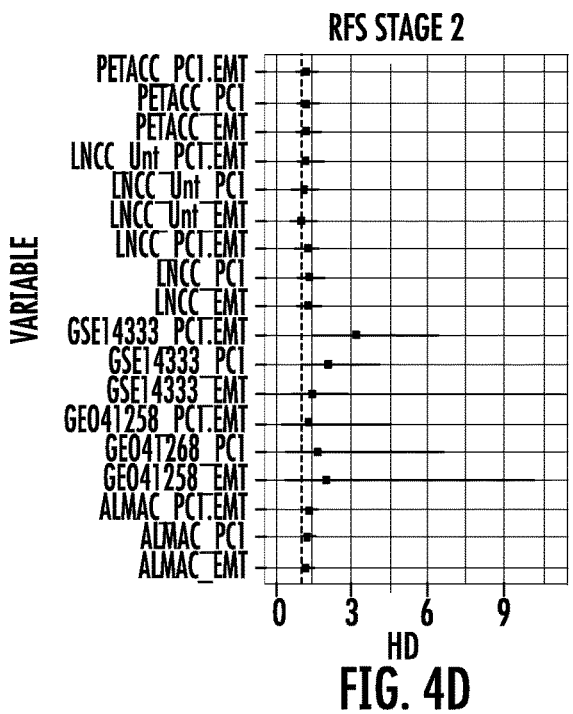
Figure 4E:
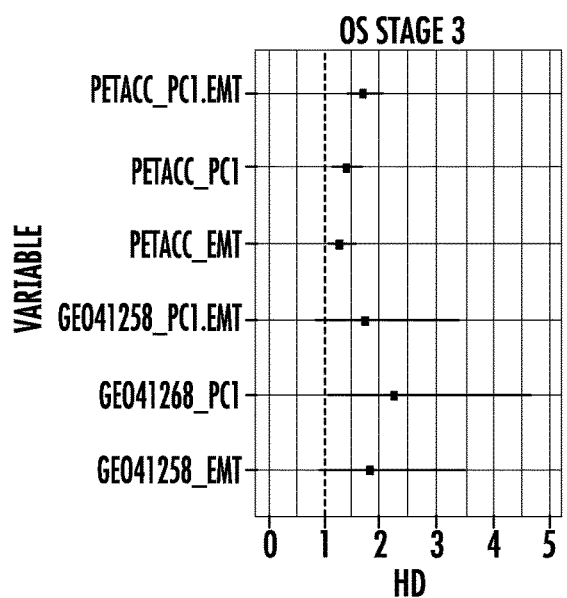
Figure 4F:
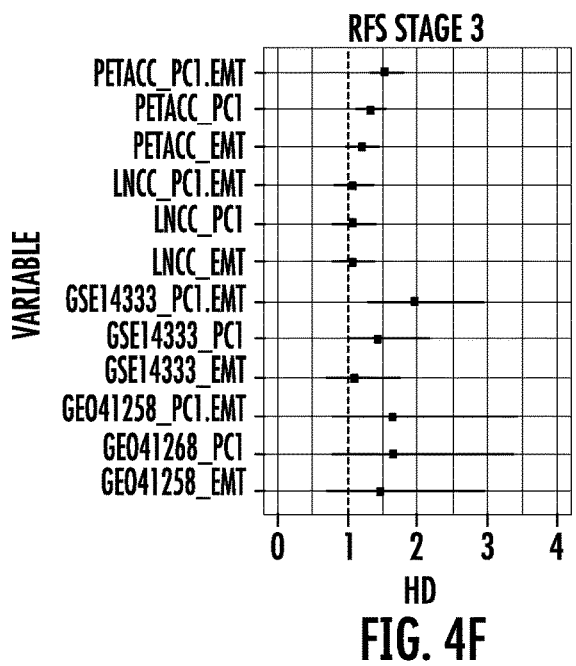
Figure 5A:
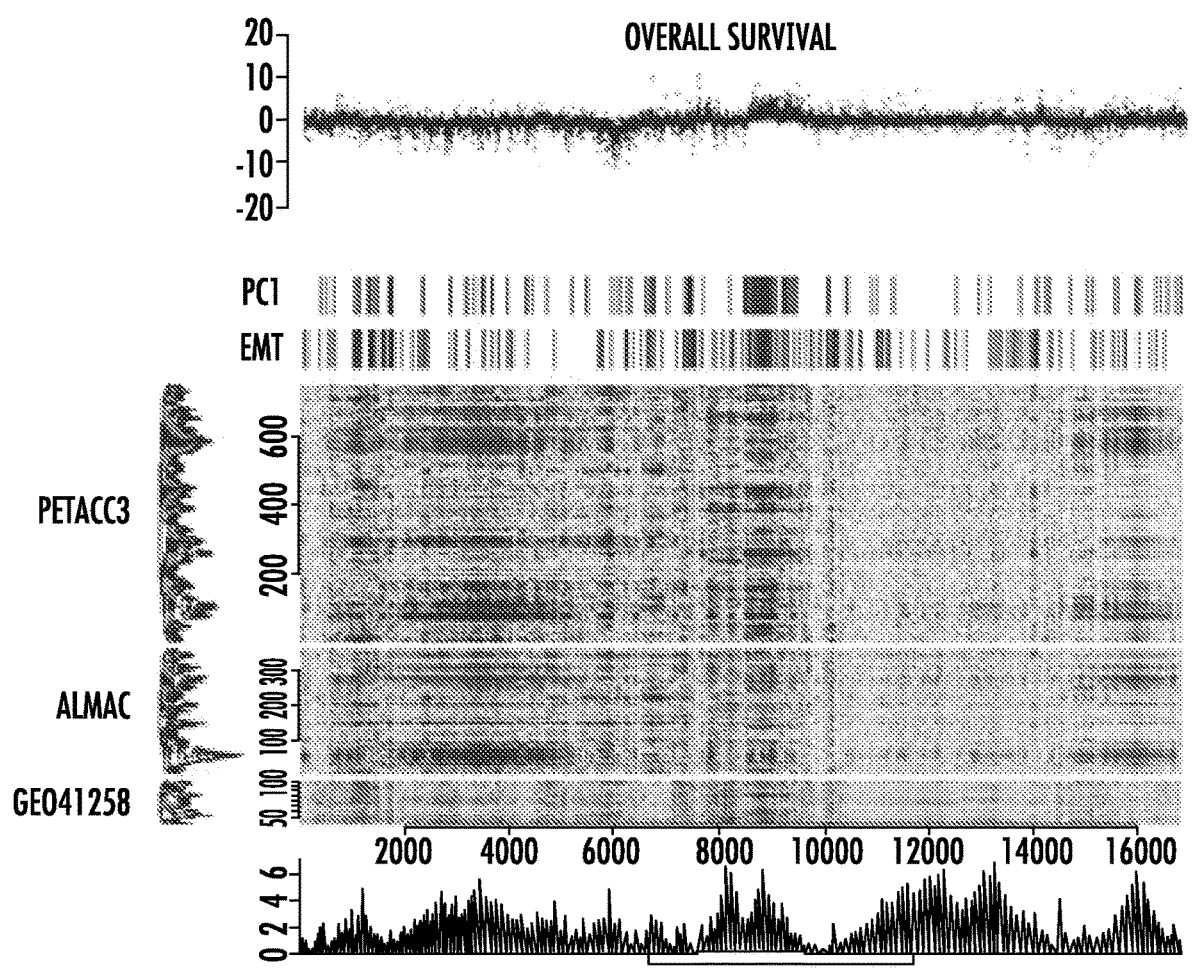
FIGS. 5A and 5B are hierarchical cluster analyses using multiple datasets, showing areas of strong overlap in gene expression accounting for the high correlation of EMT to PC1, but also showing more isolated, non-overlapped genes not strongly clustered together suggesting the potential for ΔPC1.EMT to improve outcome.
Figure 5B:
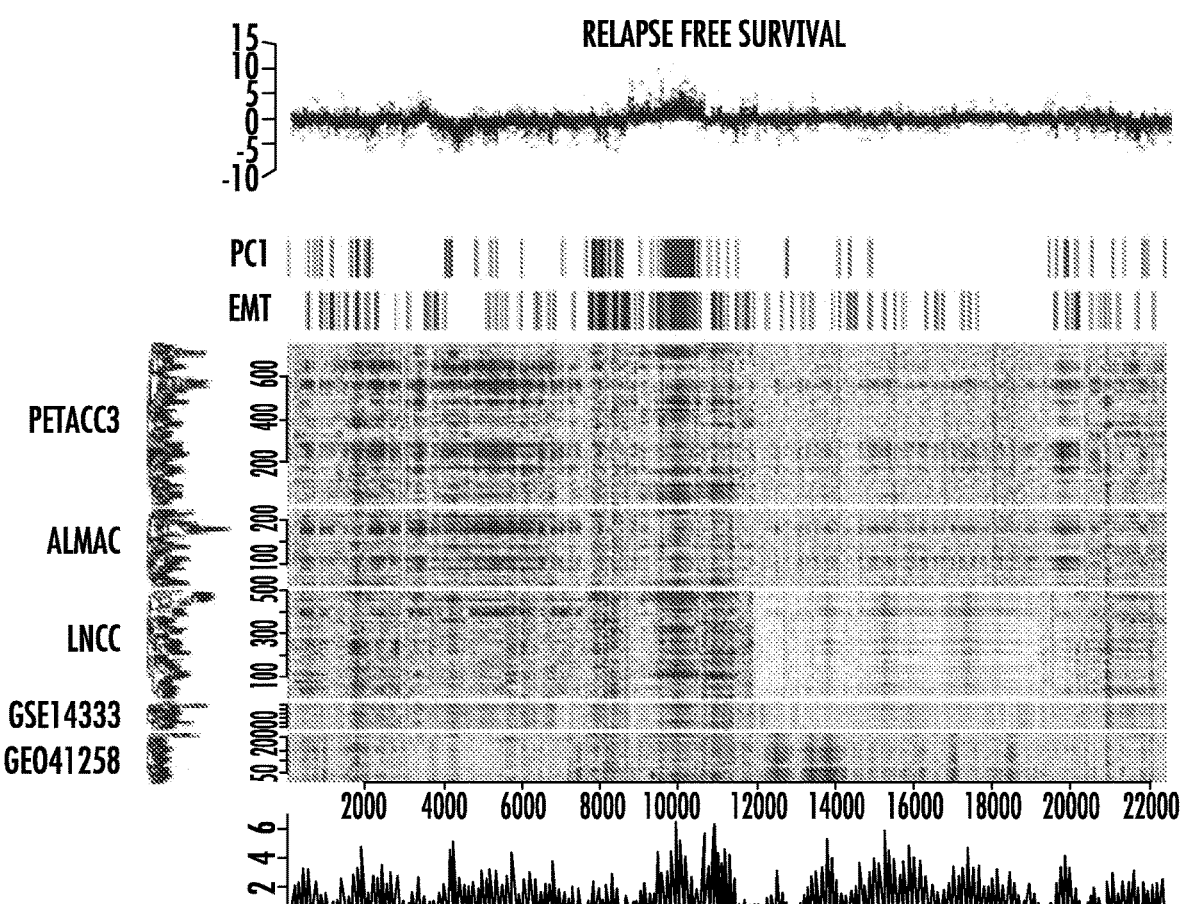
Figure 7A:
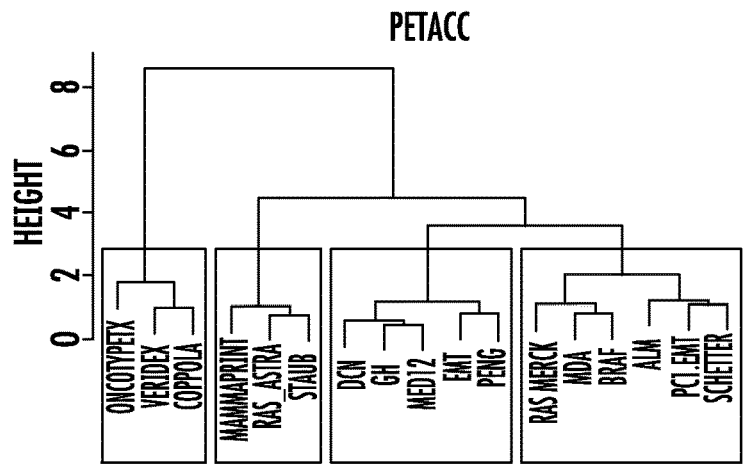
FIGS. 7A to 7F show gene clusters for PETACC (FIG. 7A), ALAMC (FIG. 7B), French (FIG. 7C), GSE14333 (FIG. 7D), GEO41258 (FIG. 7E), and TCGA (FIG. 7F) datasets.
Figure 7B:
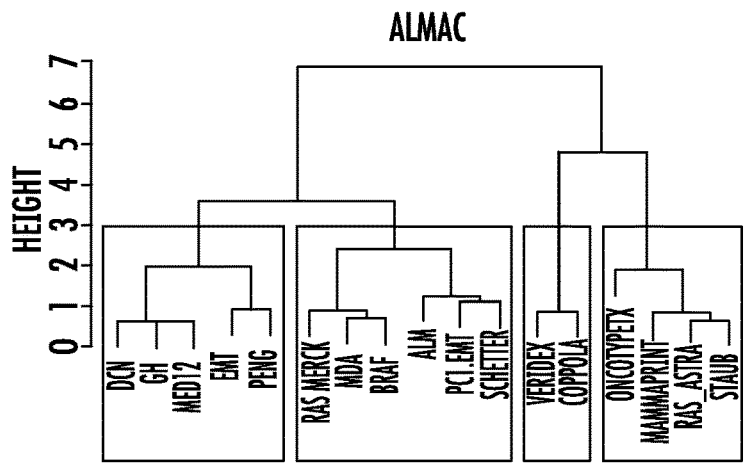
Figure 7C:
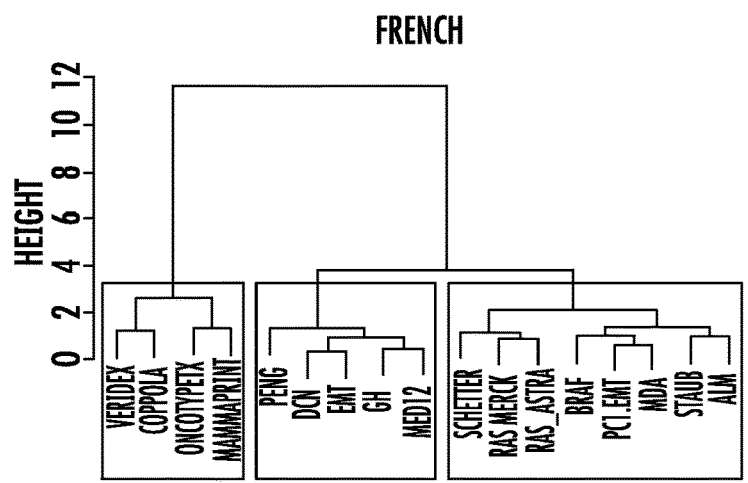
Figure 7D:
Figure 7E:
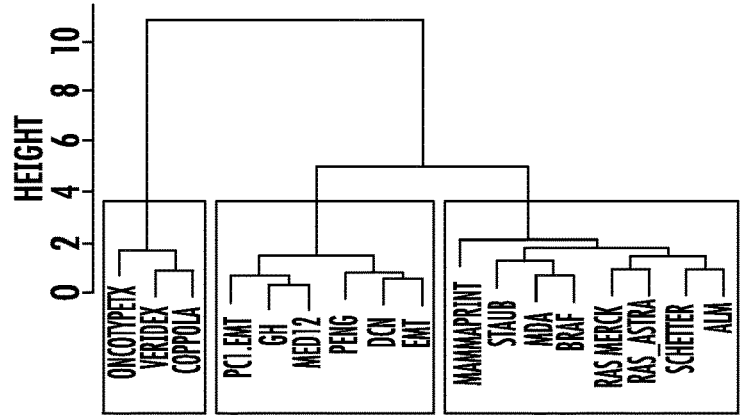
Figure 7F:
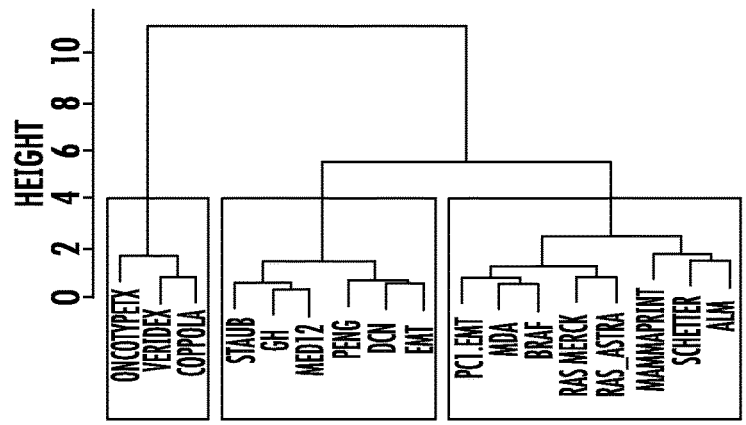

To better understand the molecular underpinnings of ΔPC1.EMT, gene expression clustering analysis was performed on the five datasets (FIG. 5A to 5B). These data show areas of strong overlap in gene expression accounting for the high correlation of EMT with PC1 (FIGS. 19A to 19E), but also show isolated, non-overlapping genes. Since the contributions of VIM (a mesenchymal gene used to create the EMT signature) and other overlapped genes were effectively diminished in ΔPC1.EMT, ΔPC1.EMT might better measure the non-EMT (epithelial) components of CRC. In addition, an analysis of the GO Process of those non-overlapping genes indicates that roughly half of the pathways were related to cell adhesion and cellular remodeling (e.g. three EMT-related pathways centered around SLUG1 were altered) (Tables 12A, 12B, 12C). Respective weighted contributions of individual signature genes of PC1 and EMT were further analyzed on the five datasets to identify the genes whose contributions changed the most from PC1 or EMT to ΔPC1.EMT (FIG. 3I). ΔPC1.EMT was represented by more epithelial and less mesenchymal gene contributions. For instance, the contribution of the epithelial marker CDH1 increased in ΔPC1.EMT, whereas the mesenchymal marker VIM and/or other EMT genes including SPARC, TCF4, COL1A2 and COL3A1 decreased.

TABLE 12A

| EMT GO Processes | | | | | |
|---|---|---|---|---|---|
| Processes | Total | p-value | FDR | In Data | Network Objects from Active Data |
| cell adhesion | 988 | 3.917E-23 | 1.389E-19 | 66 | ATR/TEM8, P-cadherin, LAMA4, FLRT2, p38 MAPK, Syk, ITGB6, EDIL3, HAS, NEPH1, COL6A1, Nectin-4, Collagen V, Calgranulin A, OSF-2, Calprotectin |

TABLE 12A-continued

EMT GO Processes

| Processes | Total | p-value | FDR | In Data | Network Objects from Active Data |
|---|---|---|---|---|---|
| | | | | | (S100A8/A9) complex, Galectin-1, CCL2, SRPX, CD24, Galpha(q)-specific peptide GPCRs, N-cadherin, Desmocollin 3, Caspr2, Annexin IX, R-cadherin, LAMA3 (Epiligrin), E-cadherin, FAT4, Claudin-7, TGF-beta 2, Collagen XII, LAMC2, EPDR1, Laminin 5, SHPS-1, Plakophilin 3, Nidogen, RHG7, SUSD5, BVES, CTGF, UFO, EPB41L5, MyHC, Claudin-4, Calgranulin B, PKC, Claudin-11, Tcf(Lef), IGFBP7, TGF-beta, Neurotractin, Cadherin 11, M-cadherin, COL5A1, LAMB3, WNT, DSC2, ADAM23, NPNT, Collagen III, Collagen IV, IGFBP7/8, Desmoplakin, JAM3 |
| biological adhesion | 995 | 5.770E−23 | 1.389E−19 | 66 | ATR/TEM8, P-cadherin, LAMA4, FLRT2, p38 MAPK, Syk, ITGB6, EDIL3, HAS, NEPH1, COL6A1, Nectin-4, Collagen V, Calgranulin A, OSF-2, Calprotectin (S100A8/A9) complex, Galectin-1, CCL2, SRPX, CD24, Galpha(q)-specific peptide GPCRs, N-cadherin, Desmocollin 3, Caspr2, Annexin IX, R-cadherin, LAMA3 (Epiligrin), E-cadherin, FAT4, Claudin-7, TGF-beta 2, Collagen XII, LAMC2, EPDR1, Laminin 5, SHPS-1, Plakophilin 3, Nidogen, RHG7, SUSD5, BVES, CTGF, UFO, EPB41L5, MyHC, Claudin-4, Calgranulin B, PKC, Claudin-11, Tcf(Lef), IGFBP7, TGF-beta, Neurotractin, Cadherin 11, M-cadherin, COL5A1, LAMB3, WNT, DSC2, ADAM23, NPNT, Collagen III, Collagen IV, IGFBP7/8, Desmoplakin, JAM3 |
| extracellular matrix organization | 413 | 2.021E−22 | 2.676E−19 | 43 | RECK, FGF2, LEKTI, COL5A2, LAMA4, ITGB6, HAS, P3H2, PAI1, COL6A1, Collagen V, OSF-2, COL4A1, GLT25D2, LAMA3 (Epiligrin), TGF-beta 2, Fibrillin 1, Collagen XII, COL1A2, LAMC2, Maspin, Tissue kallikreins, Gremlin, Laminin 5, Nidogen, Osteonectin, ELF3, CTGF, MyHC, Lysyl oxidase, PKC, TGF-beta, HAS2, Fibrillin, COL5A1, MMP-2, LAMB3, WNT, NPNT, Collagen III, Collagen IV, HAI-1, IGFBP7/8 |
| extracellular structure organization | 414 | 2.223E−22 | 2.676E−19 | 43 | RECK, FGF2, LEKTI, COL5A2, LAMA4, ITGB6, HAS, P3H2, PAI1, COL6A1, Collagen V, OSF-2, COL4A1, GLT25D2, LAMA3 (Epiligrin), TGF-beta 2, Fibrillin 1, Collagen XII, COL1A2, LAMC2, Maspin, Tissue kallikreins, Gremlin, Laminin 5, Nidogen, Osteonectin, ELF3, CTGF, MyHC, Lysyl oxidase, PKC, TGF-beta, HAS2, Fibrillin, COL5A1, MMP-2, LAMB3, WNT, NPNT, Collagen III, Collagen IV, HAI-1, IGFBP7/8 |
| system development | 4665 | 1.030E−19 | 9.920E−17 | 150 | ELF5, RECK, Tubby, FGF2, LEKTI, COL5A2, LAMA4, FLRT2, SPRR1A, p38 MAPK, Syk, N-chimaerin, IRF6, MR-GEF, CARP, Cx30, Keratin 19, BDNF, TTLL7, Plastin, HAS, Ankyrin-G, HEG1, Beta-fodrin, PAI1, COL6A1, PLA2, Collagen V, OSF-2, G-protein beta, Basonuclin-2, FAM101B, COL4A1, Sciellin, DAB2, CDH1, MAP7(EMAP115), FOG2, Galectin-1, Keratin 16, Pitx3, CCL2, Olfactory receptor, FHL1 (SLIM1), PGAR, CD24, Galpha(q)-specific peptide GPCRs, C1s, Zac1, UCHL1, FGF5, N-cadherin, TAJ(TNFRSF19), Caspr2, Prostasin, DYNLL, PDE, R-cadherin, LAMA3 (Epiligrin), E-cadherin, DKK3, TGF-beta 2, Fibrillin 1, Collagen XII, COL1A2, SPRR1B, GCNT3, SPRR3, LAMC2, SPTBN(spectrin1-4), PLA2G10, DSPP, MAP-1B, Maspin, PPL(periplakin), Tissue kallikreins, TCF7L2 (TCF4), OVOL2, Gremlin, ZCCHC24, Laminin 5, G-protein beta/gamma, Myoglobin, |

TABLE 12A-continued

EMT GO Processes

| Processes | Total | p-value | FDR | In Data | Network Objects from Active Data |
|---|---|---|---|---|---|
| | | | | | PMP22, Nidogen, RHG7, FGFR1, Neuregulin 1, Osteonectin, Vimentin, BVES, ELF3, CTGF, ADAM-TS1, Serglycin, UFO, EPB41L5, MyHC, Lysyl oxidase, PKC, Aquaporin 3, Claudin-11, Tcf(Lef), BLNK, CRMP4, SIP1 (ZFHX1B), IGFBP7, G-protein gamma, Ankyrin-B, TCF8, TUB, TGF-beta, HAS2, FA2H, Neurotractin, Kallikrein 5, Fibrillin, Cadherin 11, CCL13, DFNA5, PKC-mu, COL5A1, Kallikrein 8, GRHL2, Necdin, CAP2, MMP-2, LAMB3, MYH14, WNT5B, Galpha(t)-specific GPCRs, Keratin 5, Kallikrein 3 (PSA), ITF2, POU2F3, WNT, FGF13, ADAM23, NPNT, Kallikrein 6 (Neurosin), Collagen III, FNBP1, Collagen IV, HAI-1, ErbB3, IGFBP7/8, M-Ras, S100B, Desmoplakin, JAM3 |
| developmental process | 5978 | 4.175E−19 | 3.350E−16 | 174 | ELF5, ESE3, RECK, Tubby, FGF2, LEKTI, COL5A2, ATR/TEM8, LAMA4, FLRT2, SPRR1A, p38 MAPK, Syk, N-chimaerin, IRF6, MR-GEF, ITGB6, CARP, Cx30, Keratin 19, BDNF, TTLL7, Plastin, EDIL3, HAS, Ankyrin-G, Angiopoietin-like 2, HEG1, Beta-fodrin, MBNL3, PAI1, COL6A1, PLA2, Collagen V, OSF-2, G-protein beta, Basonuclin-2, PRR15, FALP, FAM101B, COL4A1, Sciellin, DAB2, CDH1, MAP7(EMAP115), FOG2, Galectin-1, PAPP-A, Keratin 16, Pitx3, CCL2, Olfactory receptor, FHL1 (SLIM1), PGAR, DMKN, PAR1, CD24, Galpha(q)-specific peptide GPCRs, C1s, Zac1, UCHL1, FGF5, N-cadherin, TAJ(TNFRSF19), Desmocollin 3, Caspr2, Prostasin, DYNLL, PDE, R-cadherin, LAMA3 (Epiligrin), E-cadherin, DKK3, TGF-beta 2, HOOK1, Fibrillin 1, Collagen XII, COL1A2, SPRR1B, GCNT3, SPRR3, LAMC2, SPTBN(spectrin1-4), PLA2G10, DSPP, STEAP4, MAP-1B, Chk2, Maspin, PPL(periplakin), Tissue kallikreins, TCF7L2 (TCF4), OVOL2, Gremlin, ZCCHC24, DLC1 (Dynein LC8a), Laminin 5, G-protein beta/gamma, Myoglobin, PMP22, Nidogen, RHG7, FGFR1, BICC1, LyGDI, Neuregulin 1, AP-1 mu subunits, TFCP2L2, Osteonectin, Vimentin, BVES, ELF3, CTGF, ADAM-TS1, Serglycin, UFO, EPB41L5, MyHC, Lysyl oxidase, PKC, Aquaporin 3, Claudin-11, Tcf(Lef), BLNK, CRMP4, SIP1 (ZFHX1B), IGFBP7, G-protein gamma, Ankyrin-B, LAF4, TCF8, TUB, TGF-beta, HAS2, FA2H, Neurotractin, Kallikrein 5, Fibrillin, Cadherin 11, CCL13, DFNA5, PKC-mu, M-cadherin, CLIP3, COL5A1, Kallikrein 8, GRHL2, Necdin, CAP2, MMP-2, LAMB3, MYH14, WNT5B, Galpha(t)-specific GPCRs, Keratin 5, Kallikrein 3 (PSA), ITF2, POU2F3, WNT, FGF13, ADAM23, NPNT, Kallikrein 6 (Neurosin), Collagen III, FNBP1, RBM24, Collagen IV, HAI-1, ErbB3, IGFBP7/8, M-Ras, S100B, Desmoplakin, JAM3 |
| multicellular organismal development | 5406 | 1.414E−18 | 9.694E−16 | 162 | ELF5, ESE3, RECK, Tubby, FGF2, LEKTI, COL5A2, LAMA4, FLRT2, SPRR1A, p38 MAPK, Syk, N-chimaerin, IRF6, MR-GEF, ITGB6, CARP, Cx30, Keratin 19, BDNF, TTLL7, Plastin, EDIL3, HAS, Ankyrin-G, Angiopoietin-like 2, HEG1, Beta-fodrin, MBNL3, PAI1, COL6A1, PLA2, Collagen V, OSF-2, G-protein beta, Basonuclin-2, PRR15, FAM101B, COL4A1, Sciellin, DAB2, CDH1, MAP7(EMAP115), FOG2, Galectin-1, Keratin 16, Pitx3, CCL2, Olfactory receptor, FHL1 (SLIM1), PGAR, CD24, Galpha(q)-specific peptide GPCRs, C1s, Zac1, UCHL1, FGF5, N-cadherin, TAJ(TNFRSF19), Desmocollin 3, |

TABLE 12A-continued

EMT GO Processes

| Processes | Total | p-value | FDR | In Data | Network Objects from Active Data |
|---|---|---|---|---|---|
| | | | | | Caspr2, Prostasin, DYNLL, PDE, R-cadherin, LAMA3 (Epiligrin), E-cadherin, DKK3, TGF-beta 2, HOOK1, Fibrillin 1, Collagen XII, COL1A2, SPRR1B, GCNT3, SPRR3, LAMC2, SPTBN(spectrin1-4), PLA2G10, DSPP, MAP-1B, Maspin, PPL(periplakin), Tissue kallikreins, TCF7L2 (TCF4), OVOL2, Gremlin, ZCCHC24, Laminin 5, G-protein beta/gamma, Myoglobin, PMP22, Nidogen, RHG7, FGFR1, BICC1, LyGDI, Neuregulin 1, TFCP2L2, Osteonectin, Vimentin, BVES, ELF3, CTGF, ADAM-TS1, Serglycin, UFO, EPB41L5, MyHC, Lysyl oxidase, PKC, Aquaporin 3, Claudin-11, Tcf(Lef), BLNK, CRMP4, SIP1 (ZFHX1B), IGFBP7, G-protein gamma, Ankyrin-B, LAF4, TCF8, TUB, TGF-beta, HAS2, FA2H, Neurotractin, Kallikrein 5, Fibrillin, Cadherin 11, CCL13, DFNA5, PKC-mu, COL5A1, Kallikrein 8, GRHL2, Necdin, CAP2, MMP-2, LAMB3, MYH14, WNT5B, Galpha(t)-specific GPCRs, Keratin 5, Kallikrein 3 (PSA), ITF2, POU2F3, WNT, FGF13, ADAM23, NPNT, Kallikrein 6 (Neurosin), Collagen III, FNBP1, Collagen IV, HAI-1, ErbB3, IGFBP7/8, M-Ras, S100B, Desmoplakin, JAM3 |
| anatomical structure morphogenesis | 2492 | 1.611E-18 | 9.694E-16 | 100 | Tubby, FGF2, COL5A2, ATR/TEM8, FLRT2, p38 MAPK, Syk, N-chimaerin, CARP, Cx30, Keratin 19, BDNF, HAS, Ankyrin-G, HEG1, Beta-fodrin, PAI1, COL6A1, PLA2, Collagen V, Basonuclin-2, FAM101B, COL4A1, DAB2, MAP7(EMAP115), FOG2, Pitx3, CCL2, Olfactory receptor, FHL1 (SLIM1), PGAR, PAR1, CD24, Galpha(q)-specific peptide GPCRs, UCHL1, N-cadherin, DYNLL, PDE, R-cadherin, E-cadherin, DKK3, TGF-beta 2, COL1A2, GCNT3, SPTBN(spectrin1-4), PLA2G10, DSPP, MAP-1B, Maspin, Tissue kallikreins, TCF7L2 (TCF4), OVOL2, Gremlin, DLC1 (Dynein LC8a), G-protein beta/gamma, PMP22, RHG7, FGFR1, Neuregulin 1, BVES, ELF3, CTGF, ADAM-TS1, UFO, EPB41L5, MyHC, PKC, Aquaporin 3, Tcf(Lef), CRMP4, SIP1 (ZFHX1B), G-protein gamma, Ankyrin-B, LAF4, TCF8, TGF-beta, HAS2, Fibrillin, Cadherin 11, CCL13, PKC-mu, COL5A1, Kallikrein 8, GRHL2, Necdin, CAP2, MMP-2, MYH14, WNT5B, Kallikrein 3 (PSA), WNT, NPNT, Collagen III, Collagen IV, HAI-1, ErbB3, IGFBP7/8, S100B, Desmoplakin, JAM3 |
| anatomical structure development | 5314 | 1.296E-17 | 6.934E-15 | 158 | ELF5, ESE3, RECK, Tubby, FGF2, LEKTI, COL5A2, ATR/TEM8, LAMA4, FLRT2, SPRR1A, p38 MAPK, Syk, N-chimaerin, IRF6, MR-GEF, CARP, Cx30, Keratin 19, BDNF, TTLL7, Plastin, HAS, Ankyrin-G, HEG1, Beta-fodrin, PAI1, COL6A1, PLA2, Collagen V, OSF-2, G-protein beta, Basonuclin-2, FAM101B, COL4A1, Sciellin, DAB2, CDH1, MAP7(EMAP115), FOG2, Galectin-1, Keratin 16, Pitx3, CCL2, Olfactory receptor, FHL1 (SLIM1), PGAR, PAR1, CD24, Galpha(q)-specific peptide GPCRs, C1s, Zac1, UCHL1, FGF5, N-cadherin, TAJ(TNFRSF19), Desmocollin 3, Caspr2, Prostasin, DYNLL, PDE, R-cadherin, LAMA3 (Epiligrin), E-cadherin, DKK3, TGF-beta 2, HOOK1, Fibrillin 1, Collagen XII, COL1A2, SPRR1B, GCNT3, SPRR3, LAMC2, SPTBN(spectrin1-4), PLA2G10, DSPP, MAP-1B, Maspin, PPL(periplakin), Tissue kallikreins, TCF7L2 (TCF4), OVOL2, Gremlin, ZCCHC24, DLC1 (Dynein LC8a), Laminin 5, G-protein beta/gamma, Myoglobin, |

TABLE 12A-continued

| Processes | Total | p-value | FDR | In Data | Network Objects from Active Data |
|---|---|---|---|---|---|
| | | | | | PMP22, Nidogen, RHG7, FGFR1, Neuregulin 1, Osteonectin, Vimentin, BVES, ELF3, CTGF, ADAM-TS1, Serglycin, UFO, EPB41L5, MyHC, Lysyl oxidase, PKC, Aquaporin 3, Claudin-11, Tcf(Lef), BLNK, CRMP4, SIP1 (ZFHX1B), IGFBP7, G-protein gamma, Ankyrin-B, LAF4, TCF8, TUB, TGF-beta, HAS2, FA2H, Neurotractin, Kallikrein 5, Fibrillin, Cadherin 11, CCL13, DFNA5, PKC-mu, M-cadherin, COL5A1, Kallikrein 8, GRHL2, Necdin, CAP2, MMP-2, LAMB3, MYH14, WNT5B, Galpha(t)-specific GPCRs, Keratin 5, Kallikrein 3 (PSA), ITF2, POU2F3, WNT, FGF13, ADAM23, NPNT, Kallikrein 6 (Neurosin), Collagen III, FNBP1, Collagen IV, HAI-1, ErbB3, IGFBP7/8, M-Ras, S100B, Desmoplakin, JAM3 |
| cell differentiation | 3602 | 1.740E−17 | 8.378E−15 | 123 | ELF5, ESE3, Tubby, FGF2, LEKTI, COL5A2, ATR/TEM8, LAMA4, FLRT2, SPRR1A, p38 MAPK, Syk, N-chimaerin, IRF6, CARP, Keratin 19, BDNF, TTLL7, HAS, Ankyrin-G, HEG1, Beta-fodrin, COL6A1, PLA2, Collagen V, FALP, FAM101B, COL4A1, Sciellin, DAB2, CDH1, MAP7(EMAP115), FOG2, Galectin-1, PAPP-A, Pitx3, CCL2, Olfactory receptor, FHL1 (SLIM1), PGAR, DMKN, CD24, Galpha(q)-specific peptide GPCRs, C1s, Zac1, UCHL1, FGF5, N-cadherin, Caspr2, DYNLL, PDE, R-cadherin, E-cadherin, TGF-beta 2, HOOK1, SPRR1B, SPRR3, SPTBN(spectrin1-4), PLA2G10, DSPP, STEAP4, MAP-1B, PPL(periplakin), Tissue kallikreins, TCF7L2 (TCF4), OVOL2, Gremlin, ZCCHC24, Laminin 5, G-protein beta/gamma, Myoglobin, PMP22, FGFR1, Neuregulin 1, AP-1 mu subunits, Vimentin, BVES, ELF3, CTGF, UFO, EPB41L5, MyHC, PKC, Tcf(Lef), BLNK, CRMP4, SIP1 (ZFHX1B), G-protein gamma, Ankyrin-B, TCF8, TGF-beta, HAS2, FA2H, Neurotractin, Cadherin 11, CCL13, DFNA5, PKC-mu, M-cadherin, CLIP3, COL5A1, Kallikrein 8, Necdin, CAP2, MMP-2, LAMB3, MYH14, WNT5B, ITF2, POU2F3, WNT, FGF13, NPNT, Kallikrein 6 (Neurosin), Collagen III, FNBP1, RBM24, Collagen IV, ErbB3, IGFBP7/8, S100B, Desmoplakin, JAM3 |
| tissue development | 1879 | 4.429E−17 | 1.938E−14 | 82 | ELF5, ESE3, Tubby, FGF2, LEKTI, SPRR1A, p38 MAPK, IRF6, CARP, HAS, HEG1, PAI1, PLA2, Collagen V, OSF-2, Basonuclin-2, FAM101B, COL4A1, Sciellin, DAB2, CDH1, MAP7(EMAP115), FOG2, Keratin 16, Pitx3, CD24, Galpha(q)-specific peptide GPCRs, Zac1, TAJ(TNFRSF19), Prostasin, PDE, LAMA3 (Epiligrin), E-cadherin, TGF-beta 2, HOOK1, SPRR1B, GCNT3, SPRR3, LAMC2, DSPP, Maspin, PPL(periplakin), Tissue kallikreins, TCF7L2 (TCF4), OVOL2, Gremlin, Laminin 5, RHG7, FGFR1, Neuregulin 1, Vimentin, ELF3, CTGF, Serglycin, UFO, EPB41L5, MyHC, PKC, Tcf(Lef), SIP1 (ZFHX1B), TCF8, TGF-beta, HAS2, FA2H, Kallikrein 5, COL5A1, GRHL2, MMP-2, LAMB3, WNT5B, Keratin 5, Kallikrein 3 (PSA), POU2F3, WNT, NPNT, Kallikrein 6 (Neurosin), Collagen IV, HAI-1, ErbB3, IGFBP7/8, Desmoplakin, JAM3 |
| single-organism process | 13941 | 1.487E−16 | 5.968E−14 | 290 | ELF5, ESE3, AKAP12, RECK, Tubby, FGF2, IL13RA2, LEKTI, COL5A2, PNMA2, ATR/TEM8, P-cadherin, BCMP84, LAMA4, CDS1, FLRT2, SPRR1A, INPP4B, p38 MAPK, Syk, Galpha(i)-specific prostanoid GPCRs, ATP8B2, N-chimaerin, TBXA2R, IRF6, Tubulin alpha 1A, MR-GEF, ITGB6, CARP, Cx30, Keratin 19, UBAP2L, FUT3, |

TABLE 12A-continued

EMT GO Processes

| Processes | Total | p-value | FDR | In Data | Network Objects from Active Data |
|---|---|---|---|---|---|
| | | | | | Calgizzarin, BDNF, TTLL7, Plastin, EDIL3, HAS, PTGIS, Ankyrin-G, NEPH1, Cingulin, Angiopoietin-like 2, P3H2, HEG1, Beta-fodrin, MBNL3, PAI1, COL6A1, Nectin-4, STX19, PLA2, Collagen V, MATE1, Calgranulin A, OSF-2, PPP1R14C, GPX2, GLUT3, EMP3, Synaptotagmin VII, G-protein beta, Basonuclin-2, PRR15, GPR87, DIO2, FALP, FAM101B, TMSL8, CPA4, FGD2, COL4A1, TMC4, Matriptase, MARVELD3, Calprotectin (S100A8/A9) complex, Sciellin, CYBRD1, CNK1, BSPRY, DAB2, CDH1, MAP7(EMAP115), FOG2, Galectin-1, PAPP-A, Keratin 16, Pitx3, GLT25D2, SYDE1, CCL2, SRPX, Olfactory receptor, FHL1 (SLIM1), PGAR, Galpha(q)-specific prostanoid GPCRs, KIAA1043, AKS, NAP1L3, DMKN, LIPE, Annexin VI, PAR1, MAPBPIP, CD24, Galpha(q)-specific peptide GPCRs, C1s, Zac1, UCHL1, FGF5, Tubulin alpha, Synaptotagmin, IL1RN, BPGAP1, CDP-diacylglycerol synthase, N-cadherin, TAJ(TNFRSF19), Desmocollin 3, Caspr2, PRR5, Prostasin, DYNLL, PDE, TOX3, Annexin IX, R-cadherin, LAMA3 (Epiligrin), E-cadherin, FAT4, DKK3, DOCK10, PRR5-ARHGAP8, Claudin-7, TGF-beta 2, HOOK1, Myosin Vb, PTX3, Fibrillin 1, Collagen XII, COL1A2, SPRR1B, B7-H4, GCNT3, SPRR3, LAMC2, Tricellulin, G-protein beta-4, SPTBN(spectrin1-4), PLA2G10, DSPP, STEAP4, MAP-1B, Chk2, Factor H, Maspin, PPL(periplakin), Tissue kallikreins, TCF7L2 (TCF4), OVOL2, Kallikrein 1, RASGEF1B, Gremlin, NSP1, ZCCHC24, DLC1 (Dynein LC8a), EPDR1, ATP2C2, Laminin 5, SHPS-1, G-protein beta/gamma, Gpc6, Myoglobin, Plakophilin 3, PMP22, Nidogen, RHG7, FGFR1, TRPA1, BICC1, Rab-25, HBP17, LyGDI, AOX1, Neuregulin 1, AP-1 mu subunits, TFCP2L2, SUSD5, Osteonectin, Vimentin, BVES, ELF3, CTGF, ADAM-TS1, Serglycin, ATP8B3, UFO, EPB41L5, p38delta (MAPK13), MyHC, Lysyl oxidase, Claudin-4, Calgranulin B, PKC, Aquaporin 3, FR-alpha, GPR176, Claudin-11, Tcf(Lef), WaspIP, MPP7, BLNK, CRMP4, SIP1 (ZFHX1B), IGFBP7, G-protein gamma, Ankyrin-B, LAF4, PDE7B, G-protein gamma 11, TCF8, TUB, PAK6, TGF-beta, HAS2, alpha-ENaC, FA2H, ADAM28, Neurotractin, Kallikrein 5, Fibrillin, AP1S2, Cadherin 11, CCL13, DFNA5, NGAL, PKC-mu, M-cadherin, GPR110, CLIP3, COL5A1, Kallikrein 8, GRHL2, Necdin, CAP2, MMP-2, LAMB3, SLC6A14, PTAFR, FSTL1, Aggrecanase-2, AP1M2, CEACAM6, WFDC2, MYH14, WNT5B, AP-1 sigma subunits, Galpha(t)-specific GPCRs, Keratin 5, Kallikrein 3 (PSA), ITF2, RASEF, POU2F3, WNT, F16P, TMC5, DAPP1, DSC2, Kallikrein 10 (KLK10), FGF13, ADAM23, NPNT, Kallikrein 6 (Neurosin), FXYD3, Collagen III, FNBP1, RBM24, ELP70, Collagen IV, ChAF1 subunit B, HAI-1, ErbB3, HAI-2, IGFBP7/8, M-Ras, Mucin 20, S100B, Desmoplakin, S100P, JAM3 |
| cellular developmental process | 3745 | 3.888E−16 | 1.440E−13 | 123 | ELF5, ESE3, Tubby, FGF2, LEKTI, COL5A2, ATR/TEM8, LAMA4, FLRT2, SPRR1A, p38 MAPK, Syk, N-chimaerin, IRF6, CARP, Keratin 19, BDNF, TTLL7, HAS, Ankyrin-G, HEG1, Beta-fodrin, COL6A1, PLA2, Collagen V, FALP, FAM101B, COL4A1, Sciellin, DAB2, CDH1, MAP7(EMAP115), FOG2, Galectin-1, PAPP-A, Pitx3, CCL2, Olfactory |

TABLE 12A-continued

EMT GO Processes

| Processes | Total | p-value | FDR | In Data | Network Objects from Active Data |
|---|---|---|---|---|---|
| | | | | | receptor, FHL1 (SLIM1), PGAR, DMKN, CD24, Galpha(q)-specific peptide GPCRs, C1s, Zac1, UCHL1, FGF5, N-cadherin, Caspr2, DYNLL, PDE, R-cadherin, E-cadherin, TGF-beta 2, HOOK1, SPRR1B, SPRR3, SPTBN(spectrin1-4), PLA2G10, DSPP, STEAP4, MAP-1B, PPL(periplakin), Tissue kallikreins, TCF7L2 (TCF4), OVOL2, Gremlin, ZCCHC24, Laminin 5, G-protein beta/gamma, Myoglobin, PMP22, FGFR1, Neuregulin 1, AP-1 mu subunits, Vimentin, BVES, ELF3, CTGF, UFO, EPB41L5, MyHC, PKC, Tcf(Lef), BLNK, CRMP4, SIP1 (ZFHX1B), G-protein gamma, Ankyrin-B, TCF8, TGF-beta, HAS2, FA2H, Neurotractin, Cadherin 11, CCL13, DFNA5, PKC-mu, M-cadherin, CLIP3, COL5A1, Kallikrein 8, Necdin, CAP2, MMP-2, LAMB3, MYH14, WNT5B, ITF2, POU2F3, WNT, FGF13, NPNT, Kallikrein 6 (Neurosin), Collagen III, FNBP1, RBM24, Collagen IV, ErbB3, IGFBP7/8, S100B, Desmoplakin, JAM3 |
| response to wounding | 1415 | 1.288E−15 | 4.429E−13 | 67 | FGF2, P-cadherin, p38 MAPK, Syk, Galpha(i)-specific prostanoid GPCRs, TBXA2R, ITGB6, BDNF, Plastin, PAI1, PLA2, Collagen V, Calgranulin A, Synaptotagmin VII, G-protein beta, Calprotectin (S100A8/A9) complex, FOG2, Galectin-1, CCL2, Galpha(q)-specific prostanoid GPCRs, PAR1, CD24, Galpha(q)-specific peptide GPCRs, Tubulin alpha, Synaptotagmin, IL1RN, PDE, TGF-beta 2, PTX3, COL1A2, SPRR3, MAP-1B, Tissue kallikreins, SHPS-1, G-protein beta/gamma, AOX1, Neuregulin 1, Osteonectin, Vimentin, ELF3, CTGF, Serglycin, UFO, MyHC, Lysyl oxidase, Calgranulin B, PKC, BLNK, CRMP4, G-protein gamma, TGF-beta, CCL13, PKC-mu, COL5A1, Kallikrein 8, MMP-2, PTAFR, WNT5B, Kallikrein 3 (PSA), POU2F3, WNT, Kallikrein 6 (Neurosin), Collagen III, ErbB3, IGFBP7/8, Desmoplakin, JAM3 |
| skin development | 406 | 4.949E−15 | 1.588E−12 | 34 | LEKTI, COL5A2, SPRR1A, IRF6, Collagen V, Sciellin, Keratin 16, TAJ(TNFRSF19), Prostasin, LAMA3 (Epilgrin), TGF-beta 2, COL1A2, SPRR1B, SPRR3, LAMC2, PPL(periplakin), Tissue kallikreins, TCF7L2 (TCF4), Laminin 5, FGFR1, ELF3, CTGF, Tcf(Lef), TGF-beta, FA2H, Kallikrein 5, COL5A1, LAMB3, Keratin 5, POU2F3, WNT, Collagen III, IGFBP7/8, Desmoplakin |
| regulation of cellular component organization | 1910 | 1.227E−14 | 3.692E−12 | 78 | Tubby, FGF2, p38 MAPK, Syk, N-chimaerin, CARP, BDNF, HAS, Ankyrin-G, NEPH1, Beta-fodrin, PAI1, PLA2, Collagen V, Calgranulin A, TMSL8, FGD2, Calprotectin (S100A8/A9) complex, DAB2, Galectin-1, CCL2, FHL1 (SLIM1), CD24, Galpha(q)-specific peptide GPCRs, Synaptotagmin, N-cadherin, DYNLL, R-cadherin, TGF-beta 2, PTX3, FAM110C, SPRR1B, SPRR3, SPTBN(spectrin1-4), MAP-1B, Tissue kallikreins, TCF7L2 (TCF4), Gremlin, DLC1 (Dynein LC8a), SHPS-1, G-protein beta/gamma, PRSS11 (HtrA1), PMP22, RHG7, FGFR1, Neuregulin 1, Vimentin, BVES, CTGF, EPB41L5, MyHC, Nelin, Calgranulin B, PKC, Tcf(Lef), MPP7, CRMP4, IGFBP7, G-protein gamma, TUB, TGF-beta, Neurotractin, CCL13, NGAL, PKC-mu, CLIP3, COL5A1, Kallikrein 8, Necdin, MYH14, WNT, F16P, FGF13, SH3YL1, Kallikrein 6 (Neurosin), IGFBP7/8, S100B, JAM3 |

TABLE 12A-continued

| | | EMT GO Processes | | | |
|---|---|---|---|---|---|
| Processes | Total | p-value | FDR | In Data | Network Objects from Active Data |
| cell morphogenesis involved in differentiation | 792 | 1.361E−14 | 3.854E−12 | 47 | COL5A2, ATR/TEM8, FLRT2, N-chimaerin, BDNF, HAS, Ankyrin-G, HEG1, Beta-fodrin, COL6A1, PLA2, Collagen V, FAM101B, COL4A1, DAB2, Olfactory receptor, CD24, Galpha(q)-specific peptide GPCRs, UCHL1, R-cadherin, E-cadherin, TGF-beta 2, SPTBN(spectrin1-4), PLA2G10, MAP-1B, Gremlin, FGFR1, BVES, UFO, EPB41L5, MyHC, PKC, Tcf(Lef), CRMP4, Ankyrin-B, TGF-beta, HAS2, Cadherin 11, COL5A1, Necdin, CAP2, MYH14, WNT, Collagen III, Collagen IV, ErbB3, S100B |
| cell-cell adhesion | 486 | 3.259E−14 | 8.718E−12 | 36 | P-cadherin, p38 MAPK, Syk, NEPH1, Nectin-4, Calgranulin A, Calprotectin (S100A8/A9) complex, Galectin-1, CD24, N-cadherin, Desmocollin 3, Annexin IX, R-cadherin, LAMA3 (Epiligrin), E-cadherin, FAT4, Claudin-7, TGF-beta 2, Laminin 5, BVES, CTGF, MyHC, Claudin-4, Calgranulin B, Claudin-11, Tcf(Lef), TGF-beta, Neurotractin, Cadherin 11, M-cadherin, WNT, DSC2, NPNT, IGFBP7/8, Desmoplakin, JAM3 |
| single-organism cellular process | 12767 | 8.058E−14 | 2.042E−11 | 269 | ELF5, ESE3, AKAP12, RECK, Tubby, FGF2, IL13RA2, LEKTI, COL5A2, PNMA2, ATR/TEM8, P-cadherin, BCMP84, LAMA4, CDS1, FLRT2, SPRR1A, INPP4B, p38 MAPK, Syk, Galpha(i)-specific prostanoid GPCRs, ATP8B2, N-chimaerin, TBXA2R, IRF6, Tubulin alpha 1A, MR-GEF, ITGB6, CARP, Cx30, Keratin 19, UBAP2L, FUT3, Calgizzarin, BDNF, TTLL7, Plastin, EDIL3, HAS, PTGIS, Ankyrin-G, NEPH1, Cingulin, P3H2, HEG1, Beta-fodrin, PAI1, COL6A1, Nectin-4, STX19, PLA2, Collagen V, MATE1, Calgranulin A, OSF-2, PPP1R14C, GLUT3, EMP3, G-protein beta, GPR87, DIO2, FALP, FAM101B, TMSL8, CPA4, FGD2, COL4A1, Matriptase, MARVELD3, Calprotectin (S100A8/A9) complex, Sciellin, CYBRD1, CNK1, DAB2, CDH1, MAP7(EMAP115), FOG2, Galectin-1, PAPP-A, Keratin 16, Pitx3, GLT25D2, SYDE1, CCL2, SRPX, Olfactory receptor, FHL1 (SLIM1), PGAR, Galpha(q)-specific prostanoid GPCRs, KIAA1043, AK5, NAP1L3, DMKN, PAR1, MAPBPIP, CD24, Galpha(q)-specific peptide GPCRs, C1s, Zac1, UCHL1, FGF5, Tubulin alpha, Synaptotagmin, IL1RN, BPGAP1, CDP-diacylglycerol synthase, N-cadherin, TAJ(TNFRSF19), Desmocollin 3, Caspr2, PRR5, DYNLL, PDE, TOX3, Annexin IX, R-cadherin, LAMA3 (Epiligrin), E-cadherin, FAT4, DKK3, DOCK10, PRR5-ARHGAP8, Claudin-7, TGF-beta 2, HOOK1, Myosin Vb, Fibrillin 1, Collagen XII, COL1A2, SPRR1B, B7-H4, SPRR3, LAMC2, Tricellulin, G-protein beta-4, SPTBN(spectrin1-4), PLA2G10, DSPP, STEAP4, MAP-1B, Chk2, Factor H, Maspin, PPL(periplakin), Tissue kallikreins, TCF7L2 (TCF4), OVOL2, Kallikrein 1, RASGEF1B, Gremlin, NSP1, ZCCHC24, DLC1 (Dynein LC8a), EPDR1, ATP2C2, Laminin 5, SHPS-1, G-protein beta/gamma, Gpc6, Myoglobin, Plakophilin 3, PMP22, Nidogen, RHG7, FGFR1, TRPA1, Rab-25, HBP17, LyGDI, AOX1, Neuregulin 1, AP-1 mu subunits, SUSD5, Osteonectin, Vimentin, BVES, ELF3, CTGF, ADAM-TS1, Serglycin, ATP8B3, UFO, EPB41L5, p38delta (MAPK13), MyHC, Lysyl oxidase, Claudin-4, Calgranulin B, PKC, Aquaporin 3, FR-alpha, GPR176, Claudin-11, Tcf(Lef), WaspIP, MPP7, BLNK, CRMP4, SIP1 (ZFHX1B), IGFBP7, G-protein gamma, Ankyrin-B, |

TABLE 12A-continued

| | | EMT GO Processes | | | |
|---|---|---|---|---|---|
| Processes | Total | p-value | FDR | In Data | Network Objects from Active Data |
| | | | | | PDE7B, G-protein gamma 11, TCF8, TUB, PAK6, TGF-beta, HAS2, alpha-ENaC, FA2H, ADAM28, Neurotractin, Fibrillin, AP1S2, Cadherin 11, CCL13, DFNA5, NGAL, PKC-mu, M-cadherin, GPR110, CLIP3, COL5A1, Kallikrein 8, Necdin, CAP2, MMP-2, LAMB3, SLC6A14, PTAFR, FSTL1, Aggrecanase-2, AP1M2, CEACAM6, MYH14, WNT5B, AP-1 sigma subunits, Galpha(t)-specific GPCRs, Keratin 5, Kallikrein 3 (PSA), ITF2, RASEF, POU2F3, WNT, F16P, DAPP1, DSC2, Kallikrein 10 (KLK10), FGF13, ADAM23, NPNT, Kallikrein 6 (Neurosin), FXYD3, Collagen III, FNBP1, RBM24, Collagen IV, ChAF1 subunit B, HAI-1, ErbB3, HAI-2, IGFBP7/8, M-Ras, Mucin 20, S100B, Desmoplakin, S100P, JAM3 |
| single-multicellular organism process | 7762 | 1.108E−13 | 2.569E−11 | 192 | ELF5, ESE3, RECK, Tubby, FGF2, LEKTI, COL5A2, P-cadherin, LAMA4, FLRT2, SPRR1A, p38 MAPK, Syk, Galpha(i)-specific prostanoid GPCRs, N-chimaerin, TBXA2R, IRF6, MR-GEF, ITGB6, CARP, Cx30, Keratin 19, UBAP2L, FUT3, BDNF, TTLL7, Plastin, EDIL3, HAS, Ankyrin-G, NEPH1, Angiopoietin-like 2, P3H2, HEG1, Beta-fodrin, MBNL3, PAI1, COL6A1, PLA2, Collagen V, Calgranulin A, OSF-2, GPX2, G-protein beta, Basonuclin-2, PRR15, FAM101B, COL4A1, Calprotectin (S100A8/A9) complex, Sciellin, DAB2, CDH1, MAP7(EMAP115), FOG2, Galectin-1, Keratin 16, Pitx3, CCL2, Olfactory receptor, FHL1 (SLIM1), PGAR, Galpha(q)-specific prostanoid GPCRs, LIPE, PAR1, CD24, Galpha(q)-specific peptide GPCRs, C1s, Zac1, UCHL1, FGF5, Tubulin alpha, Synaptotagmin, IL1RN, N-cadherin, TAJ(TNFRSF19), Desmocollin 3, Caspr2, Prostasin, DYNLL, PDE, R-cadherin, LAMA3 (Epiligrin), E-cadherin, DKK3, TGF-beta 2, HOOK1, Fibrillin 1, Collagen XII, COL1A2, SPRR1B, B7-H4, GCNT3, SPRR3, LAMC2, Tricellulin, SPTBN(spectrin1-4), PLA2G10, DSPP, MAP-1B, Maspin, PPL(periplakin), Tissue kallikreins, TCF7L2 (TCF4), OVOL2, Gremlin, ZCCHC24, DLC1 (Dynein LC8a), Laminin 5, SHPS-1, G-protein beta/gamma, Myoglobin, PMP22, Nidogen, RHG7, FGFR1, TRPA1, BICC1, LyGDI, Neuregulin 1, TFCP2L2, Osteonectin, Vimentin, BVES, ELF3, CTGF, ADAM-TS1, Serglycin, ATP8B3, UFO, EPB41L5, MyHC, Lysyl oxidase, Calgranulin B, PKC, Aquaporin 3, GPR176, Claudin-11, Tcf(Lef), BLNK, CRMP4, SIP1 (ZFHX1B), IGFBP7, G-protein gamma, Ankyrin-B, LAF4, PDE7B, TCF8, TUB, TGF-beta, HAS2, alpha-ENaC, FA2H, Neurotractin, Kallikrein 5, Fibrillin, Cadherin 11, CCL13, DFNA5, PKC-mu, COL5A1, Kallikrein 8, GRHL2, Necdin, CAP2, MMP-2, LAMB3, PTAFR, MYH14, WNT5B, Galpha(t)-specific GPCRs, Keratin 5, Kallikrein 3 (PSA), ITF2, POU2F3, WNT, DSC2, FGF13, ADAM23, NPNT, Kallikrein 6 (Neurosin), Collagen III, FNBP1, ELP70, Collagen IV, HAI-1, ErbB3, IGFBP7/8, M-Ras, S100B, Desmoplakin, S100P, JAM3 |
| multicellular organismal process | 8059 | 1.120E−13 | 2.569E−11 | 197 | ELF5, ESE3, RECK, Tubby, FGF2, LEKTI, COL5A2, P-cadherin, LAMA4, FLRT2, SPRR1A, p38 MAPK, Syk, Galpha(i)-specific prostanoid GPCRs, N-chimaerin, TBXA2R, IRF6, MR-GEF, ITGB6, CARP, Cx30, Keratin 19, UBAP2L, FUT3, Calgizzarin, BDNF, TTLL7, Plastin, EDIL3, HAS, |

TABLE 12A-continued

EMT GO Processes

| Processes | Total | p-value | FDR | In Data | Network Objects from Active Data |
|---|---|---|---|---|---|
| | | | | | Ankyrin-G, NEPH1, Angiopoietin-like 2, P3H2, HEG1, Beta-fodrin, MBNL3, PAI1, COL6A1, PLA2, Collagen V, Calgranulin A, OSF-2, GPX2, G-protein beta, Basonuclin-2, PRR15, FAM101B, COL4A1, Calprotectin (S100A8/A9) complex, Sciellin, DAB2, CDH1, MAP7(EMAP115), FOG2, Galectin-1, PAPP-A, Keratin 16, Pitx3, CCL2, Olfactory receptor, FHL1 (SLIM1), PGAR, Galpha(q)-specific prostanoid GPCRs, LIPE, PAR1, CD24, Galpha(q)-specific peptide GPCRs, C1s, Zac1, UCHL1, FGF5, Tubulin alpha, Synaptotagmin, IL1RN, N-cadherin, TAJ(TNFRSF19), Desmocollin 3, Caspr2, Prostasin, DYNLL, PDE, R-cadherin, LAMA3 (Epiligrin), E-cadherin, DKK3, TGF-beta 2, HOOK1, Fibrillin 1, Collagen XII, COL1A2, SPRR1B, B7-H4, GCNT3, SPRR3, LAMC2, Tricellulin, SPTBN(spectrin1-4), PLA2G10, DSPP, MAP-1B, Maspin, PPL(periplakin), Tissue kallikreins, TCF7L2 (TCF4), OVOL2, Gremlin, ZCCHC24, DLC1 (Dynein LC8a), Laminin 5, SHPS-1, G-protein beta/gamma, Myoglobin, PMP22, Nidogen, RHG7, FGFR1, TRPA1, BICC1, LyGDI, Neuregulin 1, TFCP2L2, Osteonectin, Vimentin, BVES, ELF3, CTGF, ADAM-TS1, Serglycin, ATP8B3, UFO, EPB41L5, MyHC, Lysyl oxidase, Claudin-4, Calgranulin B, PKC, Aquaporin 3, GPR176, Claudin-11, Tcf(Lef), BLNK, CRMP4, SIP1 (ZFHX1B), IGFBP7, G-protein gamma, Ankyrin-B, LAF4, PDE7B, TCF8, TUB, TGF-beta, HAS2, alpha-ENaC, FA2H, ADAM28, Neurotractin, Kallikrein 5, Fibrillin, Cadherin 11, CCL13, DFNA5, PKC-mu, COL5A1, Kallikrein 8, GRHL2, Necdin, CAP2, MMP-2, LAMB3, PTAFR, WFDC2, MYH14, WNT5B, Galpha(t)-specific GPCRs, Keratin 5, Kallikrein 3 (PSA), ITF2, POU2F3, WNT, DSC2, FGF13, ADAM23, NPNT, Kallikrein 6 (Neurosin), Collagen III, FNBP1, ELP70, Collagen IV, HAI-1, ErbB3, IGFBP7/8, M-Ras, S100B, Desmoplakin, S100P, JAM3 |
| cellular component organization | 5002 | 1.297E-13 | 2.839E-11 | 142 | RECK, Tubby, FGF2, LEKTI, COL5A2, ATR/TEM8, P-cadherin, LAMA4, FLRT2, p38 MAPK, N-chimaerin, Tubulin alpha 1A, ITGB6, CARP, Keratin 19, BDNF, Plastin, HAS, Ankyrin-G, NEPH1, P3H2, HEG1, Beta-fodrin, PAI1, COL6A1, Nectin-4, PLA2, Collagen V, OSF-2, Synaptotagmin VII, FAM101B, TMSL8, CPA4, FGD2, COL4A1, MARVELD3, Calprotectin (S100A8/A9) complex, DAB2, CDH1, MAP7(EMAP115), Keratin 16, GLT25D2, CCL2, SRPX, Olfactory receptor, PGAR, KIAA1043, NAP1L3, LIPE, PAR1, CD24, Galpha(q)-specific peptide GPCRs, UCHL1, Tubulin alpha, Synaptotagmin, N-cadherin, Caspr2, PRR5, DYNLL, PDE, R-cadherin, LAMA3 (Epiligrin), E-cadherin, FAT4, TGF-beta 2, HOOK1, Fibrillin 1, Collagen XII, COL1A2, LAMC2, Tricellulin, SPTBN(spectrin1-4), PLA2G10, MAP-1B, Chk2, Maspin, Tissue kallikreins, TCF7L2 (TCF4), Gremlin, DLC1 (Dynein LC8a), Laminin 5, SHPS-1, PMP22, Nidogen, RHG7, FGFR1, Rab-25, LyGDI, Neuregulin 1, AP-1 mu subunits, Osteonectin, Vimentin, BVES, ELF3, CTGF, Serglycin, ATP8B3, UFO, EPB41L5, MyHC, Lysyl oxidase, Calgranulin B, PKC, FR-alpha, Tcf(Lef), WaspIP, MPP7, CRMP4, Ankyrin-B, PAK6, TGF-beta, HAS2, FA2H, Fibrillin, Cadherin 11, CCL13, NGAL, PKC-mu, M-cadherin, COL5A1, Kallikrein 8, Necdin, |

TABLE 12A-continued

| | | EMT GO Processes | | | |
|---|---|---|---|---|---|
| Processes | Total | p-value | FDR | In Data | Network Objects from Active Data |
| | | | | | CAP2, MMP-2, LAMB3, MYH14, Keratin 5, ITF2, WNT, F16P, FGF13, NPNT, Collagen III, Collagen IV, ChAF1 subunit B, HAI-1, ErbB3, IGFBP7/8, M-Ras, Mucin 20, S100B, Desmoplakin |
| cellular component movement | 1526 | 1.610E−13 | 3.371E−11 | 66 | FGF2, COL5A2, FLRT2, p38 MAPK, Syk, N-chimaerin, BDNF, Ankyrin-G, Beta-fodrin, COL6A1, PLA2, Collagen V, Calgranulin A, COL4A1, Matriptase, Calprotectin (S100A8/A9) complex, CCL2, Olfactory receptor, CD24, Galpha(q)-specific peptide GPCRs, UCHL1, N-cadherin, DYNLL, PDE, R-cadherin, TGF-beta 2, COL1A2, SPTBN(spectrin1-4), PLA2G10, MAP-1B, Maspin, OVOL2, Gremlin, DLC1 (Dynein LC8a), SHPS-1, Gpc6, FGFR1, LyGDI, Neuregulin 1, Vimentin, CTGF, UFO, EPB41L5, MyHC, Calgranulin B, PKC, Tcf(Lef), WaspIP, CRMP4, SIP1 (ZFHX1B), Ankyrin-B, TGF-beta, CCL13, COL5A1, Necdin, CAP2, MMP-2, MYH14, WNT, FGF13, Collagen III, Collagen IV, HAI-2, IGFBP7/8, S100P, JAM3 |
| organ development | 3386 | 1.869E−13 | 3.750E−11 | 109 | ELF5, Tubby, FGF2, LEKTI, COL5A2, SPRR1A, p38 MAPK, Syk, IRF6, CARP, Cx30, Keratin 19, BDNF, Plastin, HAS, HEG1, PLA2, Collagen V, G-protein beta, Basonuclin-2, FAM101B, Sciellin, DAB2, CDH1, MAP7(EMAP115), FOG2, Galectin-1, Keratin 16, Pitx3, CCL2, FHL1 (SLIM1), CD24, Galpha(q)-specific peptide GPCRs, Zac1, TAJ(TNFRSF19), Caspr2, Prostasin, PDE, LAMA3 (Epiligrin), E-cadherin, DKK3, TGF-beta 2, Fibrillin 1, COL1A2, SPRR1B, GCNT3, SPRR3, LAMC2, SPTBN(spectrin1-4), DSPP, Maspin, PPL(periplakin), Tissue kallikreins, TCF7L2 (TCF4), OVOL2, Gremlin, Laminin 5, G-protein beta/gamma, Myoglobin, Nidogen, RHG7, FGFR1, Neuregulin 1, Osteonectin, Vimentin, BVES, ELF3, CTGF, ADAM-TS1, Serglycin, UFO, EPB41L5, MyHC, Lysyl oxidase, PKC, Aquaporin 3, Tcf(Lef), BLNK, SIP1 (ZFHX1B), IGFBP7, G-protein gamma, Ankyrin-B, TCF8, TUB, TGF-beta, HAS2, FA2H, Kallikrein 5, Fibrillin, CCL13, DFNA5, COL5A1, MMP-2, LAMB3, WNT5B, Galpha(t)-specific GPCRs, Keratin 5, Kallikrein 3 (PSA), POU2F3, WNT, FGF13, Collagen III, Collagen IV, HAI-1, ErbB3, IGFBP7/8, M-Ras, Desmoplakin, JAM3 |
| circulatory system development | 1023 | 2.201E−13 | 4.077E−11 | 52 | RECK, FGF2, LAMA4, p38 MAPK, Syk, CARP, HAS, HEG1, PAI1, Collagen V, COL4A1, FOG2, CCL2, PGAR, Galpha(q)-specific peptide GPCRs, N-cadherin, PDE, TGF-beta 2, Fibrillin 1, COL1A2, Tissue kallikreins, TCF7L2 (TCF4), OVOL2, Gremlin, Myoglobin, RHG7, FGFR1, Neuregulin 1, Osteonectin, CTGF, ADAM-TS1, MyHC, Lysyl oxidase, PKC, Tcf(Lef), Ankyrin-B, TGF-beta, HAS2, Fibrillin, CCL13, PKC-mu, COL5A1, MMP-2, Kallikrein 3 (PSA), WNT, Collagen III, Collagen IV, HAI-1, ErbB3, IGFBP7/8, Desmoplakin, JAM3 |
| cardiovascular system development | 1023 | 2.201E−13 | 4.077E−11 | 52 | RECK, FGF2, LAMA4, p38 MAPK, Syk, CARP, HAS, HEG1, PAI1, Collagen V, COL4A1, FOG2, CCL2, PGAR, Galpha(q)-specific peptide GPCRs, N-cadherin, PDE, TGF-beta 2, Fibrillin 1, COL1A2, Tissue kallikreins, TCF7L2 (TCF4), OVOL2, Gremlin, Myoglobin, RHG7, FGFR1, Neuregulin 1, Osteonectin, CTGF, ADAM-TS1, MyHC, Lysyl oxidase, PKC, Tcf(Lef), |

TABLE 12A-continued

| | | EMT GO Processes | | | |
|---|---|---|---|---|---|
| Processes | Total | p-value | FDR | In Data | Network Objects from Active Data |
| cellular component morphogenesis | 1137 | 3.021E−13 | 5.388E−11 | 55 | Ankyrin-B, TGF-beta, HAS2, Fibrillin, CCL13, PKC-mu, COL5A1, MMP-2, Kallikrein 3 (PSA), WNT, Collagen III, Collagen IV, HAI-1, ErbB3, IGFBP7/8, Desmoplakin, JAM3 COL5A2, ATR/TEM8, FLRT2, p38 MAPK, N-chimaerin, CARP, Keratin 19, BDNF, HAS, Ankyrin-G, HEG1, Beta-fodrin, COL6A1, PLA2, Collagen V, FAM101B, COL4A1, DAB2, MAP7(EMAP115), Olfactory receptor, CD24, Galpha(q)-specific peptide GPCRs, UCHL1, R-cadherin, E-cadherin, TGF-beta 2, SPTBN(spectrin1-4), PLA2G10, MAP-1B, Tissue kallikreins, Gremlin, PMP22, FGFR1, Neuregulin 1, BVES, UFO, EPB41L5, MyHC, PKC, Tcf(Lef), CRMP4, Ankyrin-B, TGF-beta, HAS2, Cadherin 11, COL5A1, Kallikrein 8, Necdin, CAP2, MYH14, WNT, Collagen III, Collagen IV, ErbB3, S100B |
| blood vessel development | 614 | 3.601E−13 | 6.193E−11 | 39 | RECK, FGF2, LAMA4, p38 MAPK, Syk, HAS, HEG1, PAI1, Collagen V, COL4A1, FOG2, CCL2, PGAR, Galpha(q)-specific peptide GPCRs, N-cadherin, PDE, TGF-beta 2, COL1A2, TCF7L2 (TCF4), OVOL2, Gremlin, FGFR1, CTGF, MyHC, Lysyl oxidase, PKC, Tcf(Lef), TGF-beta, HAS2, CCL13, PKC-mu, COL5A1, MMP-2, WNT, Collagen III, Collagen IV, HAI-1, IGFBP7/8, JAM3 |
| neurogenesis | 1796 | 4.204E−13 | 6.979E−11 | 72 | Tubby, FGF2, LEKTI, COL5A2, FLRT2, N-chimaerin, CARP, BDNF, Ankyrin-G, Beta-fodrin, COL6A1, PLA2, Collagen V, COL4A1, DAB2, Galectin-1, Pitx3, CCL2, Olfactory receptor, CD24, Galpha(q)-specific peptide GPCRs, C1s, UCHL1, FGF5, N-cadherin, Caspr2, DYNLL, PDE, R-cadherin, E-cadherin, TGF-beta 2, SPTBN(spectrin1-4), PLA2G10, MAP-1B, Tissue kallikreins, TCF7L2 (TCF4), ZCCHC24, G-protein beta/gamma, PMP22, FGFR1, Neuregulin 1, Vimentin, UFO, MyHC, PKC, Tcf(Lef), CRMP4, G-protein gamma, Ankyrin-B, TCF8, TGF-beta, FA2H, Neurotractin, Cadherin 11, CCL13, DFNA5, PKC-mu, COL5A1, Kallikrein 8, Necdin, CAP2, MMP-2, MYH14, WNT5B, ITF2, WNT, FGF13, Kallikrein 6 (Neurosin), Collagen III, Collagen IV, ErbB3, S100B |
| cell morphogenesis | 1047 | 5.400E−13 | 8.667E−11 | 52 | COL5A2, ATR/TEM8, FLRT2, p38 MAPK, N-chimaerin, BDNF, HAS, Ankyrin-G, HEG1, Beta-fodrin, COL6A1, PLA2, Collagen V, FAM101B, COL4A1, DAB2, MAP7(EMAP115), Olfactory receptor, CD24, Galpha(q)-specific peptide GPCRs, UCHL1, R-cadherin, E-cadherin, TGF-beta 2, SPTBN(spectrin1-4), PLA2G10, MAP-1B, Tissue kallikreins, Gremlin, FGFR1, Neuregulin 1, BVES, UFO, EPB41L5, MyHC, PKC, Tcf(Lef), CRMP4, Ankyrin-B, TGF-beta, HAS2, Cadherin 11, COL5A1, Kallikrein 8, Necdin, CAP2, MYH14, WNT, Collagen III, Collagen IV, ErbB3, S100B |
| response to external stimulus | 1775 | 7.108E−13 | 1.104E−10 | 71 | Tubby, FGF2, IL13RA2, COL5A2, CDS1, FLRT2, p38 MAPK, Syk, Galpha(i)-specific prostanoid GPCRs, N-chimaerin, TBXA2R, CARP, BDNF, Ankyrin-G, Beta-fodrin, COL6A1, PLA2, Collagen V, Calgranulin A, G-protein beta, COL4A1, Calprotectin (S100A8/A9) complex, CCL2, Olfactory receptor, PGAR, Galpha(q)-specific prostanoid GPCRs, LIPE, CD24, Galpha(q)-specific peptide GPCRs, CDP-diacylglycerol synthase, PDE, R-cadherin, TGF-beta 2, Cmtm3, SPTBN(spectrin1-4), PLA2G10, DSPP, MAP-1B, Tissue kallikreins, Kallikrein 1, G-protein |

TABLE 12A-continued

| | | EMT GO Processes | | | |
|---|---|---|---|---|---|
| Processes | Total | p-value | FDR | In Data | Network Objects from Active Data |
| | | | | | beta/gamma, Gpc6, FGFR1, TRPA1, AP-1 mu subunits, Osteonectin, Vimentin, UFO, MyHC, Calgranulin B, PKC, Aquaporin 3, Tcf(Lef), CRMP4, G-protein gamma, Ankyrin-B, TCF8, TUB, TGF-beta, CCL13, NGAL, COL5A1, CAP2, MMP-2, PTAFR, MYH14, Galpha(t)-specific GPCRs, WNT, NPNT, Collagen III, Collagen IV |
| cellular component organization or biogenesis | 5165 | 7.831E−13 | 1.178E−10 | 143 | RECK, Tubby, FGF2, LEKTI, COL5A2, ATR/TEM8, P-cadherin, LAMA4, FLRT2, p38 MAPK, N-chimaerin, Tubulin alpha 1A, ITGB6, CARP, Keratin 19, BDNF, Plastin, HAS, Ankyrin-G, NEPH1, P3H2, HEG1, Beta-fodrin, PAI1, COL6A1, Nectin-4, PLA2, Collagen V, OSF-2, Synaptotagmin VII, FAM101B, TMSL8, CPA4, FGD2, COL4A1, MARVELD3, Calprotectin (S100A8/A9) complex, DAB2, CDH1, MAP7(EMAP115), Keratin 16, GLT25D2, CCL2, SRPX, Olfactory receptor, PGAR, KIAA1043, NAP1L3, LIPE, PAR1, CD24, Galpha(q)-specific peptide GPCRs, UCHL1, Tubulin alpha, Synaptotagmin, N-cadherin, Caspr2, PRR5, DYNLL, PDE, R-cadherin, LAMA3 (Epiligrin), E-cadherin, FAT4, TGF-beta 2, HOOK1, Fibrillin 1, Collagen XII, COL1A2, LAMC2, Tricellulin, SPTBN(spectrin1-4), PLA2G10, MAP-1B, Chk2, Maspin, Tissue kallikreins, TCF7L2 (TCF4), Gremlin, DLC1 (Dynein LC8a), Laminin 5, SHPS-1, PMP22, Nidogen, RHG7, FGFR1, Rab-25, LyGDI, Neuregulin 1, AP-1 mu subunits, Osteonectin, Vimentin, BVES, ELF3, CTGF, Serglycin, ATP8B3, UFO, EPB41L5, MyHC, Lysyl oxidase, Calgranulin B, PKC, FR-alpha, Tcf(Lef), WaspIP, MPP7, CRMP4, Ankyrin-B, PAK6, TGF-beta, HAS2, FA2H, Fibrillin, Cadherin 11, CCL13, NGAL, PKC-mu, M-cadherin, CLIP3, COL5A1, Kallikrein 8, Necdin, CAP2, MMP-2, LAMB3, MYH14, Keratin 5, ITF2, WNT, F16P, FGF13, NPNT, Collagen III, Collagen IV, ChAF1 subunit B, HAI-1, ErbB3, IGFBP7/8, M-Ras, Mucin 20, S100B, Desmoplakin |
| locomotion | 1363 | 1.218E−12 | 1.777E−10 | 60 | FGF2, COL5A2, FLRT2, p38 MAPK, Syk, N-chimaerin, BDNF, Ankyrin-G, Beta-fodrin, COL6A1, PLA2, Collagen V, Calgranulin A, COL4A1, Matriptase, Calprotectin (S100A8/A9) complex, CCL2, Olfactory receptor, CD24, Galpha(q)-specific peptide GPCRs, N-cadherin, PDE, R-cadherin, TGF-beta 2, Cmtm3, COL1A2, SPTBN(spectrin1-4), PLA2G10, OVOL2, Gremlin, SHPS-1, Gpc6, FGFR1, Neuregulin 1, CTGF, UFO, EPB41L5, MyHC, Calgranulin B, PKC, Tcf(Lef), CRMP4, SIP1 (ZFHX1B), Ankyrin-B, TGF-beta, CCL13, COL5A1, Necdin, CAP2, MMP-2, PTAFR, MYH14, Galpha(t)-specific GPCRs, WNT, FGF13, Collagen III, Collagen IV, IGFBP7/8, S100P, JAM3 |
| vasculature development | 652 | 2.331E−12 | 3.106E−10 | 39 | RECK, FGF2, LAMA4, p38 MAPK, Syk, HAS, HEG1, PAI1, Collagen V, COL4A1, FOG2, CCL2, PGAR, Galpha(q)-specific peptide GPCRs, N-cadherin, PDE, TGF-beta 2, COL1A2, TCF7L2 (TCF4), OVOL2, Gremlin, FGFR1, CTGF, MyHC, Lysyl oxidase, PKC, Tcf(Lef), TGF-beta, HAS2, CCL13, PKC-mu, COL5A1, MMP-2, WNT, Collagen III, Collagen IV, HAI-1, IGFBP7/8, JAM3 |
| regulation of developmental process | 2241 | 2.383E−12 | 3.106E−10 | 81 | Tubby, FGF2, LEKTI, LAMA4, FLRT2, INPP4B, p38 MAPK, Syk, Galpha(i)-specific prostanoid GPCRs, N-chimaerin, TBXA2R, CARP, BDNF, PTGIS, MBNL3, PAI1, PLA2, FGD2, DAB2, CDH1, FOG2, Galectin-1, |

TABLE 12A-continued

| | | EMT GO Processes | | | |
|---|---|---|---|---|---|
| Processes | Total | p-value | FDR | In Data | Network Objects from Active Data |
| wound healing | 846 | 2.394E−12 | 3.106E−10 | 45 | CCL2, PGAR, Galpha(q)-specific prostanoid GPCRs, CD24, Galpha(q)-specific peptide GPCRs, IL1RN, N-cadherin, PDE, R-cadherin, LAMA3 (Epiligrin), E-cadherin, TGF-beta 2, SPRR1B, SPRR3, PLA2G10, MAP-1B, Tissue kallikreins, TCF7L2 (TCF4), OVOL2, Gremlin, ZCCHC24, Laminin 5, PMP22, RHG7, FGFR1, Neuregulin 1, Vimentin, BVES, CTGF, ADAM-TS1, Serglycin, UFO, EPB41L5, MyHC, PKC, Aquaporin 3, Tcf(Lef), CRMP4, TCF8, TGF-beta, Neurotractin, Fibrillin, CCL13, PKC-mu, M-cadherin, Kallikrein 8, MYH14, WNT5B, Kallikrein 3 (PSA), ITF2, WNT, FGF13, NPNT, Kallikrein 6 (Neurosin), Collagen III, RBM24, Collagen IV, IGFBP7/8, S100B FGF2, P-cadherin, p38 MAPK, Syk, Galpha(i)-specific prostanoid GPCRs, TBXA2R, PAI1, PLA2, Collagen V, Calgranulin A, Synaptotagmin VII, G-protein beta, Calprotectin (S100A8/A9) complex, FOG2, Galpha(q)-specific prostanoid GPCRs, PAR1, Galpha(q)-specific peptide GPCRs, Tubulin alpha, Synaptotagmin, PDE, TGF-beta 2, COL1A2, SPRR3, Tissue kallikreins, SHPS-1, G-protein beta/gamma, Neuregulin 1, Osteonectin, Vimentin, Serglycin, UFO, MyHC, Lysyl oxidase, PKC, G-protein gamma, TGF-beta, COL5A1, WNT5B, POU2F3, WNT, Kallikrein 6 (Neurosin), Collagen III, ErbB3, Desmoplakin, JAM3 |
| regulation of multicellular organismal development | 1780 | 2.396E−12 | 3.106E−10 | 70 | Tubby, FGF2, LEKTI, LAMA4, FLRT2, INPP4B, p38 MAPK, Syk, Galpha(i)-specific prostanoid GPCRs, N-chimaerin, TBXA2R, CARP, BDNF, PTGIS, MBNL3, PAI1, PLA2, DAB2, FOG2, Galectin-1, CCL2, PGAR, Galpha(q)-specific prostanoid GPCRs, CD24, Galpha(q)-specific peptide GPCRs, IL1RN, N-cadherin, PDE, R-cadherin, LAMA3 (Epiligrin), E-cadherin, TGF-beta 2, MAP-1B, Tissue kallikreins, TCF7L2 (TCF4), OVOL2, Gremlin, ZCCHC24, Laminin 5, PMP22, FGFR1, Neuregulin 1, Vimentin, CTGF, ADAM-TS1, Serglycin, UFO, EPB41L5, MyHC, PKC, Aquaporin 3, Tcf(Lef), CRMP4, TCF8, TGF-beta, Neurotractin, Fibrillin, CCL13, PKC-mu, Kallikrein 8, Kallikrein 3 (PSA), ITF2, WNT, FGF13, Kallikrein 6 (Neurosin), Collagen III, RBM24, Collagen IV, IGFBP7/8, S100B |
| chemotaxis | 748 | 2.451E−12 | 3.106E−10 | 42 | FGF2, COL5A2, FLRT2, p38 MAPK, Syk, N-chimaerin, BDNF, Ankyrin-G, Beta-fodrin, COL6A1, PLA2, Collagen V, Calgranulin A, COL4A1, Calprotectin (S100A8/A9) complex, CCL2, Olfactory receptor, CD24, Galpha(q)-specific peptide GPCRs, PDE, R-cadherin, TGF-beta 2, Cmtm3, SPTBN(spectrin1-4), PLA2G10, FGFR1, MyHC, Calgranulin B, PKC, Tcf(Lef), CRMP4, Ankyrin-B, TGF-beta, CCL13, COL5A1, CAP2, PTAFR, MYH14, Galpha(t)-specific GPCRs, WNT, Collagen III, Collagen IV |
| taxis | 750 | 2.673E−12 | 3.300E−10 | 42 | FGF2, COL5A2, FLRT2, p38 MAPK, Syk, N-chimaerin, BDNF, Ankyrin-G, Beta-fodrin, COL6A1, PLA2, Collagen V, Calgranulin A, COL4A1, Calprotectin (S100A8/A9) complex, CCL2, Olfactory receptor, CD24, Galpha(q)-specific peptide GPCRs, PDE, R-cadherin, TGF-beta 2, Cmtm3, SPTBN(spectrin1-4), PLA2G10, FGFR1, MyHC, Calgranulin B, PKC, Tcf(Lef), CRMP4, Ankyrin-B, TGF-beta, CCL13, COL5A1, CAP2, PTAFR, MYH14, Galpha(t)-specific GPCRs, WNT, Collagen III, Collagen IV |

TABLE 12A-continued

EMT GO Processes

| Processes | Total | p-value | FDR | In Data | Network Objects from Active Data |
|---|---|---|---|---|---|
| multicellular organismal metabolic process | 116 | 6.070E−12 | 7.307E−10 | 17 | Tubby, COL5A2, P3H2, COL6A1, PLA2, Collagen V, COL4A1, Collagen XII, COL1A2, Tissue kallikreins, PKC, TUB, COL5A1, MMP-2, Kallikrein 6 (Neurosin), Collagen III, Collagen IV |
| single-organism developmental process | 4620 | 6.248E−12 | 7.338E−10 | 130 | ELF5, RECK, Tubby, FGF2, LEKTI, COL5A2, ATR/TEM8, LAMA4, FLRT2, p38 MAPK, Syk, N-chimaerin, IRF6, CARP, Cx30, Keratin 19, BDNF, Plastin, HAS, Ankyrin-G, HEG1, Beta-fodrin, PAI1, COL6A1, PLA2, Collagen V, G-protein beta, Basonuclin-2, FAM101B, COL4A1, Sciellin, DAB2, CDH1, MAP7(EMAP115), FOG2, Galectin-1, Pitx3, CCL2, Olfactory receptor, FHL1 (SLIM1), PGAR, CD24, Galpha(q)-specific peptide GPCRs, Zac1, UCHL1, N-cadherin, Desmocollin 3, Caspr2, DYNLL, PDE, R-cadherin, E-cadherin, DKK3, TGF-beta 2, HOOK1, Fibrillin 1, COL1A2, GCNT3, SPTBN(spectrin1-4), PLA2G10, DSPP, MAP-1B, Chk2, Maspin, Tissue kallikreins, TCF7L2 (TCF4), OVOL2, Gremlin, G-protein beta/gamma, Myoglobin, PMP22, Nidogen, RHG7, FGFR1, Neuregulin 1, AP-1 mu subunits, Osteonectin, Vimentin, BVES, ELF3, CTGF, ADAM-TS1, UFO, EPB41L5, MyHC, Lysyl oxidase, PKC, Aquaporin 3, Tcf(Lef), BLNK, CRMP4, SIP1 (ZFHX1B), IGFBP7, G-protein gamma, Ankyrin-B, LAF4, TCF8, TUB, TGF-beta, HAS2, FA2H, Fibrillin, Cadherin 11, CCL13, DFNA5, PKC-mu, M-cadherin, COL5A1, Kallikrein 8, GRHL2, Necdin, CAP2, MMP-2, MYH14, WNT5B, Galpha(t)-specific GPCRs, Kallikrein 3 (PSA), WNT, FGF13, NPNT, Kallikrein 6 (Neurosin), Collagen III, Collagen IV, HAI-1, ErbB3, IGFBP7/8, M-Ras, S100B, Desmoplakin, JAM3 |
| cell junction organization | 237 | 7.591E−12 | 8.702E−10 | 23 | P-cadherin, HEG1, Nectin-4, MARVELD3, N-cadherin, R-cadherin, LAMA3 (Epiligrin), E-cadherin, TGF-beta 2, LAMC2, Tricellulin, Laminin 5, RHG7, PKC, MPP7, Ankyrin-B, TGF-beta, Cadherin 11, M-cadherin, LAMB3, Keratin 5, WNT, Desmoplakin |
| cell development | 1875 | 9.467E−12 | 1.060E−09 | 71 | Tubby, FGF2, COL5A2, ATR/TEM8, FLRT2, N-chimaerin, IRF6, CARP, Keratin 19, BDNF, HAS, Ankyrin-G, HEG1, Beta-fodrin, COL6A1, PLA2, Collagen V, FAM101B, COL4A1, DAB2, MAP7(EMAP115), Pitx3, Olfactory receptor, CD24, Galpha(q)-specific peptide GPCRs, UCHL1, Caspr2, DYNLL, PDE, R-cadherin, E-cadherin, TGF-beta 2, HOOK1, SPTBN(spectrin1-4), PLA2G10, MAP-1B, Tissue kallikreins, TCF7L2 (TCF4), OVOL2, Gremlin, G-protein beta/gamma, FGFR1, Neuregulin 1, Vimentin, BVES, UFO, EPB41L5, MyHC, PKC, Tcf(Lef), CRMP4, SIP1 (ZFHX1B), G-protein gamma, Ankyrin-B, TGF-beta, HAS2, FA2H, Cadherin 11, COL5A1, Kallikrein 8, Necdin, CAP2, MMP-2, MYH14, WNT5B, WNT, Collagen III, Collagen IV, ErbB3, S100B, JAM3 |
| regulation of cell adhesion | 416 | 9.894E−12 | 1.083E−09 | 30 | LEKTI, LAMA4, Syk, EDIL3, HAS, Ankyrin-G, PAI1, DAB2, Galectin-1, CD24, Galpha(q)-specific peptide GPCRs, IL1RN, PDE, LAMA3 (Epiligrin), E-cadherin, TGF-beta 2, Gremlin, Laminin 5, Nidogen, LyGDI, Neuregulin 1, EPB41L5, PKC, Tcf(Lef), TGF-beta, HAS2, MMP-2, WNT, NPNT, ErbB3 |
| multicellular organismal macromolecule metabolic process | 105 | 1.393E−11 | 1.490E−09 | 16 | Tubby, COL5A2, P3H2, COL6A1, Collagen V, COL4A1, Collagen XII, COL1A2, Tissue kallikreins, PKC, TUB, COL5A1, MMP-2, Kallikrein 6 (Neurosin), Collagen III, Collagen IV |

TABLE 12A-continued

EMT GO Processes

| Processes | Total | p-value | FDR | In Data | Network Objects from Active Data |
|---|---|---|---|---|---|
| generation of neurons | 1700 | 2.075E−11 | 2.172E−09 | 66 | Tubby, LEKTI, COL5A2, FLRT2, N-chimaerin, CARP, BDNF, Ankyrin-G, Beta-fodrin, COL6A1, PLA2, Collagen V, COL4A1, DAB2, Galectin-1, Pitx3, Olfactory receptor, CD24, Galpha(q)-specific peptide GPCRs, UCHL1, N-cadherin, Caspr2, DYNLL, PDE, R-cadherin, E-cadherin, TGF-beta 2, SPTBN(spectrin1-4), PLA2G10, MAP-1B, Tissue kallikreins, TCF7L2 (TCF4), ZCCHC24, G-protein beta/gamma, PMP22, FGFR1, Neuregulin 1, Vimentin, UFO, MyHC, PKC, Tcf(Lef), CRMP4, G-protein gamma, Ankyrin-B, TCF8, TGF-beta, Neurotractin, Cadherin 11, DFNA5, PKC-mu, COL5A1, Kallikrein 8, Necdin, CAP2, MMP-2, MYH14, WNT5B, ITF2, WNT, FGF13, Kallikrein 6 (Neurosin), Collagen III, Collagen IV, ErbB3, S100B |
| regulation of anatomical structure morphogenesis | 903 | 2.148E−11 | 2.201E−09 | 45 | FGF2, LEKTI, p38 MAPK, Galpha(i)-specific prostanoid GPCRs, N-chimaerin, TBXA2R, BDNF, PTGIS, PAI1, FGD2, DAB2, CCL2, PGAR, Galpha(q)-specific prostanoid GPCRs, Galpha(q)-specific peptide GPCRs, IL1RN, N-cadherin, PDE, R-cadherin, E-cadherin, TGF-beta 2, SPRR1B, SPRR3, MAP-1B, Tissue kallikreins, TCF7L2 (TCF4), Gremlin, RHG7, FGFR1, Vimentin, BVES, ADAM-TS1, EPB41L5, MyHC, PKC, Tcf(Lef), TGF-beta, CCL13, PKC-mu, MYH14, Kallikrein 3 (PSA), WNT, FGF13, Collagen IV, S100B |
| organ morphogenesis | 1057 | 3.234E−11 | 3.244E−09 | 49 | Tubby, FGF2, COL5A2, p38 MAPK, Syk, CARP, Cx30, HAS, HEG1, Collagen V, Basonuclin-2, FOG2, Pitx3, CCL2, FHL1 (SLIM1), Galpha(q)-specific peptide GPCRs, PDE, TGF-beta 2, COL1A2, GCNT3, DSPP, Maspin, Tissue kallikreins, TCF7L2 (TCF4), OVOL2, Gremlin, G-protein beta/gamma, RHG7, FGFR1, Neuregulin 1, CTGF, ADAM-TS1, MyHC, PKC, Aquaporin 3, Tcf(Lef), G-protein gamma, TCF8, TGF-beta, HAS2, Fibrillin, COL5A1, MMP-2, WNT5B, Kallikrein 3 (PSA), WNT, ErbB3, IGFBP7/8, Desmoplakin |
| epidermis development | 358 | 4.079E−11 | 4.008E−09 | 27 | LEKTI, SPRR1A, IRF6, Sciellin, Keratin 16, TAJ(TNFRSF19), Prostasin, LAMA3 (Epiligrin), TGF-beta 2, SPRR1B, SPRR3, LAMC2, PPL(periplakin), Tissue kallikreins, Laminin 5, FGFR1, ELF3, CTGF, TGF-beta, FA2H, Kallikrein 5, LAMB3, Keratin 5, POU2F3, WNT, IGFBP7/8, Desmoplakin |
| positive regulation of signaling | 1293 | 4.627E−11 | 4.456E−09 | 55 | AKAP12, RECK, FGF2, p38 MAPK, Syk, CARP, PTGIS, PLA2, Calgranulin A, Calprotectin (S100A8/A9) complex, DAB2, Galectin-1, CCL2, SRPX, PAR1, MAPBPIP, CD24, Galpha(q)-specific peptide GPCRs, IL1RN, BPGAP1, N-cadherin, TAJ(TNFRSF19), PRR5, PDE, PRR5-ARHGAP8, TGF-beta 2, FAM110C, Tissue kallikreins, TCF7L2 (TCF4), G-protein beta/gamma, FGFR1, HBP17, Neuregulin 1, BVES, CTGF, UFO, Calgranulin B, PKC, Tcf(Lef), MPP7, SIP1 (ZFHX1B), G-protein gamma, TGF-beta, Kallikrein 5, CCL13, DFNA5, PKC-mu, WNT, NPNT, Kallikrein 6 (Neurosin), Collagen III, ErbB3, IGFBP7/8, Mucin 20, S100B |

TABLE 12B

| | | | | In | Network Objects from |
|---|---|---|---|---|---|
| Processes | Total | p-value | FDR | Data | Active Data |
| axonogenesis | 616 | 2.613E−09 | 4.905E−06 | 29 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, SLIT2, ERM proteins, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14 |
| cell morphogenesis involved in neuron differentiation | 656 | 2.671E−09 | 4.905E−06 | 30 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, Syndecan-2, SLIT2, ERM proteins, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14 |
| cell morphogenesis involved in differentiation | 792 | 4.113E−09 | 4.905E−06 | 33 | SLUG, Ephrin-B receptors, FLRT2, FEZ1, Tubulin beta, Neuropilin-2, PLA2, SLIT3, Galpha(q)-specific peptide GPCRs, Willin, UCHL1, Kalirin, SHH, Ephrin-B receptor 2, MAP-1B, Syndecan-2, SLIT2, ERM proteins, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14, BASP1 |
| neuron projection morphogenesis | 679 | 5.898E−09 | 4.905E−06 | 30 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, Syndecan-2, SLIT2, ERM proteins, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14 |
| neuron projection guidance | 489 | 6.883E−09 | 4.905E−06 | 25 | Ephrin-B receptors, FLRT2, FEZ1, Tubulin beta, Neuropilin-2, PLA2, SLIT3, Galpha(q)-specific peptide GPCRs, SHH, Ephrin-B receptor 2, SLIT2, ERM proteins, Neuropilin-1, Ephrin-B receptor 1, Cofilin, SRGAP2, MyHC, PKC, CRMP4, PTPR-mu, Hedgehog, CAP2, MYH10, TRPC1, MYH14 |
| axon guidance | 489 | 6.883E−09 | 4.905E−06 | 25 | Ephrin-B receptors, FLRT2, FEZ1, Tubulin beta, Neuropilin-2, PLA2, SLIT3, Galpha(q)-specific peptide GPCRs, SHH, Ephrin-B receptor 2, SLIT2, ERM proteins, Neuropilin-1, Ephrin-B receptor 1, Cofilin, SRGAP2, MyHC, PKC, CRMP4, PTPR-mu, Hedgehog, CAP2, MYH10, TRPC1, MYH14 |
| single-organism developmental process | 4620 | 1.073E−08 | 6.553E−06 | 101 | SNF2L1, PAR2, c-Maf, QKI, RECK, SLUG, Alpha crystallin B, IQCJ-SCHIP1, AEBP1, Ephrin-B receptors, FLRT2, Caspase-6, SLC29A2, PEDF (serpinF1), BDH, Axin, FEZ1, Tubulin beta, Neuropilin-2, DUOX1, PLA2, LEC1, GCR-alpha, SLAC2-B, Axin2, SLIT3, TIMP2, Plakophilin 2, MAP7(EMAP115), FOG2, Calpain 5, Galectin-1, Myosin Va, SCHIP1, Galpha(q)-specific peptide GPCRs, Epsilon-sarcoglycan, Willin, UCHL1, Kalirin, SHH, DAZAP, Ephrin-B receptor 2, Decorin proteoglycan, CDX1, HMGI/Y, DUOX2, NAT-1, LDB2, MAP-1B, Chk2, HOXB9, Syndecan-2, GCR-beta, SLIT2, Polycystin 2, NNMT, ERM proteins, DZIP, Neuropilin-1, NKCC1, Ephrin-B receptor 1, AP-1 mu subunits, HNF4-alpha, Cofilin, c-Myb, DMP4, Alpha/epsilon-sarcoglycan, AML1/TRPS1 fusion protein, NOX1, Vimentin, Osteonectin, SRGAP2, MyHC, PKC, CRMP4, MGP, PTPR-mu, G-protein gamma, Hedgehog, FA2H, SLC5A1, DFNA5, AKT(PKB), PKC-mu, RILP (REST-interacting LIM domain protein), CAP2, Necdin, ECM2/SC1, MYH10, TRPC1, MYH14, TAZ, NAT-2, KCNQ1, BASP1, HNF4, STRBP, PRKD2, M-Ras, Decorin, JAM3 |
| system development | 4665 | 1.817E−08 | 9.713E−06 | 101 | SNF2L1, PAR2, c-Maf, QKI, RECK, SLUG, Alpha crystallin B, IQCJ-SCHIP1, AEBP1, Ephrin-B receptors, FLRT2, Caspase-6, SLC29A2, LZTS1, PEDF (serpinF1), BDH, Axin, FEZ1, Tubulin beta, Neuropilin-2, PLA2, LEC1, GCR-alpha, MUPP1, SLAC2-B, ERR1, SPG20, Axin2, SLIT3, TIMP2, |

TABLE 12B-continued

PC1 GO Processes

| Processes | Total | p-value | FDR | In Data | Network Objects from Active Data |
|---|---|---|---|---|---|
| | | | | | Plakophilin 2, MAP7(EMAP115), FOG2, Calpain 5, Galectin-1, Myosin Va, SCHIP1, Galpha(q)-specific peptide GPCRs, Epsilon-sarcoglycan, UCHL1, Kalirin, SHH, DAZAP, Ephrin-B receptor 2, Decorin proteoglycan, CDX1, DUOX2, NAT-1, LDB2, MAP-1B, HOXB9, Syndecan-2, GCR-beta, SLIT2, Glis2, Polycystin 2, NNMT, ERM proteins, Neuropilin-1, ENC1, NKCC1, Ephrin-B receptor 1, HNF4-alpha, Cofilin, c-Myb, DMP4, Alpha/epsilon-sarcoglycan, AML1/TRPS1 fusion protein, NOX1, Vimentin, Osteonectin, SRGAP2, MyHC, PKC, CRMP4, MGP, PTPR-mu, G-protein gamma, Hedgehog, FA2H, SLC5A1, DFNA5, AKT(PKB), PKC-mu, NELL1, RILP (REST-interacting LIM domain protein), CAP2, Necdin, MYH10, TRPC1, MYH14, TAZ, NAT-2, KCNQ1, TRPS1, BASP1, HNF4, PRKD2, M-Ras, Decorin, JAM3 |
| axon development | 680 | 2.340E−08 | 1.112E−05 | 29 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, SLIT2, ERM proteins, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14 |
| establishment or maintenance of cell polarity | 139 | 3.577E−08 | 1.473E−05 | 13 | Ephrin-B receptors, MAP7(EMAP115), SHH, MAP-1B, ERM proteins, Ephrin-B receptor 1, Cofilin, MyHC, PKC, Hedgehog, AMOTL1 (Jeap), CAP2, JAM3 |
| regulation of cell projection organization | 457 | 3.789E−08 | 1.473E−05 | 23 | PAR2, Ephrin-B receptors, LZTS1, FEZ1, GCR-alpha, SPG20, Galectin-1, CDC42EP5, Galpha(q)-specific peptide GPCRs, Kalirin, Ephrin-B receptor 2, MAP-1B, Syndecan-2, GCR-beta, SLIT2, Neuropilin-1, HNF4-alpha, Vimentin, PKC, CRMP4, AKT(PKB), PKC-mu, HNF4 |
| cell projection morphogenesis | 831 | 4.588E−08 | 1.635E−05 | 32 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, Syndecan-2, SLIT2, ERM proteins, DZIP, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14, TAZ |
| anatomical structure morphogenesis | 2492 | 6.023E−08 | 1.981E−05 | 64 | QKI, SLUG, Alpha crystallin B, IQCJ-SCHIP1, Ephrin-B receptors, FLRT2, Axin, FEZ1, Tubulin beta, Neuropilin-2, PLA2, GCR-alpha, Axin2, SLIT3, Plakophilin 2, MAP7(EMAP115), FOG2, Myosin Va, SCHIP1, Galpha(q)-specific peptide GPCRs, Willin, UCHL1, Kalirin, SHH, Ephrin-B receptor 2, Decorin proteoglycan, CDX1, DUOX2, MAP-1B, Syndecan-2, GCR-beta, SLIT2, Polycystin 2, ERM proteins, DZIP, Neuropilin-1, NKCC1, Ephrin-B receptor 1, HNF4-alpha, Cofilin, DMP4, AML1/TRPS1 fusion protein, NOX1, SRGAP2, MyHC, PKC, CRMP4, MGP, PTPR-mu, G-protein gamma, Hedgehog, PKC-mu, RILP (REST-interacting LIM domain protein), CAP2, Necdin, MYH10, TRPC1, MYH14, TAZ, BASP1, HNF4, PRKD2, Decorin, JAM3 |
| cell part morphogenesis | 855 | 8.804E−08 | 2.689E−05 | 32 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, Syndecan-2, SLIT2, ERM proteins, DZIP, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14, TAZ |
| regulation of anatomical structure morphogenesis | 903 | 9.475E−08 | 2.701E−05 | 33 | SLUG, Ephrin-B receptors, Caspase-6, LZTS1, PEDF (serpinF1), Axin, SPG20, Axin2, CDC42EP5, Galpha(q)-specific peptide GPCRs, SHH, Ephrin-B receptor 2, DDAH1, MAP-1B, Syndecan-2, SLIT2, ERM proteins, Neuropilin-1, HNF4-alpha, Cofilin, AML1/TRPS1 fusion protein, Vimentin, MyHC, PKC, PTPR-mu, Hedgehog, |

TABLE 12B-continued

PC1 GO Processes

| Processes | Total | p-value | FDR | In Data | Network Objects from Active Data |
|---|---|---|---|---|---|
| cell morphogenesis | 1047 | 1.065E−07 | 2.845E−05 | 36 | PKC-mu, MYH10, MYH14, TAZ, BASP1, HNF4, PRKD2 SLUG, Ephrin-B receptors, FLRT2, FEZ1, Tubulin beta, Neuropilin-2, PLA2, SLIT3, MAP7(EMAP115), Galpha(q)-specific peptide GPCRs, Willin, UCHL1, Kalirin, SHH, Ephrin-B receptor 2, MAP-1B, Syndecan-2, SLIT2, ERM proteins, DZIP, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14, TAZ, BASP1 |
| chemotaxis | 748 | 1.789E−07 | 4.354E−05 | 29 | CCL28, Ephrin-B receptors, FLRT2, FEZ1, Tubulin beta, Neuropilin-2, PLA2, SLIT3, Galpha(q)-specific peptide GPCRs, SHH, Ephrin-B receptor 2, Cmtm3, HOXB9, SLIT2, ERM proteins, Neuropilin-1, Ephrin-B receptor 1, Cofilin, SRGAP2, MyHC, PKC, CMTM4, CRMP4, PTPR-mu, Hedgehog, CAP2, MYH10, TRPC1, MYH14 |
| taxis | 750 | 1.892E−07 | 4.354E−05 | 29 | CCL28, Ephrin-B receptors, FLRT2, FEZ1, Tubulin beta, Neuropilin-2, PLA2, SLIT3, Galpha(q)-specific peptide GPCRs, SHH, Ephrin-B receptor 2, Cmtm3, HOXB9, SLIT2, ERM proteins, Neuropilin-1, Ephrin-B receptor 1, Cofilin, SRGAP2, MyHC, PKC, CMTM4, CRMP4, PTPR-mu, Hedgehog, CAP2, MYH10, TRPC1, MYH14 |
| establishment of cell polarity | 87 | 1.998E−07 | 4.354E−05 | 10 | Ephrin-B receptors, SHH, MAP-1B, Ephrin-B receptor 1, Cofilin, MyHC, PKC, Hedgehog, AMOTL1 (Jeap), JAM3 |
| cellular component movement | 1526 | 2.037E−07 | 4.354E−05 | 45 | PAR2, SLUG, IQCJ-SCHIP1, Ephrin-B receptors, FLRT2, FEZ1, Tubulin beta, Tensin, Neuropilin-2, PLA2, Matriptase, SLIT3, Myosin Va, SCHIP1, Galpha(q)-specific peptide GPCRs, Willin, UCHL1, SHH, Ephrin-B receptor 2, Tubulin beta 6, MAP-1B, MSN (moesin), HOXB9, Caldesmon, SLIT2, ERM proteins, Neuropilin-1, Ephrin-B receptor 1, Cofilin, NOX1, Vimentin, SRGAP2, MyHC, PKC, CRMP4, PTPR-mu, Hedgehog, AMOTL1 (Jeap), CAP2, Necdin, MYH10, TRPC1, MYH14, STRBP, JAM3 |
| multicellular organismal development | 5406 | 3.490E−07 | 7.105E−05 | 108 | SNF2L1, PAR2, c-Maf, QKI, RECK, SLUG, Alpha crystallin B, IQCJ-SCHIP1, AEBP1, Ephrin-B receptors, FLRT2, Caspase-6, SLC29A2, LZTS1, PEDF (serpinF1), BDH, Axin, FEZ1, Tubulin beta, Neuropilin-2, DUOX1, PLA2, LEC1, GCR-alpha, MUPP1, SLAC2-B, ERR1, SPG20, Axin2, SLIT3, TIMP2, Plakophilin 2, MAP7(EMAP115), FOG2, Calpain 5, Galectin-1, Myosin Va, SCHIP1, Galpha(q)-specific peptide GPCRs, Epsilon-sarcoglycan, UCHL1, PAQR8, Kalirin, SHH, DAZAP, Ephrin-B receptor 2, Decorin proteoglycan, CDX1, FRAT2, DUOX2, TMPRSS2/ERG fusion protein, NAT-1, LDB2, MAP-1B, HOXB9, Syndecan-2, GCR-beta, SLIT2, Glis2, Polycystin 2, NNMT, ERM proteins, DZIP, Neuropilin-1, ENC1, NKCC1, Ephrin-B receptor 1, HNF4-alpha, Cofilin, c-Myb, DMP4, Alpha/epsilon-sarcoglycan, AML1/TRPS1 fusion protein, NOX1, Vimentin, Osteonectin, SRGAP2, MyHC, PKC, CRMP4, MGP, PTPR-mu, G-protein gamma, Hedgehog, FA2H, SLC5A1, DFNA5, AKT(PKB), PKC-mu, NELL1, RILP (REST-interacting LIM domain protein), CAP2, Necdin, ECM2/SC1, MYH10, TRPC1, MYH14, TAZ, NAT-2, KCNQ1, TRPS1, BASP1, HNF4, STRBP, PRKD2, M-Ras, Decorin, JAM3 |
| retinal ganglion cell axon guidance | 23 | 3.907E−07 | 7.594E−05 | 6 | Ephrin-B receptors, Ephrin-B receptor 2, SLIT2, Neuropilin-1, Ephrin-B receptor 1, PTPR-mu |
| regulation of multicellular organismal development | 1780 | 4.217E−07 | 7.841E−05 | 49 | c-Maf, SLUG, Ephrin-B receptors, FLRT2, Caspase-6, LZTS1, PEDF (serpinF1), Axin, FEZ1, PLA2, GCR-alpha, ERR1, SPG20, Axin2, TIMP2, FOG2, Galectin-1, Galpha(q)-specific peptide GPCRs, Kalirin, SHH, Ephrin-B receptor 2, DDAH1, MAP-1B, Syndecan-2, GCR-beta, SLIT2, Neuropilin-1, Ephrin-B receptor 1, HNF4-alpha, c- |

TABLE 12B-continued

| | | PC1 GO Processes | | | |
|---|---|---|---|---|---|
| Processes | Total | p-value | FDR | In Data | Network Objects from Active Data |
| | | | | | Myb, DMP4, AML1/TRPS1 fusion protein, Vimentin, SRGAP2, MyHC, PKC, CRMP4, MGP, PTPR-mu, Hedgehog, AKT(PKB), PKC-mu, NELL1, RILP (REST-interacting LIM domain protein), TAZ, TRPS1, BASP1, HNF4, PRKD2 |
| locomotion | 1363 | 4.618E−07 | 8.209E−05 | 41 | PAR2, SLUG, CCL28, IQCJ-SCHIP1, Ephrin-B receptors, FLRT2, FEZ1, Tubulin beta, Tensin, Neuropilin-2, PLA2, Matriptase, SLIT3, Myosin Va, SCHIP1, Galpha(q)-specific peptide GPCRs, SHH, Ephrin-B receptor 2, Cmtm3, MSN (moesin), HOXB9, SLIT2, ERM proteins, Neuropilin-1, Ephrin-B receptor 1, Cofilin, NOX1, SRGAP2, MyHC, PKC, CMTM4, CRMP4, PTPR-mu, Hedgehog, AMOTL1 (Jeap), CAP2, Necdin, MYH10, TRPC1, MYH14, JAM3 |
| ameboidal cell migration | 203 | 4.799E−07 | 8.209E−05 | 14 | IQCJ-SCHIP1, Ephrin-B receptors, Tensin, Neuropilin-2, SCHIP1, Galpha(q)-specific peptide GPCRs, SHH, SLIT2, Neuropilin-1, Cofilin, SRGAP2, MyHC, Hedgehog, AMOTL1 (Jeap) |
| anatomical structure development | 5314 | 5.334E−07 | 8.554E−05 | 106 | SNF2L1, PAR2, c-Maf, QKI, RECK, SLUG, Alpha crystallin B, IQCJ-SCHIP1, AEBP1, Ephrin-B receptors, FLRT2, Caspase-6, SLC29A2, LZTS1, PEDF (serpinF1), BDH, Axin, FEZ1, Tubulin beta, Neuropilin-2, DUOX1, PLA2, LEC1, GCR-alpha, MUPP1, SLAC2-B, ERR1, SPG20, Axin2, SLIT3, TIMP2, Plakophilin 2, MAP7(EMAP115), FOG2, Calpain 5, Galectin-1, Myosin Va, SCHIP1, Galpha(q)-specific peptide GPCRs, Epsilon-sarcoglycan, Willin, UCHL1, Kalirin, SHH, DAZAP, Ephrin-B receptor 2, Decorin proteoglycan, CDX1, DUOX2, NAT-1, LDB2, MAP-1B, HOXB9, Syndecan-2, GCR-beta, SLIT2, Glis2, Polycystin 2, NNMT, ERM proteins, DZIP, Neuropilin-1, ENC1, NKCC1, Ephrin-B receptor 1, HNF4-alpha, Cofilin, c-Myb, DMP4, Alpha/epsilon-sarcoglycan, AML1/TRPS1 fusion protein, NOX1, Vimentin, Osteonectin, SRGAP2, MyHC, PKC, CRMP, MGP, PTPR-mu, G-protein gamma, Hedgehog, FA2H, SLC5A1, DFNA5, AKT(PKB), PKC-mu, NELL1, RILP (REST-interacting LIM domain protein), CAP2, Necdin, ECM2/SC1, MYH10, TRPC1, MYH14, TAZ, NAT-2, KCNQ1, TRPS1, BASP1, HNF4, STRBP, PRKD2, M-Ras, Decorin, JAM3 |
| regulation of developmental process | 2241 | 5.401E−07 | 8.554E−05 | 57 | c-Maf, SLUG, Ephrin-B receptors, FLRT2, Caspase-6, LZTS1, PEDF (serpinF1), Axin, FEZ1, PLA2, GCR-alpha, ERR1, SPG20, Axin2, TIMP2, Plakophilin 2, FOG2, Galectin-1, CDC42EP5, Galpha(q)-specific peptide GPCRs, Kalirin, SHH, Ephrin-B receptor 2, DDAH1, HMGI/Y, LDB2, MAP-1B, Syndecan-2, GCR-beta, SLIT2, ERM proteins, Neuropilin-1, Ephrin-B receptor 1, HNF4-alpha, Cofilin, c-Myb, DMP4, AML1/TRPS1 fusion protein, Vimentin, SRGAP2, MyHC, PKC, CRMP4, MGP, PTPR-mu, Hedgehog, AKT(PKB), PKC-mu, NELL1, RILP (REST-interacting LIM domain protein), MYH10, MYH14, TAZ, TRPS1, BASP1, HNF4, PRKD2 |
| regulation of cell development | 843 | 6.651E−07 | 1.016E−04 | 30 | Ephrin-B receptors, FLRT2, Caspase-6, LZTS1, PEDF (serpinF1), Axin, FEZ1, GCR-alpha, SPG20, Axin2, TIMP2, Galectin-1, Galpha(q)-specific peptide GPCRs, Kalirin, SHH, Ephrin-B receptor 2, MAP-1B, Syndecan-2, GCR-beta, SLIT2, Neuropilin-1, Vimentin, SRGAP2, PKC, CRMP4, Hedgehog, AKT(PKB), PKC-mu, RILP (REST-interacting LIM domain protein), TAZ |
| regulation of neuron projection development | 382 | 7.207E−07 | 1.063E−04 | 19 | Ephrin-B receptors, LZTS1, FEZ1, GCR-alpha, SPG20, Galectin-1, Galpha(q)-specific peptide GPCRs, Kalirin, Ephrin-B receptor 2, MAP-1B, Syndecan-2, GCR-beta, SLIT2, Neuropilin-1, Vimentin, PKC, CRMP4, AKT(PKB), PKC-mu |

TABLE 12B-continued

PC1 GO Processes

| Processes | Total | p-value | FDR | In Data | Network Objects from Active Data |
|---|---|---|---|---|---|
| regulation of endothelial cell migration | 125 | 7.570E−07 | 1.067E−04 | 11 | SLUG, Neuropilin-2, Galpha(q)-specific peptide GPCRs, SLIT2, Neuropilin-1, PKC, PTPR-mu, AKT(PKB), PKC-mu, AMOTL1 (Jeap), PRKD2 |
| cellular component morphogenesis | 1137 | 7.738E−07 | 1.067E−04 | 36 | SLUG, Ephrin-B receptors, FLRT2, FEZ1, Tubulin beta, Neuropilin-2, PLA2, SLIT3, MAP7(EMAP115), Galpha(q)-specific peptide GPCRs, Willin, UCHL1, Kalirin, SHH, Ephrin-B receptor 2, MAP-1B, Syndecan-2, SLIT2, ERM proteins, DZIP, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14, TAZ, BASP1 |
| cell development | 1875 | 8.084E−07 | 1.080E−04 | 50 | PAR2, c-Maf, QKI, SLUG, Alpha crystallin B, Ephrin-B receptors, FLRT2, Axin, FEZ1, Tubulin beta, Neuropilin-2, PLA2, SLAC2-B, SLIT3, MAP7(EMAP115), Galpha(q)-specific peptide GPCRs, Willin, UCHL1, Kalirin, SHH, Ephrin-B receptor 2, LDB2, MAP-1B, Syndecan-2, SLIT2, ERM proteins, DZIP, Neuropilin-1, Ephrin-B receptor 1, Cofilin, DMP4, AML1/TRPS1 fusion protein, Vimentin, SRGAP2, MyHC, PKC, CRMP4, PTPR-mu, G-protein gamma, Hedgehog, FA2H, AKT(PKB), CAP2, Necdin, MYH10, TRPC1, MYH14, BASP1, STRBP, JAM3 |
| tissue development | 1879 | 8.608E−07 | 1.115E−04 | 50 | PAR2, c-Maf, QKI, SLUG, IQCJ-SCHIP1, BDH, Axin, Neuropilin-2, PLA2, GCR-alpha, SLAC2-B, ERR1, SPG20, Axin2, Plakophilin 2, MAP7(EMAP115), FOG2, Calpain 5, Myosin Va, SCHIP1, Galpha(q)-specific peptide GPCRs, Willin, SHH, Decorin proteoglycan, DUOX2, LDB2, GCR-beta, SLIT2, Polycystin 2, ERM proteins, Neuropilin-1, NKCC1, Cofilin, DMP4, AML1/TRPS1 fusion protein, Vimentin, MyHC, PKC, MGP, Hedgehog, FA2H, AKT(PKB), RILP (REST-interacting LIM domain protein), MYH10, TRPS1, BASP1, STRBP, PRKD2, Decorin, JAM3 |
| response to external stimulus | 1775 | 9.452E−07 | 1.189E−04 | 48 | CCL28, CDS1, Ephrin-B receptors, FLRT2, BDH, FEZ1, Tubulin beta, Neuropilin-2, PLA2, HSD11B2, SLIT3, Galpha(q)-specific peptide GPCRs, Caspase-5, SHH, CDP-diacylglycerol synthase, Ephrin-B receptor 2, Decorin proteoglycan, Cmtm3, MAP-1B, HOXB9, Syndecan-2, SLIT2, Polycystin 2, ERM proteins, Neuropilin-1, NKCC1, TRPA1, Ephrin-B receptor 1, AP-1 mu subunits, Cofilin, Vimentin, Osteonectin, SRGAP2, MyHC, PKC, CMTM4, CRMP4, MGP, PTPR-mu, G-protein gamma, Hedgehog, AKT(PKB), CAP2, MYH10, TRPC1, MYH14, STRBP, Decorin |
| regulation of cell migration | 634 | 9.767E−07 | 1.193E−04 | 25 | PAR2, SLUG, CARD5, FLRT2, Neuropilin-2, PLA2, Plakophilin 2, Galpha(q)-specific peptide GPCRs, SHH, MSN (moesin), SLIT2, ERM proteins, Neuropilin-1, CRCM, Vimentin, SRGAP2, PKC, CRMP4, PTPR-mu, Hedgehog, AKT(PKB), PKC-mu, AMOTL1 (Jeap), PRKD2, JAM3 |
| regulation of epithelial cell migration | 157 | 1.082E−06 | 1.285E−04 | 12 | SLUG, Neuropilin-2, Galpha(q)-specific peptide GPCRs, SLIT2, Neuropilin-1, CRCM, PKC, PTPR-mu, AKT(PKB), PKC-mu, AMOTL1 (Jeap), PRKD2 |
| neuron projection development | 865 | 1.132E−06 | 1.308E−04 | 30 | Ephrin-B receptors, FLRT2, FEZ1, Tubulin beta, Neuropilin-2, PLA2, SLIT3, Galpha(q)-specific peptide GPCRs, UCHL1, Kalirin, SHH, Ephrin-B receptor 2, MAP-1B, Syndecan-2, SLIT2, ERM proteins, Neuropilin-1, Ephrin-B receptor 1, Cofilin, SRGAP2, MyHC, PKC, CRMP4, PTPR-mu, Hedgehog, CAP2, Necdin, MYH10, TRPC1, MYH14 |
| negative regulation of transport | 473 | 1.173E−06 | 1.320E−04 | 21 | PAR2, SLUG, Alpha crystallin B, Axin, PLA2, Axin2, Galpha(q)-specific peptide GPCRs, SHH, Synaptotagmin, MAP-1B, Polycystin 2, HNF4-alpha, PKC, FAM3D, Hedgehog, PEA15, AKT(PKB), PKC-mu, TAZ, KCNQ1, HNF4 |
| organ development | 3386 | 1.321E−06 | 1.449E−04 | 75 | SNF2L1, PAR2, c-Maf, SLUG, Alpha crystallin B, IQCJ-SCHIP1, AEBP1, Ephrin-B receptors, Caspase-6, SLC29A2, PEDF (serpinF1), BDH, |

TABLE 12B-continued

| | | PC1 GO Processes | | | |
|---|---|---|---|---|---|
| Processes | Total | p-value | FDR | In Data | Network Objects from Active Data |
| | | | | | Axin, Neuropilin-2, PLA2, LEC1, GCR-alpha, SLAC2-B, ERR1, SPG20, Axin2, SLIT3, Plakophilin 2, MAP7(EMAP115), FOG2, Calpain 5, Galectin-1, Myosin Va, SCHIP1, Galpha(q)-specific peptide GPCRs, Epsilon-sarcoglycan, SHH, DAZAP, Ephrin-B receptor 2, Decorin proteoglycan, CDX1, DUOX2, LDB2, HOXB9, GCR-beta, SLIT2, Polycystin 2, NNMT, Neuropilin-1, NKCC1, Ephrin-B receptor 1, HNF4-alpha, Cofilin, c-Myb, DMP4, Alpha/epsilon-sarcoglycan, AML1/TRPS1 fusion protein, Vimentin, Osteonectin, SRGAP2, MyHC, PKC, MGP, PTPR-mu, G-protein gamma, Hedgehog, FA2H, SLC5A1, DFNA5, AKT(PKB), MYH10, TAZ, NAT-2, KCNQ1, TRPS1, BASP1, HNF4, M-Ras, Decorin, JAM3 |
| positive regulation of endothelial cell chemotaxis | 8 | 1.903E−06 | 2.035E−04 | 4 | SLUG, PKC, PKC-mu, PRKD2 |
| cell migration | 842 | 1.986E−06 | 2.042E−04 | 29 | PAR2, SLUG, IQCJ-SCHIP1, Ephrin-B receptors, Tubulin beta, Tensin, Neuropilin-2, PLA2, Matriptase, SLIT3, SCHIP1, Galpha(q)-specific peptide GPCRs, SHH, MSN (moesin), HOXB9, SLIT2, ERM proteins, Neuropilin-1, Ephrin-B receptor 1, Cofilin, NOX1, SRGAP2, MyHC, PKC, Hedgehog, AMOTL1 (Jeap), Necdin, MYH10, JAM3 |
| positive regulation of endothelial cell migration | 65 | 2.006E−06 | 2.042E−04 | 8 | SLUG, Neuropilin-2, Neuropilin-1, PKC, AKT(PKB), PKC-mu, AMOTL1 (Jeap), PRKD2 |
| regulation of cell motility | 669 | 2.556E−06 | 2.542E−04 | 25 | PAR2, SLUG, CARD5, FLRT2, Neuropilin-2, PLA2, Plakophilin 2, Galpha(q)-specific peptide GPCRs, SHH, MSN (moesin), SLIT2, ERM proteins, Neuropilin-1, CRCM, Vimentin, SRGAP2, PKC, CRMP4, PTPR-mu, Hedgehog, AKT(PKB), PKC-mu, AMOTL1 (Jeap), PRKD2, JAM3 |
| positive regulation of chemotaxis | 115 | 2.703E−06 | 2.627E−04 | 10 | PAR2, SLUG, PLA2, Galpha(q)-specific peptide GPCRs, SLIT2, Neuropilin-1, PKC, AKT(PKB), PKC-mu, PRKD2 |
| plasma membrane organization | 143 | 2.867E−06 | 2.691E−04 | 11 | MAP7(EMAP115), Myosin Va, Rab-31, Galpha(q)-specific peptide GPCRs, Synaptotagmin, EHD3, MyHC, PKC, FA2H, AKT(PKB), MYH10 |
| developmental process | 5978 | 2.895E−06 | 2.691E−04 | 113 | SNF2L1, PAR2, c-Maf, QKI, RECK, SLUG, Alpha crystallin B, IQCJ-SCHIP1, AEBP1, Ephrin-B receptors, FLRT2, Caspase-6, SLC29A2, LZTS1, PEDF (serpinF1), BDH, Axin, FEZ1, Tubulin beta, Neuropilin-2, DUOX1, PLA2, LEC1, GCR-alpha, MUPP1, SLAC2-B, ERR1, SPG20, Axin2, SLIT3, TIMP2, Plakophilin 2, MAP7(EMAP115), FOG2, Calpain 5, Galectin-1, Myosin Va, SCHIP1, Galpha(q)-specific peptide GPCRs, Epsilon-sarcoglycan, Willin, UCHL1, PAQR8, Kalirin, SHH, DAZAP, Ephrin-B receptor 2, Decorin proteoglycan, CDX1, HMGI/Y, FRAT2, DUOX2, TMPRSS2/ERG fusion protein, NAT-1, LDB2, MAP-1B, Chk2, HOXB9, Syndecan-2, GCR-beta, SLIT2, Glis2, Polycystin 2, NNMT, ERM proteins, DZIP, Neuropilin-1, ENC1, NKCC1, Ephrin-B receptor 1, SELENBP1, AP-1 mu subunits, HNF4-alpha, Cofilin, c-Myb, DMP4, Alpha/epsilon-sarcoglycan, AML1/TRPS1 fusion protein, NOX1, Vimentin, Osteonectin, SRGAP2, MyHC, PKC, CRMP4, MGP, PTPR-mu, G-protein gamma, Hedgehog, FA2H, SLC5A1, DFNA5, AKT(PKB), PKC-mu, NELL1, RILP (REST-interacting LIM domain protein), CAP2, Necdin, ECM2/SC1, MYH10, TRPC1, MYH14, TAZ, NAT-2, KCNQ1, TRPS1, BASP1, HNF4, STRBP, PRKD2, M-Ras, Decorin, JAM3 |

TABLE 12B-continued

PC1 GO Processes

| Processes | Total | p-value | FDR | In Data | Network Objects from Active Data |
|---|---|---|---|---|---|
| regulation of cellular component organization | 1910 | 3.197E−06 | 2.881E−04 | 49 | PAR2, SLUG, ASAP, Alpha crystallin B, CARD5, Ephrin-B receptors, LZTS1, Axin, FEZ1, Stonin-1, PLA2, GCR-alpha, SPG20, Axin2, SLIT3, Plakophilin 2, Galectin-1, CDC42EP5, Galpha(q)-specific peptide GPCRs, Kalirin, Synaptotagmin, Ephrin-B receptor 2, MAP-1B, Syndecan-2, GCR-beta, SLIT2, ERM proteins, Neuropilin-1, PRSS11 (HtrA1), Ephrin-B receptor 1, HNF4-alpha, Cofilin, c-Myb, NOX1, Vimentin, MyHC, PKC, CRMP4, G-protein gamma, AKT(PKB), PKC-mu, Necdin, MYH10, MYH14, TAZ, MLLT11, HNF4, PRKD2, JAM3 |
| positive regulation of epithelial cell migration | 92 | 3.234E−06 | 2.881E−04 | 9 | SLUG, Neuropilin-2, Galpha(q)-specific peptide GPCRs, Neuropilin-1, PKC, AKT(PKB), PKC-mu, AMOTL1 (Jeap), PRKD2 |
| vascular endothelial growth factor signaling pathway | 19 | 3.646E−06 | 3.145E−04 | 5 | Neuropilin-2, Neuropilin-1, PKC, PKC-mu, PRKD2 |
| negative regulation of intracellular transport | 119 | 3.686E−06 | 3.145E−04 | 10 | SLUG, Alpha crystallin B, Axin, Axin2, MAP-1B, Polycystin 2, HNF4-alpha, PKC, TAZ, HNF4 |

TABLE 12C

Non-Overlapped Genes

| Maps | pValue | Nov Overlapping Genes |
|---|---|---|
| Immune response_Inflammasome in inflammatory response | 2.075E−04 | CARD5, IL-1RI, Caspase-5, Biglycan |
| Neurophysiological process_EphB receptors in dendritic spine morphogenesis and synaptogenesis | 2.327E−04 | Syndecan-2, Ephrin-B receptors, Kalirin, Ephrin-B receptor 2 |
| Cell adhesion_Tight junctions | 2.600E−04 | MUPP1, Claudin-3, ZO-3, CDX1 |
| Development_TGF-beta-dependent induction of EMT via RhoA, PI3K and ILK. | 6.742E−04 | SLUG, Caldesmon, Cofilin, AKT(PKB) |
| Development_Slit-Robo signaling | 2.218E−03 | SLIT2, Cofilin, SLIT3 |
| Cell adhesion_Gap junctions | 2.218E−03 | Tubulin beta, PKC, ZO-3 |
| Signal transduction_Erk Interactions Inhibition of Erk | 3.188E−03 | PKC, PEA15, AKT(PKB) |
| Development_VEGF-family signaling | 5.435E−03 | Neuropilin-1, Neuropilin-2, AKT(PKB) |
| Cell adhesion_Ephrin signaling | 7.056E−03 | Ephrin-B receptors, Ephrin-B receptor 1, Kalirin |
| Immune response_MIF - the neuroendocrine-macrophage connector | 7.501E−03 | PLA2, PKC, HMGI/Y |
| Cell adhesion_ECM remodeling | 1.052E−02 | Syndecan-2, TIMP2, MSN (moesin) |
| Development_WNT signaling pathway. Part 2 | 1.108E−02 | SLUG, ENC1, Axin |
| Cell adhesion_Chemokines and adhesion | 1.135E−02 | Syndecan-2, Cofilin, AKT(PKB), MSN (moesin) |
| Development_FGF2-dependent induction of EMT | 1.301E−02 | IL-1RI, AKT(PKB) |
| Cytoskeleton remodeling_ESR1 action on cytoskeleton remodeling and cell migration | 1.564E−02 | AKT(PKB), MSN (moesin) |
| Cytoskeleton remodeling_Regulation of actin cytoskeleton by Rho GTPases | 1.703E−02 | Cofilin, MyHC |
| Development_Regulation of epithelial-to-mesenchymal transition (EMT) | 1.840E−02 | SLUG, Caldesmon, IL-1RI |
| Development_Glucocorticoid receptor signaling | 1.847E−02 | GCR-beta, GCR-alpha |
| Transcription_Transcription regulation of aminoacid metabolism | 1.997E−02 | c-Maf, PKC |
| Neolacto-series GSL Metabolism p.1 | 2.330E−02 | FUT6, FUT2, FUT4 |
| Neolacto-series GSL Metabolism p.1/Human version | 2.330E−02 | FUT6, FUT2, FUT4 |
| Inhibition of neutrophil migration by proresolving lipid mediators in COPD | 2.330E−02 | IL-1RI, PKC, MSN (moesin) |
| Proteolysis_Putative SUMO-1 pathway | 2.642E−02 | c-Myb, GCR-alpha |

TABLE 12C-continued

| Maps | pValue | Nov Overlapping Genes |
|---|---|---|
| Non-Overlapped Genes | | |
| Colorectal cancer (general schema) | 2.815E−02 | Ephrin-B receptors, SHH |
| Transport_Aldosterone-mediated regulation of ENaC sodium transport | 2.815E−02 | GCR-alpha, AKT(PKB) |
| Regulation of lipid metabolism_FXR-dependent negative-feedback regulation of bile acids concentration | 2.992E−02 | PXR, HNF4-alpha |
| Cytoskeleton remodeling_Reverse signaling by ephrin B | 2.992E−02 | Ephrin-B receptors, Axin |
| Linoleic acid/Rodent version | 2.992E−02 | PLA2G12, CYP2J2 |
| Putative pathways for stimulation of fat cell differentiation by Bisphenol A | 3.174E−02 | GCR-alpha, AKT(PKB) |
| Development_Transcription regulation of granulocyte development | 3.174E−02 | c-Myb, PKC |
| Apoptosis and survival_Caspase cascade | 3.360E−02 | Caspase-6, AKT(PKB) |
| Cytoskeleton remodeling_Keratin filaments | 3.942E−02 | Tubulin beta, Plakophilin 2 |
| Development_MAG-dependent inhibition of neurite outgrowth | 4.144E−02 | Cofilin, MyHC |
| Regulation of metabolism_Bile acids regulation of glucose and lipid metabolism via FXR | 4.144E−02 | HNF4-alpha, AKT(PKB) |
| Cell adhesion_Cell-matrix glycoconjugates | 4.350E−02 | Galectin-4, TIMP2 |

Figure 20:
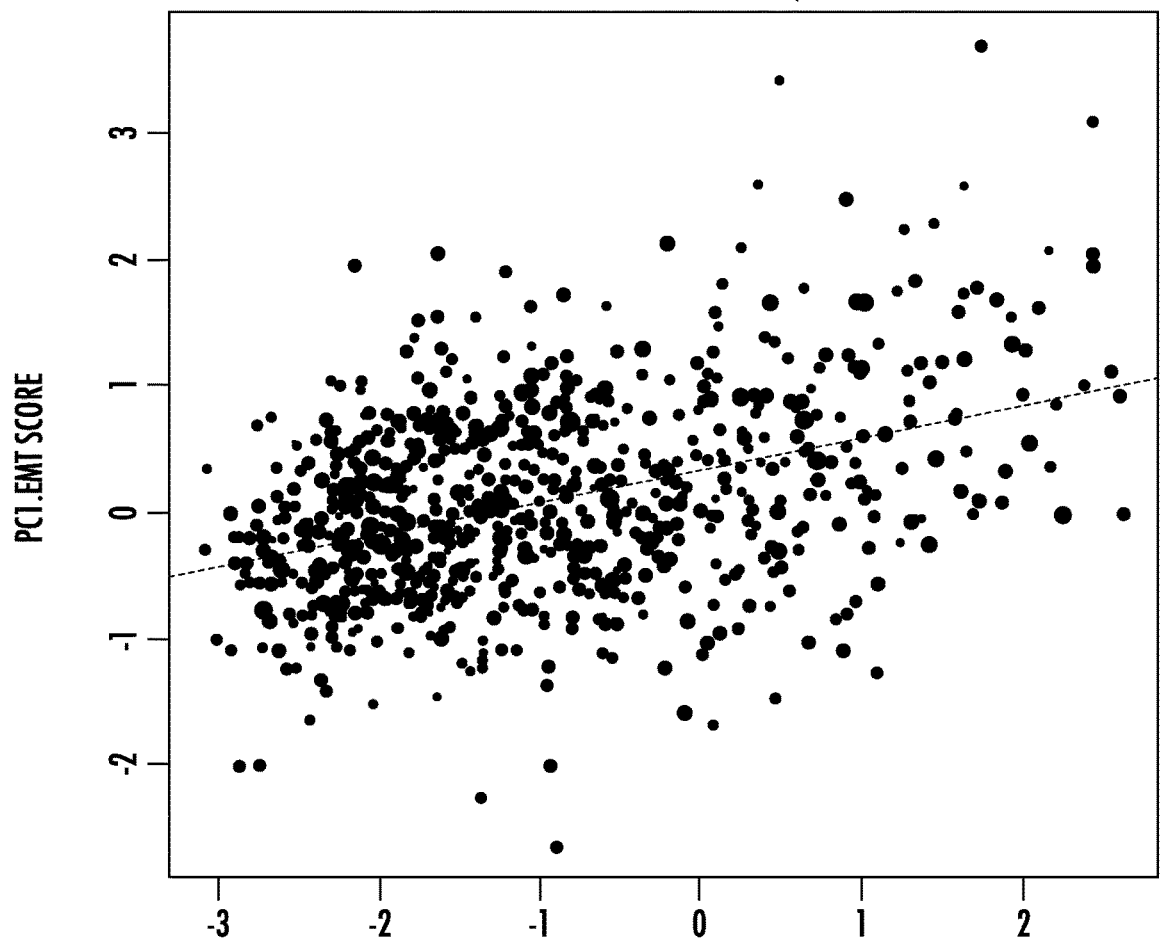
FIG. 20 is a plot showing correlation between ΔPC1.EMT and BRAF scores on PETACC dataset (n=752).
Figure 21A:
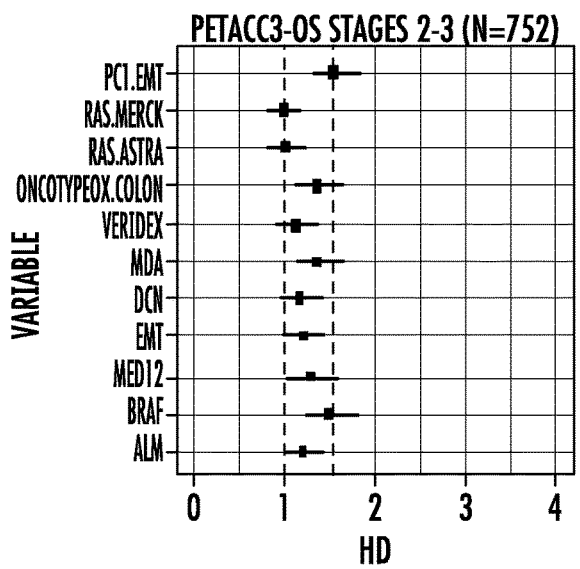
FIGS. 21A to 21H show results of OS (FIGS. 21A, 21C, 21E, 21G) and RFS (FIGS. 21B, 21D, 21F, 21H) univariate analysis of ΔPC1.EMT and other 10 known prognostic signatures on the datasets PETACC3 (FIGS. 21A, 21B), ALMAC (FIGS. 21C, 21D), GEO41258 (FIGS. 21E, 21F), LNCC (FIG. 21G), and GSE14333 (FIG. 21H), (significant prognostic values are highlighted by red and blue colors).
Figure 21B:
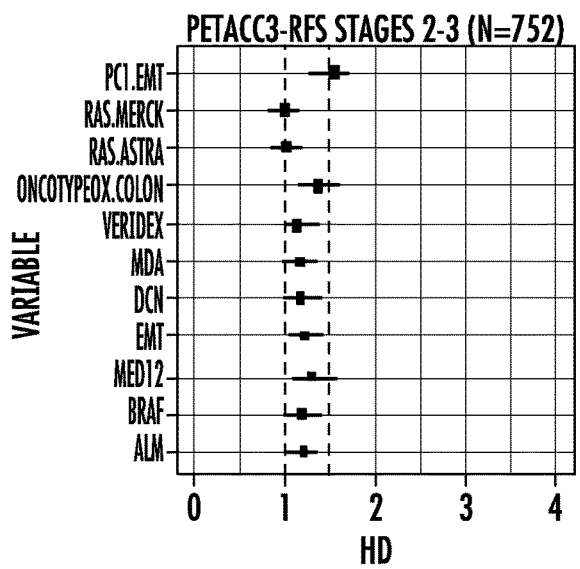
Figure 21C:
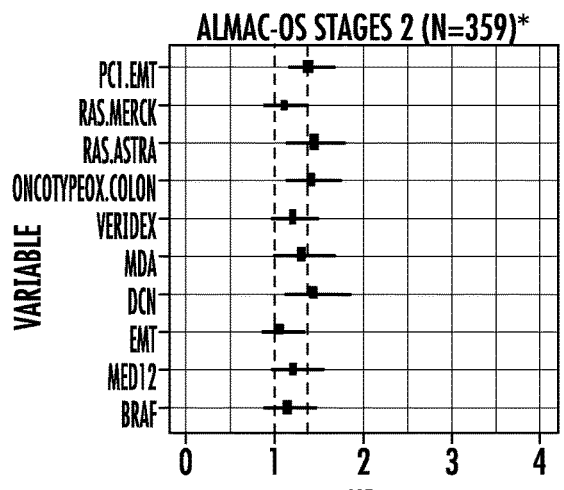
Figure 21D:
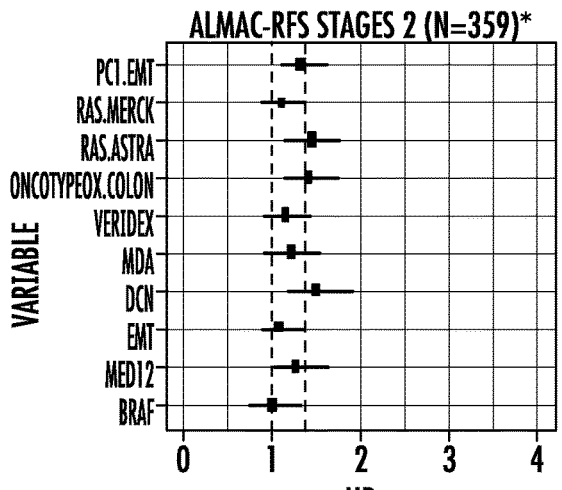
Figure 21E:
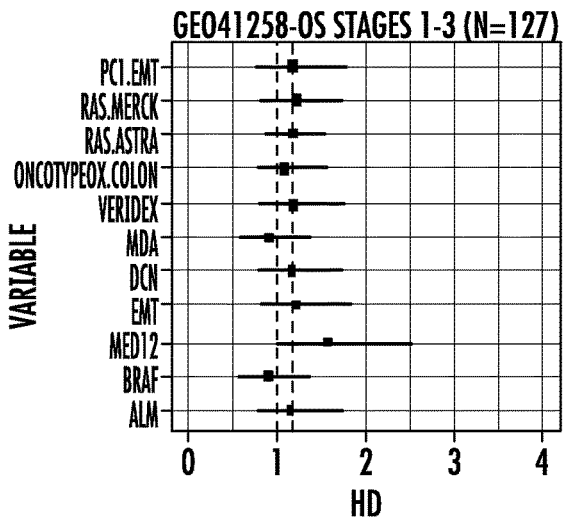
Figure 21F:
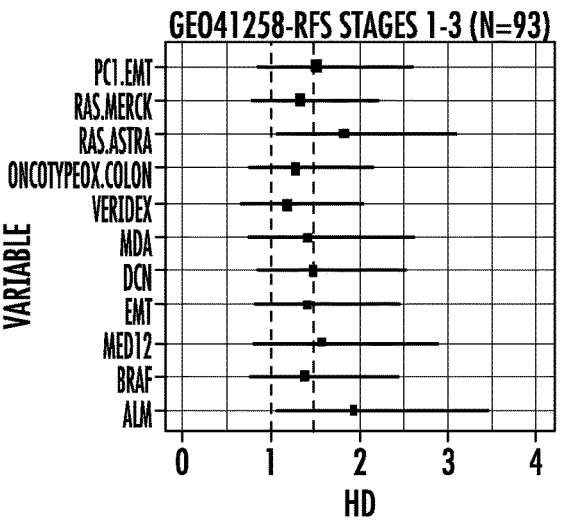
Figure 21G:
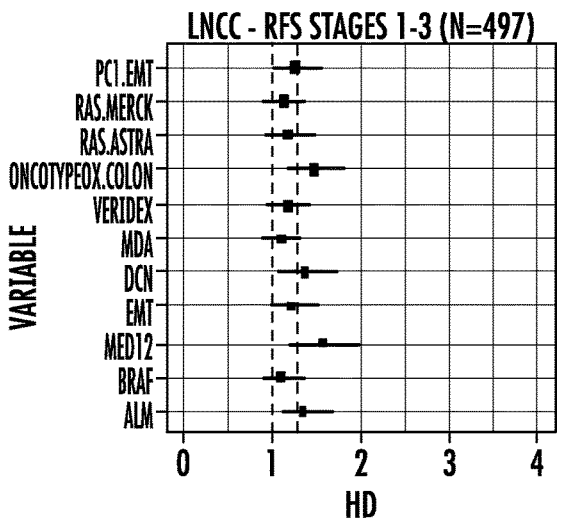
Figure 21H:
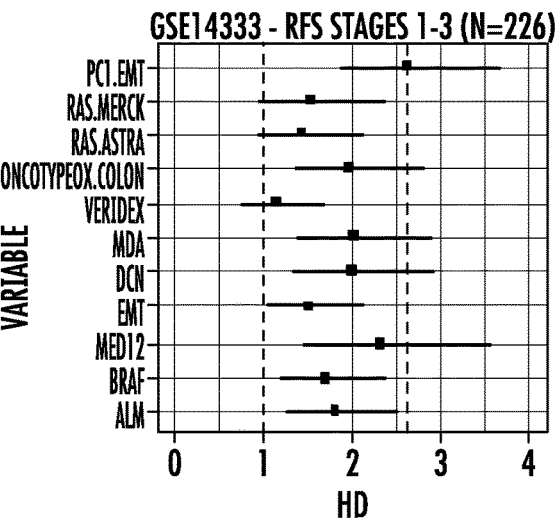

Interestingly, in comparing EMT to ΔPC1.EMT, the gene with the greatest weight change was CD24 (FIG. 3I), previously reported as a metastasis-associated gene with high expression linked to worse survival in bladder cancer (Smith, S. C. et al. Cancer Res. 2006 66(4):1917-22). CD24 was also reported as a marker of colon cancer stem cells (CSC) whose properties are thought to contribute to "metastatic traits" and therapeutic resistance (Oskarsson, T., Cell Stem Cell. 2014 14(3):306-21; Ashley, N. et al. Cancer Res. 2013 73(18):5798-809). Thus, ΔPC1.EMT may capture the epithelial CSC features in CRC, which is consistent with a recent report demonstrating that in breast cancer, CDH1 and CD24 were highly enriched in the epithelial CSCs characterized by expression of the CSC marker ALDH1, while their expression was down-regulated in the mesenchymal CSCs (CD44$^+$CD24$^-$) (Liu, S. et al. Stem Cell Reports. 2013 2(1):78-91). ERBB3 was also identified as one of the genes whose contribution was increased in ΔPC1.EMT (FIG. 3I) and was amplified, overexpressed, or mutated in human cancers (Guinney, J. et al. Clin Cancer Res. 2014 20(1):265-72). In agreement with ERBB3 activation, ΔPC1.EMT, but not EMT, was associated with activation of the RAS/MAPK pathway, evidenced by its positive correlation with various RAS and BRAF scores (Table 13 and FIG. 20). Since abnormal activation of the RAS/MAPK pathway is thought to contribute to the resistance of anti-EGFR treatments (Guinney, J. et al. Clin Cancer Res. 2014 20(1):265-72), ΔPC1.EMT-associated poor prognosis might, in part, result from RAS/MAPK-mediated drug resistance in epithelial-like CRC.

TABLE 13

| Correlations-Moffitt468 | | | | | | |
|---|---|---|---|---|---|---|
|  | d_meta | APC_ | TP53 | KRAS | EMT_Score | PC1_Score |
| d_meta | 1 | 0.09487 | 0.09409 | 0.16646 | 0.12244 | 0.26862 |
|  |  | 0.0402 | 0.0419 | 0.0003 | 0.008 | <.0001 |
| APC_ | 0.09487 | 1 | 0.13219 | 0.25802 | −0.09383 | −0.20689 |
|  | 0.0402 |  | 0.0042 | <.0001 | 0.0425 | <.0001 |
| TP53 | 0.09409 | 0.13219 | 1 | −0.08521 | −0.04201 | −0.06056 |
|  | 0.0419 | 0.0042 |  | 0.0655 | 0.3645 | 0.1909 |
| KRAS | 0.16646 | 0.25802 | −0.08521 | 1 | −0.14592 | −0.09788 |
|  | 0.0003 | <.0001 | 0.0655 |  | 0.0015 | 0.0343 |
| EMT_Score | 0.12244 | −0.09383 | −0.04201 | −0.14592 | 1 | 0.9 |
|  | 0.008 | 0.0425 | 0.3645 | 0.0015 |  | <.0001 |
| PC1_Score | 0.26862 | −0.20689 | −0.06056 | −0.09788 | 0.9 | 1 |
|  | <.0001 | <.0001 | 0.1909 | 0.0343 | <.0001 |  |
| ΔPC1.EMT | 0.3845 | −0.26895 | −0.04665 | 0.0195 | 0.38 | 0.74 |
|  | <.0001 | <.0001 | 0.314 | 0.6739 | <.0001 | <.0001 |
| RAS_Merck_ | −0.09597 | −0.15514 | −0.0884 | 0.1156 | −0.10964 | 0.01908 |
|  | 0.038 | 0.0008 | 0.056 | 0.123 | 0.0177 | 0.6805 |
| RAS_Astra | 0.08945 | −0.10735 | −0.15836 | 0.39651 | −0.01907 | 0.14859 |
|  | 0.0531 | 0.0202 | 0.0006 | <.0001 | 0.6807 | 0.0013 |
| BRAF_ | −0.10847 | −0.39096 | −0.08739 | −0.29806 | −0.04731 | 0.08427 |
|  | 0.0189 | <.0001 | 0.0589 | <.0001 | 0.3071 | 0.0685 |
| msi_high | −0.1927 | −0.33209 | −0.25961 | −0.15516 | −0.14551 | −0.02419 |
|  | <.0001 | <.0001 | <.0001 | 0.0008 | 0.0016 | 0.6016 |

|  | ΔPC1.EMT | RAS_Merck_ | RAS_Astra | BRAF_ | msi_high |
|---|---|---|---|---|---|
| d_meta | 0.3845 | −0.09597 | 0.08945 | −0.10847 | −0.1927 |
|  | <.0001 | 0.038 | 0.0531 | 0.0189 | <.0001 |

TABLE 13-continued

Correlations-Moffitt468

| | | | | | |
|---|---|---|---|---|---|
| APC_ | −0.26895 | −0.15514 | −0.10735 | −0.39096 | −0.33209 |
| | <.0001 | 0.0008 | 0.0202 | <.0001 | <.0001 |
| TP53 | −0.04665 | −0.0884 | −0.15836 | −0.08739 | −0.25961 |
| | 0.314 | 0.056 | 0.0006 | 0.0589 | <.0001 |
| KRAS | 0.0195 | 0.1156 | 0.39651 | −0.29806 | −0.15516 |
| | 0.6739 | 0.123 | <.0001 | <.0001 | 0.0008 |
| EMT_Score | 0.38 | −0.10964 | −0.01907 | −0.04731 | −0.14551 |
| | <.0001 | 0.0177 | 0.6807 | 0.3071 | 0.0016 |
| PC1_Score | 0.74 | 0.01908 | 0.14859 | 0.08427 | −0.02419 |
| | <.0001 | 0.6805 | 0.0013 | 0.0685 | 0.6016 |
| ΔPC1.EMT | 1 | 0.15645 | 0.33994 | 0.22097 | 0.14016 |
| | | 0.0007 | <.0001 | <.0001 | 0.0024 |
| RAS_Merck_ | 0.15645 | 1 | 0.48973 | 0.28309 | 0.33283 |
| | 0.0007 | | <.0001 | <.0001 | <.0001 |
| RAS_Astra | 0.33994 | 0.48973 | 1 | 0.32409 | 0.31115 |
| | <.0001 | <.0001 | | <.0001 | <.0001 |
| BRAF_ | 0.22097 | 0.28309 | 0.32409 | 1 | 0.5626 |
| | <.0001 | <.0001 | <.0001 | | |
| msi_high | 0.14016 | 0.33283 | 0.31115 | 0.5626 | 1 |
| | 0.0024 | <.0001 | <.0001 | <.0001 | |

A list of ten up-regulated and ten down-regulated genes (Tables 14A and 14B) were identified whose expression was correlated with ΔPC1.EMT in a linear model on the five datasets plus the TCGA CRC dataset (Cancer Genome Atlas Network. Nature. 2012 487(7407):330-7), and interestingly, about half of the identified genes are overlapped with the PC1 and EMT signature genes (especially PC1 down genes), suggesting these genes may maintain similar contributions between ΔPC1.EMT and parent scores. The great majority of identified genes have been reported to have biological functions related to epithelial or mesenchymal biology or to metastasis. For instance, CD109 (top up-regulated gene) has recently identified by proteomic analyses as a metastasis-associated protein marker (Karhemo, P. R. et al. J Proteomics. 2012 77:87-100), and CD109 was highly expressed in ALDH1-characterized epithelial sarcoma CSCs (Emori, M. et al. PLoS One. 2013 8(12):e84187). CDX1 and CDX2 (top two down-regulated genes) were reported as putative tumor suppressor genes whose expression was epigenetically repressed in CRC, and reduced expression of CDX1 inhibited CSC stem cell differentiation and thus promoted CSC renewal (Ashley, N. et al. Cancer Res. 2013 73(18): 5798-809). In support of this, HCT116, an epithelial, MSI CRC cell line that lacks expression of CDX1 was recently classified as a colon CSC cell line (Sadanandam, A. et al. Nat Med. 2013 19(5):619-25). In addition, reduced expression of EPHB2 was associated with metastasis (Yu, G. et al. J Cancer Res Clin Oncol. 2011 137(1):73-80) while its overexpression induced EMT (Gao, Q. et al. Hum Pathol. 2014 45(2):372-81). Another down-regulated gene, MYB, is a cell cycle gene, and its ectopic expression was reported to contribute to cell migration and invasion but to also prevent metastasis (Knopfova, L. et al. Mol Cancer. 2012 11:15). It is noteworthy that inhibition of cell proliferation is thought to be necessary in the tumor dormancy step of metastasis (Giancotti, F. G. Cell. 2013 155(4):750-64). Thus, identification EPHB2 and MYB as ΔPC1.EMT-correlated down-regulated genes further supports the notion of non-EMT contributions to metastasis.

TABLE 14A

Top ten genes positively correlated with ΔPC1.EMT

| Gene Symbol | Entrez-ID | S | num p | p value | p adj | Sum t statistics | |
|---|---|---|---|---|---|---|---|
| CD109 | 135228 | 869.79 | 5 | 0.00 | 0.00 | 75.05 | |
| AHNAK2 | 113146 | 837.41 | 6 | 0.00 | 0.00 | 79.32 | |
| GAS1 | 2619 | 806.50 | 6 | 0.00 | 0.00 | 76.57 | |
| PRKCDBP | 112464 | 806.43 | 6 | 0.00 | 0.00 | 77.90 | |
| MEIS2 | 4212 | 779.02 | 6 | 0.00 | 0.00 | 77.16 | |
| NXN | 64359 | 772.64 | 5 | 0.00 | 0.00 | 70.33 | |
| GFPT2 | 9945 | 727.95 | 6 | 0.00 | 0.00 | 72.26 | Overlapped UP |
| PMP22 | 5376 | 711.36 | 6 | 0.00 | 0.00 | 73.46 | EMT Up |
| WWTR1 | 25937 | 692.29 | 6 | 0.00 | 0.00 | 72.07 | PC1 Up |
| PTRF | 284119 | 688.52 | 6 | 0.00 | 0.00 | 71.22 | Overlapped Up |

TABLE 14B

Top ten genes negatively correlated with ΔPC1.EMT

| Gene Symbol | Entrez-ID | S | num p | p value | p adj | Sum t statistics | |
|---|---|---|---|---|---|---|---|
| CDX1 | 1044 | 860.61 | 6 | 0.00 | 0.00 | −80.16 | PC1 Down |
| CDX2 | 1045 | 845.27 | 6 | 0.00 | 0.00 | −79.41 | |
| C10orf99 | 387695 | 767.33 | 5 | 0.00 | 0.00 | −67.82 | PC1 Down |
| DDC | 1644 | 752.19 | 6 | 0.00 | 0.00 | −73.57 | |
| GPA33 | 10223 | 726.29 | 6 | 0.00 | 0.00 | −72.98 | PC1 Down |
| FAM84A | 151354 | 720.55 | 5 | 0.00 | 0.00 | −67.43 | Overlapped Down |
| NR1I2 | 8856 | 697.98 | 6 | 0.00 | 0.00 | −70.24 | PC1 Down |
| MYB | 4602 | 630.56 | 6 | 0.00 | 0.00 | −68.13 | PC1 Down |
| C2orf89 | 129293 | 616.89 | 5 | 0.00 | 0.00 | −60.62 | |
| EPHB2 | 2048 | 597.82 | 6 | 0.00 | 0.00 | −66.42 | PC1 Down |

Gene set enrichment analysis identified a variety of biological processes correlated with ΔPC1.EMT, including negatively correlated mitochondrial metabolism (Tables 27 to 42), a trait of epithelial stem cells. It is noteworthy that metastasis suppressor gene KISS1 was recently reported to promote normal mitochondrial metabolism, an anti-metastasis mechanism (Favre, C., et al. Oncogene. 2010 29(27): 3964-76). Finally, the association of the ΔPC1.EMT score with an expanded set of other known prognostic signatures was tested on the five datasets in a univariate analysis. Results showed that ΔPC1.EMT was the signature that, overall, had the highest significant prognostic value for OS and RFS across all the datasets tested (FIGS. 21A to 21H). It is of interest to mention that ΔPC1.EMT showed a relatively high correlation with the OncotypeDX™ colon signature (Genomic Health, Inc.) (Table 15), which had exploited cell proliferation as a potential prognostic marker, and GH score was found to be negatively correlated with cell cycle genes such as MYBL2 (O'Connell, M. J. et al. J Clin Oncol. 2010 28(25):3937-44), a family member of MYB as mentioned earlier. Taken together, the negative association of ΔPC1.EMT with growth properties such as mitochondrial metabolism and cell proliferation may be non-EMT processes captured by the score.

TABLE 15

Correlations between ΔPC1.EMT and OncotypeDX colon signature (GH) scores

| Datasets | Pearson's Corr. | P.value | N samples |
| --- | --- | --- | --- |
| PETACC3 | 0.36 95% CI (0.29-0.42) | <2.2e−16 | N = 750 |
| ALMAC | 0.31 95% CI (0.21-0.40) | 2.48e−09 | N = 357 |
| LNCC | 0.68 95% CI (0.63-0.72) | <2.2e−16 | N = 564 |
| GSE14333 | 0.69 95% CI (0.62-0.74) | <2.2e−16 | N = 288 |
| GEO41258 | 0.78 95% CI (0.72-0.83) | <2.2e−16 | N = 184 |

In conclusion, while EMT appears to be a dominant program in CRC, ΔPC1.EMT is far more predictive of CRC outcome (metastasis and survival) than its parent PC1 or EMT scores. Moreover, it is the "best in class" when compared to a variety of other known prognostic signatures. The subtraction of EMT from PC1 (ΔPC1.EMT) increases its bias in detecting non-EMT biology, including epithelial CSCs, thereby improving its potential to portend metastasis and providing new targets for therapy of distant disease. These observations support the hypothesis that both epithelial and mesenchymal cell phenotypes cooperate to produce metastasis (Tsuji, T et al. Cancer Res. 2009 69(18):7135-9; Nieto, M. A. Science. 2013 342(6159):1234850).

Methods

Moffitt468 and additional five independent datasets, including PTEACC31, ALMAC2, LNCC3, GEO412584 and GSE143335 (Budinska, E. et al. J Pathol. 2013 231(1): 63-76; Kennedy, R. D. et al. J Clin Oncol. 2011 29(35): 4620-6; Marisa, L. et al. PLoS Med. 2013 10(5):e1001453; Sheffer, M. et al. Proc Natl Acad Sci USA. 2009 106(17): 7131-6; Jorissen, R. N. et al. Clin Cancer Res. 2009 15(24): 7642-7651) were tested. Probe intensities were preprocessed using RMA. PC1 and EMT scores were calculated as previously described (Loboda, A. et al. BMC Med Genomics. 2011 4:9). Briefly, for each of the datasets, a score was computed for each of the 4 signatures (EMT.UP.score, EMT.DOWN.score, PC1.UP.score and PC1.DOWN.score) as the arithmetic mean of all probesets corresponding to gene symbols present in the corresponding gene signature. EMT and PC1 scores were then obtained as follows:

EMT.score=EMT.UP.score−EMT.DOWN.score

PC1.score=PC1.UP.score−PC1.DOWN.score

The ΔPC1.EMT score was computed as follows:

ΔPC1.EMT.score=PC1.score−EMT.score

Scores were standardized by subtracting the score median and dividing by the score IQR.

Pearson's product moment correlation coefficient was used to quantify the association between the scores, MSI status, and mutation status for various genes. Pathways analyses of the non-overlapped genes of PC1 and EMT signatures by GO Process were performed using the MetaCore package. A P-values cut-off of 0.05 resulted in 35 significant dysregulated pathways.

The association of gene expression with the ΔPC1.EMT.score within each of the datasets was tested by a linear regression model with the score as the explanatory variable using the "limma" R package (version 3.16.3), adjusting standard errors estimates by an empirical Bayes approach. P-values were combined across datasets using Fisher's method (MADAM R package version 1.2.2). A Bonferroni correction was applied to control for false positive results introduced by multiple testing.

Genes showing an adjusted P-value<0.00001 were split in two groups: those positively (N=2,983) and those negatively (N=2,221) correlated with the ΔPC1.EMT score. The functional tool DAVID (http://david.abcc.ncifcrf.gov/) was employed to identify annotation terms enriched within each of the groups. The 15,896 genes measured in all 5 datasets were used as background. The scores were computed from 10 signatures (RAS Merck (Loboda, A. et al. BMC Med Genomics. 2010 3:26) RAS Astrazeneca (Dry, J. R. et al. Cancer Res. 2010 70(6):2264-73), OncotypeDX colon (O'Connell, M. J. et al. J Clin Oncol. 2010 28(25):3937-44), Veridex (Jiang, Y. et al. J Mol Diagn. 2008 10(4):346-5), MD Anderson (Oh, S. C. et al. Gut. 2012 61(9):1291-8), Decorin (Farmer, P. et al. Nat Med. 2009 15(1):68-74), MED12 (Huang, S. et al. Cell. 2012 151(5):937-50), BRAF score (Popovici, V. et al. J Clin Oncol. 2012 30(12):1288-95) and ALM (Kennedy, R. D. et al. J Clin Oncol. 2011 29(35):4620-6) as described in the original study. Cox proportional hazards regression models was used in the R package "survival" (version 2.37-7) to assess association of tumor scores with Overall Survival (OS), Relapse-free survival (RFS) and Survival after Relapse (SAR).

In order to characterize the three signatures (PC1, EMT and ΔPC1.EMT), the average contribution of each gene was estimated to each of the signatures across five data sets. For each data set, a contribution was first calculated for each probe set to the PC1 and EMT signatures, respectively. The contribution was proportional to the average expression level of the probe set and inversely proportional to the number of probe sets included in the signature for the microarray platform used for the data set. Then, gene-wise contributions were estimated to each signature by summing the contributions for all probe sets corresponding to the same gene. The contributions to the ΔPC1.EMT signature were obtained as the difference between the contributions to the PC1 and the EMT signatures. Finally, a weighted average of the contributions was computed across all five data sets to obtain final estimates of the gene contributions to the three signatures. The weight for a data set was inversely proportional to the Euclidean norm of the vector of gene contributions to the PC1 and EMT signatures in the data set. A linear contrast was used to test for a trend in gene expression score with increasing stage of primary disease to distant metastasis, using PROC GLM (SAS, version 9.2).

Example 2

Table 16 summarizes the main features of the datasets used in this Example.

Based on the clustering there seem to be three stable groups of signatures: Group1: Oncotype TX, Mammaprint Coppola and Veridex; Group2: Decorin, EMT MED12, Peng and Genomic Health; and Group3: BRAF, MDA and RAS-

TABLE 16

Study Datasets

| Dataset | Institution (Article) | Accession | n | Stage | Treatment | Platform | RNA material | Survival |
|---|---|---|---|---|---|---|---|---|
| PETACC3 | BCF, Lausanne (Budinska E, et. al.) | E-MTAB-990 | 752 | 2, 3 | 5-FU/FA FOLFIRI | Almac | FFPE | OS, RFS, SAR |
| ALMAC | Queen's University Belfast (Kennedy RD. et. al.) | E-MTAB-863 E-MTAB-864 | 359 | 2 | Untreated[a] | Almac | FFPE | OS, RFS |
| French | Ligue Nationale Controle Cancer, Paris (Marisa L. et. al.) | E-GEOD-39582 | 566 | 1-4 | Treated Untreated | HGU133plus2 | Frozen | RFS |
| GEO41258 | Weizmann Institute of Science, Rehovot (Sheffer M. et. al.) | E-GEOD-41258 | 186 | 1-4 | Unknown | HGU133a | Frozen | OS, RFS |
| GSE14333 | Ludwig Institute for Cancer Research, Melbourne (Jorissen RN. et. al.) | GSE14333 | 290 | A-D | Unknown[b] | HGU133plus2 | Frozen | RFS |
| TCGA | TCGA (The Cancer Genome Atlas Network) | TCGA portal | 385 | 1-4 | Unknown | RNA-seq | Frozen | poor |

[a] no preoperative or postoperative cancer therapy within 1 year of surgery (although therapy given after recurrence was acceptable)
[b] standard adjuvant chemotherapy (either agent 5-fluouracil/capocitabine or 5-fluouracil and oxaliplatin) or postoperative concurrent chemoradiotherapy (50.4 Gy in 28 fractions with concurrent 5-fluorocil)

Correlation of PC1.EMT, PC1 and EMT Scores with Other Known Prognostic Signatures As discussed, the association of PC1.EMT with other known prognostic signatures was tested. Specifically, PC1.EMT was compared with Oncotype DX, Mammaprint, RAS Merck, RAS Astrazeneca, Genomic Health colon signature [O'Connell M J, et al. (2010). J Clin Oncol.; 28:3937-44], Veradex [Jiang Y, et al. (2008). J Mol Diagn.; 10:346-54], MD Anderson signature [Oh S C, et al. (2012). Gut. 61:1291-8], Decorin signature [Farmer P, et al. (2009). Nat Med. 15:68-74], EMT signature [Loboda A, et al. (2011). BMC Med Genomics. 4:9], MED12 signature [Huang Sl, et al. (2012). Cell. 151:937-50], BRAF signature [Popovici V, et al. (2012). J Clin Oncol. 30:1288-95], Coppola 2011 signature [Coppola D, et al. (2011). Am J Pathol. 179:37-45], Peng2010 signature [Peng J, et al. (2010). Int J Colorectal Dis. 25:1277-85], Schetter 2009 signature [Schetter A J, et al. (2009). Clin Cancer Res. 15:5878-87], Staub2009 signature [Staub El, et al. (2009). J Mol Med (Berl). 87:633-44], and ALM signature [Kennedy RD1, et al. (2011). J Clin Oncol. 35:4620-6]. The comparison was performed in all available dataset.

FIGS. 6A to 6F are pairs plots of the signature scores in PETACC (FIG. 6A), ALAMC (FIG. 6B), French (FIG. 6C), GSE14333 (FIG. 6D), GEO41258 (FIG. 6E), and TCGA (FIG. 6F) datasets. FIGS. 7A to 7F show gene clusters for PETACC (FIG. 7A), ALAMC (FIG. 7B), French (FIG. 7C), GSE14333 (FIG. 7D), GEO41258 (FIG. 7E), and TCGA (FIG. 7F) datasets.

.Merck. Some other elements moved between Group 2 and Group 3, including PC1.EMT.

Tables 17 to 24 show the correlation between prognostic signatures and OS/RFS.

TABLE 17

Univariate Cox Proportional Hazard Regression model for OS in Stage 2 and 3 - PETACC dataset

| | HR (95% CI) | P-value | n |
|---|---|---|---|
| PC1.EMT | 1.56 (1.32-1.84) | 1.16e−07 | 752 |
| OncotypeTx | 0.63 (0.53-0.75) | 4.36e−07 | 752 |
| MammaPrint | 0.75 (0.62-0.90) | 2.48e−03 | 752 |
| RAS.Merck | 0.98 (0.81-1.18) | 8.4e−01 | 752 |
| RAS.Astra | 1.01 (0.84-1.21) | 9.1e−01 | 752 |
| GH | 1.37 (1.15-1.63) | 5.32e−04 | 752 |
| Veridex | 1.12 (0.93-1.35) | 2.19e−01 | 752 |
| MDA | 1.36 (1.14-1.64) | 8.08e−04 | 752 |
| DCN | 1.16 (0.96-1.40) | 1.14e−01 | 752 |
| EMT | 1.22 (1.03-1.44) | 2.01e−02 | 752 |
| MED12 | 1.29 (1.06-1.58) | 1.12e−02 | 752 |
| BRAF | 1.49 (1.24-1.80) | 1.93e−05 | 752 |
| Coppola | 1.06 (0.89-1.26) | 5.24e−01 | 752 |
| Peng | 1.16 (0.97-1.39) | 9.39e−02 | 752 |
| Schetter | 1.32 (1.14-1.54) | 2.77e−04 | 752 |
| Staub | 0.81 (0.67-0.98) | 3.2e−02 | 752 |
| ALM | 1.18 (0.99-1.42) | 7.03e−02 | 752 |

TABLE 18

Univariate Cox Proportional Hazard Regression model for RFS in Stage 2 and 3 - PETACC dataset

|  | HR (95% CI) | P-value | n |
|---|---|---|---|
| PC1.EMT | 1.47 (1.28-1.69) | 8.98e−08 | 752 |
| OncotypeTx | 0.69 (0.59-0.80) | 1.54e−06 | 752 |
| MammaPrint | 0.75 (0.63-0.88) | 4.53e−04 | 752 |
| RAS.Merck | 0.97 (0.83-1.14) | 7.3e−01 | 752 |
| RAS.Astra | 1.03 (0.88-1.19) | 7.46e−01 | 752 |
| GH | 1.33 (1.14-1.55) | 2.42e−04 | 752 |
| Veridex | 1.19 (1.01-1.39) | 3.48e−02 | 752 |
| MDA | 1.15 (0.98-1.34) | 8.54e−02 | 752 |
| DCN | 1.20 (1.02-1.41) | 2.5e−02 | 752 |
| EMT | 1.22 (1.06-1.41) | 5.95e−03 | 752 |
| MED12 | 1.31 (1.10-1.55) | 1.92e−03 | 752 |
| BRAF | 1.18 (1.00-1.38) | 5.03e−02 | 752 |
| Coppola | 1.12 (0.96-1.30) | 1.53e−01 | 752 |
| Peng | 1.19 (1.02-1.38) | 2.67e−02 | 752 |
| Schetter | 1.27 (1.12-1.45) | 2.11e−04 | 752 |
| Staub | 0.84 (0.71-0.98) | 3e−02 | 752 |
| ALM | 1.18 (1.01-1.37) | 4.12e−02 | 752 |

TABLE 19

Univariate Cox Proportional Hazard Regression model for OS in ALMAC dataset

|  | HR (95% CI) | P-value | n |
|---|---|---|---|
| PC1.EMT | 1.38 (1.14-1.68) | 1.22e−03 | 359 |
| OncotypeTx | 0.94 (0.76-1.17) | 5.72e−01 | 359 |
| MammaPrint | 1.17 (0.91-1.49) | 2.15e−01 | 359 |
| RAS.Merck | 1.10 (0.87-1.38) | 4.32e−01 | 359 |
| RAS.Astra | 1.42 (1.14-1.78) | 2.03e−03 | 359 |
| GH | 1.40 (1.12-1.75) | 3.01e−03 | 359 |
| Veridex | 1.19 (0.96-1.48) | 1.08e−01 | 359 |
| MDA | 1.30 (1.02-1.66) | 3.24e−02 | 359 |
| DCN | 1.44 (1.13-1.84) | 3.22e−03 | 359 |
| EMT | 1.05 (0.85-1.30) | 6.38e−01 | 359 |
| MED12 | 1.24 (0.98-1.56) | 7.51e−02 | 359 |
| BRAF | 1.12 (0.87-1.45) | 3.75e−01 | 359 |
| Coppola | 1.00 (0.80-1.26) | 9.83e−01 | 359 |
| Peng | 1.04 (0.85-1.26) | 7.13e−01 | 359 |
| Schetter | 1.26 (1.08-1.46) | 3.01e−03 | 359 |
| Staub | 1.20 (0.94-1.52) | 1.43e−01 | 359 |
| ALM | 3.74 (2.92-4.79) | 0e+00 | 359 |

TABLE 20

Univariate Cox Proportional Hazard Regression model for RFS in ALMAC dataset

|  | HR (95% CI) | P-value | n |
|---|---|---|---|
| PC1.EMT | 1.31 (1.08-1.59) | 6.41e−03 | 359 |
| OncotypeTx | 1.03 (0.83-1.28) | 7.86e−01 | 359 |
| MammaPrint | 1.13 (0.88-1.43) | 3.38e−01 | 359 |
| RAS.Merck | 1.07 (0.86-1.35) | 5.33e−01 | 359 |
| RAS.Astra | 1.40 (1.12-1.75) | 2.95e−03 | 359 |
| GH | 1.40 (1.13-1.75) | 2.64e−03 | 359 |
| Veridex | 1.12 (0.90-1.38) | 3.16e−01 | 359 |
| MDA | 1.17 (0.92-1.48) | 1.99e−01 | 359 |
| DCN | 1.49 (1.17-1.90) | 1.14e−03 | 359 |
| EMT | 1.09 (0.88-1.35) | 4.15e−01 | 359 |
| MED12 | 1.29 (1.02-1.62) | 3.04e−02 | 359 |
| BRAF | 1.02 (0.79-1.31) | 8.78e−01 | 359 |
| Coppola | 1.07 (0.85-1.36) | 5.47e−01 | 359 |
| Peng | 1.06 (0.87-1.29) | 5.93e−01 | 359 |
| Schetter | 1.27 (1.08-1.49) | 3.16e−03 | 359 |
| Staub | 1.21 (0.96-1.53) | 1.05e−01 | 359 |
| ALM | 3.79 (2.98-4.82) | 0e+00 | 359 |

TABLE 21

Univariate Cox Proportional Hazard Regression model for RFS in French dataset

|  | HR (95% CI) | P-value | n |
|---|---|---|---|
| PC1.EMT | 1.37 (1.16-1.62) | 2.06e−04 | 557 |
| OncotypeTx | 0.75 (0.64-0.88) | 5.9e−04 | 557 |
| MammaPrint | 0.81 (0.67-0.97) | 2.09e−02 | 557 |
| RAS.Merck | 1.01 (0.83-1.24) | 8.98e−01 | 557 |
| RAS.Astra | 1.28 (1.05-1.56) | 1.36e−02 | 557 |
| GH | 1.53 (1.27-1.86) | 9.53e−06 | 557 |
| Veridex | 1.05 (0.87-1.27) | 6.24e−01 | 557 |
| MDA | 1.12 (0.91-1.37) | 2.92e−01 | 557 |
| DCN | 1.42 (1.14-1.77) | 2.07e−03 | 557 |
| EMT | 1.34 (1.12-1.61) | 1.71e−03 | 557 |
| MED12 | 1.53 (1.20-1.95) | 7.04e−04 | 557 |
| BRAF | 1.10 (0.90-1.34) | 3.52e−01 | 557 |
| Coppola | 1.05 (0.84-1.30) | 6.7e−01 | 557 |
| Peng | 1.31 (1.08-1.59) | 5.48e−03 | 557 |
| Schetter | 1.19 (0.99-1.45) | 7.06e−02 | 557 |
| Staub | 1.27 (1.04-1.55) | 1.99e−02 | 557 |
| ALM | 1.53 (1.26-1.86) | 1.99e−05 | 557 |

TABLE 22

Univariate Cox Proportional Hazard Regression model for RFS in GSE14333 dataset

|  | HR (95% CI) | P-value | n |
|---|---|---|---|
| PC1.EMT | 2.66 (1.89-3.73) | 1.53e−08 | 226 |
| OncotypeTx | 0.79 (0.61-1.04) | 9.06e−02 | 226 |
| MammaPrint | 0.95 (0.65-1.37) | 7.64e−01 | 226 |
| RAS.Merck | 1.54 (0.99-2.39) | 5.59e−02 | 226 |
| RAS.Astra | 1.44 (0.96-2.15) | 7.86e−02 | 226 |
| GH | 1.98 (1.38-2.84) | 2.02e−04 | 226 |
| Veridex | 1.15 (0.78-1.69) | 4.75e−01 | 226 |
| MDA | 2.02 (1.40-2.91) | 1.87e−04 | 226 |
| DCN | 2.00 (1.35-2.95) | 4.88e−04 | 226 |
| EMT | 1.51 (1.07-2.12) | 1.79e−02 | 226 |
| MED12 | 2.32 (1.49-3.59) | 1.71e−04 | 226 |
| BRAF | 1.70 (1.21-2.39) | 2.32e−03 | 226 |
| Coppola | 0.88 (0.60-1.30) | 5.21e−01 | 226 |
| Peng | 1.08 (0.79-1.49) | 6.35e−01 | 226 |
| Schetter | 0.88 (0.61-1.26) | 4.74e−01 | 226 |
| Staub | 1.15 (0.79-1.70) | 4.64e−01 | 226 |
| ALM | 1.80 (1.29-2.53) | 5.99e−04 | 226 |

TABLE 23

Univariate Cox Proportional Hazard Regression model for OS in GEO41258 dataset

|  | HR (95% CI) | P-value | n |
|---|---|---|---|
| PC1.EMT | 1.44 (1.11-1.85) | 5.66e−03 | 185 |
| OncotypeTx | 0.76 (0.58-1.01) | 5.82e−02 | 185 |
| MammaPrint | 0.88 (0.68-1.13) | 3.06e−01 | 185 |
| RAS.Merck | 1.11 (0.87-1.41) | 4.02e−01 | 185 |
| RAS.Astra | 1.18 (0.97-1.44) | 1.06e−01 | 185 |
| GH | 1.31 (1.01-1.69) | 4.06e−02 | 185 |
| Veridex | 1.09 (0.84-1.41) | 5.09e−01 | 185 |
| MDA | 1.04 (0.76-1.43) | 7.88e−01 | 185 |
| DCN | 1.19 (0.91-1.56) | 2.12e−01 | 185 |
| EMT | 1.23 (0.94-1.62) | 1.32e−01 | 185 |
| MED12 | 1.54 (1.12-2.13) | 8.07e−03 | 185 |
| BRAF | 1.04 (0.76-1.41) | 8.09e−01 | 185 |
| Coppola | 1.27 (0.96-1.70) | 9.66e−02 | 185 |
| Peng | 0.96 (0.75-1.23) | 7.67e−01 | 185 |
| Schetter | 1.02 (0.78-1.33) | 9.04e−01 | 185 |
| Staub | 0.83 (0.63-1.10) | 1.94e−01 | 185 |
| ALM | 1.29 (0.99-1.69) | 6.14e−02 | 185 |

TABLE 24

Univariate Cox Proportional Hazard Regression model for RFS in GEO41258 dataset

|  | HR (95% CI) | P-value | n |
|---|---|---|---|
| PC1.EMT | 1.76 (1.17-2.67) | 7.06e−03 | 109 |
| OncotypeTx | 0.77 (0.50-1.18) | 2.27e−01 | 109 |
| MammaPrint | 1.09 (0.72-1.65) | 6.85e−01 | 109 |
| RAS.Merck | 1.08 (0.71-1.64) | 7.33e−01 | 109 |
| RAS.Astra | 1.72 (1.13-2.63) | 1.23e−02 | 109 |
| GH | 1.52 (1.00-2.32) | 5.16e−02 | 109 |
| Veridex | 1.11 (0.70-1.75) | 6.48e−01 | 109 |
| MDA | 1.30 (0.78-2.16) | 3.07e−01 | 109 |
| DCN | 1.44 (0.92-2.25) | 1.09e−01 | 109 |
| EMT | 1.50 (0.95-2.35) | 7.91e−02 | 109 |
| MED12 | 1.54 (0.92-2.56) | 9.72e−02 | 109 |
| BRAF | 1.22 (0.75-1.98) | 4.24e−01 | 109 |
| Coppola | 1.10 (0.72-1.68) | 6.55e−01 | 109 |
| Peng | 1.17 (0.81-1.70) | 3.99e−01 | 109 |
| Schetter | 1.09 (0.69-1.74) | 7.15e−01 | 109 |
| Staub | 1.05 (0.67-1.67) | 8.21e−01 | 109 |
| ALM | 2.39 (1.48-3.87) | 3.75e−04 | 109 |

Comparison of PC1.EMT with APC Mutations

Figure 8A:
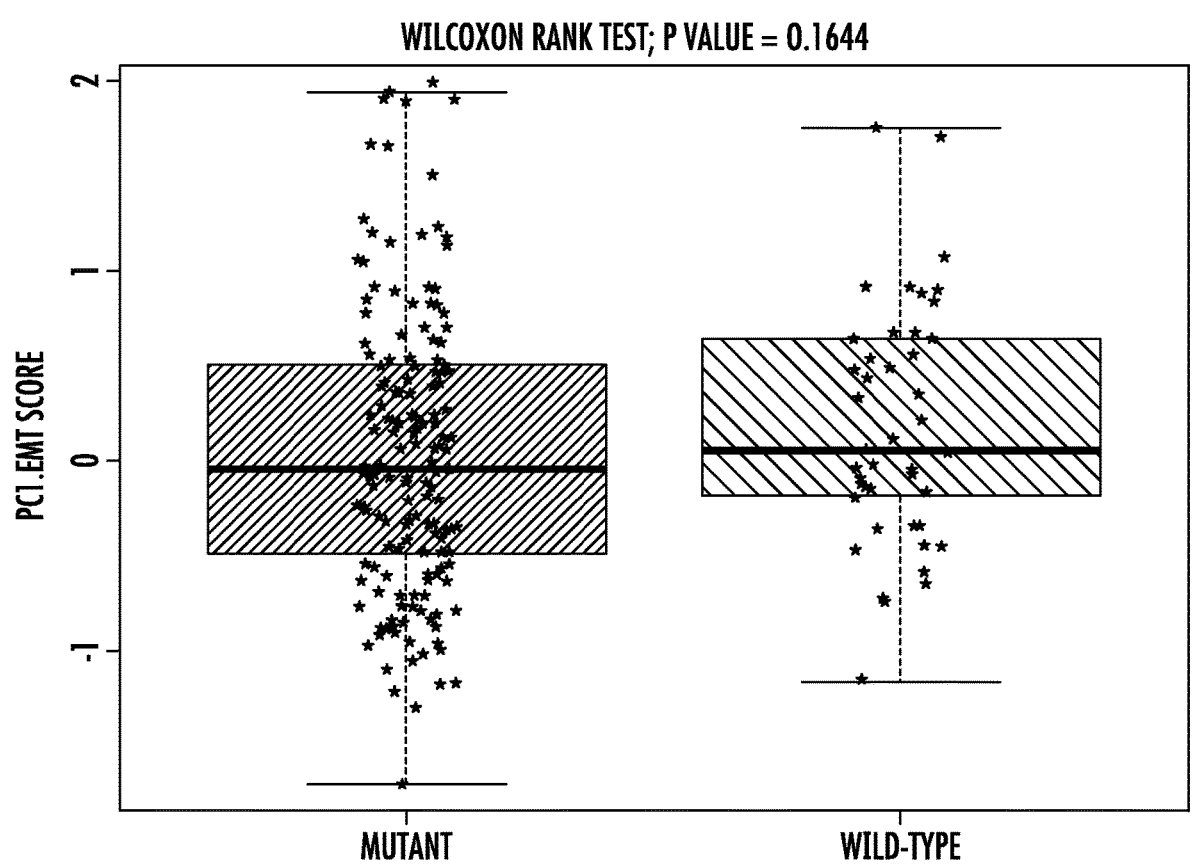
FIGS. 8A and 8B are boxplot of the PC1.EMT score intensities for APC detrimental mutations or wild-type analyzed by Wilcoxon Rank test (FIG. 8A, p=0.1644) or Kruskal-Wallis Rank test (FIG. 8B, p=0.0181).
Figure 8B:
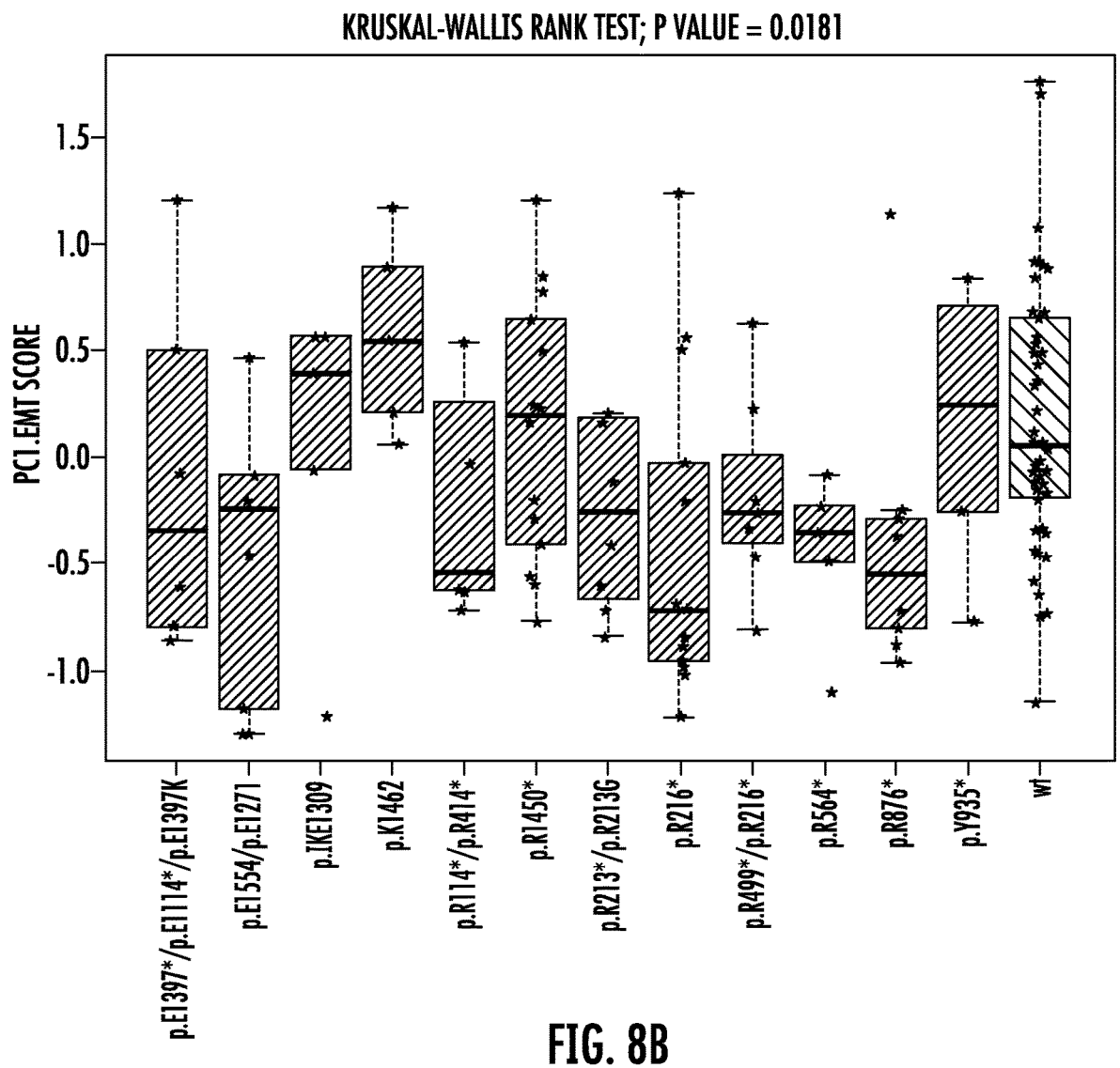
Figure 9A:
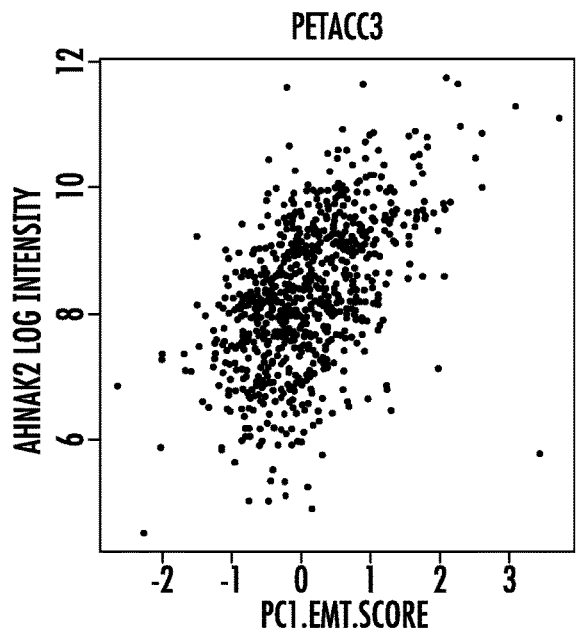
FIG. 9A to 9D are plots of AHNAK2 gene log intensities as a function of PC1.EMT score intensities in PETACC (FIG. 9A), French (FIG. 9B), GEO41258 (FIG. 9C), and ALAMC (FIG. 9D) datasets. Example of gene positively correlating with the score
Figure 9B:
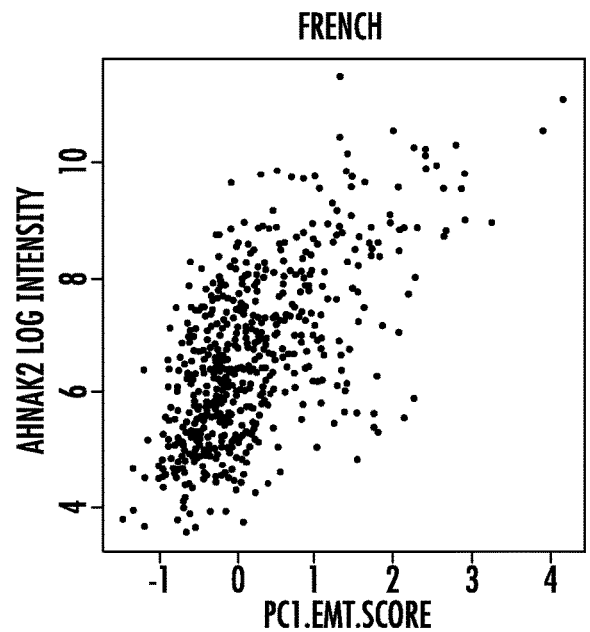
Figure 9C:
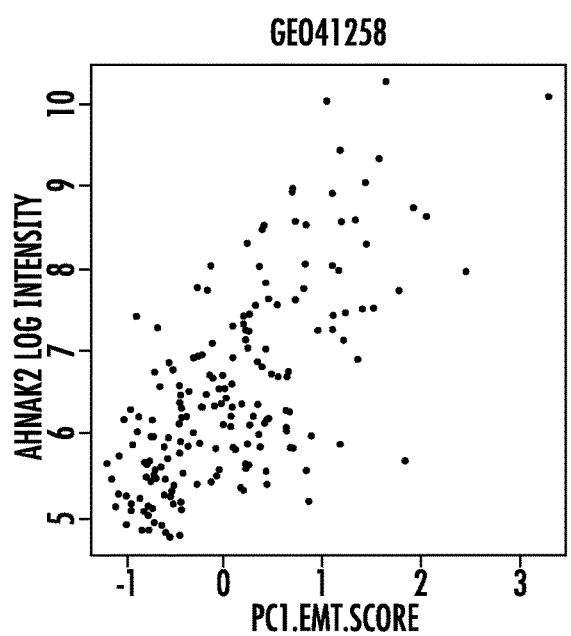
Figure 9D:
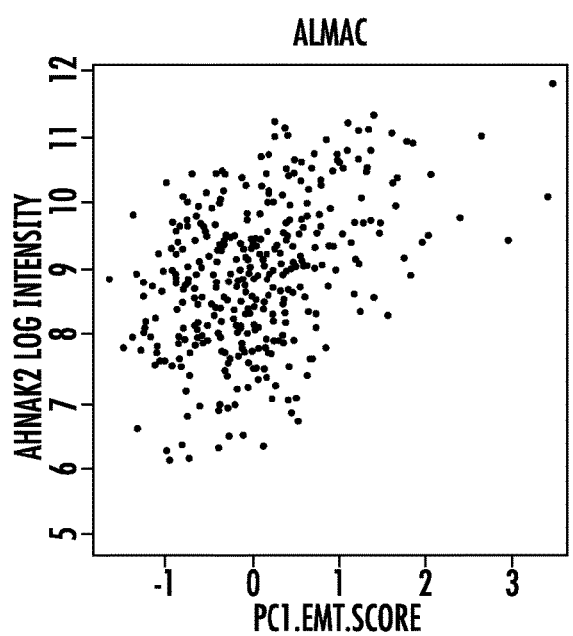
Figure 10A:
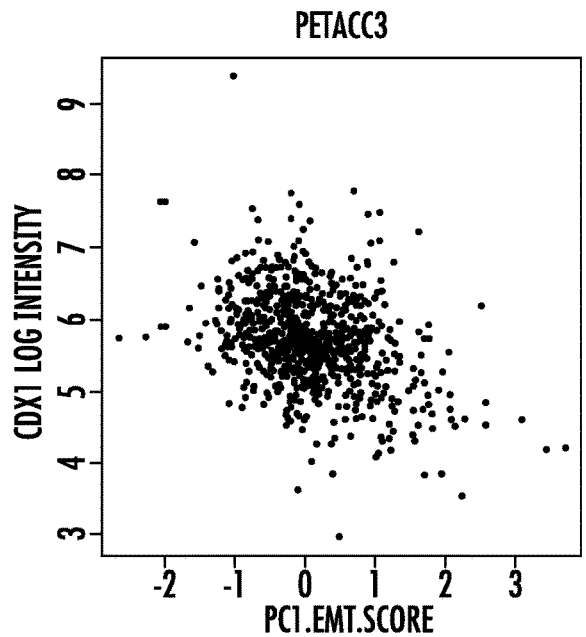
FIG. 10A to 10D are plots of CDX1 gene log intensities as a function of PC1.EMT score intensities in PETACC (FIG. 10A), French (FIG. 0B), GEO41258 (FIG. 10C), and ALAMC (FIG. 10D) datasets. Example of gene negatively correlating with the score
Figure 10B:
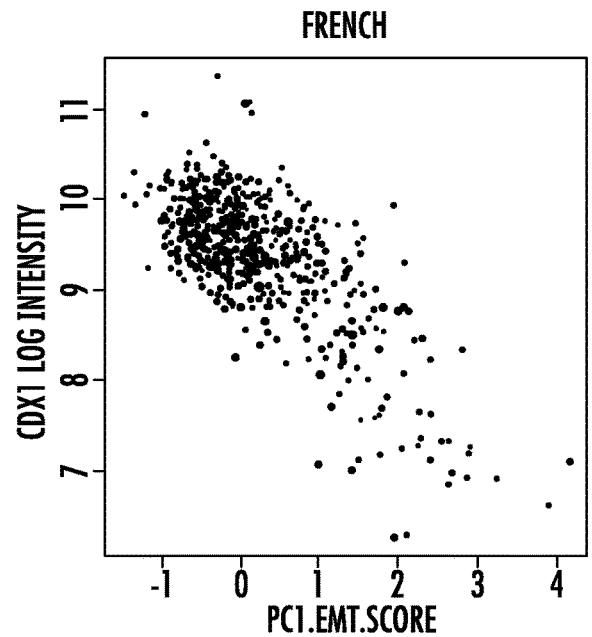
Figure 10C:
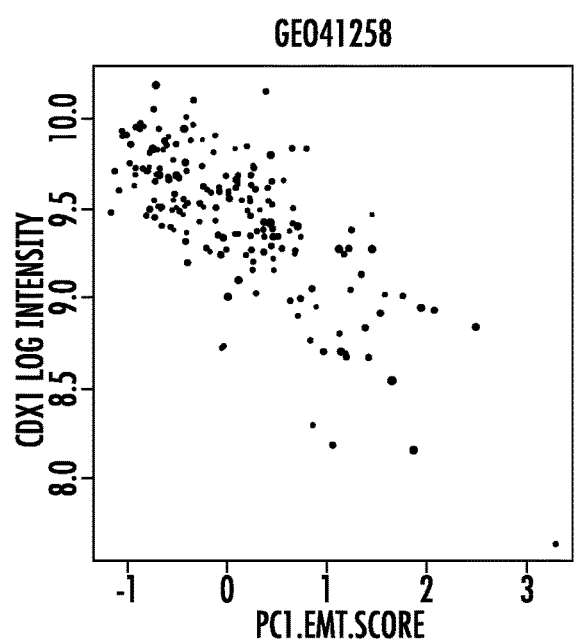
Figure 10D:
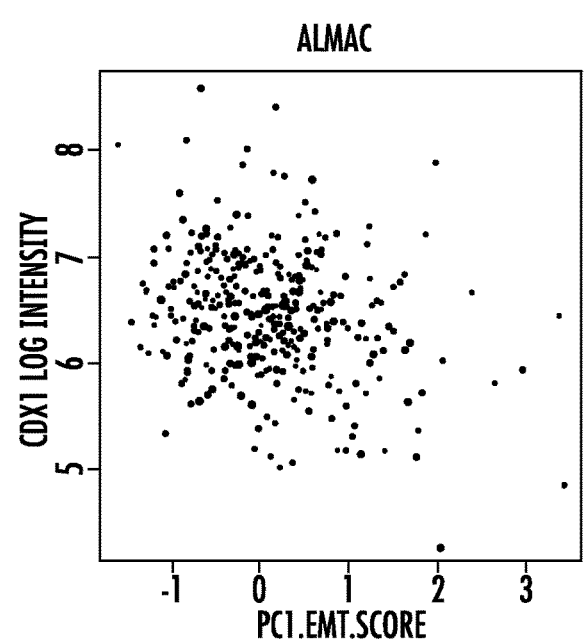

PC1.EMT was compared with APC mutation status. For this analysis TCGA dataset was used. FIGS. 8A to 8B are boxplots with PC1.EMT score split by APC mutation status (WT VS all detrimental mutations or WT VS specific mutation type (known COSMIC)). No clear correlation was seen between PC1.EMT score and APC mutation status. However, some specific APC mutations showed lower score compared with WT.

Genes Correlating with PC1.EMT Signature Score

In order to have clues concerning the biological functions captured by the PC1.EMT score, we identified genes which expression correlates with the score using a linear model including only the PC1.EMT score. We used a meta-analytic method (Fisher) to merge the results across all 6 datasets. Tables 25 and 26 show the top 10 most consistent positive and negative correlating genes.

TABLE 25

Top 10 genes positively correlating with PC1.EMT score

| Gene.Symbol | Entrez-ID | S | num.p | p.value | p.adj | Sum t statistics |
|---|---|---|---|---|---|---|
| CD109 | 135228 | 869.79 | 5 | 0.00 | 0.00 | 75.05 |
| AHNAK2 | 113146 | 837.41 | 6 | 0.00 | 0.00 | 79.32 |
| GAS1 | 2619 | 806.50 | 6 | 0.00 | 0.00 | 76.57 |
| PRKCDBP | 112464 | 806.43 | 6 | 0.00 | 0.00 | 77.90 |
| MEIS2 | 4212 | 779.02 | 6 | 0.00 | 0.00 | 77.16 |
| NXN | 64359 | 772.64 | 5 | 0.00 | 0.00 | 70.33 |
| GFPT2 | 9945 | 727.95 | 6 | 0.00 | 0.00 | 72.26 |
| PMP22 | 5376 | 711.36 | 6 | 0.00 | 0.00 | 73..46 |
| WWTR1 | 25937 | 692.29 | 6 | 0.00 | 0.00 | 72.07 |
| PTRF | 284119 | 688.52 | 6 | 0.00 | 0.00 | 71.22 |

TABLE 26

Top 10 genes negatively correlating with PC1.EMT score

| Gene.Symbol | Entrez-ID | S | num.p | p.value | p.adj | Sum t statistics |
|---|---|---|---|---|---|---|
| CDX1 | 1044 | 860.61 | 6 | 0.00 | 0.00 | −80.16 |
| CDX2 | 1045 | 845.97 | 6 | 0.00 | 0.00 | −79.41 |
| C10orf99 | 387695 | 767.33 | 5 | 0.00 | 0.00 | −67.82 |
| DDC | 1644 | 752.19 | 6 | 0.00 | 0.00 | −73.57 |
| GPA33 | 10223 | 726.29 | 6 | 0.00 | 0.00 | −72.98 |
| FAM84A | 151354 | 720.55 | 5 | 0.00 | 0.00 | −67.43 |
| NR.1I2 | 8856 | 697.98 | 6 | 0.00 | 0.00 | −70.24 |
| MYB | 4602 | 630.56 | 6 | 0.00 | 0.00 | −68.13 |
| C2orf89 | 129293 | 616.89 | 5 | 0.00 | 0.00 | −60.62 |
| EPHB2 | 2048 | 597.82 | 6 | 0.00 | 0.00 | −66.42 |

FIG. 9A to 9D are plots of AHNAK2 gene log intensities as a function of PC1.EMT score intensities in PETACC (FIG. 9A), French (FIG. 9B), GEO41258 (FIG. 9C), and ALAMC (FIG. 9D) datasets. Example of gene positively correlating with the score. FIG. 10A to 10D are plots of CDX1 gene log intensities as a function of PC1.EMT score intensities in PETACC (FIG. 10A), French (FIG. 0B), GEO41258 (FIG. 10C), and ALAMC (FIG. 10D) datasets. Example of gene negatively correlating with the score In order to interpret the list of genes found to be correlating with PC1.EMT score, gene enrichment analysis (GSEA) was performed using DAVID bioinformatics DB. Genes were split in two groups: list of genes found to be significantly positively correlated with PC1.EMT at an adjusted p value<0.05 (N=2351) or negatively correlated (N=1339). The two lists were submitted to the DAVID webpage and compared to the total number of analyzed gene (N=22946). Tables 27 and 28 show the top clusters of terms found to be enriched when using Functional annotation clustering tool:

TABLE 27

Top 10 Annotation clusters found enriched among genes positively correlating with PC1.EMT score (DAVID DB)

| Annotation Cluster 1 Category | Enrichment Score: 45.78660446516211 Term | Count | % | PValue | Fold Enrichment | FDR |
|---|---|---|---|---|---|---|
| SP_PIR_KEYWORDS | signal | 704 | 30.1 | 0.0000 | 1.8 | 0.0000 |
| UP_SEQ_FEATURE | signal peptide | 704 | 30.1 | 0.0000 | 1.8 | 0.0000 |
| SP_PIR_KEYWORDS | glycoprotein | 820 | 35.1 | 0.0000 | 1.6 | 0.0000 |
| UP_SEQ_FEATURE | glycosylation site:N-linked (GlcNAc . . . ) | 781 | 33.4 | 0.0000 | 1.6 | 0.0000 |
| SP_PIR_KEYWORDS | disulfide bond | 571 | 24.4 | 0.0000 | 1.7 | 0.0000 |
| UP_SEQ_FEATURE | disulfide bond | 553 | 23.6 | 0.0000 | 1.7 | 0.0000 |
| GOTERM_CC_FAT | GO:0044421~extracellular region part | 285 | 12.2 | 0.0000 | 2.2 | 0.0000 |
| SP_PIR_KEYWORDS | Secreted | 376 | 16.1 | 0.0000 | 1.9 | 0.0000 |

TABLE 27-continued

Top 10 Annotation clusters found enriched among genes positively
correlating with PC1.EMT score (DAVID DB)

| Category | Term | Count | % | PValue | Fold Enrichment | FDR |
|---|---|---|---|---|---|---|
| GOTERM_CC_FAT | GO:0005576—extracellular region | 444 | 19.0 | 0.0000 | 1.7 | 0.0000 |
| GOTERM_CC_FAT | GO:0005615—extracellular space | 180 | 7.7 | 0.0000 | 1.9 | 0.0000 |
| Annotation Cluster 2 | Enrichment Score: 39.79319232227263 | | | | | |
| Category | Term | Count | % | PValue | Fold Enrichment | FDR |
| GOTERM_BP_FAT | GO:0007155—cell adhesion | 233 | 10.0 | 0.0000 | 2.5 | 0.0000 |
| GOTERM_BP_FAT | GO:0022610—biological adhesion | 233 | 10.0 | 0.0000 | 2.5 | 0.0000 |
| SP_PIR_KEYWORDS | cell adhesion | 145 | 6.2 | 0.0000 | 2.8 | 0.0000 |
| Annotation Cluster 3 | Enrichment Score: 28.110221475114905 | | | | | |
| Category | Term | Count | % | PValue | Fold Enrichment | FDR |
| GOTERM_CC_FAT | GO:0005578—proteinaceous extracellular matrix | 129 | 5.5 | 0.0000 | 2.9 | 0.0000 |
| SP_PIR_KEYWORDS | extracellular matrix | 103 | 4.4 | 0.0000 | 3.5 | 0.0000 |
| GOTERM_CC_FAT | GO:0031012—extracellular matrix | 134 | 5.7 | 0.0000 | 2.8 | 0.0000 |
| GOTERM_CC_FAT | GO:0044420—extracellular matrix part | 57 | 2.4 | 0.0000 | 3.5 | 0.0000 |
| Annotation Cluster 4 | Enrichment Score: 25.22234604850097 | | | | | |
| Category | Term | Count | % | PValue | Fold Enrichment | FDR |
| GOTERM_BP_FAT | GO:0009611—response to wounding | 177 | 7.6 | 0.0000 | 2.5 | 0.0000 |
| GOTERM_BP_FAT | GO:0006954—inflammatory response | 110 | 4.7 | 0.0000 | 2.6 | 0.0000 |
| GOTERM_BP_FAT | GO:0006952—defense response | 165 | 7.1 | 0.0000 | 2.1 | 0.0000 |
| Annotation Cluster 5 | Enrichment Score: 15.441501146605358 | | | | | |
| Category | Term | Count | % | PValue | Fold Enrichment | FDR |
| GOTERM_BP_FAT | GO:0001568—blood vessel development | 88 | 3.8 | 0.0000 | 2.7 | 0.0000 |
| GOTERM_BP_FAT | GO:0001944—vasculature development | 89 | 3.8 | 0.0000 | 2.7 | 0.0000 |
| GOTERM_BP_FAT | GO:0048514—blood vessel morphogenesis | 72 | 3.1 | 0.0000 | 2.6 | 0.0000 |
| GOTERM_BP_FAT | GO:0001525—angiogenesis | 53 | 2.3 | 0.0000 | 2.7 | 0.0000 |
| Annotation Cluster 6 | Enrichment Score: 14.094253321991394 | | | | | |
| Category | Term | Count | % | PValue | Fold Enrichment | FDR |
| GOTERM_CC_FAT | GO:0044459—plasma membrane part | 444 | 19.0 | 0.0000 | 1.5 | 0.0000 |
| GOTERM_CC_FAT | GO:0031226—intrinsic to plasma membrane | 250 | 10.7 | 0.0000 | 1.5 | 0.0000 |
| GOTERM_CC_FAT | GO:0005887—integral to plasma mmbrane | 242 | 10.3 | 0.0000 | 1.5 | 0.0000 |
| Annotation Cluster 7 | Enrichment Score: 13.217589093630473 | | | | | |
| Category | Term | Count | % | PValue | Fold Enrichment | FDR |
| GOTERM_BP_FAT | GO:0030198—extracellular matrix organization | 48 | 2.1 | 0.0000 | 3.5 | 0.0000 |
| GOTERM_BP_FAT | GO:0043062—extracellular structure organization | 61 | 2.6 | 0.0000 | 2.8 | 0.0000 |
| GOTERM_BP_FAT | GO:0030199—collagen fibril organization | 21 | 0.9 | 0.0000 | 5.5 | 0.0000 |
| Annotation Cluster 8 | Enrichment Score: 11.92555541984095 | | | | | |
| Category | Term | Count | % | PValue | Fold Enrichment | FDR |
| GOTERM_MF_FAT | GO:0030247—polysaccharide binding | 59 | 2.5 | 0.0000 | 2.9 | 0.0000 |
| GOTERM_MF_FAT | GO:0001871—pattern binding | 59 | 2.5 | 0.0000 | 2.9 | 0.0000 |
| GOTERM_MF_FAT | GO:0005539—glycosaminoglycan binding | 55 | 2.4 | 0.0000 | 3.0 | 0.0000 |
| GOTERM_MF_FAT | GO:0030246—carbohydrate binding | 99 | 4.2 | 0.0000 | 2.1 | 0.0000 |
| GOTERM_MF_FAT | GO:0008201—heparin binding | 41 | 1.8 | 0.0000 | 3.0 | 0.0000 |
| SP_PIR_KEYWORDS | heparin-binding | 25 | 1.1 | 0.0000 | 3.1 | 0.0004 |
| Annotation Cluster 9 | Enrichment Score: 11.186259107509017 | | | | | |
| Category | Term | Count | % | PValue | Fold Enrichment | FDR |
| GOTERM_BP_FAT | GO:0006928—cell motion | 128 | 5.5 | 0.0000 | 2.0 | 0.0000 |
| GOTERM_BP_FAT | GO:0016477—cell migration | 80 | 3.4 | 0.0000 | 2.2 | 0.0000 |
| GOTERM_BP_FAT | GO:0051674—localization of cell | 82 | 3.5 | 0.0000 | 2.0 | 0.0000 |
| GOTERM_BP_FAT | GO:0048870—cell motility | 82 | 3.5 | 0.0000 | 2.0 | 0.0000 |
| Annotation Cluster 10 | Enrichment Score: 10.235463831336938 | | | | | |
| Category | Term | Count | % | PValue | Fold Enrichment | FDR |
| SP_PIR_KEYWORDS | membrane | 930 | 39.8 | 0.0000 | 1.3 | 0.0000 |
| UP_SEQ_FEATURE | topological domain:Extracellular | 445 | 19.0 | 0.0000 | 1.4 | 0.0000 |
| UP_SEQ_FEATURE | topological domain:Cytoplasmic | 535 | 22.9 | 0.0000 | 1.4 | 0.0000 |
| SP_PIR_KEYWORDS | transmembrane | 697 | 29.8 | 0.0000 | 1.2 | 0.0000 |

TABLE 27-continued

Top 10 Annotation clusters found enriched among genes positively correlating with PC1.EMT score (DAVID DB)

| | | | | | | |
|---|---|---|---|---|---|---|
| UP_SEQ_FEATURE | transmembrane region | 693 | 29.6 | 0.0000 | 1.2 | 0.0000 |
| GOTERM_CC_FAT | GO:0031224—intrinsic to membrane | 778 | 33.3 | 0.0019 | 1.1 | 2.7902 |
| GOTERM_CC_FAT | GO:0016021—integral to membrane | 740 | 31.6 | 0.0120 | 1.1 | 16.1249 |

TABLE 28

Top 9 Annotation clusters found enriched among genes negatively correlating with PC1.EMT score (DAVID DB)

| Annotation Cluster 1 Category | Enrichment Score: 14.055636116126923 Term | Count | % | PValue | Fold Enrichment | FDR |
|---|---|---|---|---|---|---|
| SP_PIR_KEYWORDS | mitochondrian | 148 | 11.1 | 0.000 | 2.7 | 0.0000 |
| GOTERM_CC_FAT | GO:0005739—mitochondrion | 172 | 12.9 | 0.000 | 2.3 | 0.0000 |
| GOTERM_CC_FAT | GO:0044429—mitochondrial part | 111 | 8.3 | 0.000 | 2.7 | 0.0000 |
| SP_PIR_KEYWORDS | transit peptide | 91 | 6.8 | 0.000 | 2.9 | 0.0000 |
| UP_SEQ_FEATURE | transit peptide:Mitochondrion | 90 | 6.8 | 0.000 | 2.9 | 0.0000 |
| GOTERM_CC_FAT | GO:0031980—mitochondrial lumen | 60 | 4.5 | 0.000 | 3.8 | 0.0000 |
| GOTERM_CC_FAT | GO:0005759—mitochondrial matrix | 60 | 4.5 | 0.000 | 3.8 | 0.0000 |
| GOTERM_CC_FAT | GO:0019866—organelle inner membrane | 59 | 4.4 | 0.000 | 2.6 | 0.0000 |
| GOTERM_CC_FAT | GO:0005740—mitochondrial envelope | 67 | 5.0 | 0.000 | 2.3 | 0.0000 |
| GOTERM_CC_FAT | GO:0005743—mitochondrial inner membrane | 54 | 4.1 | 0.000 | 2.5 | 0.0000 |
| GOTERM_CC_FAT | GO:0031966—mitochondrial membrane | 63 | 4.7 | 0.000 | 2.3 | 0.0000 |
| GOTERM_CC_FAT | GO:0031967—organelle envelope | 78 | 5.9 | 0.000 | 1.8 | 0.0005 |
| GOTERM_CC_FAT | GO:0031975—envelope | 78 | 5.9 | 0.000 | 1.8 | 0.0006 |
| GOTERM_CC_FAT | GO:0031090—organelle membrane | 115 | 8.6 | 0.000 | 1.5 | 0.0090 |
| SP_PIR_KEYWORDS | mitochondrion inner membrane | 30 | 2.3 | 0.000 | 2.3 | 0.0522 |
| Annotation Cluster 2 Category | Enrichment Score: 8.18712581462025 Term | Count | % | PValue | Fold Enrichment | FDR |
| SP_PIR_KEYWORDS | oxidoreductase | 79 | 5.9 | 0.000 | 2.1 | 0.0000 |
| GOTERM_BP_FAT | GO:0055114—oxidation reduction | 83 | 6.4 | 0.000 | 2.0 | 0.0000 |
| GOTERM_MF_FAT | GO:0009055—electron carrier activity | 38 | 2.9 | 0.000 | 2.5 | 0.0008 |
| Annotation Cluster 3 Category | Enrichment Score: 7.53962677068125 Term | Count | % | PValue | Fold Enrichment | FDR |
| GOTERM_CC_FAT | GO:0005759—mitochondrial matrix | 60 | 4.5 | 0.000 | 3.8 | 0.0000 |
| GOTERM_CC_FAT | GO:0031980—mitochondrial lumen | 60 | 4.5 | 0.000 | 3.8 | 0.0000 |
| GOTERM_CC_FAT | GO:0070013—intracellular organelle lumen | 155 | 11.6 | 0.002 | 1.2 | 2.6842 |
| GOTERM_CC_FAT | GO:0031974—membrane-enclosed lumen | 160 | 12.0 | 0.002 | 1.2 | 3.2888 |
| GOTERM_CC_FAT | GO:0043233—organelle lumen | 155 | 11.5 | 0.005 | 1.2 | 6.3798 |
| GOTERM_CC_FAT | GO:0031981—nuclear lumen | 85 | 6.4 | 0.974 | 0.8 | 100.0000 |
| Annotation Cluster 8 Category | Enrichment Score: 3.2818754734384727 Term | Count | % | PValue | Fold Enrichment | FDR |
| GOTERM_MF_FAT | GO:0050662—coenzyme binding | 32 | 2.4 | 0.000 | 2.5 | 0.0039 |
| SP_PIR_KEYWORDS | FAD | 19 | 1.4 | 0.001 | 2.5 | 0.8215 |
| GOTERM_MF_FAT | GO:0050660—FAD binding | 14 | 1.1 | 0.001 | 2.8 | 1.9608 |
| SP_PIR_KEYWORDS | Flavoprotein | 17 | 1.3 | 0.002 | 2.4 | 2.9944 |
| UP_SEQ_FEATURE | nucleotide phosphate-binding region:FAD | 12 | 0.9 | 0.002 | 2.9 | 3.9729 |
| UP_SEQ_FEATURE | binding site:FAD | 7 | 0.5 | 0.003 | 4.7 | 4.6852 |
| Annotation Cluster 9 Category | Enrichment Score: 2.851945270321666 Term | Count | % | PValue | Fold Enrichment | FDR |
| GOTERM_BP_FAT | GO:0006399—tRNA metabolic process | 22 | 1.7 | 0.000 | 2.8 | 0.0532 |
| GOTERM_BP_FAT | GO:0034660—ncRNA metabolic process | 32 | 2.4 | 0.000 | 2.1 | 0.2343 |
| GOTERM_BP_FAT | GO:0008033—tRNA processing | 15 | 1.1 | 0.000 | 3.0 | 0.7601 |
| SP_PIR_KEYWORDS | trna processing | 13 | 1.0 | 0.001 | 2.9 | 2.1777 |
| GOTERM_BP_FAT | GO:0034470—ncRNA processing | 23 | 1.7 | 0.006 | 1.8 | 10.9528 |
| GOTERM_BP_FAT | GO:0006396—RNA processing | 38 | 2.9 | 0.493 | 1.0 | 99.9995 |
| Annotation Cluster 4 Category | Enrichment Score: 5.213585990413278 Term | Count | % | PValue | Fold Enrichment | FDR |
| GOTERM_BP_FAT | GO:0051186—cofactor metabolic process | 35 | 2.6 | 0.000 | 2.7 | 0.0003 |
| GOTERM_BP_FAT | GO:0006732—coenzyme metabolic process | 29 | 2.2 | 0.000 | 2.8 | 0.0015 |
| GOTERM_BP_FAT | GO:0051188—cofactor biosynthetic process | 19 | 1.4 | 0.000 | 2.9 | 0.1099 |
| GOTERM_BP_FAT | GO:0009108—coenzyme biosynthetic process | 15 | 1.1 | 0.000 | 3.3 | 0.2645 |

TABLE 28-continued

Top 9 Annotation clusters found enriched among genes negatively correlating with PC1.EMT score (DAVID DB)

| Annotation Cluster 5 Category | Enrichment Score: 5.180163320241737 Term | Count | % | PValue | Fold Enrichment | FDR |
|---|---|---|---|---|---|---|
| SP_PIR_KEYWORDS | nad | 34 | 2.6 | 0.000 | 2.7 | 0.0005 |
| UP_SEQ_FEATURE | nucleotide phosphate-binding region:NAD | 18 | 1.4 | 0.000 | 3.5 | 0.0163 |
| UP_SEQ_FEATURE | binding site:NAD | 13 | 1.0 | 0.000 | 3.9 | 0.1612 |
| Annotation Cluster 6 Category | Enrichment Score: 4.169776745163271 Term | Count | % | PValue | Fold Enrichment | FDR |
| GOTERM_CC_FAT | GO:0005777~peroxisome | 29 | 2.2 | 0.000 | 4.0 | 0.0000 |
| GOTERM_CC_FAT | GO:0042579~microbody | 29 | 2.2 | 0.000 | 4.0 | 0.0000 |
| SP_PIR_KEYWORDS | peroxisome | 25 | 1.9 | 0.000 | 4.1 | 0.0000 |
| UP_SEQ_FEATURE | short sequence motif:Microbody targeting signal | 10 | 0.8 | 0.001 | 3.6 | 2.3847 |
| GOTERM_CC_FAT | GO:0044438~microbody part | 10 | 0.8 | 0.002 | 3.3 | 3.4172 |
| GOTERM_CC_FAT | GO:0044439~peroxisomal part | 10 | 0.8 | 0.002 | 3.3 | 3.4172 |
| GOTERM_CC_FAT | GO:0005778~peroxisomal membrane | 7 | 0.5 | 0.018 | 3.2 | 23.3418 |
| GOTERM_CC_FAT | GO:0031903~microbody membrane | 7 | 0.5 | 0.018 | 3.2 | 23.3418 |
| GOTERM_CC_FAT | GO:0031907~microbody lumen | 4 | 0.3 | 0.069 | 4.1 | 63.9846 |
| GOTERM_CC_FAT | GO:0005782~peroxisomal matrix | 4 | 0.3 | 0.069 | 4.1 | 63.9846 |
| Annotation Cluster 7 Category | Enrichment Score: 3.5116212942526577 Term | Count | % | PValue | Fold Enrichment | FDR |
| GOTERM_MF_FAT | GO:0031406~carboxylic acid binding | 24 | 1.8 | 0.000 | 2.4 | 0.2300 |
| GOTERM_MF_FAT | GO:0005504~fatty acid binding | 11 | 0.8 | 0.000 | 4.2 | 0.3148 |
| GOTERM_MF_FAT | GO:0033293~monocarboxylic acid binding | 12 | 0.9 | 0.001 | 3.2 | 1.6436 |

GSEA was performed also using gene sets obtained from the MSig database (DB) [Subramanian, A, et al. (2005). Proc. Natl. Acad. Sci 102:15545-15550] (MSigDB) which includes C2 (curated gene sets—Chemical and Genetic Perturbations, Biocarta and KEGG), C3 transcription factors, C5 GO biological process terms, C6 (Oncogenic signature) and C7 (immunologic signatures). The analysis was done using "Romer" algorithm (similar to Gene Set Enrichment Analysis (GSEA)) and the same linear model used to identify genes correlating with PC1.EMT score. The p values obtained across the 6 datasets were merged using Fisher method. Tables 29 to 42 list the top 5 signatures found to be positively or negatively correlated with PC1.EMT within each of the tested Msig.DB.

TABLE 29

Top 10 Chemical and Genetic Perturbations found enriched among genes positively correlating with PC1.EMT score (MSig.DB)

| | S | num.p | p.value | p.adj |
|---|---|---|---|---|
| CHARAFE_BREAST_CANCER_LUMINAL_VS_BASAL_DN | 82.89 | 6 | 0.00 | 0.00 |
| CHARAFE_BREAST_CANCER_LUMINAL_VS_MESENCHYMAL_DN | 82.89 | 6 | 0.00 | 0.00 |
| TONKS_TARGETS_OF_RUNX1_RUNX1T1_FUSION_ERYTHROCYTE_UP | 82.89 | 6 | 0.00 | 0.00 |
| KIM_WT1_TARGETS_SHR_UP | 82.89 | 6 | 0.00 | 0.00 |
| DELYS_THYROID_CANCER_UP | 82.89 | 6 | 0.00 | 0.00 |
| CASTELLANO_NRAS_TARGETS_UP | 82.89 | 6 | 0.00 | 0.00 |
| GAUSSMANN_MLL_AF4_FUSION_TARGETS_F_UP | 82.89 | 6 | 0.00 | 0.00 |
| FRIDMAN_SENESCENCE_UP | 82.89 | 6 | 0.00 | 0.00 |
| ROZANOV_MMP14_TARGETS_UP | 82.89 | 6 | 0.00 | 0.00 |
| PETROVA_ENDOTHELIUM_LYMPHATIC_VS_BLOOD_DN | 82.89 | 6 | 0.00 | 0.00 |

TABLE 30

Top 10 Chemical and Genetic Perturbations found enriched among genes negatively correlating with PC1.EMT score (MSig.DB)

| | S | num.p | p.value | p.adj |
|---|---|---|---|---|
| WALLACE_PROSTATE_CANCER_UP | 71.41 | 6 | 0.00 | 0.00 |
| WATANABE_COLON_CANCER_MSI_VS_MSS_DN | 66.08 | 6 | 0.00 | 0.00 |
| SERVITJA_ISLET_HNF1A_TARGETS_DN | 62.72 | 6 | 0.00 | 0.00 |
| SANSOM_APC_TARGETS_UP | 61.54 | 6 | 0.00 | 0.00 |
| ZHOU_PANCREATIC_EXOCRINE_PROGENITOR | 58.18 | 6 | 0.00 | 0.00 |
| STEIN_ESRRA_TARGETS_UP | 56.70 | 6 | 0.00 | 0.00 |
| BURTON_ADIPOGENESIS_5 | 55.36 | 6 | 0.00 | 0.00 |
| LE_NEURONAL_DIFFERENTIATION_DN | 55.23 | 6 | 0.00 | 0.00 |

TABLE 30-continued

Top 10 Chemical and Genetic Perturbations found enriched among genes negatively correlating with PC1.EMT score (MSig.DB)

|  | S | num.p | p.value | p.adj |
|---|---|---|---|---|
| JEON_SMAD6_TARGETS_DN | 55.01 | 6 | 0.00 | 0.00 |
| LIEN_BREAST_CARCINOMA_METAPLASTIC_VS_DUCTAL_DN | 53.98 | 6 | 0.00 | 0.00 |

TABLE 31

Top 10 Biocarta pathways found enriched among genes positively correlating with PC1.EMT score (MSig.DB)

|  | S | num.p | p.value | p.adj |
|---|---|---|---|---|
| BIOCARTA_LAIR_PATHWAY | 59.63 | 6 | 0.00 | 0.00 |
| BIOCARTA_CLASSIC_PATHWAY | 58.59 | 6 | 0.00 | 0.00 |
| BIOCARTA_EPHA4_PATHWAY | 55.32 | 6 | 0.00 | 0.00 |
| BIOCARTA_COMP_PATHWAY | 54.60 | 6 | 0.00 | 0.00 |
| BIOCARTA_MONOCYTE_PATHWAY | 52.03 | 6 | 0.00 | 0.00 |
| BIOCARTA_GRANULOCYTES_PATHWAY | 50.87 | 6 | 0.00 | 0.00 |
| BIOCARTA_INTEGRIN_PATHWAY | 48.92 | 6 | 0.00 | 0.00 |
| BIOCARTA_LYM_PATHWAY | 48.22 | 6 | 0.00 | 0.00 |
| BIOCARTA_VITCB_PATHWAY | 45.75 | 6 | 0.00 | 0.00 |
| BIOCARTA_FIBRINOLYSIS_PATHWAY | 45.37 | 6 | 0.00 | 0.00 |

TABLE 32

Top 10 Biocarta pathways found enriched among genes negatively correlating with PC1.EMT score (MSig.DB)

|  | S | num.p | p.value | p.adj |
|---|---|---|---|---|
| BIOCARTA_MITOCHONDRIA_PATHWAY | 42.23 | 6 | 0.00 | 0.01 |
| BIOCARTA_RANMS_PATHWAY | 42.16 | 6 | 0.00 | 0.01 |
| BIOCARTA_PTC1_PATHWAY | 41.78 | 6 | 0.00 | 0.01 |
| BIOCARTA_ATRBRCA_PATHWAY | 35.39 | 6 | 0.00 | 0.09 |
| BIOCARTA_NUCLEARRS_PATHWAY | 34.73 | 6 | 0.00 | 0.11 |
| BIOCARTA_CELLCYCLE_PATHWAY | 33.34 | 6 | 0.00 | 0.18 |
| BIOCARTA_G2_PATHWAY | 32.93 | 6 | 0.00 | 0.21 |
| BIOCARTA_CASPASE_PATHWAY | 31.86 | 6 | 0.00 | 0.31 |
| BIOCARTA_MCM_PATHWAY | 31.75 | 6 | 0.00 | 0.33 |
| BIOCARTA_G1_PATHWAY | 29.41 | 6 | 0.00 | 0.74 |

TABLE 33

Top 10 KEGG pathways found enriched among genes positively correlating with PC1.EMT score (MSig.DB)

|  | S | num.p | p.value | p.adj |
|---|---|---|---|---|
| KEGG_AXON_GUIDANCE | 78.73 | 6 | 0.00 | 0.00 |
| KEGG_FOCAL_ADHESION | 78.73 | 6 | 0.00 | 0.00 |
| KEGG_ECM_RECEPTOR_INTERACTION | 78.73 | 6 | 0.00 | 0.00 |
| KEGG_GLYCOSAMINOGLYCAN_BIOSYNTHESIS_CHONDROPTIN_SULFATE | 75.07 | 6 | 0.00 | 0.00 |
| KEGG_REGULATION_OF_ACTIN_CYTOSKELETON | 71.57 | 6 | 0.00 | 0.00 |
| KEGG_LEUKOCYTE_TRANSENDOTHELIAL_MIGRATION | 70.00 | 6 | 0.00 | 0.00 |
| KEGG_CELL_ADHESION_MOLECULES_CAMS | 67.30 | 6 | 0.00 | 0.00 |
| KEGG_PATHWAYS_IN_CANCER | 67.17 | 6 | 0.00 | 0.00 |
| KEGG_COMPLEMENT_AND_COAGULATION_CASCADES | 63.45 | 6 | 0.00 | 0.00 |
| KEGG_HYPERTROPHIC_CARDIOMYOPATHY_HCM | 61.53 | 6 | 0.00 | 0.00 |

TABLE 34

Top 10 KEGG pathways found enriched among genes negatively correlating with PC1.EMT score (MSig.DB)

|  | S | num.p | p.value | p.adj |
|---|---|---|---|---|
| KEGG_PEROXISOME | 64.02 | 6 | 0.00 | 0.00 |
| KEGG_SELENOAMINO_ACID_METABOLISM | 63.30 | 6 | 0.00 | 0.00 |

TABLE 34-continued

Top 10 KEGG pathways found enriched among genes negatively correlating with PC1.EMT score (MSig.DB)

|  | S | num.p | p.value | p.adj |
|---|---|---|---|---|
| KEGG_BUTANOATE_METABOLISM | 60.53 | 6 | 0.00 | 0.00 |
| KEGG_CITRATE_CYCLE_TCA_CYCLE | 60.25 | 6 | 0.00 | 0.00 |
| KEGG_TRYPTOPHAN_METABOLISM | 55.30 | 6 | 0.00 | 0.00 |
| KEGG_VALINE_LEUCINE_AND_ISOLEUCINE_BIOSYNTHESIS | 52.23 | 6 | 0.00 | 0.00 |
| KEGG_PYRUVATE_METABOLISM | 51.60 | 6 | 0.00 | 0.00 |
| KEGG_MATURITY_ONSET_DIABETES_OF_THE_YOUNG | 50.94 | 6 | 0.00 | 0.00 |
| KEGG_ARGININE_AND_PROLINE_METABOLISM | 49.03 | 6 | 0.00 | 0.00 |
| KEGG_VALINE_LEUCINE_AND_ISOLEUCINE_DEGRADATION | 47.23 | 6 | 0.00 | 0.00 |

TABLE 35

Top 10 transcription factor targets found enriched among genes positively correlating with PC1.EMT score (MSig.DB)

|  | S | num.p | p.value | p.adj |
|---|---|---|---|---|
| V$AP1_Q6_01 | 82.89 | 6 | 0.00 | 0.00 |
| V$AP1_Q4_01 | 82.89 | 6 | 0.00 | 0.00 |
| TGANTCA_V$AP1_C | 82.89 | 6 | 0.00 | 0.00 |
| V$AML1_01 | 81.51 | 6 | 0.00 | 0.00 |
| V$AML1_Q6 | 81.51 | 6 | 0.00 | 0.00 |
| GGGTGGRR_V$PAX4_03 | 81.51 | 6 | 0.00 | 0.00 |
| V$AP1_C | 80.70 | 6 | 0.00 | 0.00 |
| V$STAT5B_01 | 80.70 | 6 | 0.00 | 0.00 |
| V$NFKB_Q6 | 80.12 | 6 | 0.00 | 0.00 |
| CAGCTG_V$AP4_Q5 | 79.67 | 6 | 0.00 | 0.00 |

TABLE 36

Top 10 transcription factor targets found enriched among genes negatively correlating with PC1.EMT score (MSig.DB)

|  | S | num.p | p.value | p.adj |
|---|---|---|---|---|
| V$MYCMAX_01 | 56.53 | 6 | 0.00 | 0.00 |
| V$PPARG_01 | 44.02 | 6 | 0.00 | 0.01 |
| V$E2F1_Q6_01 | 40.53 | 6 | 0.00 | 0.04 |
| V$E2F_Q4_01 | 40.43 | 4 | 0.00 | 0.04 |
| V$E2F1_Q4_01 | 40.17 | 6 | 0.00 | 0.04 |
| SGCGSSAAA_V$E2F1DP2_01 | 39.82 | 6 | 0.00 | 0.05 |
| V$E2F_Q6_01 | 38.66 | 6 | 0.00 | 0.07 |
| V$E2F_Q3 | 38.63 | 6 | 0.00 | 0.07 |
| V$E2F1_Q3 | 38.54 | 6 | 0.00 | 0.08 |
| V$HNF4_01 | 38.20 | 6 | 0.00 | 0.09 |

TABLE 37

Top 10 GO Biological Process terms found enriched among genes positively correlating with PC1.EMT score (MSig.DB)

|  | S | num.p | p.value | p.adj |
|---|---|---|---|---|
| TISSUE_DEVELOPMENT | 82.89 | 6 | 0.00 | 0.00 |
| ORGAN_DEVELOPMENT | 81.51 | 6 | 0.00 | 0.00 |
| CELL_SUBSTRATE_ADHESION | 78.29 | 6 | 0.00 | 0.00 |
| CELL_MATRIX_ADHESION | 77.92 | 6 | 0.00 | 0.00 |
| REGULATION_OF_CELL_GROWTH | 77.92 | 6 | 0.00 | 0.00 |
| REGULATION_OF_BIOLOGICAL_QUALITY | 77.48 | 6 | 0.00 | 0.00 |
| MULTICELLULAR_ORGANISMAL_DEVELOPMENT | 77.48 | 6 | 0.00 | 0.00 |
| ANATOMICAL_STRUCTURE_DEVELOPMENT | 77.11 | 6 | 0.00 | 0.00 |
| CELL_MIGRATION | 76.54 | 6 | 0.00 | 0.00 |
| NEGATIVE_REGULATION_OF_GROWTH | 76.23 | 6 | 0.00 | 0.00 |

TABLE 38

Top 10 GO Biological Process terms found enriched among genes negatively correlating with PC1.EMT score (MSig.DB)

|  | S | num.p | p.value | p.adj |
|---|---|---|---|---|
| ORGANIC_ACID_METABOLIC_PROCESS | 48.24 | 6 | 0.00 | 0.00 |
| COENZYME_BIOSYNTHETIC_PROCESS | 46.92 | 6 | 0.00 | 0.00 |
| CARBOXYLIC_ACID_METABOLIC_PROCESS | 45.86 | 6 | 0.00 | 0.01 |
| RRNA_METABOLIC_PROCESS | 42.57 | 6 | 0.00 | 0.02 |
| RIBOSOME_BIOGENESIS_AND_ASSEMBLY | 41.80 | 6 | 0.00 | 0.03 |
| ENERGY_DERIVATION_BY_OXIDATION_OF_ORGANIC_COMPOUNDS | 40.96 | 6 | 0.00 | 0.04 |
| CELLULAR_PROTEIN_COMPLEX_DISASSEMBLY | 40.52 | 6 | 0.00 | 0.05 |
| RRNA_PROCESSING | 40.44 | 6 | 0.00 | 0.05 |
| GLYCOPROTEIN_BIOSYNTHETIC_PROCESS | 39.42 | 6 | 0.00 | 0.07 |
| MACROMOLECULE_BIOSYNTHETIC_PROCESS | 39.27 | 6 | 0.00 | 0.08 |

TABLE 39

Top 10 Oncogenic signatures found enriched among genes
positively correlating with PC1.EMT score (MSig.DB)

|  | S | num.p | p.value | p.adj |
|---|---|---|---|---|
| ESC_V6.5_UP_EARLY.V1_DN | 82.89 | 6 | 0.00 | 0.00 |
| CAHOY_ASTROGLIAL | 82.89 | 6 | 0.00 | 0.00 |
| PTEN_DN.V2_UP | 81.51 | 6 | 0.00 | 0.00 |
| BMI1_DN.V1_UP | 80.70 | 6 | 0.00 | 0.00 |
| BMI1_DN_MEL18_DN.V1_UP | 79.31 | 6 | 0.00 | 0.00 |
| RPS14_DN.V1_UP | 78.73 | 6 | 0.00 | 0.00 |
| ATF2_S_UP.V1_DN | 77.92 | 6 | 0.00 | 0.00 |
| TGFB_UP.V1_UP | 77.35 | 6 | 0.00 | 0.00 |
| MEL18_DN.V1_DN | 77.11 | 6 | 0.00 | 0.00 |
| KRAS.DF.V1_UP | 77.11 | 6 | 0.00 | 0.00 |

TABLE 40

Top 10 Oncogenic signatures found enriched among
genes negatively correlating with PC1.EMT score (MSig.DB)

|  | S | num.p | p.value | p.adj |
|---|---|---|---|---|
| MYC_UP.V1_UP | 57.05 | 6 | 0.00 | 0.00 |
| RPS14_DN.V1_DN | 49.57 | 6 | 0.00 | 0.00 |
| STK33_NOMO_DN | 49.13 | 6 | 0.00 | 0.00 |
| RB_DN.V1_UP | 46.95 | 6 | 0.00 | 0.00 |
| STK33_DN | 43.77 | 6 | 0.00 | 0.00 |
| GCNP_SHH_UP_LATE.V1_UP | 38.67 | 6 | 0.00 | 0.02 |
| E2F1_UP.V1_UP | 37.70 | 6 | 0.00 | 0.03 |
| PRC2_EZH2_UP.V1_UP | 37.46 | 6 | 0.00 | 0.04 |
| EIF4E_UP | 32.51 | 6 | 0.00 | 0.22 |
| RB_P130_DN.V1_UP | 32.13 | 6 | 0.00 | 0.25 |

TABLE 41

Top 10 immunologic signatures found enriched among genes positively correlating
with PC1.EMT score (MSig.DB)

|  | S | num.p | p.value | p.adj |
|---|---|---|---|---|
| GSE1432_6H_VS_24H_IFNG_MICROGLIA_UP | 82.89 | 6 | 0.00 | 0.00 |
| GSE14350_IL2RB_KO_VS_WT_TREG_DN | 82.89 | 6 | 0.00 | 0.00 |
| GSE17721_12H_VS_24H_LPS_BMDM_UP | 82.89 | 6 | 0.00 | 0.00 |
| GSE24142_EARLY_THYMIC_PROGENITOR_VS_DN3_THYMOCYTE_ADULT_UP | 82.89 | 6 | 0.00 | 0.00 |
| GSE24634_TEFF_VS_TCONV_DAY10_IN_CULTURE_DN | 82.89 | 6 | 0.00 | 0.00 |
| GSE26495_NAIVE_VS_PD1HIGH_CD8_TCELL_DN | 82.89 | 6 | 0.00 | 0.00 |
| GSE3337_CTRL_VS_16H_IFNG_IN_CD8POS_DC_UP | 82.89 | 6 | 0.00 | 0.00 |
| GSE360_DC_VS_MAC_T_GONDII_DN | 82.89 | 6 | 0.00 | 0.00 |
| GSE3982_DC_VS_TH1_UP | 82.89 | 6 | 0.00 | 0.00 |
| GSE3982_DC_VS_TH2_UP | 82.89 | 6 | 0.00 | 0.00 |

TABLE 42

Top 10 immunologic signatures found enriched among genes negatively correlating
with PC1.EMT score (MSig.DB)

|  | S | num.p | p.value | p.adj |
|---|---|---|---|---|
| GSE27786_ERYTHROBLAST_VS_MONO_MAC_UP | 59.14 | 6 | 0.00 | 0.00 |
| GSE18791_CTRL_VS_NEWCASTLE_VIRUS_DC_8H_UP | 56.51 | 6 | 0.00 | 0.00 |
| GSE18791_CTRL_VS_NEWCASTLE_VIRUS_DC_6H_UP | 54.69 | 6 | 0.00 | 0.00 |
| GSE27786_LIN_NEG_VS_BCELL_UP | 52.38 | 6 | 0.00 | 0.00 |
| GSE27786_LIN_NEG_VS_NEUTROPHIL_UP | 52.37 | 6 | 0.00 | 0.00 |
| GSE14308_TH2_VS_INDUCED_TREG_DN | 52.07 | 6 | 0.00 | 0.00 |
| GSE18791_CTRL_VS_NEWCASTLE_VIRUS_DC_14H_UP | 51.65 | 6 | 0.00 | 0.00 |
| GSE14350_TREG_VS_TEFF_IN_IL2RB_KO_DN | 49.37 | 6 | 0.00 | 0.00 |
| GSE18791_CTRL_VS_NEWCASTLE_VIRUS_DC_4H_UP | 49.23 | 6 | 0.00 | 0.00 |
| GSE18791_CTRL_VS_NEWCASTLE_VIRUS_DC_10H_UP | 48.84 | 6 | 0.00 | 0.00 |

Figure 11:
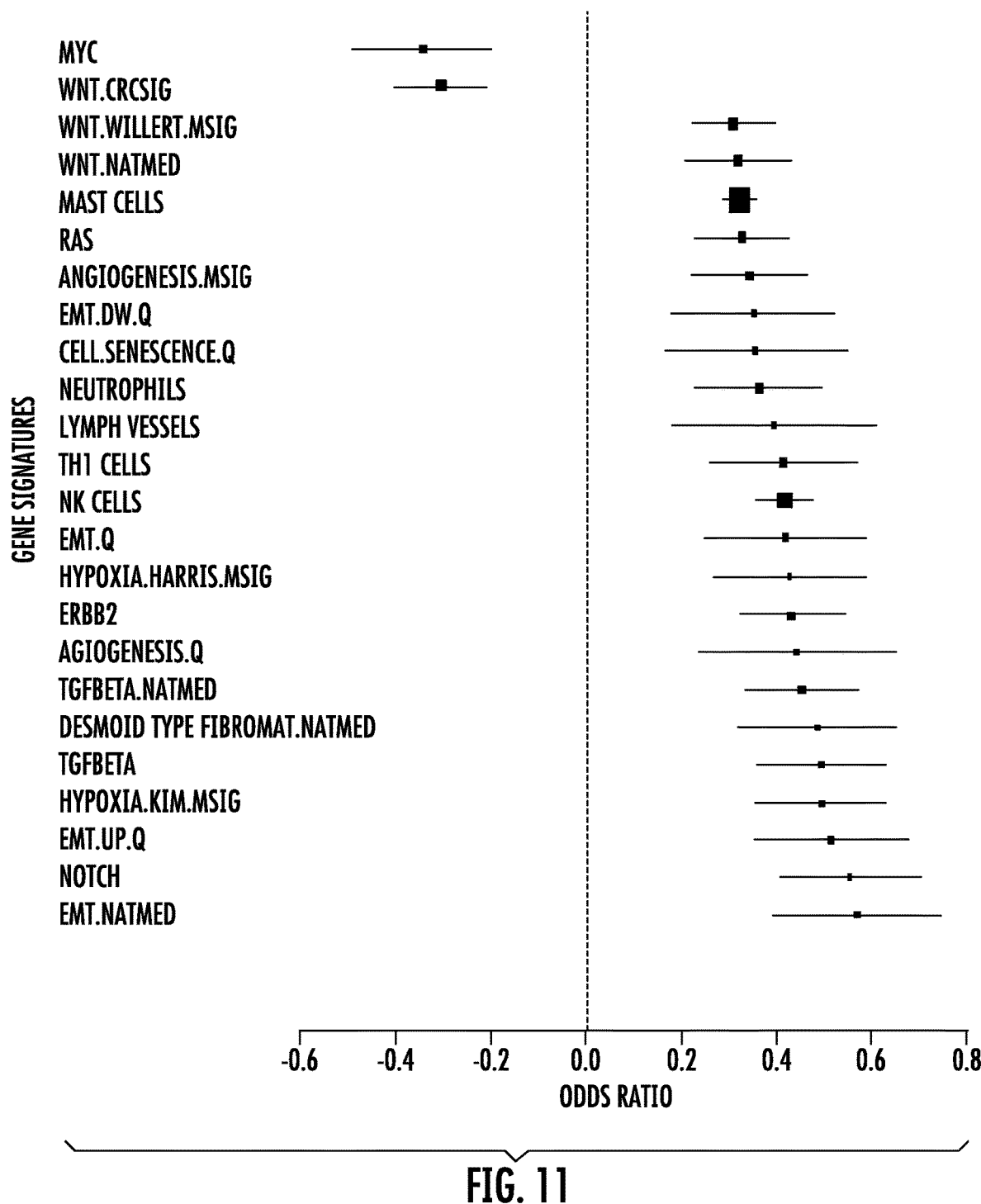
FIG. 11 is a forest plot showing correlation between PC1.EMT score intensity and relevant gene signatures. Only signatures showing an absolute estimated coefficient above 0.3 and an adjusted p value bellow 0.05 were plotted.

PC1.EMT score expression was also compared with a set of 75 gene signatures designed to capture some biological functions. Those signatures were obtained from different sources (databases, literature, etc.). The correlation coefficients were combined using DerSimonian-Laird (DSL) meta-analytic method. FIG. 11 is a forest plot showing correlation between PC1.EMT score intensity and relevant gene signatures. Only signatures showing an absolute estimated coefficient above 0.3 and an adjusted p value bellow 0.05 were plotted.

The enrichment analysis evidenced that PC1.EMT is still strongly associated with EMT. For instance, response to wounding, cell motility, extracellular matrix remodeling, activation of TGFbeta signalling, angiogenesis are all well known phenomena associated with EMT. Activation of Notch signaling was also observed, which has been also suggested to be involved in EMT.

The role of WNT signalling in EMT has been also described in literature. However, contradictory results were observed with different WNT signatures showing different behavior (some positively and other negatively correlated). This is also in line with the APC mutations results, where it was observed that only specific mutations were showing lower PC1.EMT score compare to WT.

Concerning the negatively correlated features, there was a clear effect in the mitochondrial metabolism and function. Activation of MYC was also inversely correlated with PC1.EMT score.

PC1.EMT and Clinico-Pathological-Molecular Features

Figure 12A:
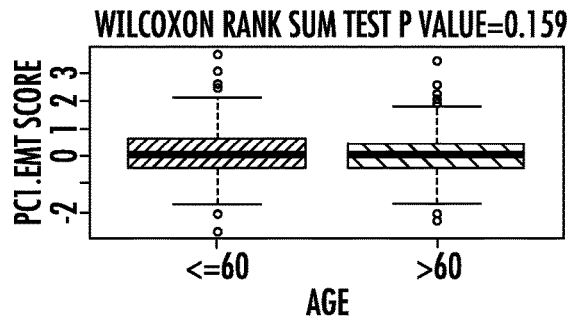
FIG. 12A to 12U are boxplots of PC1.EMT score split by the clinico-pathological-molecular features age (FIG. 12A), gender (FIG. 12B), stage (FIG. 12C), T.stage (FIG. 12D), N.stage (FIG. 12E), grade (FIG. 12F), adj. treatment (FIG. 12G), lymphovascular invasion LVI (FIG. 12H), perineural invasion PNI (FIG. 12I), bowel obstruction (FIG. 12J), positive margin (FIG. 12K), mucinous (FIG. 12L), tumor site (FIG. 12M), left or right tumor site (FIG. 12N), MSI (FIG. 12O), PIK3Ca (FIG. 12P), TP53 (FIG. 12Q), LOH18
Figure 12B:
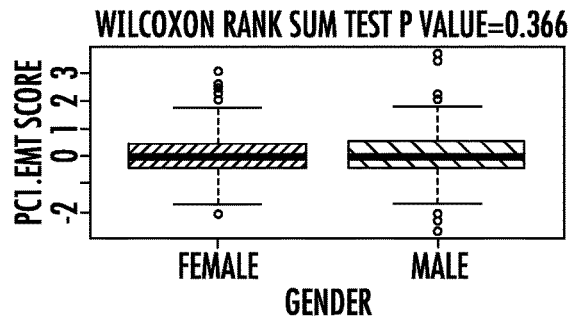
(FIG. 12R), BRAF (FIG. 12S), PIK3Ca (FIG. 12T), and TYMS using the PETACC dataset.
Figure 12C:
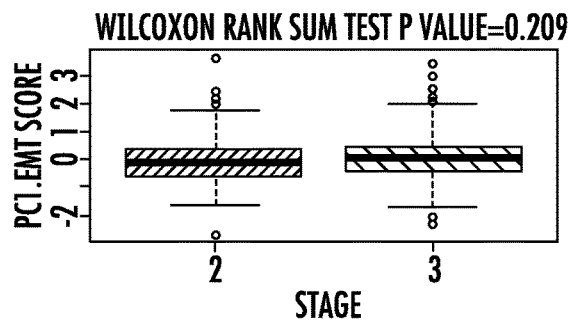
Figure 12D:
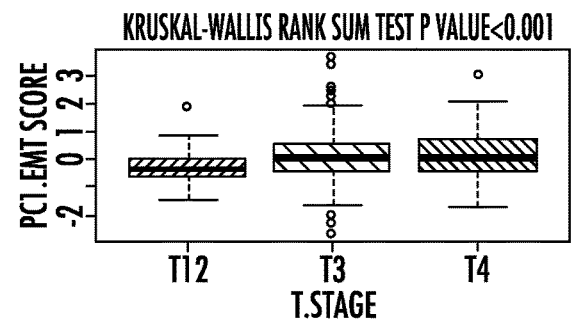
Figure 12E:
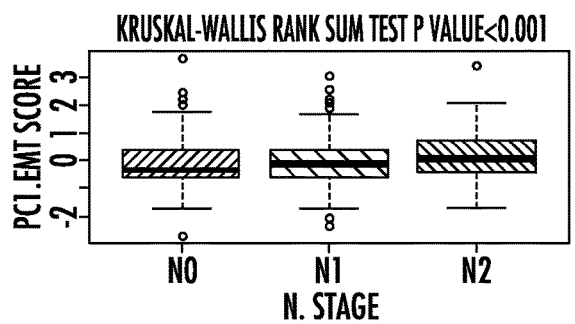
Figure 12F:
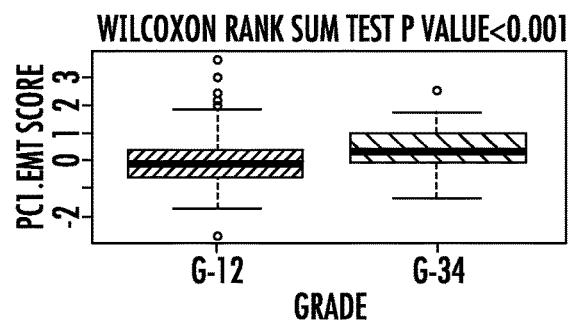
Figure 12G:
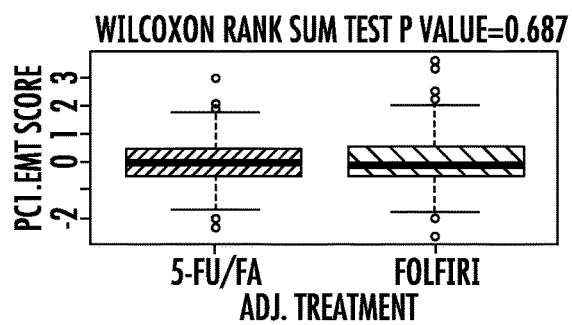
Figure 12H:
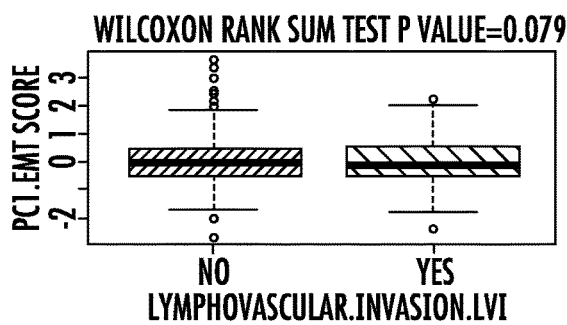
Figure 12I:
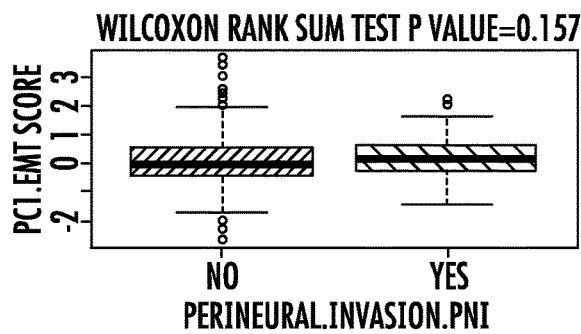
Figure 12J:
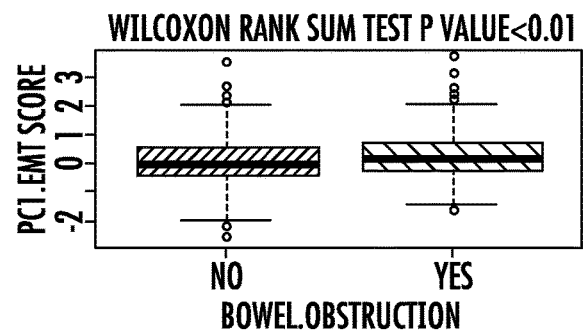
Figure 12K:
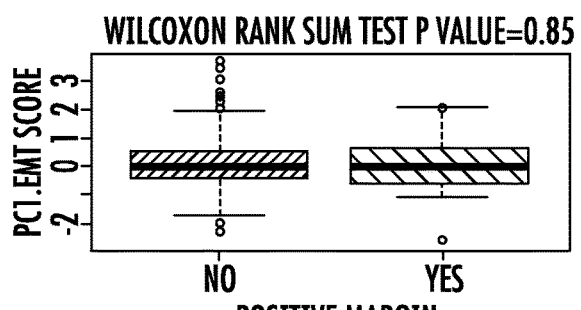
Figure 12L:
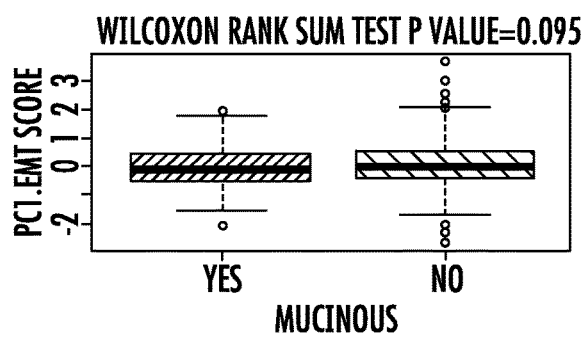
Figure 12M:
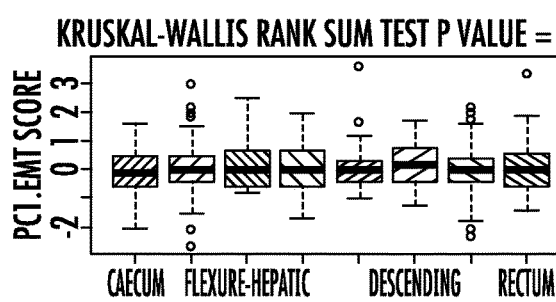
Figure 12N:
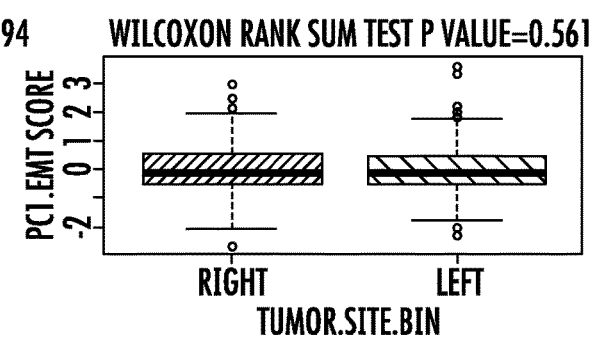
Figure 12O:
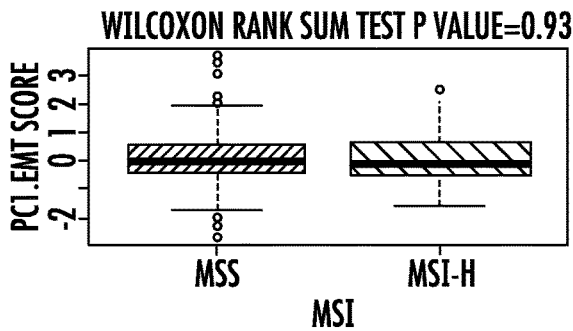
Figure 12P:
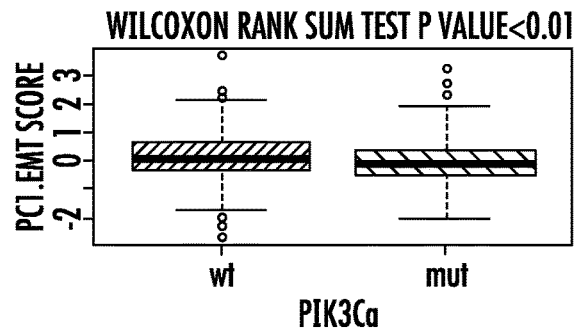
Figure 12Q:
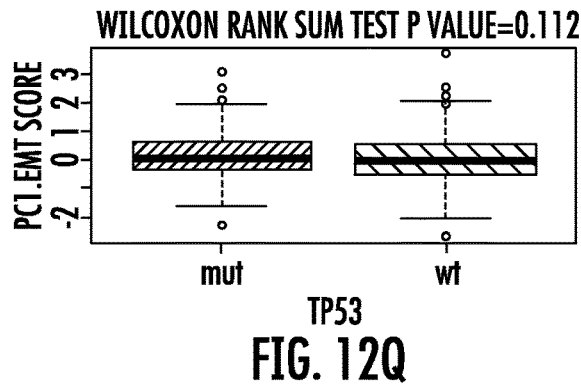
Figure 12R:
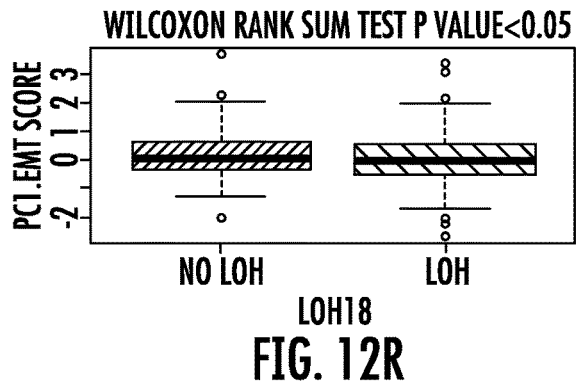
Figure 12S:
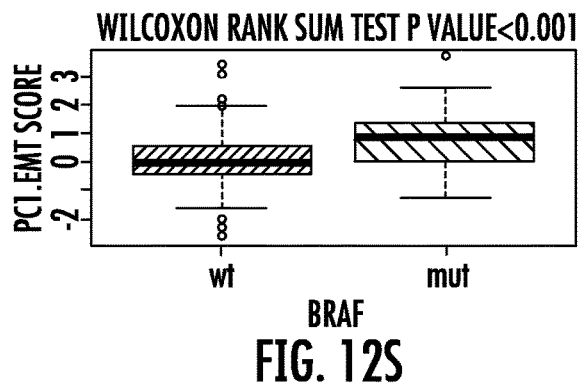
Figure 12T:
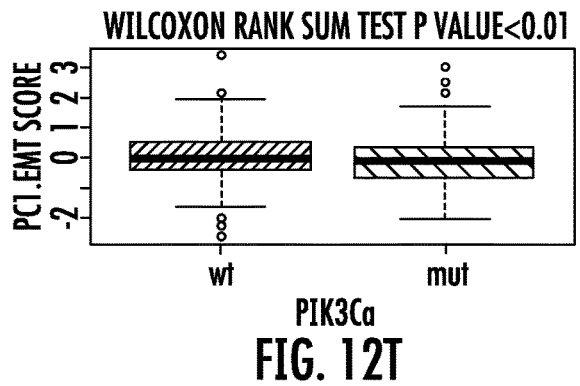
Figure 12U:
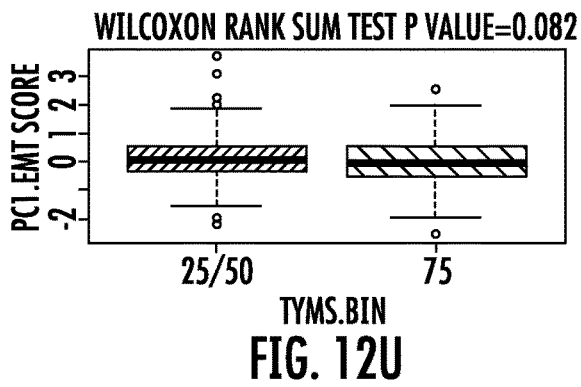
Figure 13A:
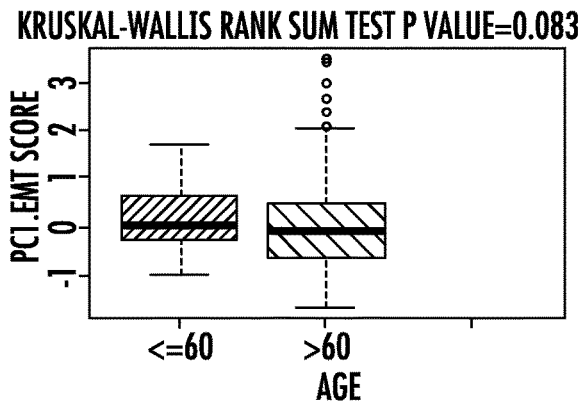
FIG. 13A to 13G are boxplots of PC1.EMT score split by the clinico-pathological-molecular features age (FIG. 13A), gender (FIG. 13B), stage (FIG. 13C), T.stage (FIG. 13D), mucinous (FIG. 13E), tumor site (FIG. 13F), and left or right tumor site (FIG. 13G) using the ALMAC dataset.
Figure 13B:
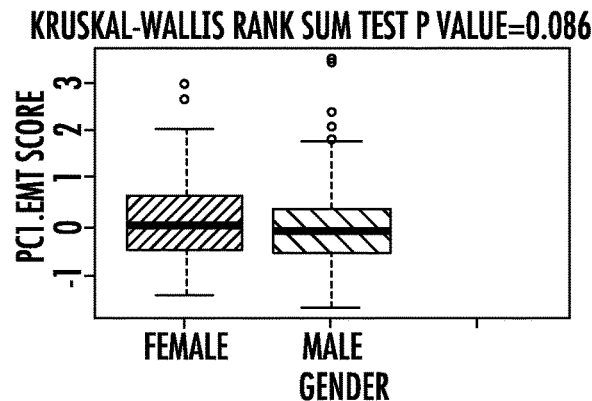
Figure 13C:
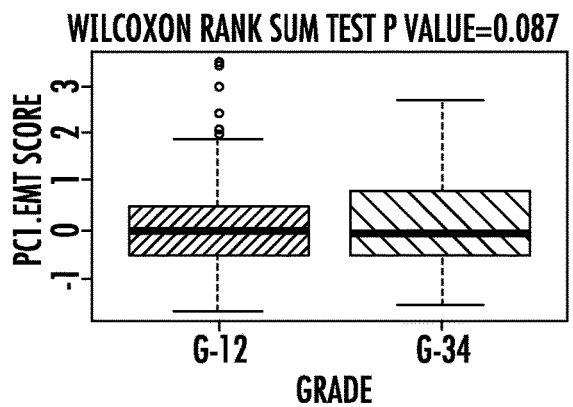
Figure 13D:
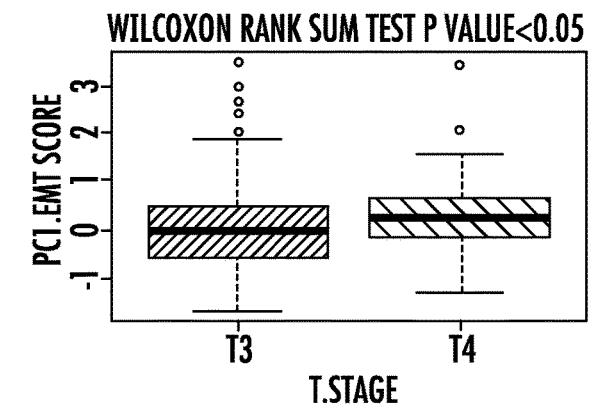
Figure 13E:
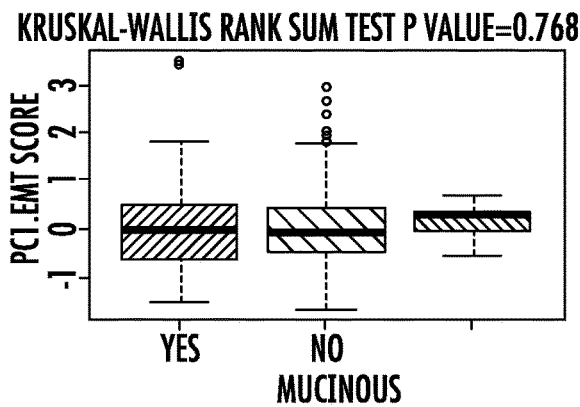
Figure 13F:
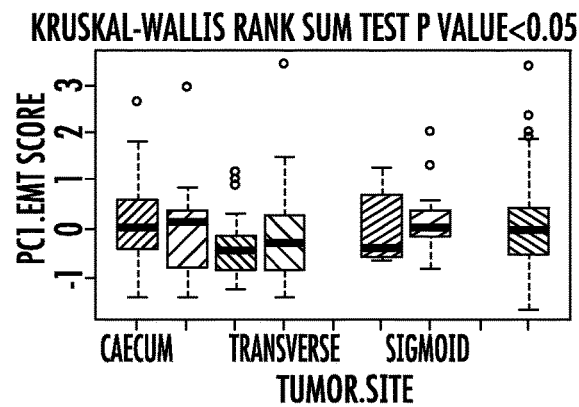
Figure 13G:
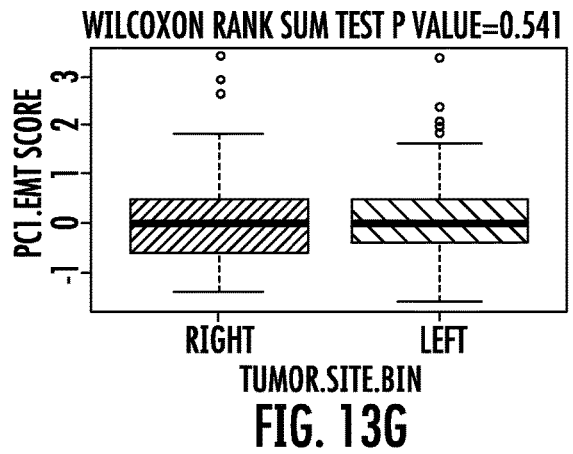
Figure 14A:
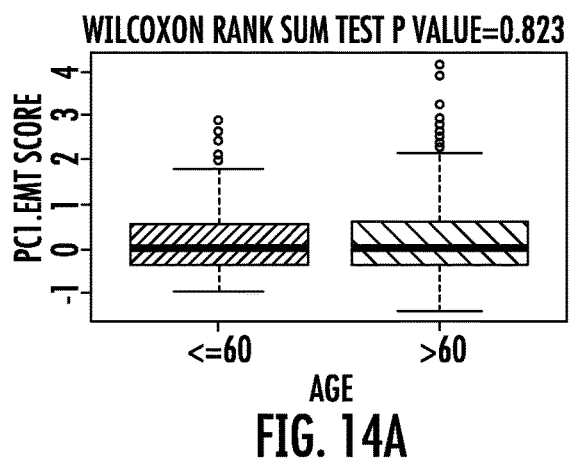
FIG. 14A to 14K are boxplots of PC1.EMT score split by the clinico-pathological-molecular features age (FIG. 14A), gender (FIG. 14B), stage (FIG. 14C), KRAS (FIG. 14D), MSI (FIG. 14E), KRAS (FIG. 14F), BRAF (FIG. 14G), TP53 (FIG. 14H), CIMP (FIG. 14I), adj. treatment (FIG. 14J), and CIN (FIG. 14K) using the French dataset.
Figure 14B:
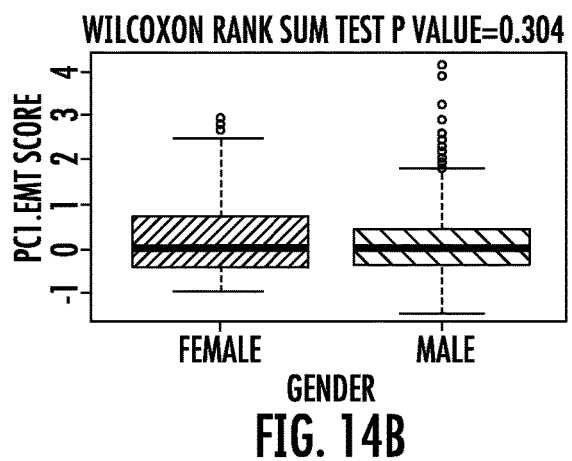
Figure 14C:
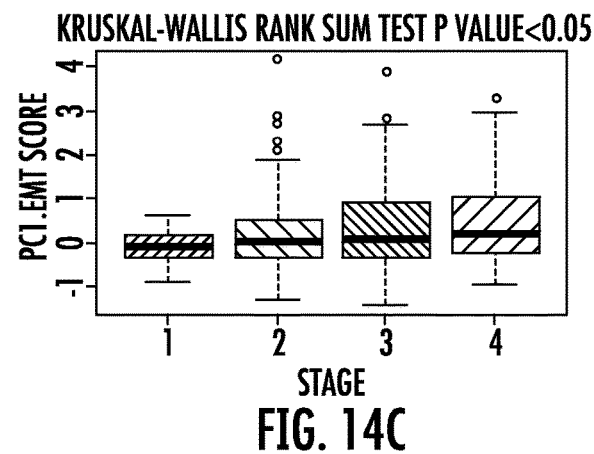
Figure 14D:
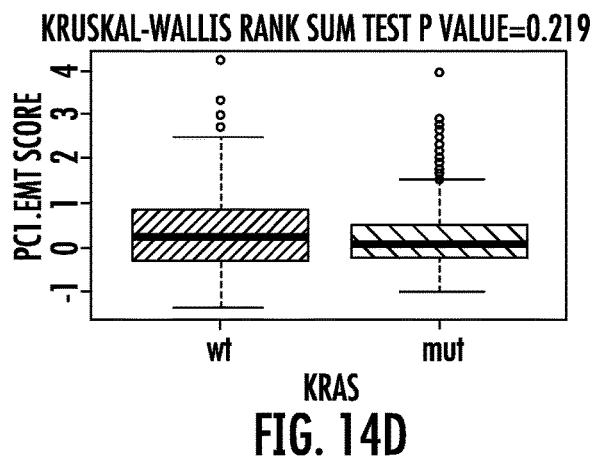
Figure 14E:
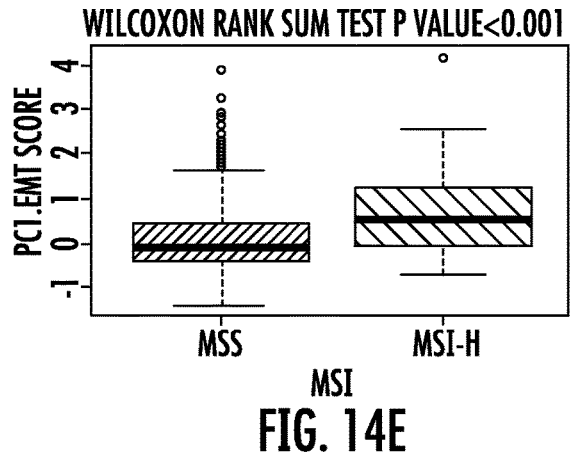
Figure 14F:
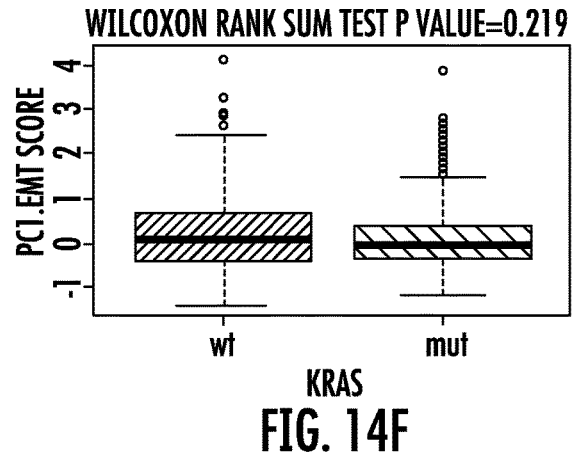
Figure 14G:
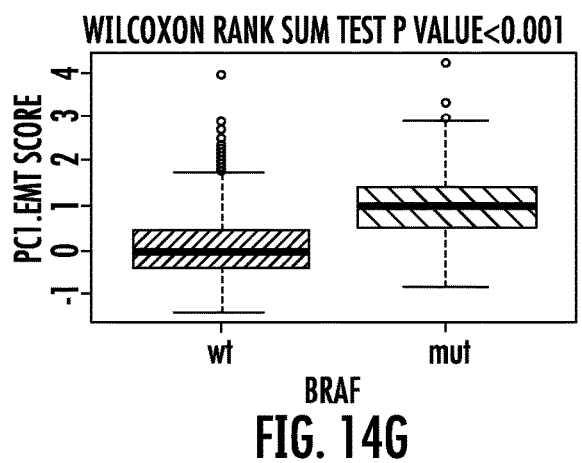
Figure 14H:
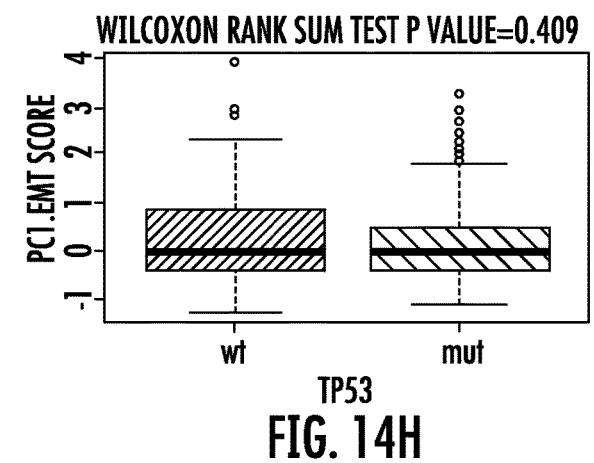
Figure 14I:
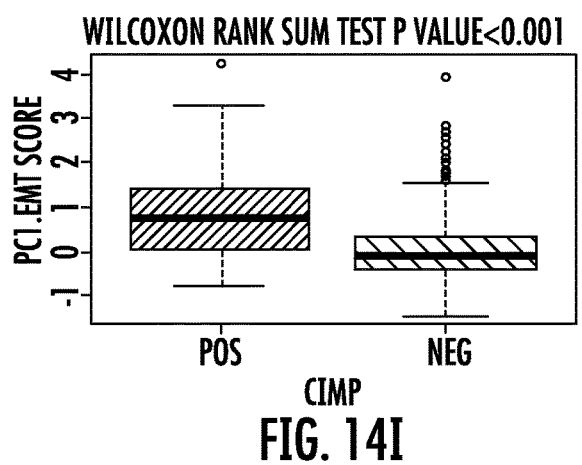
Figure 14J:
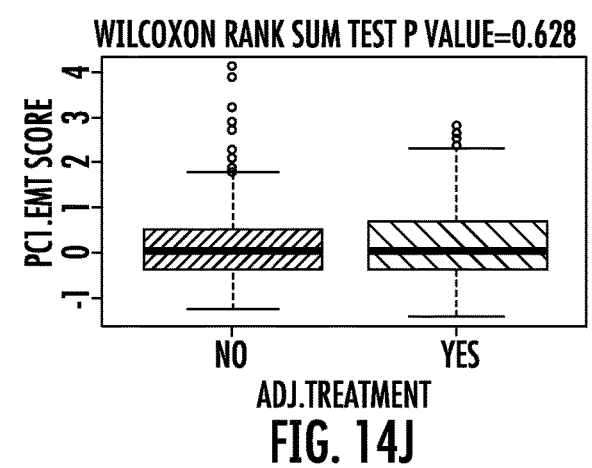
Figure 14K:
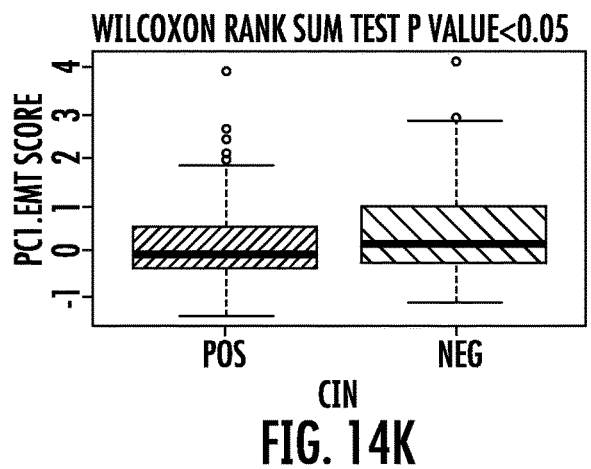
Figure 15A:
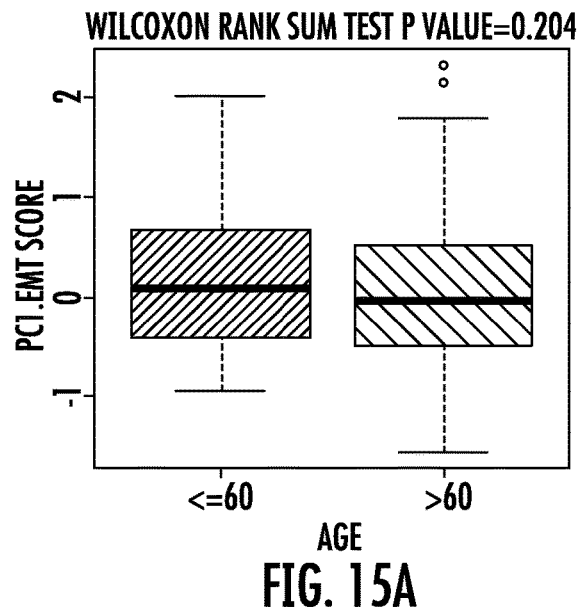
FIG. 15A to 15D are boxplots of PC1.EMT score split by the clinico-pathological-molecular features age (FIG. 15A), gender (FIG. 15B), Dukes stage (FIG. 15C), and tumor site (FIG. 15D) using the GSE14333 dataset.
Figure 15B:
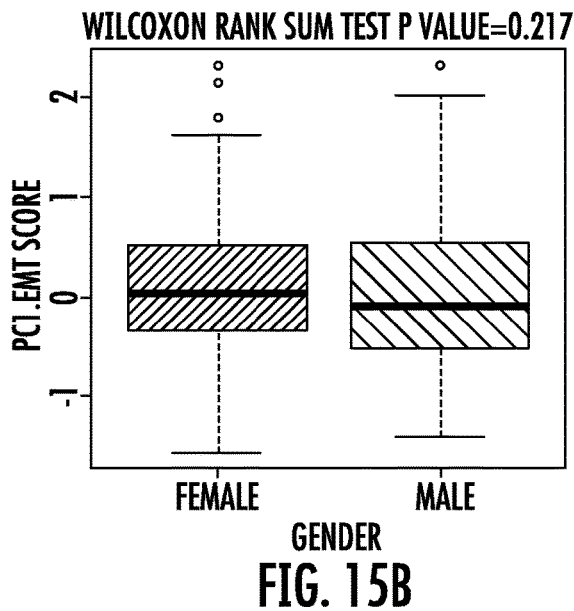
Figure 15C:
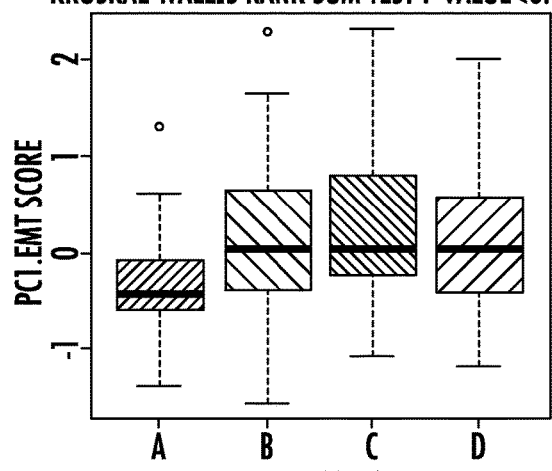
Figure 15D:
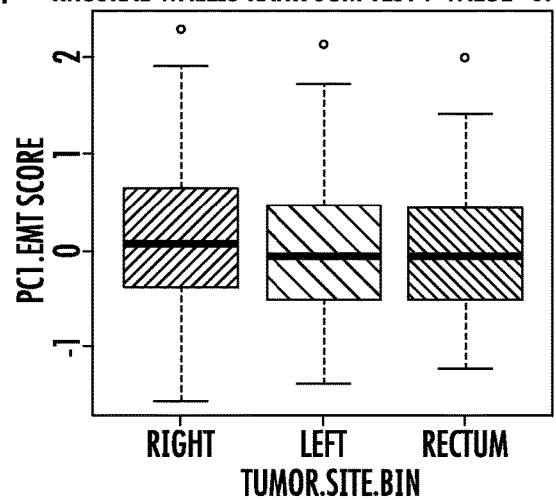
Figure 16A:
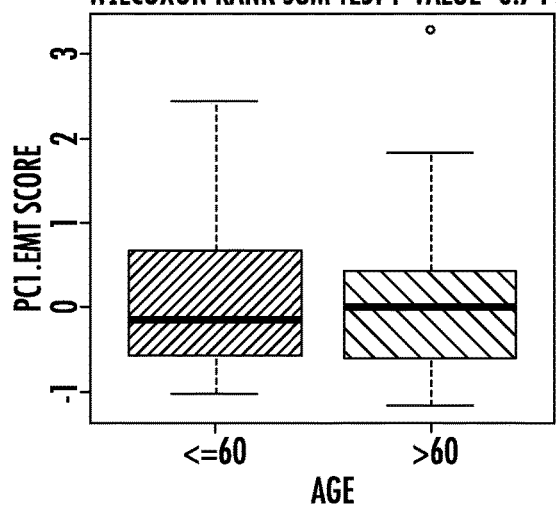
FIG. 16A to 16I are boxplots of PC1.EMT score split by the clinico-pathological-molecular features age (FIG. 16A), gender (FIG. 16B), stage (FIG. 16C), T.stage (FIG. 16D), N.stage (FIG. 16E), tumor site (FIG. 16F), left or right tumor site (FIG. 16G), MSI (FIG. 16H), and TP53 (FIG. 16I) using the GEO41258 dataset.
Figure 16B:
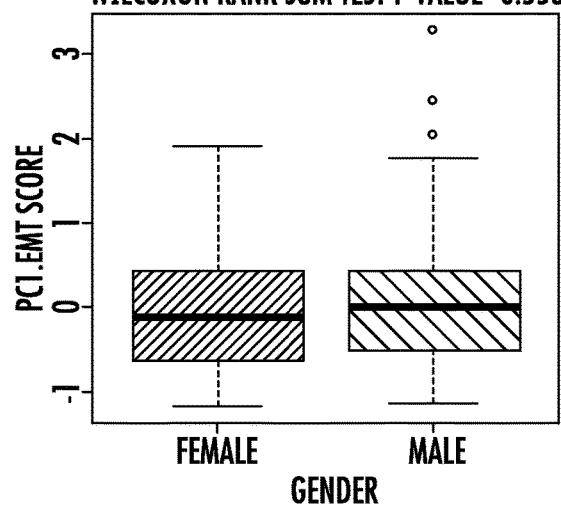
Figure 16C:
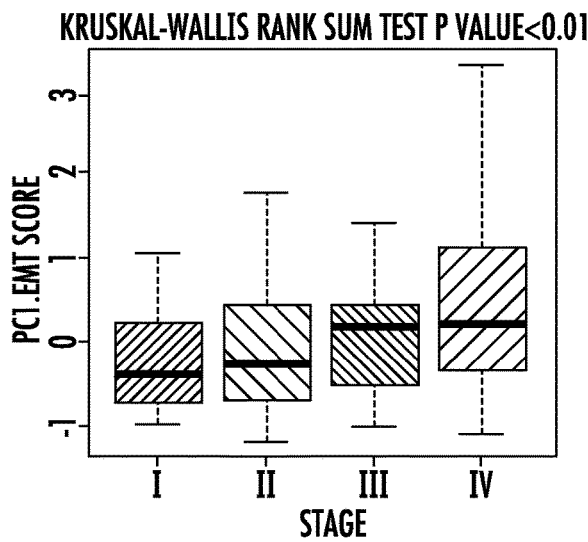
Figure 16D:
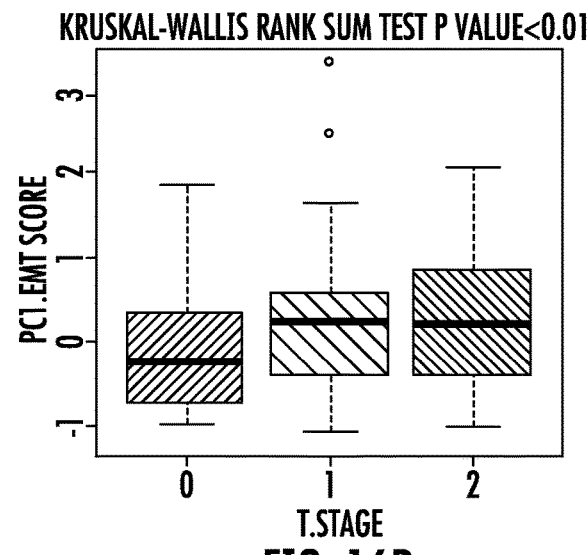
Figure 16E:
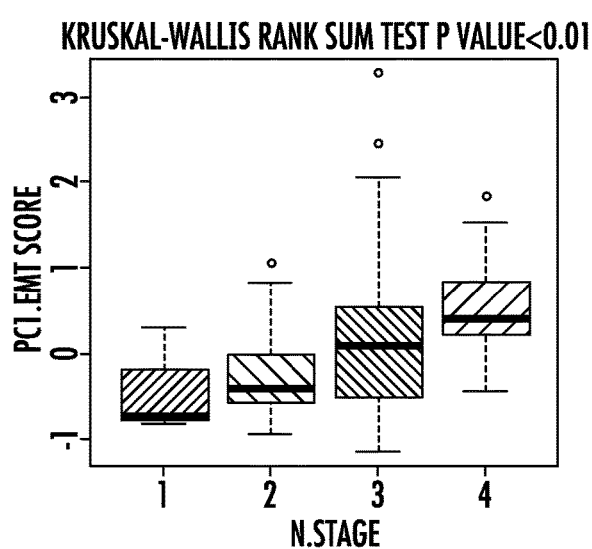
Figure 16F:
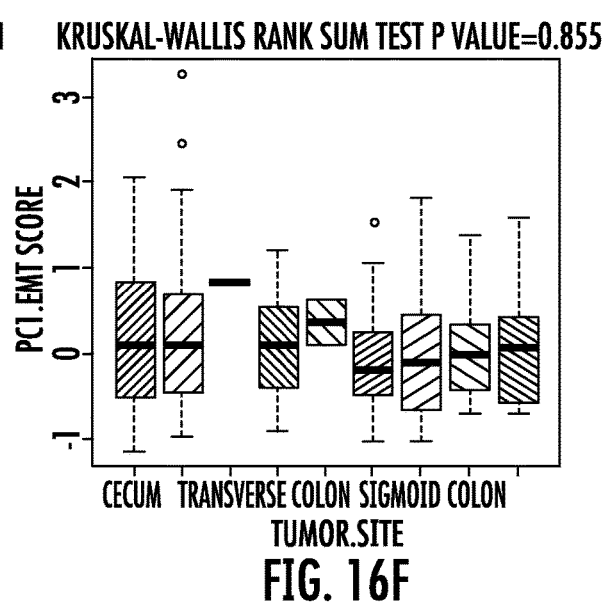
Figure 16G:
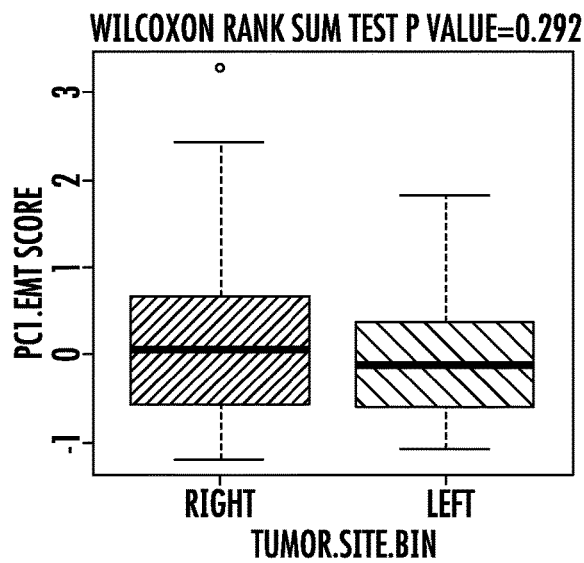
Figure 16H:
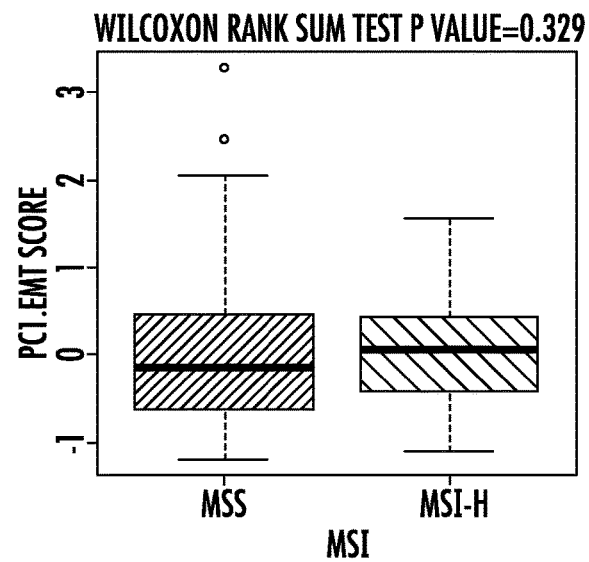
Figure 16I:
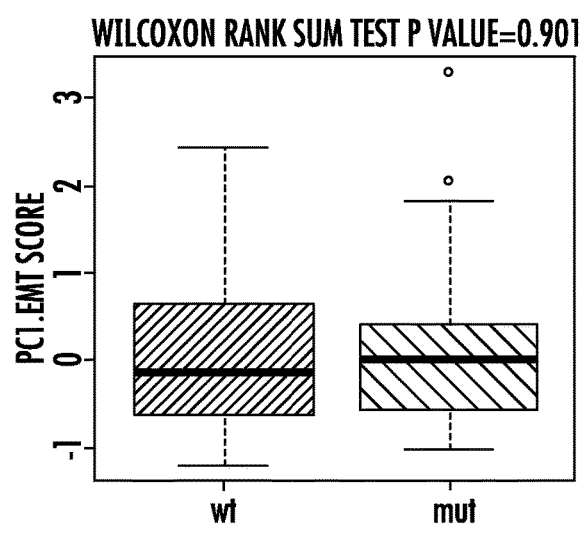
Figure 17A:
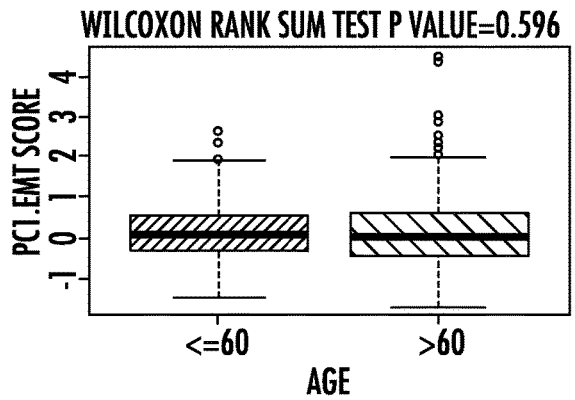
FIGS. 17A to 17L are boxplots of PC1.EMT score split by the clinico-pathological-molecular features age (FIG. 17A), gender (FIG. 17B), stage (FIG. 17C), T.stage (FIG. 17D), lympovascular invation (LVI) (FIG. 17E), perineural invasion (PNI) (FIG. 17F), mucinous (FIG. 17G), tumor site (FIG. 17H), left or right tumor site (FIG. 17I), MSI (FIG. 17J), KRAS (FIG. 17K), and BRAF (FIG. 17J) using the TCGA dataset.
Figure 17B:
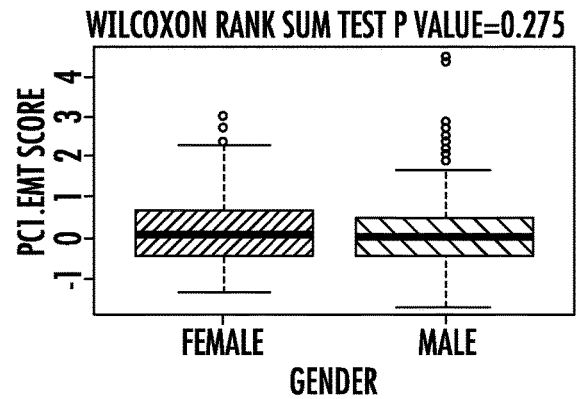
Figure 17C:
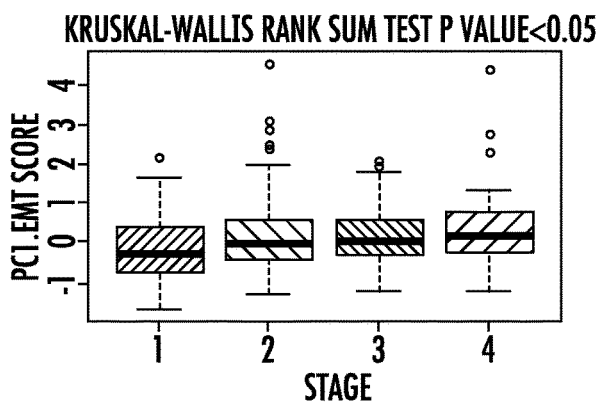
Figure 17D:
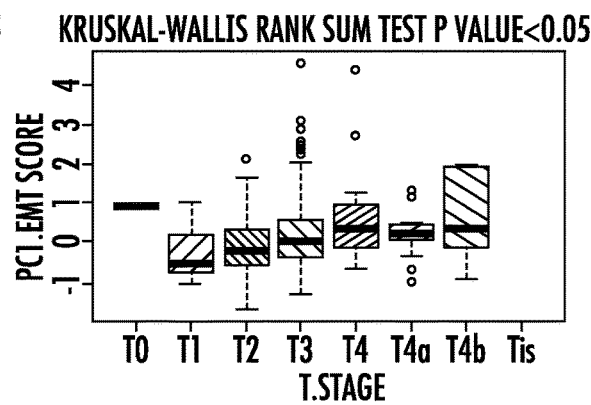
Figure 17E:
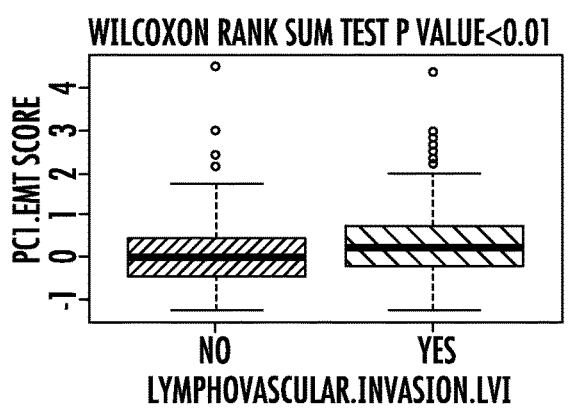
Figure 17F:
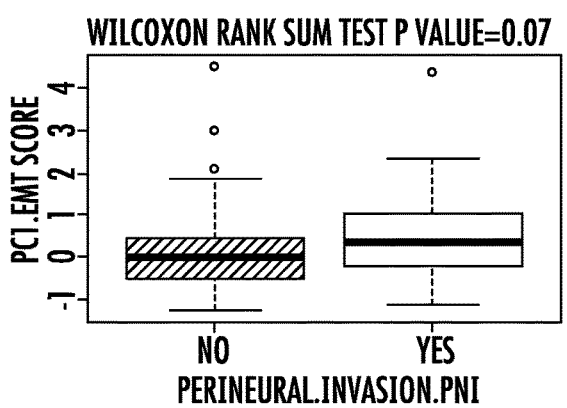
Figure 17G:
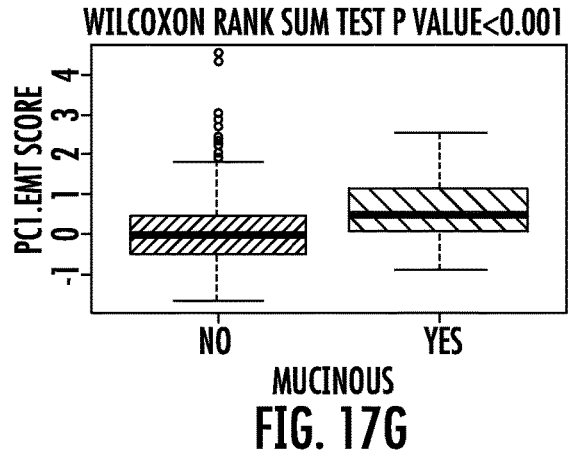
Figure 17H:
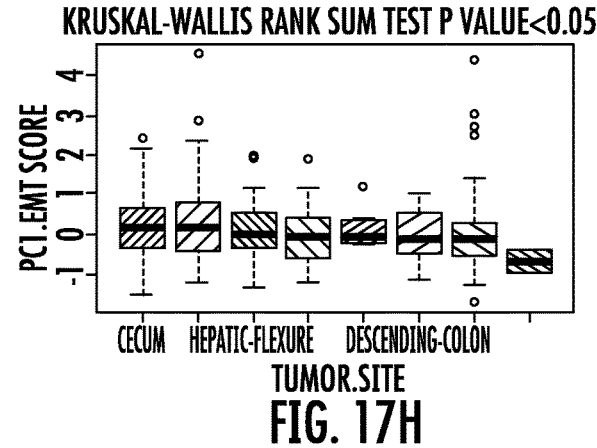
Figure 17I:
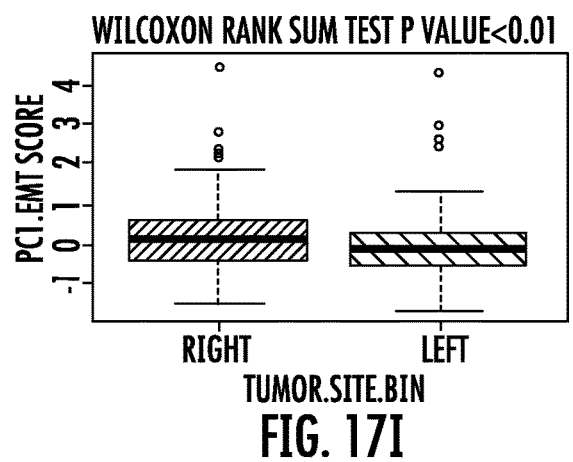
Figure 17J:
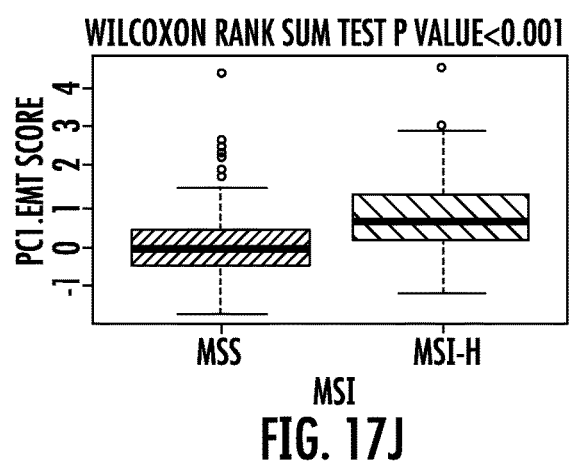
Figure 17K:
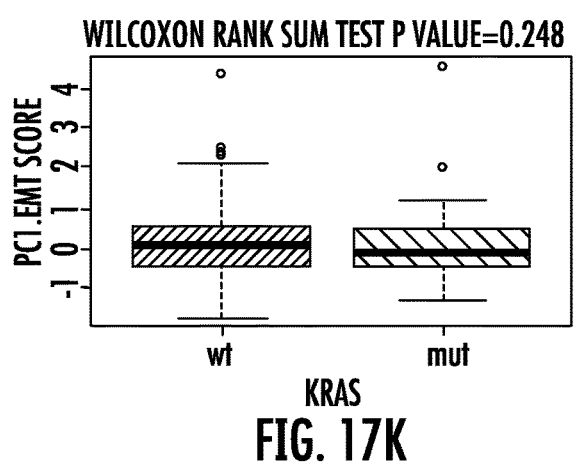
Figure 17L:
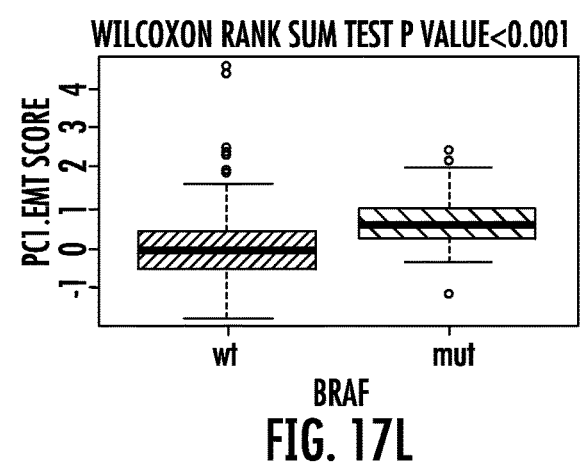

The expression of PC1.EMT score was also compared with the available Clinico-Pathological-Molecular features for each datasets. FIG. 12A to 12U are boxplots of PC1.EMT score split by the clinico-pathological-molecular features age (FIG. 12A), gender (FIG. 12B), stage (FIG. 12C), T.stage (FIG. 12D), N.stage (FIG. 12E), grade (FIG. 12F), adj. treatment (FIG. 12G), lymphovascular invation LVI (FIG. 12H), perineural invasion PNI (FIG. 12I), bowel obstruction (FIG. 12J), positive margin (FIG. 12K), mucinous (FIG. 12L), tumor site (FIG. 12M), left or right tumor site (FIG. 12N), MSI (FIG. 12O), PIK3Ca (FIG. 12P), TP53 (FIG. 12Q), LOH18 (FIG. 12R), BRAF (FIG. 12S), PIK3Ca (FIG. 12T), and TYMS using the PETACC dataset.

FIG. 13A to 13G are boxplots of PC1.EMT score split by the clinico-pathological-molecular features age (FIG. 13A), gender (FIG. 13B), stage (FIG. 13C), T.stage (FIG. 13D), mucinous (FIG. 13E), tumor site (FIG. 13F), and left or right tumor site (FIG. 13G) using the ALMAC dataset.

FIG. 14A to 14K are boxplots of PC1.EMT score split by the clinico-pathological-molecular features age (FIG. 14A), gender (FIG. 14B), stage (FIG. 14C), KRAS (FIG. 14D), MSI (FIG. 14E), KRAS (FIG. 14F), BRAF (FIG. 14G), TP53 (FIG. 14H), CIMP (FIG. 14I), adj. treatment (FIG. 14J), and CIN (FIG. 14K) using the French dataset.

FIG. 15A to 15D are boxplots of PC1.EMT score split by the clinico-pathological-molecular features age (FIG. 15A), gender (FIG. 15B), Dukes stage (FIG. 15C), and tumor site (FIG. 15D) using the GSE14333 dataset.

FIG. 16A to 16I are boxplots of PC1.EMT score split by the clinico-pathological-molecular features age (FIG. 16A), gender (FIG. 16B), stage (FIG. 16C), T.stage (FIG. 16D), N.stage (FIG. 16E), tumor site (FIG. 16F), left or right tumor site (FIG. 16G), MSI (FIG. 16H), and TP53 (FIG. 16I) using the GEO41258 dataset.

FIGS. 17A to 17L are boxplots of PC1.EMT score split by the clinico-pathological-molecular features age (FIG. 17A), gender (FIG. 17B), stage (FIG. 17C), T.stage (FIG. 17D), lympovascular invation (LVI) (FIG. 17E), perineural invasion (PNI) (FIG. 17F), mucinous (FIG. 17G), tumor site (FIG. 17H), left or right tumor site (FIG. 17I), MSI (FIG. 17J), KRAS (FIG. 17K), and BRAF (FIG. 17J) using the TCGA dataset.

PC1.EMT high score was usually associated with higher T and N stages, higher grade, mucinous histology. It was also higher in the right sided, MSI-High, BRAF V600E mutants and CIMP positive.

PC1.EMT and Copy Number Variations (CNVs)

Figure 18A:
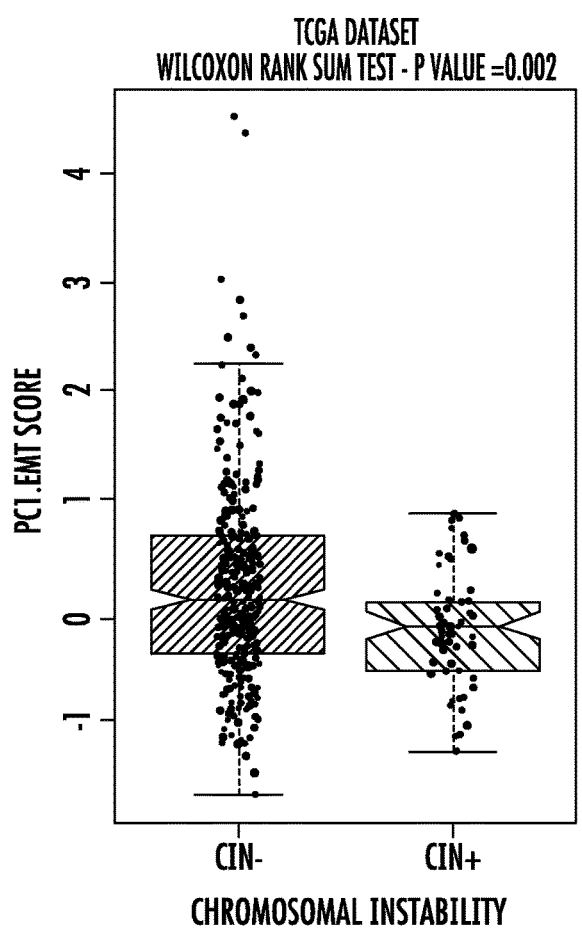
FIG. 18A to 18B are boxplot of the PC1.EMT score split by chromosomal instability (CIN) status in TCGA (FIG. 18A) and French (FIG. 18B) datasets.
Figure 18B:
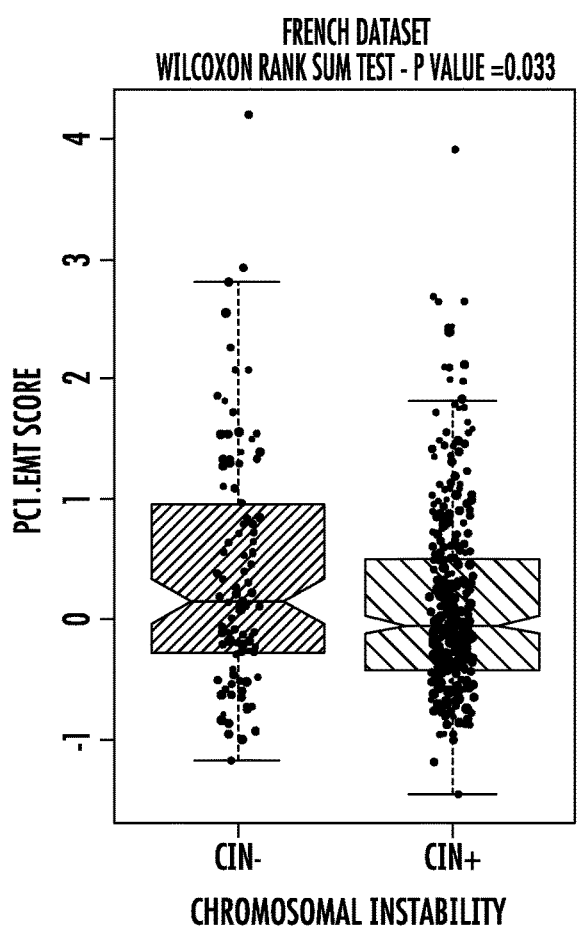
Figure 19A:
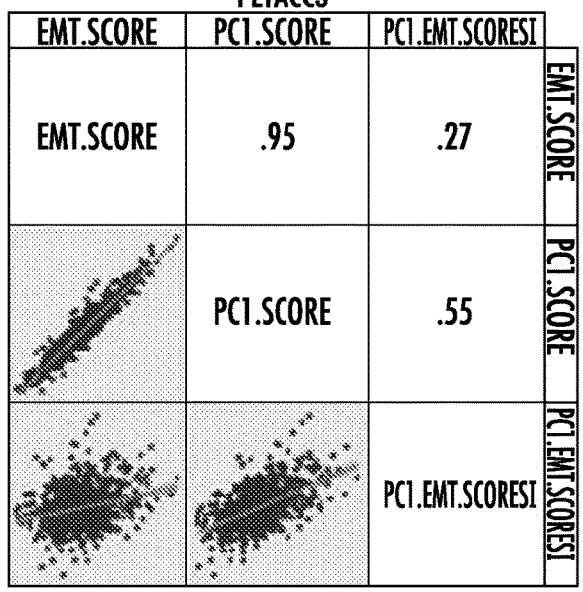
FIGS. 19A to 19E are show correlations between EMT, PC1 and ΔPC1.EMT scores on the datasets PETACC3 (FIG. 19A), ALMAC (FIG. 19B), GSE14333 (FIG. 19C), GEO41258 (FIG. 19D), and LNCC (FIG. 19E).
Figure 19B:
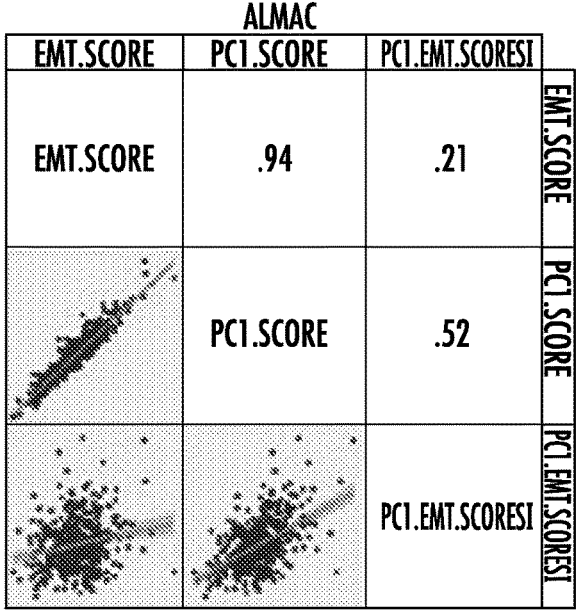
Figure 19C:
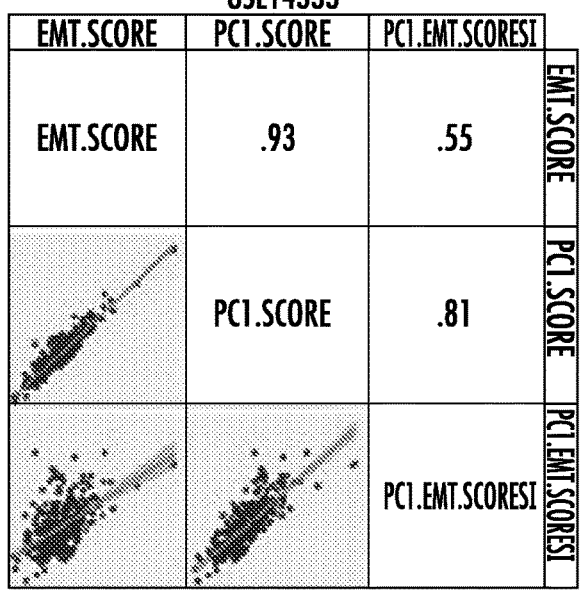
Figure 19D:
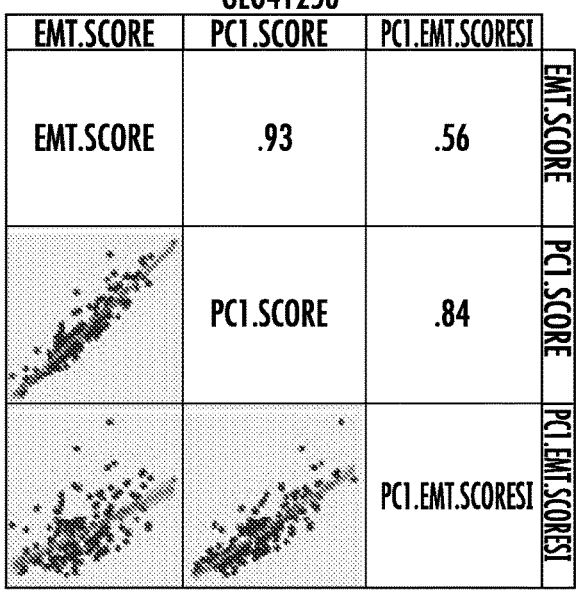
Figure 19E:
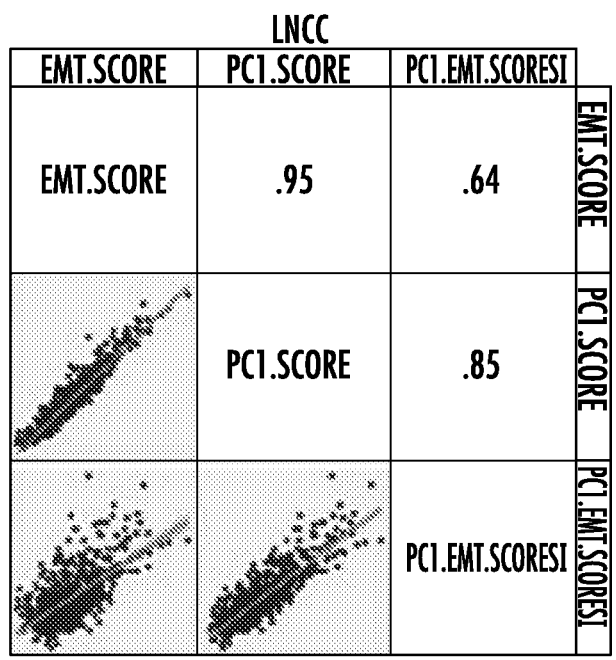

In order to assess if PC1.EMT is or not correlating with chromosomal instability (CIN), TCGA samples were split based on the number of chromosomal rearrangement observed. The CIN status was assigned according to CGH alteration profile. A CIN rate was designed as the proportion of chromosomes showing gain (segmented ratio>0.5) or loss (segmented ratio<-0.5) events (excluding sex chromosomes). A tumor having an alteration rate superior to 10% was considered CIN+, otherwise CIN-. FIG. 18A to 18B are boxplot of the PC1.EMT score split by chromosomal instability (CIN) status in TCGA (FIG. 18A) and French (FIG. 18B) datasets. PC1.EMT high score was associated with lower chromosomal instability.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a human patient with Dukes B colorectal cancer with adjuvant chemotherapy the method comprising:

(a) assaying colorectal cells from the human patient for the expression level of ten (10) or more genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, or their corresponding expression products, and ten (10) or more genes associated with SEQ ID NOS: 160, 173, 177, 190, 192, 213, 223, 230, 241, 248, 276, 280, 289, 295, 310, and 405-508, or their corresponding expression products, and using normalized values of the expression levels to calculate a colorectal cancer (CRC) score;

(b) assaying colorectal cells from the human patient for the expression levels of ten (10) or more genes associated with SEQ ID NOS: 1-149, or their corresponding expression products, and ten (10) or more genes associated with SEQ ID NOS: 150-310, or their corresponding expression products, and using normalized values of the expression levels to calculate an Epithelial to Mesenchymal Transition (EMT) score; and (c) calculating the difference between the CRC score and the EMT score to arrive at a Recurrence Signature Score that determines that the patient with Dukes B colorectal cancer has a high risk of recurrence of colorectal cancer and would benefit from adjuvant chemotherapy; and d); and treating the patient from step d) above with adjuvant chemotherapy.

2. The method of claim 1, further comprising displaying or outputting to a user, user interface device, computer readable storage medium, or local or remote computer system the calculated risk of colorectal cancer recurrence.

3. The method of claim 1, wherein the chemotherapy comprises a 5-fluorouracil (5-FU) therapy.

4. The method of claim 1, wherein increased expression of the genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, or their corresponding expression products, increases the CRC score; and wherein increased expression of the genes associated with SEQ ID NOS: 160, 173, 177, 190, 192, 213, 223, 230, 241, 248, 276, 280, 289, 295, 310, and 405-508, or their corresponding products, decreases the CRC score.

5. The method of claim 1, wherein increased expression of the genes associated with SEQ ID NOS: 1-149, or their corresponding expression products, increases the EMT score; and wherein increased expression of the genes associated with SEQ ID NOS: 150-310, or their corresponding products, decreases the EMT score.

6. The method of claim 1, wherein the expression levels are normalized by quantile normalization.

7. The method of claim 1, wherein the normalized expression values of the expression levels for each assayed gene are given equal weight in calculating the CRC score.

8. The method of claim 1, wherein the normalized expression values of the expression levels for each assayed gene are given equal weight in calculating the EMT score.

9. A method for treating a human patient with of Dukes B colorectal cancer with adjuvant chemotherapy the method comprising:
(a) assaying colorectal cells from the human patient for normalized expression values of ten (10) or more genes associated with SEQ ID NOS: 1-149, ten (10) or more genes associated with SEQ ID NOS: 150-310, ten (10) or more genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, and ten (10) or more genes associated with SEQ ID NOS: 160, 173, 177, 190, 192, 213, 223, 230, 241, 248, 276, 280, 289, 295, 310, and 405-508;
(b) inputting the normalized expression values into a computer programmed to execute an algorithm to convert the normalized expression values to a Recurrence Signature Score indicative that the subject would benefit from adjuvant chemotherapy, wherein the algorithm gives reduced weight to the normalized expression values for genes that are listed more than once in step a); and further wherein the algorithm converts the normalized expression values for the genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404 and the genes associated with SEQ ID NOS: 160, 173, 177, 190, 192, 213, 223, 230, 241, 248, 276, 280, 289, 295, 310, and 405-508 to a colorectal cancer (CRC) score, wherein the algorithm converts the normalized expression values for the genes associated with SEQ ID NOS: 1-310 to an Epithelial to Mesenchymal Transition (EMT) score, wherein the Recurrence Signature Score is determined by calculating the difference between the CRC score and the EMT score; and
c) treating the human patient with Dukes B colorectal cancer and a high risk of colorectal cancer recurrence by providing adjuvant chemotherapy.

10. The method of claim 9, wherein increased expression of the genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, or their corresponding expression products, increases the CRC score; and wherein increased expression of the genes associated with SEQ ID NOS: 160, 173, 177, 190, 192, 213, 223, 230, 241, 248, 276, 280, 289, 295, 310, and 405-508, or their corresponding products, decreases the CRC score.

11. The method of claim 9, wherein increased expression of the genes associated with SEQ ID NOS: 1-149, or their corresponding expression products, increases the EMT score; and wherein increased expression of SEQ ID NOS: 150-310, or their corresponding products, decreases the EMT score.

12. The method of claim 9, wherein the chemotherapy comprises a 5-fluorouracil (5-FU) therapy.

13. The method of claim 9, wherein the expression levels are normalized by quantile normalization.

14. The method of claim 9, wherein the normalized expression values of the expression levels for each assayed gene are given equal weight in calculating the CRC score.

15. The method of claim 9, wherein the normalized expression values of the expression levels for each assayed gene are given equal weight in calculating the EMT score.

16. A method for treating a human patient with Dukes C colorectal cancer, wherein the subject is treated with surgery but is not treated with post-operative adjuvant chemotherapy within 6 months of surgery, the method comprising:
(a) assaying colorectal cells from the human patient for the expression level of ten (10) or more genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, or their corresponding expression products, and ten (10) or more genes associated with SEQ ID NOS: 160, 173, 177, 190, 192, 213, 223, 230, 241, 248, 276, 280, 289, 295, 310, and 405-508, or their corresponding expression products, and using normalized values of the expression levels to calculate a colorectal cancer (CRC) score;
(b) assaying colorectal cells from the human patient for the expression levels of ten (10) or more genes associated with SEQ ID NOS: 1-149, or their corresponding expression products, and ten (10) or more genes associated with SEQ ID NOS: 150-310, or their corresponding expression products, and using normalized values of the expression levels to calculate an Epithelial to Mesenchymal Transition (EMT) score; and
(c) calculating the difference between the CRC score and the EMT score to arrive at a Recurrence Signature Score that determines that the patient with Dukes C colorectal cancer has a low risk of recurrence of colorectal cancer and would not benefit from adjuvant chemotherapy; and
d) treating the patient from step d) above with surgery but not with post-operative adjuvant chemotherapy within 6 months of surgery.

17. The method of claim 16, further comprising displaying or outputting to a user, user interface device, computer readable storage medium, or local or remote computer system the calculated risk of colorectal cancer recurrence.

18. The method of claim 17, wherein the chemotherapy comprises a 5-fluorouracil (5-FU) therapy.

19. The method of claim 16, wherein increased expression of the genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, or their corresponding expression products, increases the CRC score; and wherein increased expression of the genes associated with SEQ ID NOS: 160, 173, 177, 190, 192, 213, 223, 230, 241, 248, 276, 280, 289, 295, 310, and 405-508, or their corresponding products, decreases the CRC score.

20. The method of claim 16, wherein increased expression of the genes associated with SEQ ID NOS: 1-149, or their corresponding expression products, increases the EMT score; and wherein increased expression of the genes associated with SEQ ID NOS: 150-310, or their corresponding products, decreases the EMT score.

21. The method of claim 16, wherein the expression levels are normalized by quantile normalization.

22. The method of claim 16, wherein the normalized expression values of the expression levels for each assayed gene are given equal weight in calculating the CRC score.

23. The method of claim 16, wherein the normalized expression values of the expression levels for each assayed gene are given equal weight in calculating the EMT score.

24. A method for treating a human patient with Dukes C colorectal cancer, wherein the subject is treated with surgery but is not treated with post-operative adjuvant chemotherapy within 6 months of surgery, the method comprising:
   (a) assaying colorectal cells from the human patient for normalized expression values of ten (10) or more genes associated with SEQ ID NOS: 1-149, ten (10) or more genes associated with SEQ ID NOS: 150-310, ten (10) or more genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, and ten (10) or more genes associated with SEQ ID NOS: 160, 173, 177, 190, 192, 213, 223, 230, 241, 248, 276, 280, 289, 295, 310, and 405-508;
   (b) inputting the normalized expression values into a computer programmed to execute an algorithm to convert the normalized expression values to a Recurrence Signature Score indicative that the subject would not benefit from adjuvant chemotherapy, wherein the algorithm gives reduced weight to the normalized expression values for genes that are listed more than once in step a); and further wherein the algorithm converts the normalized expression values for the genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404 and the genes associated with SEQ ID NOS: 160, 173, 177, 190, 192, 213, 223, 230, 241, 248, 276, 280, 289, 295, 310, and 405-508 to a colorectal cancer (CRC) score, wherein the algorithm converts the normalized expression values for the genes associated with SEQ ID NOS: 1-310 to an Epithelial to Mesenchymal Transition (EMT) score, wherein the Recurrence Signature Score is determined by calculating the difference between the CRC score and the EMT score; and
   c) treating the human patient with Dukes C colorectal cancer with surgery but not with post-operative adjuvant chemotherapy within 6 months of surgery.

25. The method of claim 24, wherein increased expression of the genes associated with SEQ ID NOS: 7, 13, 18, 19, 30, 38, 43, 45, 52, 59, 67, 69, 76, 94, 95, 97, 98, 100, 101, 103, 104, 106, 122, 123, 127, 134, 135, 139, 142, 148, and 311-404, or their corresponding expression products, increases the CRC score; and wherein increased expression of the genes associated with SEQ ID NOS: 160, 173, 177, 190, 192, 213, 223, 230, 241, 248, 276, 280, 289, 295, 310, and 405-508, or their corresponding products, decreases the CRC score.

26. The method of claim 24, wherein increased expression of the genes associated with SEQ ID NOS: 1-149, or their corresponding expression products, increases the EMT score; and wherein increased expression of the genes associated with SEQ ID NOS: 150-310, or their corresponding products, decreases the EMT score.

27. The method of claim 24, wherein the expression levels are normalized by quantile normalization.

28. The method of claim 24, wherein the normalized expression values of the expression levels for each assayed gene are given equal weight in calculating the CRC score.

29. The method of claim 24, wherein the normalized expression values of the expression levels for each assayed gene are given equal weight in calculating the EMT score.

* * * * *

UNITED STATES PATENT AND TRADEMARK OFFICE
CERTIFICATE OF CORRECTION

PATENT NO. : 11,035,006 B2
APPLICATION NO. : 14/907372
DATED : June 15, 2021
INVENTOR(S) : Michael Schell et al.

Page 1 of 1

It is certified that error appears in the above-identified patent and that said Letters Patent is hereby corrected as shown below:

In the Claims

Column 250, Lines 64-66, for claim reference numeral '1', "chemotherapy, and and d) and treating the patient from step d) above with adjuvant chemotherapy" should read, --chemotherapy, and d) and treating the patient from step c) above with adjuvant chemotherapy--.

Column 251, Line 31, for claim reference numeral '9', "A method for treating a human patient with of Dukes B colorectal cancer with adjuvant chemotherapy the method comprising" should read, --A method for treating a human patient with Dukes B colorectal cancer with adjuvant chemotherapy the method comprising--.

Signed and Sealed this
Fifth Day of April, 2022

Drew Hirshfeld
*Performing the Functions and Duties of the
Under Secretary of Commerce for Intellectual Property and
Director of the United States Patent and Trademark Office*